United States Patent
Safadi

(10) Patent No.: US 9,944,988 B2
(45) Date of Patent: Apr. 17, 2018

(54) MODULATION OF NLGN4 EXPRESSION, NK CELL ACTIVITY IN NON-ALCOHOLIC FATTY LIVER DISEASE (NAFLD)

(71) Applicant: HADASIT MEDICAL RESEARCH SERVICES AND DEVELOPMENT LTD., Jerusalem (IL)

(72) Inventor: Rifaat Safadi, Nazareth Elit (IL)

(73) Assignee: Hadasit Medical Research Services and Development Ltd., Jerusalem (IL)

( * ) Notice: Subject to any disclaimer, the term of this patent is extended or adjusted under 35 U.S.C. 154(b) by 0 days.

(21) Appl. No.: 15/256,781

(22) Filed: Sep. 6, 2016

(65) Prior Publication Data

US 2016/0369347 A1 Dec. 22, 2016

Related U.S. Application Data

(63) Continuation of application No. 14/963,319, filed on Dec. 9, 2015, now Pat. No. 9,469,855, which is a continuation of application No. 14/501,160, filed on Sep. 30, 2014, now Pat. No. 9,243,294.

(60) Provisional application No. 61/884,153, filed on Sep. 30, 2013.

(51) Int. Cl.
| | |
|---|---|
| *C07H 21/02* | (2006.01) |
| *C12Q 1/68* | (2018.01) |
| *A61K 31/7088* | (2006.01) |
| *A61K 45/06* | (2006.01) |
| *C12N 15/113* | (2010.01) |
| *A61K 31/713* | (2006.01) |
| *A61K 31/7105* | (2006.01) |

(52) U.S. Cl.
CPC ........ *C12Q 1/6883* (2013.01); *A61K 31/7088* (2013.01); *A61K 31/713* (2013.01); *A61K 31/7105* (2013.01); *A61K 45/06* (2013.01); *C12N 15/1138* (2013.01); *C12N 2310/11* (2013.01); *C12N 2310/14* (2013.01); *C12Q 2600/158* (2013.01)

(58) Field of Classification Search
CPC .......................... C12N 15/111; C12N 15/113
See application file for complete search history.

(56) References Cited

U.S. PATENT DOCUMENTS

| | | |
|---|---|---|
| 4,816,567 A | 3/1989 | Cabilly |
| 5,641,870 A | 6/1997 | Rinderknecht |
| 5,910,573 A | 6/1999 | Pluckthun |
| 7,579,392 B2 | 8/2009 | Gan |

FOREIGN PATENT DOCUMENTS

| | | |
|---|---|---|
| EP | 0404097 | 12/1990 |
| WO | 93/11161 | 6/1993 |
| WO | 93/15210 | 8/1993 |
| WO | 96/13583 | 5/1996 |
| WO | 96/37621 | 11/1996 |

OTHER PUBLICATIONS

Bian and Ma (2012) Liver fibrogenesis in non-alcoholic steatohepatitis. Front Physiol 3: 248.
Bird et al., (1988) Single-chain antigen-binding proteins. Science 242(4877): 423-6.
Björkström et al., (2010) Expression patterns of NKG2A, KIR, and CD57 define a process of CD56dim NK-cell differentiation uncoupled from NK-cell education. Blood 116(19): 3853-64.
Bolliger et al., (2001) Identification of a novel neuroligin in humans which binds to PSD-95 and has a widespread expression. Biochem J 356(Pt 2): 581-8.
Bolliger et al., (2008) Unusually rapid evolution of Neuroligin-4 in mice. Proc Natl Acad Sci U S A 105(17): 6421-6.
Clackson et al., (1991) Making antibody fragments using phage display libraries. Nature 352(6336): 624-8.
Cooper et al., (2001) Human natural killer cells: a unique innate immunoregulatory role for the CD56 (bright) subset. Blood 97(10): 3146-51.
Holliger et al., (1993) "Diabodies": small bivalent and bispecific antibody fragments. Proc Natl Acad Sci U S A 90(14): 6444-8.
Huston et al., (1988) Protein engineering of antibody binding sites: recovery of specific activity in an anti-digoxin single-chain Fv analogue produced in *Escherichia coli*. Proc Natl Acad Sci U S A 85(16): 5879-83.
Kohler and Milstein (1975) Continuous cultures of fused cells secreting antibody of predefined specificity. Nature 256(5517):495-7.
Lopez-Vergès et al., (2010) CD57 defines a functionally distinct population of mature NK cells in the human CD56dimCD16+NK-cell subset. Blood 116(19): 3865-74.
Marks et al., (1991) By-passing immunization. Human antibodies from V-gene libraries displayed on phage. J Mol Biol 222(3): 581-97.
Melhem et al., (2006) Anti-fibrotic activity of NK cells in experimental liver injury through killing of activated HSC. J Hepatol 45(1): 60-71.
Moreira (2007) Hepatic stellate cells and liver fibrosis. Arch Pathol Lab Med 131(11): 1728-34.
Morella (2010) Dissecting CD56dim human NK cells. Blood 116: 3689-3691.
Muhanna et al., (2007) Lymphocyte-hepatic stellate cell proximity suggests a direct interaction. Clin Exp Immunol 148 (2): 338-47.
Muller et al., (1998) A dimeric bispecific miniantibody combines two specificities with avidity. FEBS Letters 432(1-2): 45-49.

(Continued)

*Primary Examiner* — Amy H Bowman
(74) *Attorney, Agent, or Firm* — Roach Brown McCarthy & Gruber, P.C.; Kevin D. McCarthy

(57) ABSTRACT

The present invention provides a method of diagnosing and/or monitoring a liver disorder in a subject. The method calls for isolating an immune cell population from a biological sample of the subject; and detecting expression level of an NLGn4 gene product in the immune cell population using NLGn4 specific primers or NLGn4 specific probes.

9 Claims, 7 Drawing Sheets

(56) References Cited

OTHER PUBLICATIONS

Sans et al., (2000) A developmental change in NMDA receptor-associated proteins at hippocampal synapses. J Neurosci 20(3): 1260-71.

Seki et al., (2011) Antitumor immunity produced by the liver Kupffer cells, NK cells, NKT cells, and CD8 CD122 T cells. Clin Dev Immunol 2011: 868345.

Wang et al., (2010) Delivery of siRNA therapeutics: barriers and carriers. AAPS J 12(4): 492-503.

Zapata et al., (1995) Engineering linear F(ab')2 fragments for efficient production in *Escherichia coli* and enhanced antiproliferative activity. Protein Eng 8(10): 1057-62.

Zelber-Sagi et al., (2011) Nutrition and physical activity in NAFLD: an overview of the epidemiological evidence. World J Gastroenterol 17(29): 3377-89.

Clinical Trial No. NCT01133184: Improved Prevention of Perinatal Hepatitis B Transmission. Updated May 27, 2010, http://www.clinicaltrials.gov/ct2/show/NCT01133184?term=nct01133184&rank=1.

https://en.wikipedia.org/wiki/Small_interfering_RNA—obtained Jul. 27, 2015.

Page 661 left column Microbial Mol Biol Rev. Dec. 2003; 67(4): 657-685 http://www.ncbi.nlm.nih.gov/pmc/articles/PMC309050/).

Wittrup et al., Knocking down disease: a progress report on siRNA therapeutics, Nat Rev Genet. Aug. 18, 2015; 16(9):543-52 (10 pages).

Abu-Tair et al., (2013) 1102 Neuroligin-4 receptor silencing increased human natural killer activity and decreased hepatic stellate cells activation. Journal of Hepatology 58: S450 (1 page).

Leone et al., (2010) Structural insights into the exquisite selectivity of neurexin/neuroligin synaptic interactions. The EMBO journal 29(14): 2461-2471 (11 pages).

Yanagi et al., (2012) Identification of four novel synonymous substitutions in the X-linked genes neuroligin 3 and neuroligin 4X in Japanese patients with autistic spectrum disorder. Autism research and treatment 2012: 724072; 5 pages.

SEQUENCE LISTING

```
<160> NUMBER OF SEQ ID NOS: 20

<210> SEQ ID NO 1
<211> LENGTH: 338857
<212> TYPE: DNA
<213> ORGANISM: Homo sapiens

<400> SEQUENCE: 1
atctctcttt ttcttgcaga accgtctctc tcccttctct gtctcttagc acagagctct        60
tattcagcca ctagcttggc ccttcctgct tcaattgtaa tgcttgttct gcccgtccac       120
agactattgg cggcagaaac aacgaatttc ctccaaacta ggcggtgttg gtggctcttg       180
cattcctctg gatgaggaaa tctagttggg gggttccaga aggggaaggc tcctgggctt       240
tcaatacatc ctcctgaatc atacctcgtt tcgggttccc tagaaaaatc tggacgtgta       300
aaaagaactc ttaacggccg atgcagctct tccaaagcta aggtaggtgc agttttaaga       360
cctgtctctg ggacattatt ctcattttaa aaagccgttt aaacattttg acttgcagca       420
aaggatggaa agcctcactg cagatacttg agcttcactt catctgatct ttatttttc        480 cttttatgat tattaatatt atttttggaa aatttggaca ggactttctc ccatctgtct       540
```

-continued

```
cgctgcattt cttaggtgtg ggtgggagtg tagaccttca tacggttttt acatgcaacc      600
tctccacaga aatatttggt tttattttca cttaaagaga aaaatccaga ccaccgttgt      660
ttggaagcgt tttgctgcaa tcagctattt gaacggctct ggggccgtgt gtgatgtgtt      720
tacaaagtag cgctgccttc cacacaaata aacagaagac tgtggcgggg agaggaggaa      780
aaaaatatat atgtatctgc agtacaggga aagaaggag agaagcggcc agggctggag       840
atggtgaagg caggaagact tctgcaaact gtgaggcatg ggaggctttt cttttctttt      900
tctctccccc cccaccccc cccttattc tttaagaaaa ctgtcagcta ccaccgcctg        960
gggtgctttt ttgaggggtt ggggggtgc tgttaaccag aaagaaaaag ggaaaaccgg       1020
cttggttggg gtcgcattta agcgattttt tttccctcct tcatctccgg gcctcggata      1080
agatgacggc ttgggtgatg cacgaaataa cgcacgtgat tgattagacc tggcttggct     1140
tggctaggga acgatccagg cgcgctggag accccgcgtg aagatgaaat gacggtagct     1200
ccgggctgct tctgtaaacc ggggagcggg ctccatgcac cccttcccg tgtgtgtggg      1260 tttcgaggcg ggtgggaagg gtgaggcaag ccgcagaagg agggtagagc tggtggtttt    1320
gcttctttcg gagcctttga gtgtagtctg aaccttgag gggggcgcgg ggggcttgc      1380 agctgccgcc ctgggaacca tctctgaact gcccgctttt ccgaaggagc ggaaaagttg     1440
gaagctgcga ggacagacta ccggagcccct ggtctgggtc tcggggatc tggagcccta    1500 gtcggtgccc actgagaaca ccccttctcg gagcgagggt gtcgggggga gtgttaagcc    1560
tgcggggcgc acggtccgcc agtccccgag gtggggacgg gggaggaggc tgaggagtcg    1620
gttccaatag gcgcaccacc tctacagccc tggaaaacgc aaccgccacc ccctcttccc    1680
ttccatccca tcccaagcct ctctgctgtc ccgggccgat tcatctcgt ctcttccccc    1740 gcctccccgc ttccccgcct cccaattccc gcgcggctcg gctcagcccc ttcccactcc   1800
agtgggcaga actgatggag aagatccgcc aagcgcgcag ccggcggcgg aggagacagt   1860
gcggggtggg cgaggggctt cgagaccacg cagagagaga gtgaacttca gtcctgaccc   1920
ctccccaagg ccgcggctgg ggcgcccaca gcccgcgctg gcacccgcgt ggcctgacct   1980
gcggaagcgc gagcggggat gaggtaggga gaggaggta ggtgccgctc ggctgcagat    2040
gatgcgtggg tgggggcctt gctgtgggag gagaggccca ggtcccggcc tgcgccctcc   2100
actccgcggc tgctccctcc gcctctggtt ttccaagagg ccggtcgcta ccccggagga   2160
cactctcatc cttcagtcag tctcctggac accccttcct cctcctgtcc ctcaacctga   2220
cctggctctt tcgcccctcc gagaaccggt aggctgggt ccctcggcgg ggttctcctg    2280
ggccgcaccc gaagctttgc gccccggta tccgggccca gtgctccgtg caaccctggg    2340
cccgagcgca cgattccggc gcctgctcgc gccagacac agcgcccttt cttcccggag    2400 cggcggggc gggagcaggg gggtcaggcc aacccttgca ccccgaggc ctggcccggg     2460 ccaccctggg aacggatgtt ctgcatggag agcgagggggc agccggagga cgtcctccgc   2520
atcatacccc tccccttccc cagaaggctt tttttttttc cggactgcgg gtttcttttt    2580
ctctgccttc ttcctctgaa cctacggcag gtgtcagcct cttttgtgt atgtgctgct     2640 gctatctcgg ggatgcggg ggagggggtg caggaggcag cgtgaagggg tcctaggagg    2700
ttccggcggg gttttggccc ctgcggtgcg ccggggcttg caactcgccc gggtgctggg   2760
cgcgcgcgtc acgaattcag cctagggctt gggcgagtct gcgggagtg aggacagagg    2820 atcccgatct gtcatttgga cccaacttaa gaaatttggg gtgggggttg ggtggggggtt  2880 ttggaactaa gcaggtgatg ttcttgcgag ctggatccac aaggtggtag tatggcttct   2940
```

```
ttttatttttt attttatttt atttctattt ggtcatttttt tttgggggggg gcggtggttt    3000 gttgttgttg ttgttgctct tatcttatgc tttttgaagg catccgttgc ccgtaggggtt    3060 tacatcggag cgcgttgcat tatattttct tgaaaggggg tggtgtgcgt gagctcccat    3120
ctcagaatca gccctttccgg tgatgtgagg aaggcaaaag caaaaaaaaa aaaaaaaaaa    3180
aaaaaaaaaa aaagaaaaaa agaaagaaaa aaaaggaaaa gaaaaagttt agggagacct    3240
cgttatcctg acgaagcaga attgccagtt tgtgtgggcg ttctgcgggc aacatagaag    3300
tgcatgctta agaaatccgg ggtagcttcc ttctccagct agaaattaaa tggccagggt    3360
gcaaacacct gactttgatg agaacaaagc ggcagaaact gcaagagacc tgcatggttt    3420
gaatggacgc actgagcctt ttcctagggg atggcagagc ggggtgaaat cagatagcaa    3480
agaaatctgc cgttttgtgg gggcagattt ggagagtgga gaattatttc atacctttag    3540
ttggctgtgg ggaagatgtt agcagtaatc cattaaatcc tcagcataga ttttcctgtg    3600
gaaatgagca aaatgttaag tggggaggg atggctaatg gcacatggtt gcattaatcc    3660
ctgtatttcc agaaaaaaat atggaatttc tgtgtatcct aaaattaaga atacaggaat    3720
ttcatggaga actctgcaag catgtatttt ctcagattag aaattcagta ttttattact    3780
caatgaaatg tagaatgcgt gtgtgtgtat gtgtgtatac agacatacac acacgcattc    3840
tacatttcta catatatgtg tgtgtgtgtg tatatatata tatatatata tatatatata    3900
tatatggcca ttttaaagag tattttcttt gacatgtaag aacataatca gggccagttg    3960
tagcaagtgg aaaattactt catcagtttt aagtcagtag attaaaatgg aaggcttcat    4020
ttttttttga aatcagaata ataattgcat tttcataata atgcctgtgc gtggatgcag    4080
ttttaaagat gctttgatgt tttcttctcc agtggaagaa ttgctacttt tctttgcgtt    4140
ttatttaaat aaactaatgc cgagtataca gttggccctc aaaccagtaa cctagctgat    4200
ttttacccaa acctgagaat gtaacagata cttgataagg gactggtggc tgcataaggt    4260
agataatgaa gttatcttga tgctgtgaaa tttacaagca gacttgaaag aatttgaaag    4320
ttcatagttg ttggcctgga atgtagccta atggtaaata tatagatttt ttaaaatttg    4380
tgaacttggc tatttcattg ttttgtgtgt agtaatttgt ggaaagctta tagtctctcc    4440
acaaagatga gagtgttgac tgactccgca acagagactt gcttttggaa gtgcagggggt   4500 ctctttaaaa gccatttgga atactgtgct tttatttcta gaccacaacc aaaaggttct    4560
caaaaaacta aacattcaag tgcacgaggg aatgacctcc gtttaacatt ctttctttt    4620 aattggtacg ccacatttca aaccttttgt aatactgttg aatattgcca ataatgcaac    4680
ttgttgagcg aatgcattgc attcaaatga agtagcaata tacaaatatt ttaagtcctt    4740
tagtatcctc cttctaaaga taggcttatc tggttaaaat atacttatat tccaaataag    4800
gtgagagttg gtcttaagat gtgaatgtca agtgtaagag acacgatttt agtttgtaaa    4860
ccagaatgta ttcttctgt actgcttttct gccttttaac aatatgtatt ctattcccaa    4920
atggggaaat atgttcagtt tagtttaaat ctgttgctct ttttgtgtgt gtttttgtct    4980
gagtactgta cttttttcaga ggagagactt cgtctcctat ttaattatgt gaatggatat    5040
tcagacagat ttgaatagcc accactgatt tcttaaactc ctgagctacc agttttaaat    5100
caaagataca tcttttgcac agtcaattag aggaagtgag aatcaaaatt gaagcccagg    5160
ctgctgaggc aattaggtca tctgctgtgc tctctactac cattcactca acgaatattt    5220
tccagttctg tcattttttct ctaaacaacc tacatttgga ctttgaaagg ctccactgtt    5280
```

| | | | | |
|---|---|---|---|---|
| ctttgttaag | tgaacggcag | tgtaggaagc | ccttcctcat | ttttcttgga | gcacagtagc | 5340 |
| acacatgaac | aagaaaaaaa | agaaggtgat | agctcctagc | agtttgtcat | tgtgccattt | 5400 |
| ataggctttg | aataaatgta | tagatgaaaa | ggctttccct | ctgcaggtgg | ttacattaaa | 5460 |
| caaaaaataa | gtaaataaaa | gcctcataaa | atcattacgg | gagtggaagg | ttggtggtgg | 5520 |
| aaaacagccc | atctacctcg | ggctgagatt | tcaaacttta | gacatctcgt | gttcagttca | 5580 |
| cgtgtcccag | tgtgtgcgg | aacacctcca | tacaccacat | cttcccaagg | cactctcatc | 5640 |
| ttcccagaaa | tggtacctga | aggagaacag | acctaacccc | aacaatacta | aaatacgtat | 5700 |
| ataaaaaact | atatatagta | agatatgtat | cctactatat | aatatatata | tggtaataca | 5760 |
| tattatagta | aggtctgcat | catgtatata | aaaatacact | atatatctta | ttattatata | 5820 |
| tatagtgaga | tgaggtgtat | taatccattc | tcaggctgct | aaaaaagaca | tacccaagac | 5880 |
| tgggtaattt | gtaaaggaaa | gaggtttaaa | tgactcacag | ttcagcatgg | ctggagaggc | 5940 |
| ctcaggaaac | ttacaatcat | ggtggaaggg | gaagcaaata | cttccttctt | cacatgatgg | 6000 |
| caggaaggag | aggaatgaga | accgagtgaa | gggggaaacc | ccttataaaa | tcaacagatc | 6060 |
| ttgtgagaac | ttactcacta | tcataagaat | agcatggggc | aaactgcccc | catgattcaa | 6120 |
| ttacttccca | ccacatccct | ccacgacacg | tggggattat | gggagctaca | atccaagatg | 6180 |
| aggtttggtg | gggacaaagc | caaaccatat | catgaggttt | tattgaattt | atttgagaca | 6240 |
| ggaaaagagt | aatcctccat | aatttagaaa | ggagatgaag | tacaatgaac | atttaggtcc | 6300 |
| tcattagttg | aggaatacat | ttcaaagaga | gaaatgttaa | tttcagtata | gtgctaatga | 6360 |
| aacgatctag | gctttcactg | ctctctggaa | atgtggataa | atggcccaga | attttgtttg | 6420 |
| ggttgtttta | tttaaaatgt | atattatata | aagaaatcat | ggtttgtcaa | agtaacagag | 6480 |
| tgctatttt | ggcttacaac | aggactttct | tagctccacc | tgttaatatc | ggtgatcatt | 6540 |
| ttggttttaa | gaggctggta | cctgattgga | tgatgaaaac | ttggatctca | agccatcac | 6600 |
| cccagacatg | tgattttatt | aacatctgtg | ggcatctgtc | cggctcccac | atcaacccctt | 6660 |
| catccaggct | cattttctgt | ttgttttttgt | ttggttgttt | gtatgctttg | gttggggaga | 6720 |
| ggggacacgg | attttgctaa | gggcacctttt | tcaggagtg | aaacttagcc | tgtcatataa | 6780 |
| gctgaaaagg | aacttgggtt | gttttcaagtt | gcattacttg | gtaagttttt | ggatccttta | 6840 |
| aaaaagaaag | gactgaggtt | actaaaagtg | ttattggcac | tgataaaaga | gctatggtga | 6900 |
| attgtggttt | gttttttgtaa | agtgcagaaa | aggcctcttt | ggttctgtga | tgatggctgt | 6960 |
| ggtgaagttg | catgcggtgc | catttttccat | gtttagtatt | tcaacaccac | caatatgtgg | 7020 |
| ctctggagta | tgggacgggc | aagtccaaga | actcagtgag | gcatgccgtg | tgactccaat | 7080 |
| ggtcagagct | gttcagcatg | gaactgtggt | ctcaaaagca | tggggatgg | gggcagaaga | 7140 |
| agctcgctgc | aactgagtgc | ctttaactta | ttccactctt | cagtactctc | tgtgactata | 7200 |
| actctgtgaa | tgggttaggt | ggggaaactc | acaaaagtaa | atgcatgttt | tcacaaacaa | 7260 |
| aatatgtcat | tgttaactgt | tttcctaagt | gagacaatat | gccctcatgc | cctgaagcta | 7320 |
| catggtaaga | atggcagtgt | gtatgagcgg | gtgtatacac | atacatgtat | gcatatgcta | 7380 |
| acacattaac | taggaactag | tctttgctga | aaatgttttt | ctcagccatt | gcaacacatt | 7440 |
| agataaaagc | aaatatatat | atatatatat | atatatatat | atatatatat | aatataagaa | 7500 |
| ggaaaaatgt | ggttttccat | tattttcttt | ttcttatcct | catcattcac | caaatctata | 7560 |
| ttaaacaact | cataacatct | ggcctgggta | atagagtgag | accccaactc | cacaaagaaa | 7620 |
| caaaaattaa | aaacaaatta | gccgggcctg | atggcaagta | cctgtggttc | cagctgaggt | 7680 |

```
gggaggatca cttgagccca ggagttcagg gctgcagtga gctatgatta cgccagtgta   7740
ctccagcctg ggagacagag caagaccccta tctctaaaaa tataaataaa taaataaata   7800
aataataaat aaaaatagaa aatgtacaat gaaagttata agttggcca ggcgtggtgg    7860 ctcacgcctg taatcccagc actttgggag gctgaggtgg gcgaatcacc tgaggtcagt   7920
agttcaagac tagcctggcc aacatggcga atcctgtct ctactaaaaa tacaaaaact   7980
agctgggtgt ggtggtgtgt gcctgtaatc ccagctatac aggaggctga ggccggagaa   8040
ttgcttgaac ctgggagggg gaggttgcag tgagccaaga tcgtgccatt gcactgtagc   8100
ttgggtgaca gagcgagact ctgtctcaaa aaaaaaaaa aaaaaaaga aagttataaa    8160 gttacctatg atgggtctgg atgtactcct tatttaggag tgaagacatt cgttaacatg   8220
agacctaagt aagtagaaag tatgtgttta agggacaggt gtccattttc tctaggtctc   8280
ctggaagctt tttttttcta atttgagtac tagttccaaa aaggtgtta ccgcctatgt    8340 ttatagtgaa actatctatg tgtgacaaaa ttctaccctc tcttgtccat caatattgtg   8400
caatgttgtg tacttgtatg gagaaataga caacttttac aaagatcaaa ctaggcaccc   8460
tttaccaacg ctaaactcat aaccctttta tctgcctttg tagaagattc tcacctttat   8520
ttctcttggt ccctctgaga aatatttttcc tctgagacaa tgcaatctat gcctcatctt   8580
taagcaatcc tagctcacca gtatgagtaa tgttgtctat ttttaaggtt atctcattat   8640
tctaaaagac tttaaattgt tgaaaaataa attgtgtgag gggtggtaga gtttgaaaca   8700
attatctgtg atgttaccag atattttaga ctaaaatata ttagaatcca aggtattgtt   8760
catgccttaa aaatgctgaa atatctgact gttgcttatt aattttaaaa agaatatagg   8820
aaatagccat taattaatga ggctgttttcc actaccacat aaaaaaaaaa aaagctcaca   8880
ggtgcctgta tgttttttgtc gaatcaaagt aatctgcttt atgtatgcat ttattcatag   8940
aatttactaa aatcaaaatc aaggttttat aaatataggg tttgacaaag ttttaaaata   9000
taaccagcta tacaaatatg gcatgtggga aattctatta aattgtcatg aacatgcttc   9060
tttgtcattc caggagtctt tcttttcatt actctttcct atttgatctg ttattctata   9120
gaattatctt cattttctct ttaatacttt aaggatccct gagaccttgt cactcatcca   9180
aatagaataa aggaatgagg gaagaaagaa ggaagggaag aaggaaggaa gaaaggacgg   9240
aaggaagaag gaagggatgg aggaacgaag ggaggaaggg agggaaggaa agaaggaagg   9300
aaggaaggaa gaaagaaaga aagaaagaaa gaaagaaaag agaaaggaa ggaagaaagg    9360 aagcagggag ggagggagaa ggatgataga tcgaagggaa ggagagaagg agggaaggag   9420
ggaaagaaga aaggaaggaa agaaagaaga gaaaaggaa ggagagaggg agggaatgaa    9480
ggaaagaagg aaagaaggaa ggaaagaaag aagagaaaaa gaaggaagga aggagggaag   9540
gaaggaagga aagaagaaag gaagggaaga gggaaggaag ctgtggtttc tgtgcaccat   9600
taactaacaa tagctcctgt gaaccagcct ggaagttcat tcaccacata caatatagtt   9660
tcttttggaa aatgcatgtc aaactatata tatggtttgt gtgtgtgtat atatatatat   9720
acacacacac acatacatat atatacgtat atatgtatat acatataaaa tttgcatgta   9780
cttttcatac aaaagaacaa gaactatata tatacaatat atatacattg gaatatattt   9840
attatagatg tatatggatt ttactatata ttatttcttg aaaaagtata agaactcccg   9900
aatcagggat tctttcttga agaggctgcc tggtccaata ttttttggaaa accatatatc   9960 atttgcctct cttcaattat atcctgaaaa tggacacatt atggccttaa agtctcctgt  10020
```

-continued

```
actaatgggt ttagcagctg tgacggataa cttagggttc tttgtaatga gtttaaacca    10080
aattaaccac aagagtgttg agaatacttc tgttgacaca gagcagaaag aagtactaac    10140
agggtatgaa gatacttgaa agtgtttaaa ttaccaagac tacttggaga tatgaacttg    10200
ttggtttttt tctttatttc acgaatttat tcaaaacttg ttgagtacca ataagtgggg    10260
tacaaagaag atgaaattgc ttatctttcc tatattaacc atacactaat gttattttgc    10320
acctctggtt ttatgtttaa gaacaaataa gttttaccag aattttttctt ctggtgtgtg    10380 tgtgtgtgtg tgtgtgtgtg tgtgtgtggg tttaatctct catgtcctat ttcaaaagtt    10440
aaggaaaaca acagcttgat tcagtcttca tacatctttc ttaaatagtt aagggcaaaa    10500
tcatcagagc tacatagccc aaatattagg aattaggttc atgttcgaat tctcagaggg    10560
taattatata gttcgatttt aacttcttca acagaccgac tactacagtt gatgagcaag    10620
gagatgaaag tatttgataa acatcatgga gttaatatga ttcttgaggg aggggagaag    10680
gctgcttgtc ttaggtaatg cttttgaggg taggtttgtc ctagccttga ggtagcaggc    10740
ttgctctgtt ggctgaagaa gccttaacat gcatgcccgt attgcaaatt tacccacatg    10800
ccaactgtat gctgtgggaa gaaatgaata atgtagatgc cattcaggg aattaggcgg    10860 aacggataga cttagtgcat cagaaccaat gagaagtaga caagacatttt agaaaatagc    10920 aacagcaatg aaaacaaata taagtaaacc acaatcaaaa cccttacatt tgggtttcta    10980
gttgcctgtt accacagagg gttctggtta ctagctaaaa tgtaacccag taggaaggtc    11040
aagacaaggc ccctcatgct gtctcaaaca gtaacaaaca gtaaggatga cccagggaga    11100
aagggtaaca agttacatgg aagttaaata ccagttacct gtgcagagac tgaaaacata    11160
aagcagacac aggaatggca gtagtagaaa gtggggaaaa tctgaatttg ttgcagcata    11220
aaaccaacca accaaccccta gtgagggaat caatacctca aaaaaaaaat cttctgacaa    11280
tctaggttca tggtagagat taaacggtac catattatga ggacagaaca ataaatcaca    11340
catggcttcc catagaattt gtgtgacagt ggttgtgtac tatgattcag tctgtcatga    11400
caatttcacc agtaaaataa ccttccagga tttatttgat atctcaattg ataagcctcc    11460
cgtaagtgaa taaccagaat atgacataat ttataaaaat taacttaaaa ttacacaaga    11520
agttatgtgt ctagtcattt cacaatcaaa tgtatttagg catttaatct agtaagatcc    11580
caaataataa aaaattgttt cttttctagac caacatgtat cctgatgtta taaatacata    11640
tgtaaattat atacatatat ttgtatatgt aaaatacaca tacatttaca tatgcataca    11700
tagctcactt tttattgggg agcacatctt cctgaaggtt tttcaaagaa taattattct    11760
acctgtaatg ctgtagcagt atttgtaaaa agttcaaatg tggctgggta cagtggctca    11820
tgcctgtaat tccagcattt tgagaggcca aggaaggagg gttacttgag cccaggactt    11880
tgagaccagt ctaggaaaca ccatccatac gaaaaaaatt taaaaataag tcaggtgtgg    11940
tggtgcatgt ctgtagtccc tgttactcag gaggctgagg tgtaaggctc acttgaggag    12000
tatatcagga gtttgaggct gcagtgagct atgacctcac tactgcattg cagcctgggc    12060
aacagagtga cactccatct cttaaaaaga attcaaatgc ctcatttatc tggacagaat    12120
ttgattggtg ttattctatt gctgaataat tccagggtat gcatttacct tttctctatt    12180
gactttaaac atagcttatg aaaacaaac aaacaaaaac caaacagagg agtttgcaaa    12240 actatatttta aaagtaaacc atactccctc acccctgact ccacaaaaat actgtttaat    12300
gtagagaaac cacagacggt gcagccccca aatctggagc atcctcaggt acctgggggc    12360
attctggagt gaggggctga gcctcagagg catttggtca cacttgggtg gggatgcctc    12420
```

```
attggctagt gaagaagcag ctgtctcttc catgtagtgg tcagttgtgg cctctcctgg   12480
aagggaattt atccagcagt gtgtgttcct gaagatgcta atagcaaatt atgttcagtg   12540
aagccagctg catcctgttg gtcttgctag tcccgggatt cttgccacag caggtcagaa   12600
tggaagggag ctgcttatct ttcctcctta cttcctctcc ccatcccagc tctcatctga   12660
catccttcca acacctatat gacaggaaaa aaattctctc ttcaaattaa gaaaagggtc   12720
tggtctgggt acgatggctc atgcctgtaa tcccagcact tgggaggac gaggtgggtg    12780 gatcatatga ggtcaggagt tcaagtagtg aaaccccatc tctactaaaa atacaaaaat   12840
tagccaggtg tggtggcacg tgcctgtagt cccagctact caggaggctg aggcaggaga   12900
atggcttgaa ctcaggagtc ggaggttgca gtaagctgat atcacgccac tgcactccag   12960
cctgggcgac agagcaagac tctctctcaa aaaaaaaaa aaaagtgttt gagtatttac    13020
tctccacatc tttcagctat ttcacttcac tgggagtaga caggacagga tggctccagg   13080
gacagtgcta ttgttacctt gttatccact tccaatttgg aaaggtaaaa atatgcttca   13140
gtgtctacta aattgcctgc attgaatttg aagtacagtt tgttgggata ctcatgatga   13200
aattggaaaa cagaatcaca gattgttagg acttgaatgt acttgagcaa tcatttgtat   13260
tccctcatgt acacaaggaa attgagtcac agagagtttc agtgatttat cctcatcctt   13320
tttttttttt tttgagacgg agtttcgctt tcgttaccca cgctggagtg caatggcgca   13380
gtctcggctc accgcaacct ctgcctccca ggttcaagtg tttctcctgc ctcagtctcc   13440
caagtagctg ggattacagg cacacaccac cactgctggc taatttttgta tttttagtag   13500 agacagggtt tctccatgtt ggtcagctgg tctcgaactc ccgacctcag gtgatccacc   13560
tgccttggcc tctcaaagtg ctgggattac aggcgtgagc caccatgccc ggccgtgatt   13620
tatctccata attttaaaca ctatccctgc aatgaaaaag gaataccccc aattttttaac   13680 atatctgctt acgccagttc atgacaagct tacaaaatta gaagtaattt taaatgggca   13740
aaataaagca aagtgcatta tttaattttc aaaacagact tttctttatt atgcagcagc   13800
gatttaaaca gataaatcat ttctatgaaa gggactagca gagaaagcag gaaaagacat   13860
gtcccacatt aaaagctgaa cttgttggtg ggaactcatt ttgtttatg agttatgatg    13920 aatgcacctt agctgtttct aaccccgctc ccattccctg ttttttatttg taagtcagaa   13980 cccagcattt ttacatttttt tgaagtgtta attaattgcc tttgtttaat gcaccttgct   14040
gtgtctcaag cattgttaag aaaggataag atcttttttca gggatgattc tttcctttcc   14100
ttacagggct ttgtctgtga tgagaacttt ctatacacat attttttcttt ttaagagacg   14160 gggtctcact atgttgcgca ggctggtctc gaacgcctgg gctcaaggga tccttcggac   14220
tgacctcctg aaatactggg attactggtg cgagccaccg cacttggctc tatctttctg   14280
caaaaactgg tggattctac ttctctctcc atctatgttt agtcctggga gatataatca   14340
agagaaaaga aacatctacc ttcattagat taagagtcaa acaaaagggc ctagaggcaa   14400
agaggctcca cgaccctctt ttgcgggtga gcctgtgcat tgaaatcctc agcttcaaag   14460
agacacagaa ggcaaaatag gaagttggat ttgcaggagt tagtctcttg gagggtcttg   14520
taaaattgaa gggttcacat atgccctgtc aactctccaa gagagagatg acttggtgaa   14580
atctgtattt tgtgatgatt agtctttctc agagggctgg ttcaagggca aacgaagggc   14640
agaataagga cttgcagatg tgttaagaac agaacccgct gtgttgtgcg tcaacgacaa   14700
aagcccactc cactcctgac attcatattt tggggtaact gttttttgca gtgcagacct   14760
```

```
gtgaaacctg gagtattttc agtcacagct tttatcgaga tgctttctgt tgacctgaga    14820
attaattatg gtttgtcaaa cagcttgacg accttgtcag tggtgttttt tggttttttac   14880 aactccccat ctaaggattt gagaatgccg cagtggataa aactgtgtga ctgacgttca    14940 ttatttttt ccacaatgct ttaaagtaag tgcgctggga atgctccatt tattatgtag     15000
aggagagaca tttccaaact ttaactttgt tgctgttgct tttgtacact gaggcattga    15060
ttctgcagga ttaaaagaag gtgctgatta ttccatttgg tggaaagttt caggagtgga    15120
agccagcaga attgttccac tgagatgata attctgactc tttgattctt acacattgac    15180
tacttttaca aaatacaaac ctgttttaat ctttttaaag dacatttgtg cgctactgtt    15240
ttcatttttt aaaataacct tttaaaaatt ttaggatagt ttcaggtttg ctgaaaggtt    15300
gcaaagatag tacagagagt tactctttaa ctccacacgc atatcgcatc ttacgtgacc    15360
atctgttaca cttaaggaac caacattagt acgttactaa gaactgacat cacaatttgt    15420
ttggatttca ctggtgtcca cctaatgtcc tttttctctt ctgaggtacc atctgaaata    15480
ccacactgca tggatttgcc ctattttctt agcctcatct agtctgtgac agtttctcag    15540
tttttccttg ttttcatga ccttaatagt tttgaggtat taatgtcatg gagaatgtcc     15600
accaactaga gccagtctga tgttttagac aggggtatgt gtttggggga ggaaatccac    15660
agagatgaag gtttccttca tctcacccta gcaacggtga ctactgtcca gaagactttt    15720
gctgctggtg ttggctttga tcacctggct gacagagagt ttgtcacttt tctctgctgt    15780
aaagttgtac tctcccctcc ctgcccaagt ctagtctttg aaaccaagtc cctaaagtgg    15840 ggtggggtg ggagaagagg cagaattaag ctccactttc cggatggtgg aatatcgata     15900
aattatttgg aattcttctc taagaaagat gggtctctcc cctttattta cttaatcaat    15960
catttatatc agtatggaca catggatatt ttagatatgc tttgggctac attgctgtga    16020
cttattccac tttatattcc ttgtggccat gatgtagaca ccagagagtc tattcacttg    16080
aatagcaagt aaatgagggg actcaatggt aaatgactct tagagaaact ctcagccctg    16140
ctggttcatg gatgctcagc ttgcaaaaac accttcttcc atcaggaaac ctcagtggat    16200
gggcaaacat tacagcgtcc ttgaatatgc ttcattgctt taatctacga acttcctatg    16260
cagtaagcaa aaccacccat accacagctt aagagtgggg ctttcctccc aacactcatc    16320
ctagtgtctt tgataaaga ggtataaagt tgaaggaaca tgttactaac cagaagactt      16380
ccagaggacc ccattgatca gggtagatga atggctgtgt gcgtcttgtc acaaccatca    16440
gtatttcaaa aggtgatatc atcctcttaa ccttatgatg tgttttaaca taaaatttta    16500
atatgcatac aggcggttat tacttaagca ttgcttaaga agcagtcttt ttttttaat     16560 tcatgtaact ggatctattc tctgaataag gaatataagc aaatcgtagc catttcaagg    16620
actctttttt ttttttttta aatggagtct tgctctgtcg cccaggctgg agtgcagtgg    16680
cgcgaccttg gctcactgca acctccacct cctggttcaa gccattctcc tgtctcagcc    16740
tcccaagtag ctgggattac aggtgcccac gagcacacca ggctgatttt tgtgttttta    16800
gtagagatgg tgtttcacca tgttagccag gctggtctcg aactcctgac ctcagatgag    16860
ccgcccacct caacctcctg acgtgctggg attacagaca tgagccactg tgcccagcct    16920
caaggaggct tttaagggca ggatgttttt ttttcttatg gtgaaggaat gaagagtagt    16980
atgggaaaga aatacagaaa ctttgaaaaa agaaatgtaa aactggatca tcattccata    17040
ggctagtagt taatagtaaa taactgtata gtttgttcaa gggattttgt gaatatttta    17100
aacacagatg ataattctct atctacatct acgtgtttac ctgcatttat atcatatgta    17160
```

```
cgtatggaca tatatatttg cctgtagatc acatctttgt atggtatctg taccaatatt    17220
agagtctata gctacagcat atcaataaca gtatctattc ttatctatat cttaatcata    17280
tctatttttg tatctgtaca catatcttta ccgatattca cattatattt ctatgtctag    17340
atctatatat atctctatct ataccatttt gaactttaca tttcctacag tatgatagca    17400
taagctattt taggattatt aaaaatcttc ataagcattg ttttcatgg ttaattttct     17460 caaaagacta tgctttaaca tacccagttc tttatatatt ttttgacatt tggcttattt    17520
taatgttttt gctcctctaa tgtattttc tttttttact ccacacccct cccgcctcta     17580
attttcaaat tgggcattct tcattatagg ggcattgctt attttctttt gtatgtttca    17640
aaaaacattc tgcattggtc tgtacacatt tttccctctt gtatcccttc tgtaaacatt    17700
tgtattcact tgaaacctta tggaatattt tactacagaa aatttctggt tatgataaaa    17760
aaaggcagag aagatagaat aaaggatccc atgtgcccat cagttggctt cagcaattat    17820
gaatggatag cctaatcttt agtatctaac ttcattcata tttccattct tattatggca    17880
tgatgtaatt catttaaaga tatgtctgta cgttgctcta aaatatagga accattttat    17940
tttacacagc tgcagaatct tttccatgcc taaaattatc aacagtagtt cctctgtatc    18000
atccactata aagttgtaac tgtcaaaatg atcttctcgt agttttgtaa ctcacgcaag    18060
gtcaaggtct agcactgcaa taggttgatt tgtcttttac atttcttta attgatatag      18120 cttccctatc tttttatgca cattcttgtt gaaaaaactg ctcttttac tctacatgaa     18180 agtgggtttt agaattggaa aatgtagttg tcaagttatt ttagaaggaa cgtgtgtatt    18240
ttccgtaatg cacagtctta agttactaac tccttaggag caaacgctgt gtgacttggt    18300
agtgttctac ccagaaggaa tgctgctggg taaatttggc cagctacgtg acagctcttt    18360
ggactcagta tatctcagtt ttatctatt ttaacaaggt tttattttga agacagggtc     18420
tcgctctgtc gcccatgctg gagtgcagtg atgcaatcat agctcgatgc ggtcttgaac    18480
ttctgggctc aagcaatctt cccacctcag cctcatatta tctagtacct ggcagagata    18540
cagatctgat gagaagcaaa gatagagggg tgtcagaagg tagcttttgt tgcaccatta    18600
catacataca cacacacaca cacacacaca cacacacaca aacgggcgca cacgcacgca    18660
caaagaatca actgcaattt tttcctcttt gccaacccac agttaagtaa aattattagt    18720
tctattgaac tccacattgc atgtgatatt ttgaatgata gaggctaaag agaggccaaa    18780
gagggaggat tgcttgaggc caggagttca agacgagctt cgacaacata atgagaccgc    18840
gtttctacag aaaaaaagaa aaaaaatagc cagatgtgat ggctcgctcc tgtaatccca    18900
gctactggag aggctgagac aggaggatgg cttgagccga ggagttggag gctgcagtga    18960
actctgatag tgccactgca ctccagcctg ggtgacagag agattctgtc tctaaaaaac    19020
aggaaaaata tgactaaaga aaaccaaact aatctaatct atacagttat agatagttgg    19080
ctatcattct tatgctaatg taagtatgcc tcattttaag aagagttgtg tgtgtgtatg    19140
tgtgtgtatc tgtgagtgtg tgtgtatgca tgatataaat ccagacttct aagcgagtat    19200
cagggatggt gaactattat tagtagatca ttggaacctg ttacacaagg atgcactaga    19260
gaattttaca aactattaaa ttctgtataa tttaaaatgt gacttgattt actcagatat    19320
tttaaaagga tgcatgtctc ttacaaaaca agatttacta actttggtgc tcttgacgtt    19380
gaggctggat aattctttgt tgtggtggct gtcctgtgcc ttgcgtgatg ctgaatggta    19440
ttgctggact caagcttcta ggtgcccgtt gtatacacgt tcctgtttta aaaaaaactt    19500
```

```
atataaattt aacgggcaca agtgctgttt tgttacatgg atatattgca tagtgatgaa   19560
atctgggttt ttagtgtaac caccacccaa ataacataca ttgtatccat taagtaattt   19620
ctcattcctc atcatcctac caccctccca ccttttgat tctccagggt ctattattcc   19680
actctctgtg tccatgtgta cacattattt agctcccact taggagtgag gacatgtggt   19740
ttttgacttt ctgtttccga gttgtttcac ttaaggtaat ggcctccagt tccatccatg   19800
ctcctgcaaa agagatagtt tcgttctttt tatggctgaa taatatttcg ttattcatat   19860
ataccacatt ttctttattc atttatccat tgatggatgc ctagctggat tccatatctt   19920
tgctattgtg aatagtgcgg tattaaacgt atgcgtgcag gtatccttt gacatagcga   19980 tttctttta tttgcgtaga tacccagtag tgggattgct agataagatg gtagttctat   20040
ttttagttct ttgaggactc tccatactgt tttccataga acttatacta atttacattc   20100
ccatcaacag tgtatgtgga ttcccttctc tctgcatcct catcaacctc tgttatgttt   20160
tgagtttgac atccacaatg tctgcagaca gtctcagata tcccctggg agtaaaatcc   20220 atcccagtta aaaagctctg ttatgaaatg aggtgtactt attccaagtt ttacatgggg   20280
aatttcactg gtttttgggt tctagtagcc ccgacgtgta tactgggcat gaccagataa   20340
gataaactgg gcaaagagtg caatgagaga tagtaaccac attattttgg aagatgtttt   20400
tcataaccag aatagacttt atgaattcta tcaattgtaa tgagaatcgg attgacattt   20460
ggggacagtt aatataacgc acgttatccg aaaggaggtg gcattgattt atataagtga   20520
gagcttacga gaaaacaaag actggaaata aagaaaaaga aaatccttga taagtatctg   20580
atagaacaaa gtgcagaacg aaatgcagct agcttatcta aaatttgggca aaatcatgtt   20640 ccaaatgaaa gctcagtaga tgggaagaga gtatttgaac atttgatgtg aaaaatgaga   20700
tttactgttc cacagatatg aacacattga tgagagctgt cagttattag aacttattaa   20760
catcaatggg aacaccagaa atgtgctgca cagaaaatta aatttaagac tgtttgaaaa   20820
tggtgttata ttttctgaac tgttacattg attgattaaa attagattat ccaacaaaat   20880
aagaactttt gatattctgt gagtgaatat gagatgaatt tatgtggcag atgtgttttt   20940
aaaagatgta ttattaaccg cagagattca gaattaatgt cgccaacccc aaagaatgca   21000
gtataacatt tgtcataagt gacctcataa taggttattt tataatatcg ttttaatttt   21060
tgataataaa tggacacctt ttacatcttt aataataaaa ggatatatgc aaaaccagtt   21120
atttttattc caatgttaat aaaatagcaa taagcctcat ttcatttgaa gcaccaactt   21180
tcactccata tcaaatttct aaaagtctgg gagatactca ccaactagtc aagaagattt   21240
tcattctata aaattgtata atgcagtgaa tcctgttctt ttcccatatg catttattta   21300
atatttatat ttgatacaag gaatctatat tattttcatt aagccactca taaacgtaag   21360
tgttttactt cttcttgggt acatttttaa aaatttggtt acattttga gatgttgatg   21420 ccatggttaa aatattccaa ctaagtaatg ggatgggttt acaataagtt tttgctctac   21480
aaggaaatag gtcaataaat caggctccag ccaattatag gagaaaagga aaagttaact   21540
tattatacat tattgcacac agtgtttgat gtatgtatgc aaattgctcc caaatacagt   21600
ttggttgcag ttgtgctcca catttatggt ggatgcagtt ttgaatatgt gcagagagaa   21660
tatattctga cctcattcat caatgtgatg caaatgtgta gaaatggcaa ggtcattttt   21720
gtatgatgat aaaatgcctg tttgaaagta aactcatcca cccatccatc caaaggttgc   21780
attttctcaa ttcccaattc taaatatgtc tgtgtgtgtg tgtgtgtatg tgtgtgtgag   21840
agagagagag agagaatcta gtgcaatttt attgttctac tttgttccag gcttgacatt   21900
```

```
ttagtgattg aaactaaaat accttgattc ttaccctcta attttacaaa taaaatctgg  21960
tttactgtta tggattgaac tgtgttacag attgaattgt gttccccaaa aagatatatt  22020
gaaatcctaa tgcccagcac ctcagaatgt gatcttattt tgaaataagg tctttgcaga  22080
tgtaattaca atgaggtgat taaggtggcc cttattccgt acaactggtg tcgtaaccac  22140
catgtgaaga cacagacact cacagggtga agacggccat ctgatgatgg aaggttggca  22200
tgatgcagct acaaaaaggg aatgccaagg attactggca actccctgaa tttagaagag  22260
acaggaaagt atcctcacca agaaccctca gagggagcat ggccaacatc atgattttgg  22320
acttctagac ttcagaactt tgagagagta tattcctgtt tcctgagaca taagccttgt  22380
gattcttttt gatagtaact ctaggaaact catacaccaa gacacagagt tatttattta  22440
aattcatttt ttttcattta aaaatactta tttgacaaag actgtaatat ggaaagtgtc  22500
cagtgtgatg actggatgta cgtatacatt gtgtaacaat gatcacaatc aaattaatga  22560
acatatcact catagcccat gtggtacata atggatggac ctgaagttat gcagccagct  22620
tggggcagag ctgggtttga agggcagact cctcacccag ccacacttgt cttccagaat  22680
cactttcaca tcgtcatgag gattttagag actccactgc tccatgtcac tgcatcaaca  22740
cattgtggag tgggggggtct cataattcat tgcaggtgtc tgaagatcaa cagttgggtt  22800
tcccttccct caactgtaaa atgagtgagt tggacctgtc tccagggcct ttctaagcta  22860
tatgatttga gaacaatgat cattgtaatt aagacgcttg acttgaatac tgctcatttt  22920
aaaccatgat tagggatatg agatgctccg tgtgttttct aaataaactt cattgtgacc  22980
tggttaagtg ttggatatga attggcaaga ggaggcttgc tagtagaaat ggtgtaattt  23040
aaaacccatt cacaagtatt tacacactgc aagacatcta gatcctcaga agtcaggtag  23100
tatcctaaaa gcacagtgtg taatttatgg tagataattg aaattgcact gaaattgaac  23160
ttggtggtgg ggagtacact tcatagtatt caattttttgc cttcacttta ttctatgtct  23220
gactctcagg aaataggaac tgcaacgttg ggtttctcca gtgtattttc aacttcaaac  23280
ttgtgaattg taaccatta aacaaatgat caaacactac atctttccct gctcttgtat  23340
ggacatagag ttttgttatt catgccttct cttttcttat ctgggaagag atctttctta  23400
acctttagaa attggattaa tgcgaccctc tttaacctca catttgatgt gaatgtcaga  23460
acttttttgaa acttagctgt gcttttagta cactgatcac tgagtgcccg ttgactggca  23520
ggcactgggc tgctcagtga ggtaggtgaa gaagagacac cagctccctc ctggagtgtg  23580
tgctctgctg gaggataaag acacttatca agcaatagca taaatgcttc tgacaccatg  23640
actctaatca gagtggcaca gccaatgggc atgggctag gagaatatga gaattcgtag  23700
gtatggggat gctgtcaggg ttcatgaaag gtcttcccaa tgatgagaaa actgcaagtt  23760
gggaggaggt agaaataact gaaagaaatg gttgtagaga tgaatacatt gggggatgat  23820
cgtgttgcag ggtgacatct tttagtgata aaagggatag agtttgagct cctgctgcag  23880
accctcagcg atgtgttgta atggtaagaa ttggctcatg gtttcctggt tgcctgatt  23940
gctgcatcca caaaccatg ggttctgggg ttaattccca tccattttgt tgctgaattt  24000
ctcagaatga tagtcttcgg tacattgtta ctgaaaggag gtgctaaacc caatgtcttc  24060
attgcttttg aagcagatgg tccagtgtag tgtttctcaa acataagcat cagagtgtcc  24120
tagaggtctt gttaaaggca aattgctggg atccatccca ggagtttctg agtcagcaga  24180
tctgagatgg gacccataat tccccagttg aagttgccgt tactggtctt gggatcactc  24240
```

```
ttttagaact actgccttag ggtatttctg ggttacatgt gcacacatga cctgcttaag   24300
ttttgagctc aacattctgt tttattcctt cctgttcaga ggccggcatc cacagctctg   24360
ggtctcatca tttgcttttt gtcatccagt tgtgctctac tgatttataa gttatcttta   24420
tgttttcagt ttcccagtca attcaagcca atgcatattt attgggcatc taccatgtgc   24480
tatggactgt gagggactta agattaata acaacaacca taaaaactca ttgacgtgct   24540
gggcattatt tatttcccca tggcccccaa atgctaggct tatcattcaa acactacag    24600 caacttgaag gcagcagatt gtttctcatt tcagggatcc acaggtatat ggcttctcaa   24660
acgaaggtct ggtaattcca ggctgcatgc agctattctt cctttaaaga ctgagaaacc   24720
atgcatacaa catcttttct tccttcttcg tttatacatt tgataactat gtactgacat   24780
cttactttga gaaggtcacc atgccagata ccgtcagtga tagaaacaca gataagattc   24840
aacctctgat cccagggaga ctctcagtaa ggaagagaaa atgagaaatg aaagtaccta   24900
tactacaagg catgcacgtc acacattcca taagtgggta aaaacacaga ccttggcagc   24960
acagaatctt gttttccatt tgtgtcattt aggacactgc attggttatc tattgctgca   25020
taaaaaattc ttctaaacct taggttaaaa ctgcaaacat ttatcatctc atgcatttct   25080
atacatcagg gatttaggag cagtgtagct ggccagttct agctcagggt ccgtcatgat   25140
gttgtggtca agttgtagac agggcttgca gttttatgac ggtgttggag aatctcactt   25200
atgtgtcact tggcaggagg cttcagttct tggccacatg ggcttctccc tagggctaga   25260
cgtgtgacat taacagctgg cttttctgaa agtgaggaga gaaagaggga ggctgaaaga   25320
gagtctaagg tgaaagccac acactcttag aacttgatct tggaggtgac accttgtcac   25380
ttttgcactt gatttggagg tgacaccttg tcacttttgc tacatgctat tggttgttca   25440
aatcaaatct ggcaccatgt ggatgaggat tccaggaagg tgttaattgc aggtgtcagt   25500
tggccatctc agaagctaga ctatcaccag aagctcttcc aaaggaggtg gcttatgagc   25560
tgcatagaat tttgtcataa ggacaaagga gaaagtgtga acaaacacat aggtacagca   25620
agtgttgagg aatgggctgt gttgtgttga tgttgtctc aagggcatgt tgagtttggg   25680
tgatgaaatt gaaatcagat catttcaggt ggtgcaactt gatggtaagc catatagatg   25740
ttattctgta ggcaatgggg caatcatatt aggactttg cagaattatt taaggaatag    25800
cagtttcatg atagtagagg tagggataga agacagaagg tcagtaatgc aagttgagat   25860
ctagttatag attcaactgt ggtagagatt gaggaaatgg ggatggcatg aggctctgca   25920
gaggcattgg aaggatgata ctgatagaat cttgcaaact attggataga ggccaagaca   25980
atgaataacc atccaaggtt gcagttatgg gtggagttgt ccagttaaga aaagggagag   26040
agttcagagg taggtgaagg tcagcattat tagatgcttt ggagacacat gagactgaca   26100
gagatgttta ctatttttt tggtgattat aaggtaatca atagactttg agagattact    26160 gttttcagt cttccatatt atgttgcttg gatgcatttt tctttttcc tgaaacttgg     26220 cagacatatc cattatcaag acgttttcag aggggcatgg tggctcatgc ctgtaaatcc   26280
agcactttgg gaggctgaag caggattgct tgagctcagg agttggagac cagccggggc   26340
aacatggtga aactccatct ctacacaaag tacaaaaatt agtcaggcat ggcagcatat   26400
gcctgtagtc ctacctactc gggaggctga ggttggagga ttgcttgagc ctgggaggcg   26460
gaggctgcag tgagcccaga tcacactact gcactccatc ttgggtgaca cagtgagacc   26520
ctgtctcaaa aaaaaaaaa aaagaaaat gaaaagacct tttcaaccat tctaatcata    26580
attccaagac ctatttgtgt cctgacttca agagcaggta ctcttattga gaaacatttc   26640
```

```
tgtaattgtt cccacttccc ttataccttt ttttctgaca gcaggtggca tcccctcagt    26700
tgtctagctg accactggaa gggctgaccc ctcaacaaac ccatatcctg cttggagttt    26760
ctctataggc cctgtcttat ttattgctcc tgctttgagt aactttctcc ttcctcaaat    26820
ctattcttct aattttcctt cactgcctat taattgaact gactttttctg attgtctgtt   26880 cctcctgcct ttgcagttac tgtcgctccc taaattccat cctcgaatca ctcctcttcc    26940
ttccgtactg tcctatgtag ctttgcatct actcatggtt tgatgattat ttccatcgga    27000
gagaccacag gggtctctat cttctgctct cacttctctt ccaagttcct tcctgccctt    27060
acagctcccc tttcaacaac attgcctata tgctctggcc aaaactcaat tcagtgttcc    27120
caaaattgtc ccatcatctt tcttgccaag cttaccctgc tccctgctca tggcatcttc    27180
tcctctcaat tcctcatctt ggatttgaat cccctctctt tcccatcccc agtgtaaatc    27240
actttcagaa ataacaggtc ctgtcatttc ttcttctgag atacatctgt actttccttg    27300
gtcatcttct cactttatgt gttactattt taatcatatc ctgtctatga cttgtacact    27360
ctccaatcta ttttttaaagc tattctttct tcatcttcac aaataattga ttatgtaaga   27420
ctactatctc gttcaaaatt cataaacaag catccactgt gcttcaccac ctgccccatc    27480
tccgccgtta caactgcagt catcatttta ctcctctggg tgttatactt catcctccac    27540
ccaacctgag tatggatagg aatcactgca tttcaccttg gtttcttgct ttttctcatt    27600
cttctcaggc tctctttcaa cctggaatac tgttattttc ccatctccac accttattca    27660
tgactgaggg ctaaaatgct gtttctttca ctgctctctc taacatgcat tgtttgtatt    27720
cctctgtggt agtcatcaat ttccattaca gaggccagga gacctgatac tttcttgagt    27780
gtgaatttca gtagttgacg tcttgtgtct cagtttcctc agctgttgag ggctgtgaga    27840
agagtaccta cctcgaggga tgtttgcaaa ataaataagt taaggtcagg cactgtggct    27900
catgcctgta atccaagcac tttgggaggc tgaggcagga ggactgcttg atcccaggag    27960
ttcgagacca gcctgggcaa catagggaga ccctgtctgt acaaagaata ataataataa    28020
taataaaaat taggcaggta tgatggcaca tgcctgtgat cccagctact tgggaagctg    28080
agacaggagg attgcttgag cctgggtatt caaggttata atgagctagg attgcaccat    28140
tgcactccag cgtgtgtgac agagcaagat cttgtaaaaa aaaaaaaaaa aaaaagaaaa    28200
ggaaaggaat aaattaagca tataaagcac tttaaaacag gtatttagaa agtgttgaag    28260
gcggccttga cattacttat ctttggccca tccttgtctt tctccttcgt agtctaaaat    28320
gttttacaaa ggactgtttc tcatgacact gagaatgaac cccaaattcc tttcactgac    28380
ctattccact tttatacagt aagcctcttg ctcacttctc caccttcatc ccaggccatc    28440
ctcttctcac tgaactgctg tcccagtcct cttttggttt tgtgatctga gtggataccg    28500
tgttaggaca ttttttgtgtg ccactccctc tgcccagagc accctgtcct gttcccattt   28560
aaagtgggtt ccaccctcga ttgtgttctt atttaaccca ttatttactt tcttctctga    28620
gctcacctga tctcaaaggc ttttttattc tttgtctact tatggatatg tgtggaggat    28680 ctgggggggtt agtgaatttt tctctgcatt ctctaaacat gtgtattgca tgaatctgga   28740
atagatcagc ccttactggg tatttattaa agaaatgagt agttgtaaga cactctatag    28800 atattcatttt aatgaatgag aaaatcaaat gttgcctggt aaaaacaagt gttaagtcag   28860
ctatcacagt tttctgagat atgcagccaa gccaggagga ctgagggaag gatgtctttc    28920
attgtaaaat caacgcactg taggggaaag ttcctctctc acctaaggga atatcgatct    28980
```

```
tccttgattg tttgctttgg tatttctaaa ttagcatgat ttaccaaaaa tgtttggatc    29040
actcagtaca tgcatgtgat tttttctaaa tggctatctt taaaaaaact tcctcatctg    29100
tattaatgtc cctagagttt ttacattttt tgcctgtatt tcattaaaga tgatgtcata    29160 gaaaatttt gtcaaatttc tcattctggt ccgtgcctgg aagattgaca gtgatgcagt    29220
ctaagaaagt tcaggatttt gaggtttaat catttacatt ctaacactaa agctacaaat    29280
ctgccgtgca gtgttgctta cttctactgc tcactggatg gatgagtcta tgtgcttttt    29340
aaattcctta taaagatgtg ggtcaaaact agcagtgtgg tcaataaatt aatttcttga    29400
gagtttatca gaattgtggg atgatttggg aggagcaaaa ttgtgtaaaa tcaatcctct    29460
atttttaaac ttattcttct aaaattctaa atagaatttt tttattcatt aatattttct    29520
tgatttcata atgctaaaaa ttaagtaaga tgaatgttgt gttgagaaat gggagcaaat    29580
ccaagaccaa aaatcagatg atttattaaa tttgcaagtt aaaaaaataa atacagtttg    29640
aaagattgct ctgtttgagg aaaggacata caattttgtt gagataactt agggtacaaa    29700
tcaaggtcat ttatgttcat ttgaacattc atattcacat ccggaaatat ccagaatgac    29760
tacactaaaa cctgcaggta aattctttc tcagctgagc ataccatatt gttgtagtta    29820
atcaagaaat ctaccaaaat taaatttgtc ctcctacttt ttagtttaga aatttagggg    29880
gtcactggga ctcaaaagaa aattcaataa ataatggacc atcctagaga tacttctttt    29940
taacttaaaa atccctctga gatatcctca ggtttttaaaa atacctttgt attttcctgt    30000
ttttgtgtgt gtttgtgtag gcctacatct tcatattagt catcagtgtt gtcagaacct    30060
tggctagaat catagtctag acctcttgag gtcactgggt ggttggctac attttccacc    30120
tcttgctttt catgggtccc actctgagaa acatgctcct tctctctctc tcctctttca    30180
aggtcatctt tgaggacatc ttctgaagct ttttctgaga tgctgcctct tctgagcacg    30240
acactgtcta ttcttgtatc accagtatag gagctcatgc aatttgtaag cacttgcctt    30300
aatgatgcgc tccctgaaag accctgagga gagggatcag gtggcgttca tctttaggat    30360
cccttccctg tcctcacagc acattcatgg tccacgttca gcaaacactt gtacaatgac    30420
atgacttagg gtttctagac aatctgtatt gtaattctg ttgatataaa gggataacat    30480
tagcatcata tgaaaagtca gagttctatc aatgtcatct tgatgaaaat atttatatcg    30540
ttatatctta tgtcctaggt gtcttcttga ctgactaccc agggcgagtt ggaatggcta    30600
tgtgcatctc tctgaacccc caaatcttta gttgtaatga tgaacttaca tggagaggct    30660
tattcgaaac gtcattatag tgtggatgat aaccttctta gtttccacag ctgatattcc    30720
tccaaagttt tgtatgcttt gactaatgta ttctctttat gctaagcttt ctttaaaatg    30780
atatgaatgt tccataaatg ctgattttt tgttttttg agacagggct tcactctgtc    30840
acccagggtg gagtgcagtg gcgtaactac agctcactgc agcctctgct cctgggctca    30900
agcaatcctc ccacctcagc ctgtggagta gctgggacta caggcgtgca ccaccaaacc    30960
tcgctaattt ttgtattttt ttgtagagac agagtttcgc catgttgccc aggctggtct    31020
caaattcctg agctgaagca atcctccctc ctcagcctcc cgaagtgctg ggattacagg    31080
catgagccac cacgcccggc cccataactg ttagtttaat tagcaccttt ctgctttagt    31140
tcatgttgac tattgaaaat ctatcatcct gtataattaa tgttttttaaa agatactttt    31200 agatagtgat caaaaactta tttattaagt agaatgtaaa ttattacaaa tgatatgaat    31260
accataggat aaagttttta tatgacaact tagattataa aatgcaattc tagccaggca    31320
cattggctca tgcctgtaat cccagcactt tgggaggccc agcaggcacc aaccgcttgc    31380
```

```
ttccaggagt tcgagagcaa ccagggcaac atagtgagac tccgtctcta taaaaaatac   31440
aaaaaaaaaa aaaaatagct gagcatggtg gtgcatgcct gtagtcccag ctattcagga   31500
gactgaggtg agaggattgc ttgagcctgg gaggttgagg ctgcagtgat ccaaggttgc   31560
accgttgcac tccagtctag gcaacagata aatatgagta caaatggctg atcatcttca   31620
tattaatatg aaattgcatt ttttgataca ggatctcgtt ctgtcttgtg gccttctgta   31680
ataggttatc ttgtccaaat tctggaataa agtccagaag aattttaatc tagataattt   31740
attctttaac ctttgaaata ttgtatcagc tacatgacaa tggcttataa ctagctctaa   31800
ataaatgaaa taacgtttgc gagagtgaat cacatcactg agaaccaagg ggaaacatga   31860
aatagtgatt atttgaacag agagtgttag tggtctgcat tctgccttgc acccaaatgg   31920
catcacctat gggtgtgata aaagcccct gcctttctct ccctcctcag tgcttgggat   31980
ttccaacaac agcaaaagag aagccaggaa gaatgctgtg ttgtgagtac ccccaggaag   32040
ggttttcctt tatgaagagg cagacctagt taggaaatac ataaccatgg actgcaggaa   32100
agacagttga gtctgcatgg aggatagaga ccagggaccc cataaaagga gaggtggtga   32160
ccgaggcctg caggatgcat ggaaacattc ctgacctcaa gggcagcaac tgtgaacaca   32220
ctcctactag gcagaactag aatggatgaa cagagttctt ttcagggaga ctcaccaggt   32280
agatgactac acatgagaca cttttttttt tttttttttt tttttttttt tgagacagag   32340
tctcgctctg tcgcccaggc tggagtgcag tggcgccatc tcggctcact gcaagctccg   32400
cctcccgggt tcacgccatt ctcctgcctc agcctcctga gtagctgaga ctacaggcgc   32460
ccgccaccac gcccggctaa ttgttttgta tttttagtag agacagggtt aaaccgtgtt   32520
agccaggacg gtcttgatct cctgacctcg tgatccgccc acctcggcct cccgagtagc   32580
tgggattaca ggcgtgagcc accgaaacac tttcagtggg aatattttgt tccatcagat   32640
tttagcaata tcggatttga aaatagggga agcacacaca gatacaatta gtttcaccat   32700
ctcacttgtg tatttaaaca aacctgtaaa caaagctaag cgaaccaaga aacaaacaaa   32760
acctcaaacc taatacagta ataataggct gggggtggtg gctcatgact attattaatc   32820
tcagcacttt ggtaggctaa tacagaagaa ttgcttgagc ccagagttcg agaccagcct   32880
gggcaaaata gtgagatcct atctctataa agattattta aaaaattagc caggtttcga   32940
ggcatccacc tgtagtccca ggtacttggg aggctgagag gcaggggat cacctgagcc   33000 taggaatttg agattacagc cagctgtgat cgtgccattg aattccagcc tgggtaaaag   33060
agtgaggtct gtctccaaag ttaataaata agtaaaataa taataataat ttttaccgta   33120
tcacaaaaaa tatagccagt cagatacaat gcacactaat tattgtaaaa ttttctgaaa   33180
cacacataca tcactaactt gataattgta aatttaacac tgattggagg gtgtgaacaa   33240
aggtatgatc aagtaaaata aatgtatagg caatttcaaa gtcttaataa tacaatttca   33300
agagctaata ttaattgagc atttactata tgcacactca tgcatcatgg gactgtgttt   33360
ggtgctaata tcacaaaact ttatttttc ttccactggt aattttgtc actgttgaaa   33420 actgtttcag ccatggatcc ccacagtgcg gagattgcgg gatgtgggag agaaatgatg   33480
gtctcaatcc ccacctgagc cagtgtccta tggcaggcag gtgaaagcca agccacccag   33540
cttgagttct ggctccactt ttatagttct gtggtgttgg gcaggttagc taatctgtcc   33600
ctgcattagt gttctcaact aatggggata aagctcacat ataccttata tgtttttgga   33660
gacaattaag agttagtata tgtaaagaat tcagcaagtt agatgctgac ccactatgta   33720
```

```
catattagct attataactt attattcgga caaacagcta atgcatgtgg agcttaatac   33780
ctaggtgacg ggttgatagg tgcagcaaac cactatggca cacgtttacc tatgtaagaa   33840
acctgcacat tctgaacatg tatcccggaa cttaaagtaa aataaaaata aaaaataaaa   33900
aaataactat tattactact attattagaa ttgtttggat gaggaggtag cttgatatct   33960
tgaaaaaatg catggtcttt ggagtcaaga taggtcttac tccctgcttc agtgagctgc   34020
gttacttaac acctggatat catttttttc ccaatgtaaa ataagatgtc ataataactc   34080
ctgcccttgg ctgtagaagg gtcagtgaag atgaatgtta ttatgattgt tgttaaatat   34140
aaattcattt ttacaaatac agtttcatca acaatattta tgataatgcc tattaataac   34200
aaaatgtgct aggtgttatg agaaatcaaa aacatagtta aaatatgatc ttgtcttcct   34260
gtaatttaat aatgtgctgg ctcattagct atgaaaccca aaggcctttat ctactttgta   34320
ttaatatttt ttcaagcatg gaagtaagcc cagaagggta ttgagtgatg tatcctcttc   34380
ttcccttacc atctttccta tagatgcaaa atcctgagtg tgaaaggcca cgtggtactc   34440
tgttagatat ctcgcaggtg ttacttatcg atggttcttg cttaaaagta gaaggaggag   34500
tgtcgcatga gacgcatcct ataaagagag cattccgggt gagatggcaa gaaaaactcc   34560
gaatggtcct gagatgataa ctgatccaat ggagatgata tatctgttca gttgacgcaa   34620
acataattgc ggtttatacc cgtgaatgta aggcaaaaac tgcaattacg cttgcaccaa   34680
cctaatatat atatcttttg gagacagggt cttgctctgt cgcccaggct gtagtgtagt   34740
ggtgcgatca cagctcactg cagcctcaac ctcccaggct caagtgatcc tcccacctca   34800
gcttcctgag tccgctggga ccatagacac atgccgccac atccagctaa ttttgagata   34860
agttttcttg cagtagagtc aatggcagtg ttgttctgac cttctgccac agcaaaacat   34920
ctctgcaggt tgaggattag ttcttgcaaa taagtgattt ctaaatgatt gattggttct   34980
tttcacacat tttgcagatt tctttttatta aacaagttat atctaatgga gaaatacagt   35040
gagttgatga tctccaacaa aactttaatg ccacccagat caatgccaac cagattatga   35100
gttgcccatt ggaaacctca aggagtcttc attgattttg tattctcaaa ctgcatgtgt   35160
gtgctaaaat ggttgcatag agattccaca tgcagccatg catgtgtgta ggtgctccca   35220
ctagactagt tccttgactt attagggaac aagttaagaa ttacttcatg tcatgatcgg   35280
ctagttcttg taactaccca taagaaagct tataaggaat gtcacattgg ttttgaaaca   35340
atatcatctc ttttactgat ggagagaggt atgttttttct tttttttttt aaatagggaa   35400
caatgtgcta agatggaaaa aaaaaatcaa gtaggtttcc agggaggcat ttttttttt   35460
ttttttttt ttttgagacg gagtctcgtt ctgtcgccca ggcgggagtg ctgtggcgcg   35520
atctccgctc actgcaagct ctgccttccg ggttcacgcc attctcttgc ctcagcctcc   35580
cgagtagctg ggactacagg cgcccgccac tgcgcccggc taatttttttg cattttagt   35640
agagacgggg tttcaccgtg gtctcgatct cctgacctcg tgatccgccc acctcggcct   35700
cccagagtgc tgggattaca ggcgtgagcc accgcgcccg gcccagggag gcattttaa   35760
aggcaccatc tcagaaggac gaggcaatgg taagtatcag gaatagttat tggcgagtcc   35820
agcacagcag tcaatgactg tgttctggac tgcaccgttg gactcgggaa ccactgtgtg   35880
gccaggctgt gggctccggc agttgttcaa aaccctgaac ctggagctca gaccagaggg   35940
ttgtatggga ggctcactgt cattcattgt aaccctaaga acctcatcct tccttgagcc   36000
cgattgttcc catctgatca gagccttagat gcaagattgg gaagaaaggt ggtggagttg   36060
gggtctgcct ggaggacagc ccaggtgagt catgcatggc tgggagagca gtaggttcat   36120
```

```
tctcaccacc tcatttttct aaggggaaac agatccacaa gggagggtca gccccagatc   36180
attggccaca cttatgggaa acatgtgctg ctgttacgca ggccccttca ttctgtttgc   36240
atgctctcct tgtaacccct gggcctatca ggacgccagg gtgtctgttg aagaggcat    36300 ccaagaagga tctttaggct gcaggatgga agcacacact acagcatgac cttaggtaga   36360
tggttcattc attaccttt aatatcttcc tctttctttg ctgtcaaaca tgggtaataa    36420
aatacctaac ctgtcatatt ataagaagta attgaggcca ggtgcagtgg gtcatgcctg   36480
taatcccaac acgttgggag gctgaggagg gagaatcact tgggttcagg agttcgagac   36540
cagcctgggc cacacagtga gacttcatct ctacaaaaaa tttaaaaatt agccagacat   36600
ggtgatgcac acctgtagtc ccagctactt gggaggctga ggtgggagga tcgcttgagc   36660
tcaggagttt gaggctgtgt agctgtgatt gctccactgc actccagcct ggccaacgag   36720
caagaccctg tctcaaagaa aaaaaaaatt aggtgaaaac aatgtctatg caacgctcag   36780
tgcctggtga tgtctaagga atgcccaaac tttctaggta aggggtaggg gatgcattgg   36840
gtgagagtcc cattggatga gcatgaatgg gaactcatca atattgctga aagtgcctga   36900
tccagaatta aaatatttca acagaaaatt cagaggaaac tttagaatgc tgaaaaatgc   36960
catattggtc agtcttactg gttaatcgac ttttctgaag tacatacaca cttttttttt   37020
atttgagata gaatctcgct ctttcatcca ggctgtagtg cagtggcaga atttcagctc   37080
actgcaacct ccacctccca ggttcaagtg attctcctgc ctcagcctcc cgagtagctg   37140
ggattacagg cacccactgc aacgctcagc tagttttttgt attttttagta ggggtgaggt   37200 tttaccatgt tggccaggct ggtcttgaac tcctgacctc aggtgatctg cctgcttttg   37260
cctcccaaag tgctgggatt acaggtgtga gccacaactt ccttcccacc cagctaattt   37320
ttgtattttt agtagaggca gggtttcacc atgttgacca ggctggtctc gaactcctga   37380
cctcaagtga tccatccgct ttggcctcca aaagtgctgg gattacaggc atgagccact   37440
gtgcccagca cacacttcac tttggatcaa gcccccttta gagcatctga acttctttttc   37500 cagtcccttg ttccacccag gcaatcccaa gcctggtgcc ttcctatctc tagccttttga  37560 tttaggctat tctgtctgcc tgtgtgcaac atttcctttc cctccttact gaagttctac   37620
cccatcctgt gttgcatgag ttgatggata attttgaaaa aataattatt ggtaatcatt   37680
aacctctact gacttatttc attgatgcat ttttgagcct ggttaaacca agtctagcag   37740
tgctttcgga ttacttttggt ggtgaaaatt gtttacttaa aaaaaaaaaa acaatttgaa   37800
acaaataaaa gtagaaagca gtggtttcaa gctcatttgg agtgtccaaa gtgacatgcc   37860
tggaaattta ggattttgaa ataattgtct gctcctcctc atggccacac ttcggggtac   37920
atctcataaa gtagacaaac acagatgaag gtcacctgtc tgactcactg tatgtaaacc   37980
tctcagaaat tcacccttgg ctgcactgct caccggaagt ccatttttctt ctagagtaaa  38040 gatttgcaat gatctaggac tcaaaaagtc catcttgggc catttgaatg acccccagcat  38100 ctcattttac ccttttgtatt tgtagcccct gcagagtggg gttcaaaatg tcagacaggt   38160
actactagta caggcagagg ggacactcag accatgagat ccttctcact gtctggacat   38220
tagaaagaga gcagagccca aggaaaagat atgggtagaa tactttttgtg atatacagct   38280 gtgagcccat gttagtggag atatttcaca attgaaaatc tggacccttc cccacaaact   38340
caaattttag aaaggttcat ctgatgcttt catacatctc aagtaaatgg ctctgtcttt   38400
tcatggttca gctgcaaatc tgaagtcttt acaatttgat tgcttaaata ttggttattg   38460
```

-continued

```
acaaattttc ttatcaattt gaatgttgta gcttccaaac ttttgtcaaa atttagacca    38520
caaaggcctt ttgagtatct ctttaatgat tgccagataa ttttcctatc catggctttc    38580
tctttacaga ataaaacttc agtatttttc cttgattcta gaagattgtc aaggtcatgt    38640
cctttatgga actcttgttt ccaacaaagt tgattttaa acatctctcc atatttcctg     38700
ccataaacaa atactaggtt ttgttttca aagataattt gtaatttata aagaaagatt    38760
aatgctgtcc cacctccccc atttgatcat taacatacaa attggaagaa atcatactt    38820
ggaaaaatga ttgatcagct gttttgctatt tttatctagt atagatttat ttgtcttatc   38880
aaaggtaaaa cgaataaagg tacacatcat ttttcatcag catatacagc taaataatca    38940
ataatgatac attatgtaaa tccctttggc tcctgaatta cacgactttc ttttttttcca   39000
ttttcttttt tttcaacctg gatgagtctt aataaataat caaggcctga agtctaagaa    39060
atgtttgtct tctctctcac acttacagcc tttggaacag gaacccaatg cagcattggt    39120
tgtaattatt tcagtagctg cagtgcaaag cacattcagg tgaatataat cagactgtcc    39180
tagttccaag gagaagcagt agtaacaggt ctggcatcag gctcagagct atagacgagt    39240
cacagcttat aatatgatag actcactta tgaaacccaa agggaacatt atataaagtg    39300
cacaatcatg agaaggaaat gagaacttct gaacctagga cttttttaaa attgttttac    39360
catatgcact taggttcaaa ctacatttga aaccactggg cattatcagt atgtctctgc    39420
aagagtcagc tactgctttt gcttaattgg tagctgcatt ttctcttaag gggggaatgc    39480
tttggagtgt gttttcctga taatttggag tggtctttgc tgaatggtga tcctaggttg    39540
gaatttccta cattgtacac caagaatcag ttggctggat gaaaaacaag tgacaaaggg    39600
ttttccttt cccagtattc tcaaaatcct cagtaagaac tgaaggcatc atgactcttc     39660
agtgacatca gttgtccttg aggagggtg gaggatttcg tggagacaca cataggcctg    39720
ataatgagga catctatgct gtaatccagc tctgctgcta attagttgtt tgcaattact    39780
aggttttgg tatgtttaaa gactgcagag acaggcattc attcctttt actatgaaga    39840
atgtgtgaat gtaaattaag aaccacagct agctgagaag tacaaataat ttgtgaagcc    39900
tatttaatac tcgaaaattt caatttatgt cagttcattc aattttttcta catacagttg    39960
actgaacact ttctggtttt gtaaccccta ttagggaaaa ttctttgcaa tggattttca    40020
tgataatctg gatagtctta gtgatcttat gttagaattt atttattgc taggatgact    40080
tagtccaatt caaaactgat gatcaagaaa aattcctttc atggcattcc tgaaaacata    40140
atttttaagt caagggatga tcaggataat tctaggggcc tgtaagtttg aacattgaga    40200
ttgttgatac taagttctga acacatatta cccaaatgaa tctttttatta aacatttgt    40260
ggtttcaaag gacatagagt agttatgcaa atcaatgtgg tgcagcaact acagtataac    40320
cttcagatgt tagggaatca acgactaaaa aaaaaaaagg acagtatttg aatgttatta    40380
caaagacacc tgcgattctt gaaggacatt tcaaaggcag acaatggggt aaattgtgat    40440
tgaaatacac gcgcaatctc tatgatatgc tccttccact tagaaagtgg gatgaaagct    40500
catcaattga agagtaattg ctaaaaaaga tttctcctct atctagcttg ggagtattta    40560
ggagctaatc agagtatttc gtcttctcgg aaattaaaag agatgaacag agttgtgcag    40620
acatggggaa aataaagttt agtttaatat ttagatttta aaattagtac ttgatggaca    40680
ttttaaaaag tgtacaatta tcaaaacttc aatatctaat ccttttatgt aaactatggt    40740
ggatacatgg aaacaccagg gacgggtgct ggttcttgtt aacttttctt tctctgtcag    40800
ccacaagagt gcctgtccca tagcagtaaa ctaataagta tttgctaaat taagaagtgg    40860
```

```
gaagggcgtt gtaggttatt gatcaaacga aaataaatat attttgttgt ttattcaaaa    40920
atttccccga cttaattttt ttaaaatgta acttaattt ttaaagctca tctgtgtttc      40980
tttgttttgt gtcgagtcaa agattatttt atgtcaatta ccttttcatg ctgaggcaac    41040
agtttcagtt ttcccattct gcaaaactaa tttcctgatt cctctctcac cagggaccat    41100
tcccctccaa aatcctacaa ggtgggtcca tgacatctgc tagagaaaaa gagggacatg    41160
ttggagcgat aggattccca tgggcactga catactggcc tctggggata ggaagattaa    41220
tgcttagtac aagaaagaag gaaaagaagg ccttggcgag gactgtttta tctcagcatt    41280
tctcagaagc tccttcagtg gagacttcgc ctgggacctt cgccccacct tcttctaatg    41340
gcacttcctc cctgtggggc tccacgcggg acattacgtc ggtgatgcgt agggcatcgg    41400
gtgcggaaat gtgtgcgtgc ctcctggcgt gtgcgtgcct tctggcgtgt gcctgtgcgt    41460
gtacgtgcgc atgcgtccgc ctcccgggtt cacgccattc cctggcctca gcctccgggg    41520
tagctggggc tacgggcgct cgcttttttt tttttttttt gtattttag tagggacggg      41580 gtttcaccgt gttagccagg acggtctagg aaattttaa gccactctga ctaaagaagg       41640
tggagttggc cgggcgcggt ggctcaaacc tgtaatccca gcactttggg aggccgaggc    41700
gggcggatca ctaggtcagg agatggagac catcctggct aacgcggtga aaccccgtct    41760
ctactaaaaa tacaaaaaaa ttagccgggc gcggtggcgg gcgcctgtag tcccagctac    41820
tcgggaggct gaggcaggag aatggcgtga acccgggagg cggagcttgc agtgagctga    41880
gatcgtacca ctgtactcca gcctggttag agtttatatt tcctttaaat ttctagagaa      41940
aacagattgt catgtatttt tatagagaca aaatactgat gaaggtgata tacaggtagc     42000
ttaattatga tttttctaag atttaattag atggtaaatt tacagtaatt attaatatgt      42060
tcactgcttt tattaaaaac catcaattct gaatccacaa tgacacaaat ggtgagtaag    42120
gcttatgtct tgtatctgtg ttcttcagt gcttaaatgt caagagaaa acaaagactt       42180 ttaacatgat ttttaaggaa cgttttcatt ctatggtggt ttctaatgta tgtgtttgtc      42240
tttagacttc ctttatcctt ttcctttcat ctctttctca aactcataag gtttcctttg     42300
tgcagatact tttttgcctg tttttcctcc ctagtttatg ctgcttttct gtcaagaggc    42360
tatatttcag aatgggaaaa aagggcaagc atatatagtt aaatgaatca ttttacactg    42420
tttgtaagtt attatacata agctaatgtt tgatctctgg aggataaaaa tgagctcaag   42480
tttgagcaaa tgatggtgcc gcacacatgc cctaccttat ggtgagtcaa ctatggccta    42540
tgggtggtgg ccaattttg taaataaaat gttttgcaac ccaaccacac acttaaattt      42600
acattttcat atatggttct tttatactac agtgccagag tggaatggtt gccccagaca    42660
ctgcatggcc tacaaagcct aaaatattta tcatgtgatc ctttaccaga aaacattggc    42720
aatgcatact ttggcaattc atggtgatca tctttgggcct atgagttaat gcatccgtgc  42780
atacatttta aattagaaat atgtaataca ttagcattaa caacagagca tatgcttttg     42840
tattaggaat tctatgaatg catgcactac aactcttaaa cacagagcaa gtttaaagcc    42900
tggcatctgg ggtgtatgga tgagtggggc ctgggaacac ccttgaattt tacctgtaaa   42960
atttatgtgc accagggaaa gattcagtgg cgttcaacaa cacaagaagc tgcagctggt    43020
tcgtgtgggt tttcattggt ggtctctagc tgctcaagtg atggattcca gttgctggtt    43080
gatctctctt agggctaagg ttcattattg cacagattga tcttggagaa acatcttgac   43140
tgtttttttc acactccaat ccatttgttt tatgatctag aagaaggaa cgcttaaatg      43200
```

```
caaacaatta ttgtgatttt tattccgctt cactgaactt tttaatgaag tgcattttgt    43260
acagttaaaa ccaggggtt cctggattct attttttgtg ggaattttg agagagaagt     43320 aattctgact cagtacgctt ccttggagtg ataattaat attaatgggg aatggaattg    43380
ttttgtcttt cgctggcatg ttgttctctg ccacacctgg catgctgtgg acctgtagta    43440
aatattaact aaatatattt tagacacaga tgattaagga tcttttgctg aaaaacattc    43500
tcttaatctt ttatacttcc ctttccacag tgcctgctga aaacatgaat ttcaattgtg    43560
tttctaagtc ttggtcaatt taagtgtgac atggggtgat ggggaaatag cagttaggac    43620
taaaggtaga aggtaacatg atccatgtga attgtggtca gtgcaaaggc ctggaacagc    43680
ggtcactctt tcctgtccat gaacctttgt gctattcctc tttgtacaca gtttaaaata    43740
taaataagaa aatgtcatgc tgccaagtat gtatcacagt gcaggccacg tagaagatgc    43800
tttatatgtg ttggatgcag gccagtgttc tcaactcagc agtttcagag gaagtgaaac    43860
aagccctggc tggaaaccag tagccgtaag gtctaagtcc tggctgagca gtccaaatgg    43920
gttccctaac ctattgccca tcccctcagc taagaagggc aggcagtgcc cctgggcaat    43980
gctggtttta tccaactctc agaaggcgcc attctttgcc tacgctctcc cgtgtattgg    44040
tccaaagccc accaacttcc tgagtggagt tccttcacat tctgcagaaa accttctgtg    44100
gtgctttaac attggatggg aagatgaagt tatcttgggc tctgggctat gttagtcatg    44160
ttttggtaaa cgaagcattc tgttttcacc aggggatgag taggtataat tttccttctt    44220
gagttttgca aacctgggtg gagaagaaaa tcagtgcaat gtcttatgaa tttttttttt    44280
aatagaagat agcaacttgg aagcaattga gtgttgagtc taagagattc cccaccccc    44340 ccagcatttg ttctgatctc atatatatgt acagaaaaat ataaattatt tagcattgac    44400
ttatctgtaa ttaagtcttc taaaaggact actgttttag ctgctatatt ttcttctcaa    44460
ttacttggaa aatttaaacc ttccttgggg aatgtttagt ctttcacttg tccttttaat    44520
ggtaattgat tggattgttc aaattatgct gttctgagaa gaagttaaca aataaaatct    44580
ggcaaagtaa taagcaaatg gcatcaggta aatgaaaaga acagcacact gtgtccagtg    44640
atatgtgtct tcactaatt cttacctttc aaaagttgaa gattgataat caaggtaaac      44700
tttaaaatgg aaaatttgcc agctacagat tttaaagttc ataaaaggtg gttttttgat    44760
agcttttgtt gctactattt ccatttagcc tttataata attagttaaa aatctcaact     44820
aattcttttg ataagatatc ataggttgta ttttcaatg tttaagccag atacttgctt     44880
aaaaatcagt taattaactg agagtgaata attgtcattt attattttat atttgaaata    44940
ttaggttata gtttaaacat tttacttaaa gtgtaactag aatactggac acattttgct    45000
aacactcagt gttttcaggt gtttttaaaa tcatcaccat ttctatggtt aagtcttaga    45060
acaacactct gaaatgatgt ggcatcaacc atctgagaaa gtaattaaaa gggataaaat    45120
agtaccacat gagttgggat tccttgacta tccaaccaaa aaattaccga ttttaggaaa    45180
cattctattt aatctaatta tccttcaaag tgagtggacc tttgacgtca ttttcaacag    45240
cagtgccatc ttgttttgt gtagttgaag atcagttcat tgatcttatg tctcaggaag    45300
aaattgcagt atttcttttt tgtctttttt tttttgaga cggagtcttg ctctctcgtc     45360
caggctggag tgcagtggcg cgatctccgc tcactgcaaa ctccgcctcc cgtgttcatg    45420
catatctcct gcctcagcct cccaagtggc tgggactaca ggcgcccacc accactcctg    45480
gctaattttt tgtatttta gtagagacag ggtttcacca tgttagccag gatggtctcg    45540
atctcctgac ctcgtgatct gcccgcctca gcctcccaaa gtgctgggat tagaggcgtg    45600
```

```
agccaccgtg cccggccagt atttattttt ttggtgttta aaaggttaaa ctgctttgga    45660
aagaaatttc aaaatgattt gggttttccg ggcttagaaa gcagactcca gctctaatag    45720
tatatgcttt ttttctacaa atgttttcca ctagatggtt atagagaatc gtttcaattg    45780
atttctttct gatgtcttct ctatttggaa atgcagtcgt tcacatctaa tggacacttt    45840
ctagcagccc tgtttcatcc ctcctgtata cttcttaact aggattccag aaggagcagt    45900
cacatttgtt tttccttact ttccactcct tcttcagcat gttcatgttc tcagctgtaa    45960
cacataatca caaacttaat ggtttgaaga acactcattg gtaaacatgg ttctggaggc    46020
cactttctga aatggacctg gtggagctac aatcttagtg tcagcagggc tccttccttc    46080
ggaaggctcc aagggagaat ctttctcctt gtcgttttcc cccatggagg ctacctgcgt    46140
tccttagctg ttgtggcagg tcacatctcc ctctctgact ctgaccctcc tgcctccctc    46200
ttgtaagggc ccttgtaatg ccactgggct cacccagcta acccaggatc atctctttat    46260
ctcaaaatcc ttaacttaat cacatctgca aagtcccttt gccgtgaaag gtcacatatt    46320
cacagactct ggggattaag atgtggatag ctttggggac agtgcattat tcagcctcag    46380
gatgctataa tcgtatgatt gatgcatctc aggggtcatc ttagttggcc tctgcaacat    46440
cttctcccct cttgatacct ttcctgggat gctttcctca acatctttga caacactctt    46500
gttttccctt tttctccctg atggctgctt ttctctttat tttccttctt cccttgtctc    46560
tttccctcct ccttgctcca tctcccttgg gaatcccatt gtacattgta tactcgatgg    46620
aaggtatgtt tggaatatta tcacgtgtgt gaccaaagac tgatggccag tgaaatggtc    46680
ttaggtgatt tggccctaag ttcccttttc tatcccattt catgacatct gtctacatat    46740
cctgtgtctc aggcatgttg aaggacacac aaccttctgg taccagcagt gtttagccac    46800
agacctccgt gtcactgtta ttgctacctt cctcccttgc ctgactttc tccctgcagt    46860 ggaggtccta atgattccac attcacctga aagtcatttc tcaagggagc cttccatgac    46920
ctgctccccc tctataatca tgtatccaaa agagtacccc catgataacc ctctttcctc    46980
tcttgttaat ttcaatgcct tacttcccta ccagactaaa aattcccctg aatacaggaa    47040
atatcttacg ttattgtaat caccactccg tctaatgcag tgccccactg ctatggtttg    47100
aatatcccct ccgaaactta tgttgaaact taattctcag tgtggcagta ttaagaggtg    47160
ggcctttaag aggtgattgg atcaaggatt aatggattaa tgtgtaaaag gattaattgg    47220
ttaagaagaa ggagagagac ctgaggtagc actgagccct ttggctatgt gataacatgg    47280
gccacctcag gaatcagcag agagtcccta ttagcaagaa gcttctcatc agatgcagcc    47340
ccttaacctt ggacttctca gcccccagaa ctttaagaaa taaattcctt ttgttcataa    47400
agttactcag tttcagatgt tctcttataa gcagcgggaa acaggactac taagacacac    47460
agtcaaaaat tatttattaa attaataata ttaccataaa atcatagtag ttaaatctgt    47520
gtttagagat agtttcactc cttttagtct atcacttttta aatctacgta ttcatgttag    47580
ttccgtggta tgagcgtctg tgtgcatagc tgtaattata gtgtaataga ttactaaagc    47640
agtcatgaaa cacttgaggg ttctttgtac caccgctcaa atttatttac atccatacac    47700
acttgtcaaa agaggtagag agtttcagat gcccttaact atccttattc cccacaggcc    47760
taccctcata tttctgatag cagctgatat accagggaga ctgaaaatta agttccatcc    47820
taagcacaga gacttaagag ttgctgtcac ttagagagag agagaagcaa actattggtg    47880
cctccgaatg caatattggt tttccccaaa gaatgcttta tcttcgcttt acttaaagaa    47940
```

```
aaaagcaggg cagggcagtg gaaatgaact gataaccttg tgtctgtgga tataactctg    48000
ctccagggaa gacattaaag ggtaatgctt tgaaaataac atcaagaaat gaaagttaac    48060
ataaaaaaaa aaaagctgtc agtactttag gtgttccaaa gtcctgtgga gagtggctta    48120
actggagttt atagcaactc tgagacattt tttttagta cagttctgcc actactttct     48180
atgtttataa acaatgaaca gatgcattca gtgctagtta cctagaatca actctcatac    48240
ccagcattac actcgaacgt tgaatgttgt attagtccgt tcttgcattg ctttaagaaa    48300
atacctgagg ctgggtaatt tataaaggaa agaggtttaa ttggttcatg gttctgcagg    48360
atgtacagga agcatagggg ttttgcttc tggagagtcc tcagggaact acaatcttg      48420 gcggaaggta aagggggagt gagctttctt acatggccgg agcaggagga agagagagag    48480
aggggcaagg tgctgcacac ttttaaacaa ccagatctca tgagaactca ctcactatac    48540
agtaccaagg gggccgatgc taaaccattc atgagaactc cgcccccatc atccagtctc    48600
ctcccaccag gccccacctc catcactggg aattacagtt cgacaggaga tttggatagg    48660
gacacatttt catcttaatt tgtatttttgg tatagtttca taggaaagat ttaggttggt   48720
gttctctcgc atggaaattc acttagagct tttacttgct tgttacttgt tttaaagcct    48780
ttccaattga accaatttat taagggcatc tatttaattt tctatggtaa atgtactaaa   48840
aactagaaga gatcttactg ccttgatact agtttattgc ttgttttatta ggtgccctga  48900 aaagataact ttagcatcca ctgcttgcta accatccttg tcttcagcat cattagaaga   48960
tacgaaggag taaggaacgt gcttatgaga aaacagaagc tatggcatcc cccatcatag   49020
ccacatgagt cttgaatagg ccgcctgctt ctctgtcttc ttttttgcaag tgggttgcat  49080 cctagctttg gtggtgtcct tgtaactttg gaattgcctt tgagagaaga ccagtctgtc   49140
tctttccagc tgctggacct gagagattgg gctgcaggtg gcaaatggtc gctactgaga   49200
aaactgaaag caatgacagc catataatat ggtgtgaaca ccatatggat caaactggga   49260
catcacagtc agcacacact catccaattc tcagaccaag gcacaccatg aaattctgac   49320
atttaggttt cctgcctctt aggaattcca tcaaaattat ataagtagca ctattctaaa   49380
ttttaaccta ctatcatttt aaaaaatgac ttactcacag ccctaacact catcggagca   49440
ggttgatatt gtagaaaact ctagccctat gcaactggag tgatcttgat gctaagacaa   49500
tatgacccaa agccttgtcc tttcctcttg gctatatgaa tattttctaa cttttgtgaa   49560
caaaatatgc ctctttttcc tcatgatggt gtttcaaaat gagtcgatgg gtgttttca    49620 gttattagtg gataggagct ctcttagctt agtccttcaa aagcttgtgt ttgatgttgt    49680
agctttgtaa attatctcaa tgtatgcata cacacatact cccctaccaa aaaaggtcaa    49740
tagatgctta gaattccttc cttccttcct tccttccttc cttttttca gggtcttgct     49800 ttgtcgctca ggctggagtg tagtagtaca atcatagctc actgcagctt tgagttcctg    49860
ggctcaagta atcttcccat ctcacacctc agcctctcct gggaccacag gcatgcacca    49920
ccacacccag ctgatttaaa atttgttttt ttagagacac ggttttccta tgttgttcag    49980
gctggtctcg aactcctgga ctctagtgat cctcctgtct tgtgctcctt ggattacagg    50040
cataagccgc cacgcccagc cacgtagtat ttctatattt tacttttagc ataagtccgt    50100
gaaagaacta tatttctcat gctttgttca actgtgcaca tcatgatgtt gaaggatttg    50160
cacgatggct atgatggtgg ctgtcactgc actacaatac tttttttgaa aataagtgaa    50220
atattcattg ttcactagaa tagtcttaca ggcatttgtt tctttagaat ttggaaactt    50280
ctttttatat tcatggtcgt atttcattct gctagcagtt taggcagatt caatctgtcc    50340
```

```
cactttccag tggtagaaac agtgtgaaga agtgaagtag ttgttggaaa atcactgtgg    50400
tttgcttccc agggggttgcc ttgtccactg attacaaaag tatcataaca catggcatct    50460
tcccacaagg agtttagagt ttgaaaagtc aatgtattaa tgtacatagg ggacccactt    50520
ccactcaaag caaacattga gtcaggtatc agagctcggt gggtgaacac gatggcattt    50580
aattatccta aattacttta tataatcaat atctactaac tgcctttgtt atgatgctac    50640
ccatcatttt tggagtcaca agctttcaac ctttgtctaa ctaaaagatg gatatctgca    50700
ttttatatta ggtggtctgg aagccatagt aatattagag agcacatagg gaatgtttta    50760
gtccatttgg gctactataa ggaaatacca tagactgtgt agcttataaa caacagacat    50820
ttattgctca attctggagg ctgggagtcc aagatcaagg tatggcagat tcagtgtctg    50880
gtgagcaccc acatcctggt ttgtagatgg tgccttctcc ctgtatcctc atgtggtaga    50940
aggggtgagg gagctgagtt cccttttatg agggcactaa tcccattcat gaggctccaa    51000
cctcatgacc tcatcacctc ccaaggacct cgcctcctga taccatcatc ttgggggtca    51060
caatttcaac ataggaattt ggaggggcac aaacattcag atcatagcag ggagagagat    51120
gagccttgcc caactccatg aagccatcta gatttttttca gtctcagtcc tatttccatt    51180
ttttaatgtt gagttttgaa ctctattaat gtctcctggt attttcaaaa ctttgtagag    51240
ctttcatcat caatattaaa cctttcacat tcaaaggaca tgattatttt gtgtgagtag    51300
cgtgttgtta tttgacaaat gagtacaatt ataaataaat cttgaccatc ttgatagagg    51360
aaataaatgc acgtgtcaag atatactata atgcttttgt aatcaaaaca atgatggggc    51420
caggcgcagt ggctcacgcc tgtaatccca gcactttggg attacaccca ctgaggtggg    51480
tggatcactt gaggtcagga gttcgagacc accctggcca acatggtgaa accccatctc    51540
tactaaaaat acaaaaatta gccaggcatg gtggtgcacg cctgtaattc cagctactca    51600
ggaggctgag gcaggagaat cgcttgagcc caggaggcag aggttgcaat gagtcaagat    51660
ggtgtcactg cattctagcc tgggcaacag agtgagactc tgtctcaaaa acaaaacaat    51720
caaacaaaaa gcaatgatgg atagaacagg gtattattta aatgaaaact gtaaggggag    51780
ttgtatgctc tcaaatgtca ttatgcacag tctaatattt tcccttttac tttgtcactc    51840
tacctgctaa tttgcttcct taattcagag ttatgtcttt ggttattagt tataatatag    51900
gctgacagtt atgtagcgtt tcttctgtgc taggacctgt tccaagtgct ttttatatta    51960
actcattggt ctcaaccact ctacctgata gttaccatta gtattagttt cctatctgtg    52020
ctgcagtaac aagttactac agactagtg gctgcttaca gctctagagg tcagaagtcc    52080
aaaatgagcc ttaggaggct aaaatcaagg tatcatcagg acaccgttct ttttggaggc    52140
tctaggagag gacagatttc cctgcctttt ccagattcta gagacttctt actctccttg    52200
gctcataagt tccttctctgc accttcaatg ccagtagatt gagtccttct cattctgtca    52260
tctttctggt tcttcctctt ttcttttttcc cttttctact tataaggatc cttgtgatta    52320
tgtggaccca ctggataacc tggaatcatc tccccatttc gaggtctgct gactgggaac    52380
cttaattcta cctgcctctt tcatttgaat ctcttttcca tgtaaggtca cacaaagtca    52440
caagttcttg tattaacaca tggtcatccc gggggggtccg ttattctgca gaccacacag    52500
ttgttatctt cattttacag acaagaaaga caaacagtga gagttaaatc acttactcag    52560
ggttgttggg ctgctaaatg gtagagccag ttaaaattag gagtgtacac agggaagcta    52620
ggcagtgttg tggtcaaggg ccttggcccc ctgaaggttc aatgaaaaat catggagaca    52680
```

```
aagtgattttt tactgtccac tcaactggat tgcacagagg gagagagaga ccaggagcct    52740
ggctggctgg tgagaaattc ttacccttg gccagcagtg tgggttcctg ggttctctgc     52800
actgtggctt ccaaaagagc agagcgtctt tgttgacccc gctcgctgtg tcataactgt    52860
aggggccaag gctctttact ccctaaaatt ttaatgaaaa atcactgact aggcagactg    52920
attaacagga gaaatgacat tacaagtgta tttaatgcag atacacagga gcctttggaa    52980
tgaagatcta ccctccaaat gaggtccaga agcttataca ccatcctgag gttacagaaa    53040
gagtgggggc ttggatccca gtaaaacagg tgatgggagg gggaggtgag gaattctgtt    53100
gaggagatta ttagaacaga gattaacttg taaagagttc tctttgaaaa ttaaatgatc    53160
cttggagaca cccttggaaa actgtctgct caggtgtggt tttatcttgt tttttttttt    53220
tttttttctg taatagataa tgatataact tgaaggggtt gaaaaacaac tgtaggttgt    53280
caaatgtatc ccatatccta gccctcactt ctggttccat cttactttc tatgtaagtt     53340 ttcacttcta gttctatttc ttacttagaa attgtgttaa tcactggtat aagtagcatc    53400
tttgccagat aaaaggaaa acaaaaaca atgctttat gacgatatgt gggagaaaag       53460
aatgtaatag tacttgagaa atattggaac tggttaaata ctagatggtg ttgggtagtg    53520
tttaataaaa tgattatatt tcatagagaa cattttctct acgctgaggc agaaatacag    53580
agataatttt atactatact catcctttct cctaatcata ttattttta aaattcaagt     53640 tagaatttga gtgattgtat tgctgctgtg ctgttttct cagaggaaaa atcatagcaa     53700
attatttcaa agatagatgg agaacatggt gtttctctat atccaggttg gattgaatgt    53760
tgtattagcc aatggaaacc ttcctcttca ccctctggag ggtcacggaa aatcatgtca    53820
caaaaggcag attaatagaa agcaatacat atttattaag ttgtagattt gtgtaacaca    53880
ggagccttca gaatgaggac acaaagatac aggggagact gtccaatttt ttttttattt    53940
caacttattt tagattcagg gggtacatgt gtaggtttgc tagatgggaa tattgcgtga    54000
tgctgaggta tagggtacaa ttgatcccaa tcaatggtgg taagcatagt gaccaccagc    54060 tagttttca gtcctcaccc tactcacttc ccattctagt agtcccctgt gcctattgct     54120
cccgtcttta tttccgtgtt ttctcaagct cccacttata agtgagaaca tgcagtattt    54180
ggttttctgt ttttatgttg actcacttag gataatggcc tccagcagta tccatgtttc    54240
tgcaagggac ctgattttgt tctttttcat ggttgcatag tattccacag tgcatatgtg    54300
gagaccacat tttcttatt tattccaccc accactgatt ggcatctagg ttgattccat     54360
gtctgtcttt gctattgtga atagtactac agtgaacata caaatgcatg cgtctttttt    54420
gtagaacgat ttatttcct ttgagtatat acccagtaac gggattgctg ggtcaaatgg     54480
tagttttgtt tcatttaagt cctttgagaa atctccaaac tacttccac agtggctgaa     54540 ctaatttaca atctcagcaa gaatgtataa gtgttcctt tttctctgca aactcactgg     54600
catctgttat atatttttt ttttgactat ttaatgatgg cctttctgac tggtgtgaga     54660
tggtttctca ttgtggtttt gatttacatt tccctaatga tcaatgatgt ggagcatttt    54720
tcagatgttt attgattgct tatatgccct cttttgagaa gtgtgtgttc atgttctagg    54780
cacagttttt ttttgttttt tgttttgttt tgttttgttt tgtttgagac agagtctagc    54840
tctgttgccc aggctggagt gcagtagcac catctcggct cactgcaacc tctacctcct    54900
gggttcaaaa atcctgcct cagcctccta agtaggtggg attacaggtg cccaccacca     54960
tgcctggcta attattttgt atttttttag tagagacagg gtttcaccat gttgccagg     55020 ctagttttga gctcctgacc tcaagtgatc tgctgcctcg gcctcctgaa gtgctaggat    55080
```

```
tacaggcgtg agcgaccact accagcccct tggcacagttt ttaatggggt tatttggaaa   55140
ctcagttttt atgctaaggt tcaactaact gtggacaacc cagtagaaat agggttggac   55200
aaaaagggcc tgatctaaag ctaatggact gagtggggaa acccagccag gtctgtctgc   55260
ctagattctt cttggcctct ctgagcagca ttccttctgg gtgtgaggta ggaccctctg   55320
tggaatgggg ggtcttagga cctacagtca aaaaggcagg tcagaggatt tatttatggc   55380
cagtgtttac agaaaggcag gggaaagttg aggtcatctt tttttggttt catgggtgct   55440
ttgtggggaa ggggtctggt ttgtatgacc tgctttaggg aggagggatt ccagttccta   55500
tggccagcct tcggggagaa tggaattgag agacaacagg tcaggggagg gtcagagaaa   55560
aaccttttgc ctctgaggct gctgaagcct tcattttgtg gtatcattct ctgagcccca   55620
acaacacaaa ttttttttaac ttcatgcaaa actcttaggt cagttgagcc tagaatacag   55680
gtttctacgc tgtgtggcta agtacggtc cttccctcct ctccacaggg agcagatgaa    55740
atttattttg gaggaagtta actcagaata gaaggaccca gagatgtcag agagtggagt   55800
gggggcgaga gcccagactc cgtatctgtc ctgagaaagt taggacataa ggacccacag   55860
acatcagaga gtggagtagg ggtgagggcc cacgctctgt gtctgtaagg gaattgtcta   55920
cactctgcat actcacagcc atcagctttc ttgttcttcc ttccaagttg aaagtcactg   55980
gactccttca gtccatcct ggaggatccc tttcttggta aactgaactg gcagagaaaa    56040
gtattccata actggcattt ggaggccatt tgggcctatt acttatttac tgtacaatat   56100
gttcacctgc tgaggaagga cccctggcta tccacacaga cctgattctt aagtgagaaa   56160
agacagtctt acatcctaga tatttttgag aagctttcaa taagaaattc tttttaaaaa   56220
ttgaaaaaag aatcatctgg aggtagcaca gacaacacca accaagaaaa caagagacaa   56280
aatttctaat ctgtaacttg taggagatat gatgaaatag tgactcataa aaaacatggg   56340
aattctatta aaatgtgaca tattaggcaa attaaataat cagattggag aacgattatg   56400
aggatatctc caatggacaa aactttaatg agagagagat agcaaaatgg aaaggaacga   56460
atatggagac tctaggaatc tgacattcga agagtatttt caggaaggac aacagaaatac  56520 aaataagcaa aagtgactta tgaataattt ttaaaataat cccagcattg agggatctac   56580
acttccaggc ttatgaaaca acactcaggg ctcaccatag tgaatgaatt gaaactccaa   56640
actacaaaag cacattgcga gatttcagaa gaacaaatat atagggaaga tcctaagagc   56700
ttggaggctg tattaggccg ttcttgcatt gatataaaga aatacccgag actgggtaat   56760
ttacaaagaa aagaggttta attggctcat ggttctgcag gccgtacagg aagcatggcg   56820
gctcctgggg aggcctcagg aacgtgtcaa tcatgacaga aggtgaaggg aaagcaggca   56880
catcttacat ggctggagca cgaggaagag agagagagga cgtgctacag cctttcaaac   56940
caccaggtct cctgagaact cactcactat acagtaccaa ggggtgtgta cagtaccatt   57000
caagagaact ctgctcccca tgatgccatc acctcccacc aggcccctc tccaacactg    57060 gggattacaa ttcaatatga gatttgggca gggacacaga tccaaatcat atcagaggca   57120
aagaaaaaaa acttattaag aatcaagaat ttgtaatgtc atagaatgct tcatgtcttc   57180
actgaacgtt aaaagataga aactttcaca attctaagaa aaaacaattt actacgtaga   57240
actcttggag caaactgtcc atgggcaggc agggtcaagg catttacact gatgtagcat   57300
ttccgaaaat ttacctttg tgcaccctt cttggaaagc tgtgtgatta tgtcttcctt     57360
caaacagcgg aataaatgac aaatagaaag atggggaatc caaggaacag tggccttcac   57420
```

```
agaagagagc tgaaagaatg caggtctcag attaatgccc agagcaggct gggacagctg   57480
gaatcctaga gtgagacttc aaggagaaag tacataaaag aaaaggaaat gagccatttg   57540
accatgtaga aatagtactt gagatgggct ttagttccct tggaacattc agaaaaattg   57600
aacaatagac acacagaaaa gcatgaaatg aaaatgtgaa gttgttgttg tctccagata   57660
aaacaggagg caattcaatg aaggagattt aattagagta gaatgcttca ttcaggagtg   57720
attattaatt gcacagttac aataaagtta aagagagaag gccaggtgta gtggctcacg   57780
cctgtaatcc cagcactctg ggaggccaag ataggcagat ctcttgagtc caacagttcg   57840
agaccagcct gggcaatgtg gcgaaatccc acctctacaa aaaattcaaa aattatctgg   57900
gcatggtggt gtgtggctgt agtcccagtt actgcagagg ctgaggtggg aagattgctg   57960
gagcctggaa ggttgggggct gcggtgagtt gtgactgtac cattgcactc cagcctgggc   58020
aacagagcaa gaccctgtct cgaaaaaaca aaaggcaga aggggcaaat agagtggtgg   58080
ttgcccattg ataatttata ggtaatatct aaaaataata tatcaagaaa aaatagcata   58140
aactattact tagaaatatc atagagcata tatttggaga ggagaagcta agaaatctga   58200
aagcatttgc tttctaaagc aagtgtggtc atgggatgtt gtatgttggg caagaaagtg   58260
ctgtttgttg tgcaaataac acttgtagta gtttgacctt taaaacttca tgcatgcctt   58320
tctttattga aacaaaattt tttcaaaaga aaaatgataa ggccaagatt gaatggtatg   58380
tgaatgtgaa tatgacagtt aaaagcatga tttctcaaat gtacctgccc attggaatca   58440
cctggagaat gtaataggta ttaatgcctg tgctgtggtc ctccagagat tctgacttgc   58500
tcggtctgca atgcagactg ggcagtgaaa ttttccaatt ctccttaggg attctaagat   58560
gcagcagagt ttaggaagca tggatctagg tagctcagat tcttacttga atttaaaaat   58620
ctctagctgg gtgcagtggc tcatgcctgc aatcccagca ctttgtgctg ggctgaggtg   58680
ggaggattgc ttgagcccaa gagttccaga ccagcctggg caacatagcg tgcctgtgtt   58740
cccagctatt caggagactg aggtgggagg ttcgcttgag ccctggaggt caaggctgca   58800
gtgagctgag attataccgc tgcactcaag cctgggcaac agagtgagac cctgtttcaa   58860
aaaaaaaaaa aatcttgtcc agtgttctct tcaccaagat acagtggttt cagtaataaa   58920
ctactactaa catgatgatt tagattgagc caacttcatc actcagtcat ttctttgtta   58980
tctgatatgt tctttatgga aaggctttaa ttgcttgaaa atgacctaat gcttctccca   59040
agcttcccat ttttttttcc ctttcttaac tgaagtcaca gaatgttctc gtgtgtggaa   59100
tgctttgtct atcctacggg aagccaattg tgcatggctc atggcgccat gctggcttaa   59160
ttgttccaat tcctcctgtt tctccgacca cacatgaggt tgaattaaat ataatttcct   59220
cagtttgcat ttcccaggca gtcgtcctaa gtggcttctt ggaggagctc tgtgcattcc   59280
actggtctaa ttctgtgatg cccttttaact cgagggccaa ggacataatt accagctcta   59340
gaaattcgtt ccgtggtcaa ggatgcttgt gcagaggcca aattttcttt cattataatt   59400
tggcctttgc caagcttcaa agtgaagggg attgagttcc tactaaagag tattggcacc   59460
taggaagtga atgctttctc tatcttttgc agctagtgtg ttctacattt cttcaatgta   59520
ccttctgcct ggtaaatgtc agattattg ttgatcatcc tcaggtgta gttctttgtg   59580 ttgttaaata agaacccagt ggcttaaaag cattggcttt tgagaagtca tttttatcct   59640
ggatgataac tcaaatccat gcagtgctga tatttacagc tgggaggtga catgatctta   59700 tccttttggtc tgttgctcaa attattgatt tcagtaggac ttactggctc ccttctgtct   59760
tggggatacc tttgatctgt cttgccttgg gggacccctcc ctctgacctg gaatagcagc   59820
```

```
ctatttccac aagaagggac cctctgagag aggacagtct tcataccgcc tcttccgatt    59880
ttcctttatc ttttatgggt tttggcttta aactttact cttagaatgt ccttaaagct    59940
aatgattttt taatgttctc tagtgtatta ctaaaagctc ttcatctact tgaaagactg    60000
gggcaggaag attgcttgag cccaaaaggt cgaggctgca gtgagttgtg atcctgccac    60060
tgtattccag cctgggtgac agagcaagac cctgtctcaa aaaataaaaa aggacaggtg    60120
cagtggctca cgcctataat cccagcactt gggaggctg aagcaggagg attgcttgaa    60180
gccagagttc tagaccagcc tgcaacatag agagacccat ctcttcaaaa aataaaaaaa    60240
aaatagctgg acatgatggc acacccctgt agtcccagct tcttgtgggg ctgagaccag    60300
caggaggact tctagagcct aggaattcca ggatgcagtg agcaatatgt atgtgttaat    60360
acatagtgaa accagttatt ggagaattag tatatgtcct cccacaaatt cagtatgttt    60420
tcctaattat ccaattaatt caaagggcat aaacataata gatgcaaatt attttacgtt    60480
ttttgtttaa aaacctttt gactgaatca gtctatgacg ctttagtatt tgaagttgcg    60540
gacagaactt agtcttaaga tagcactcgc tttgttgata gatttccatg gagggaattt    60600
ttgccagatg ataatttagc ttgaagatgt tatagatgtg gacagtcaca ccctctaagt    60660
tacacagtct ggggtgggcc aattgaaaag aacatgcaga aacacaggct tgttaaggga    60720
taattaaacg tgggggaaat agaacagtca tggcagagga tttaatagg tttaattggg    60780 ttaggaagaa taggccggag tgaaagaata gctcttaata ggaggtctag aaatagccaa    60840
ggaaagcatt aattgcagaa atctgtgac atctgattac tgtagtgaaa gaaagatcca    60900
cctttaaaaa tcctatctat acagaaagaa gtgatagga gaagaaaatc ttcccacgga    60960
catatttaag aaaaacagtg gggaggtttg agatttcaaa gggccatggt tcaggttata    61020
attcaaaaga gaggcaaatg atagtcctac tcttcttgag tttcaggaag ggggaggatt    61080
ttgccacttg ctgtgaaata attttggagc ttctataacg ttgatccttt catcctattt    61140
tttcttggac ttgggatgtg gggagtggat aagatgggga tggagaagaa gcagggttg    61200 aaatgcctct tttgattctg ttcattcccg gaattcttct ccatgggcct taaagagtag    61260
agactccttc ccggtgcatg acatccagtg gccaattaat gaaactttat ttcctcagat    61320
aagttccctt cctccattaa tttgtgggaa ttcagatgaa aacttacttg gactgtggtt    61380
ttctatgtgt ttgtgaatgg aaggacatgt tgtctttga ccttccttta gtttcacgtc    61440
ttagtcttga tatttaagta gctttggttc agacagagaa ggaccatgtg tgcagttgct    61500
gggactgctc tctagcttgg aggttccctg gtcttgggaa agatctccct gcccctatgca    61560 ggtggcatag atgtttaatt ttctacatga gagaagcgct agagtttttt tattcattac    61620
ttgtgtgcac agctgtggcc tctagggaag ctcagctgag gtggtctcag gttccaccaa    61680
aggttaccgg ggagagatga ctaggaagac aggaagacct gtctcacttg ggagggtatg    61740
gcaagagcta ggcaagacct cctggtggag atatttgcct tttattcttt cttttttttt    61800
tttttttttt tttgagacag tttcactctg tcacccgggc tgaagtgtag tggtgcgatc    61860
atggctcaca ccaacctccc cgtctcgagc tcaagccatc ctcccacctc agcctcttga    61920
gtagctaggg ctacaggcat gcaacaccat gtccagctaa ttttaaatt attttagaa    61980 acaaggtttt gccatgttgc ccagactggt cttgaactct taggctcaag tgatcctccc    62040
gcctcagcct ccgaaagtgt tgggattata ggcatgagcc atgttgcctg acccatttat    62100
tctcaagtac ttatgctcag ggcaggtctt ccaagggaag agaacagcca gataagactc    62160
```

```
gtatgagata gctgaggagg tggcatttca tccttccatg cacatgctcc ttatccacaa   62220
gcagaaagct gtaacctttg ctgtccccac taggtcatga taggtagata cgcaggtgat   62280
gaccacagac tggcaattag ccaaggattc tcagctgtgc acgctacatg tgtgagtgtg   62340
tgtgacagat ccctttggcg gtttggtgga aaattgatac attttgtaaa aatgatatgt   62400
ttaagtcata caataaggta aataacgcat aaaaggaaat cggttttatt gaaatagtta   62460
ccaaggtata ttaatattaa tatttaaagt tggtgcagtg gctcatgcct gtaaacacca   62520
gcatttgggg aggctgaggt gagaggattg cttgaggcca ggagttcaag accagcctgg   62580
ccaacaaagt gagactctgt ttctacaatc aataaaataa aaaataaaaa taaaagata   62640 tatttaaact gggctacagt aatacatgtg catctttatt gtgtgctaag tacctggatc   62700
tacttaagag gttcgtaata gtcacaattt caaagtacaa taagcgtaaa cagtattttg   62760
ggatatctgt gataacagtg ttaagtgtcc tacctacacg ggtaatggaa gcaaatacta   62820
aatttcagtg catggtagtg aaactaaaga tgtaattact tttgcccatt gcaatttgta   62880
gaacccatgg aatctatcta aagactcctg ggtggcaaag gataaatgct tgagggtatg   62940 atacccatt cttcatgatg tgattattac atattgcatg cctgtatcaa aacaactcat   63000
gtgccccata tatatatata tgtatatgta tatacacctg ctatgtactc acaaaaaaat   63060
aaataaagac acctgggtgg gattggggtt tttggactta gggtggagaa catctgcatt   63120
tagaattgta tagaggaaag gttttgattt atttattata cctctgtttt ctttaaaaaa   63180
cctgcatgtg tagtaggaat tttgccagag gtgggaatgt gagagtcact agtttgcagc   63240
atagagcatt ctatactgag ataattattt ttatgtcaaa aagaaagtga agaatctggc   63300
agattagaat cttcatgtta ttttcattta aaaagcttgg aagtgtcaat atcaattaat   63360
attgactgct atttactgac attttttggca aaaaacattt cattttaatg aattttgtct   63420
tgtttgaatg tttgtaaggc tttggaggta gttttaggag atagttgcct ttgattcctg   63480
aggtatattc ttgggtctac cctgattctg tctcttgact ttgcacctct ttccttcctg   63540
aaccctgttt aaaagagcct tccttttacg actctttttct tccatcctat tcttccttcc   63600
catgctaatg tgagacacag aggtttttat gagaagcctg ttgtctatat gctggatctt   63660
ggaagccttg gttatttcct agagatggaa ggtctgatct cagttaagtt ctgacccag   63720 gacaagaagc ctctctggag taactgactc actgggatag agcctgtttt cacaaattaa   63780
tattcctgtc tggggagggc agaggaaaca ttttggggag tgggtggagg tgatgaggtt   63840
caagcctgag gatgaagctt gccttttcctg ggagcttgta cagtgtcata ctcaggaaat   63900
aaactgtgtg ggaaaggtgg tgtttagtaa tctagagccg aacaccttgt aaggccctca   63960
ccttgtcatt ctgcactgtc agaagcacat gagaaaagag tgtaggctgc cagagcaagc   64020
atcacaccga aataggaact tctcagatag agccgtctgc ctaaaacaaa gtaaccttag   64080
caaataggat ctgtgctaca gaaaatggag cactctagcc agggttgtga gatggagctg   64140 gtcctgggt cacaggtggt gtcttgggaa acgttctgaa gacactcagc ttttcggata   64200
ttgcacagtt cattaggaga ggtatgggca gtggttatga agctccttat gtaagagaca   64260
tagagataca ctcaacagta ttactccaga ggggttctggc tcctgtcttg cacttgggag   64320
tacacacttg ttcttgtcca cattaacctc caactgtcca catgatcaac catctgcaga   64380
cccactgcca gttgagggtc gtgccaggtc agaagtacta actgcaggtt aaactgtgct   64440
atttagaaat tgagtgtttt tttccttactc aaactgacag ttttccttttg tagaagaact   64500 cactcagctt ccactctggc ttaaatattt cctttacatg atcaatatta tctctgtcca   64560
```

```
tcagatacag caatgagaaa gccttttaaa ggaaatgagg ttaaaagtga ctgggtatct    64620
agaattcttt attttgtttg ctaaattgca ggcaaatata ttcccagaac tagttgtgat    64680 acctttcag aaactggctt atttgacatt ggctgaaagt aatactctaa cactttactg    64740
ctgtgtcaat gagtgaaatt cctgcaggca aaaacaatag ggactacatc gtgaagccta    64800
tgagaatttt atggtggaaa catgagtgga gcaggtggtg gaagtagctc atcttctgtg    64860
gttgtggtac ccacaggaga tgagctaagg agaatgccct gaaacctaac cttgccaatt    64920
ttctgtcttc tgtgtcctgg ttccttctgg tttccttgtg tctcttttct tccttttaat    64980
ttaatagtgt ttactgaaga ccttctgtct tccaagttca agtattagtc atctctgggc    65040
tttgccctta gatacttatc atagtctagc aatgaatgta agcattgagg aagtaatggt    65100
gacataatgt gaatgttcag tgtggtatca tcttccccac tctttgtaaa tcttggtggt    65160
cttaattctt gaatgtcaat gcttaccccc tctatgctgt ctttacagaa gtcctctggc    65220
ctagctctct ctacatgtct aaaattgtag aagcatcttc tgggcactcc attgcaaagt    65280
ccattctgca gaagcccacc atcccacaga aggagcaggt gggaggcagt ggaccacagg    65340
ctggctgcat ggtagcaatt gaaaagcaat ggagcacagg ctggcttcat ggtaacagtt    65400
gaaaagcaat ggagcacagg ctggcttaat tgtagcaatt gaaaggcaag cttcatctca    65460
tcagctggag tgtttactac ttgaggatgg gtacttgatt ggtgtatctt tacattttat    65520
caaaatgggt ttcaccttgg aagcattcag tggtacctca gtgaataatt gtaattagct    65580
aggatttctt tggggaatac ttattgttct aaatttatat gtgtttacat atatgtactg    65640
tattagtctt ttttcacact gctgataaag acataccgga gactgggtaa tttataaaga    65700
aaaagagatt taatggactc acagttccat gtggttgggg aggcttcaca attatggcaa    65760
aaggcaaggt aagaacaaag gcatgtctta catggcggaa ggcaaaaaga gagagcttgt    65820 tcagggaac tcctcattat aaaaccatca gatctcatga gacttactat cacgagaaca    65880
gtatggggga aactgccctc ttgattcagt tatctcccac agggtccctc tccctatacg    65940
tgggaattat gggagctaca attcaagatg agatttgtgt ggggacacag tcaaaccata    66000
tcacatacat atgcatatct ttatgtaagg tgtgtgaata taggtgtgta tattcatata    66060
ctcttgtact ttctcaaaca caaaccatag cacgtgcaat aatatccttg agttacatct    66120
gctactctgc ccattttaca cataagagat ggaagcattg atggttatat taggtagggt    66180
tctctagagg aacagaacta ataggacaga tagatatata aagggagtt tatcaagtag    66240 tatttgttca cacgatcaca aggtcccaca acaggccatc tgcaagctga ggagcaagga    66300
agccagtccg aatcccaaag ctgaaggact tggagtctga tgtttgaggg caggaagcat    66360
ctagcacagg agaaagatgt agacttagag gctaagctag tctagtcttt tcatgttttt    66420
ctgtctctgc tttatatttg ctggcagctg attagatggt gcccacccag attaagggtg    66480
ggtctgcctt cccagcccct ctgactcaaa tattaatctc ctttggcaac accctcagag    66540
acacacccag gatcaatact ttgcattctt caatccaatg aagttgacac tcagcattaa    66600
ccatcacaat ggtgtataca cccttctctg gttgctgatg gagttaaagt gagagccagg    66660
atttgaatca tagtcataaa actgcacaaa acctctgccc catactacct cccagataca    66720
taatacacac atgagtaggt gttttttgtgc ctgttatagt gcatttgagc ctgttgttct    66780
tagtttgctc ttatgtagga ccatctctct gaaaacagat gatcagcatc atatgcaaca    66840
ggtagtattg attatctgta gcataaaggc atggaacacg ggattttcag ggaatggagt    66900
```

```
aggaaaaatt cctgaaccta agcagcttaa tagtttaata tttcacttgg ttagttcgaa    66960
tatatatgtt catatgcaca tgcatgaaat gacatggata aaataagttt taatgtattg    67020
tatctatata aatctcttta aacctcaaaa aatgtatata tccaaactaa ttatttgtca    67080
gtctctccct ctctttctcc ctctctctct ttccacgtat ttatatataa atatttctgc    67140
aaactaacca actgaaatat taagctccta tctatgtttt atatgtattt ctgcaaatag    67200
ccaaccaaaa tattaaagca attaaactcc taaatataat atttctttta tctattatat    67260
tatttcttca aactaaccaa ttgaaatatt aagcttctat gttttatata tataaagtat    67320
ttctccaaat aaccaagcaa aatattgagg tattaagctc ctgtgaatgt tttatattat    67380
tctatgtata tagaataata tattttatat gttttttatt atattttata ttattctata    67440
tgtagaataa tatattttat atcctatatt atatatagaa taatatattt tatatcctat    67500
attatatata gaataatata ttatatatcc tatattatat atagaataat atattttata    67560
tcctatatta tatatagaat aatatatttt atatccctata taatatatag aataatatat    67620
tttatatcct atataatata tagaataata tattttatat cctatataat atatagaata    67680
atatatttta tatcctatat aatatataga ataatatatt ttatatccta tataatatat    67740
agaataatat attttatatc ctatataata tatagaataa tatattttat atcctatatt    67800
atatatagaa taatatattt tatatcctat attatatata gaataatata ttttatatcc    67860
tatattatat atagaataat atattttata tcctatatta tatatagaat aatatatttt    67920
atttatattt tattttttata atatattttg taatatatat gttttttata tatagaataa    67980
tatattttat attattctct ctctatatat agcaggttag tttgaagata tctatacgta    68040
taatatatta aaatttattt ttggccaggc gcgttggctc acgcctgtaa tcccagcact    68100
ctgggaggcc aaggcgggcg gataatgagg tcaggagttc aagactagcc tggccaatat    68160
ggtgaaaccc tgtctctact aaaaatacaa aaaattagct gggcatgggg gcatatgctt    68220
gtagtcctgg ctactcagga ggctgaggca agataatccg ggaggcagaa gttgtagtga    68280
gccgagatct caccactgca ctccagcctg ggtgacagag tgaaactctg tctcaaaaaa    68340
aaaaaaaatt attttataga tataatttca tatatgataa gttaaagtac aaactcttga    68400
aacaactcct cttatatatg aggggaaaga agaagattat ttgtacagta caattagtac    68460
agtgaattct gggaaaaagt cagtaaatac tcatttcaaa tcctcatgta caattcaagt    68520
aaagaaaaat ctggtggcat ttttatatcc tgctaataaa ggttatctgg tgttggaaaa    68580
catattttat tttacatgt acatagtagg tgtatatatt tgtgggtaca tgagatattt    68640
tgatataggc atatgtgtaa aaatcacatt agaataaatg gagtatacat cacctgaagc    68700
atttatcatt tctttgtgtt acagactttc caattatgct tttagttatt taaaaatata    68760
cagtaaatta atgttgactg cagtcaccct gttgtgctat caaatactag atcttattca    68820
ttctgtctat attttgtgc ccattaacca tcctcacttc tctctctctc ccattaccct    68880
tcccagcctc tggtagccat cattctactc tctgtctccc tgactgcaac tgaaagaaat    68940
atttttaaag aataggctgg aaggccacac tgactctcac tgtttctggc acactaaacc    69000
ttgccatttt ctgcagtagg gattgtctcg cttcagttat gccttgctac ttcagtgaag    69060
gactttctgt tcccactggg ctcctatact gagtctgctt tggagataat agtctgagat    69120
gtcagagcgt cttagtggtg aaagcaactt aagaggtcac tggcacaagc cctcgttttg    69180
cagtggaggg agttgatggc gagggcactt ggctaattag tgaccagggc tatagcaggc    69240
tcaggttcca tgactgtgct taccatggct ggcaggatcc cagggctttt ctgtgtaata    69300
```

```
tgtgggtgga tggtctattg ccttgggctt gtcgcataat catggagaaa acagtttata   69360
ttttcccttc aattttaaaa tccaagatag tttgatagca catgggaaaa taaagtcatt   69420
gagtaaaact tatacggatg agaatctttt gattaaattt tcattgtaaa ataatcatag   69480
tcataaaaag tgtatcaaaa tgtgtatttg gatattcatt ttaaagagta aaaataatc    69540 agatacatag tattgtaccc actgacagac aaggaaagag aacattccca ctgtttttat   69600
atatcagtgt gagttgcttc cctctctcct acctttcagt gaaatctaat cccccaagat   69660
ttggttttca tactgtcctt gctgtatatt tcaggacaaa catagctctg agcaatatat   69720
tgtttagttt tactattatg taaataaaat cacactattt gtagtcttct gtgacttgcc   69780
ttttatgttt gagattttcc cattttcctc catatatctg tattttattc attttgact    69840 gttttgtaaa gccttctgtt ttaatatgcc aacattatt tattcattat cctatttatg    69900
gatatctgga ttgtggcaat attttttgca attataattg gggcttattt atcctcagca   69960
aactaacgca ggaacagaaa accaaacacc gcatgttctc actcataagt gggagctgaa   70020
tgatgagaac acatggacac atgggggagg gaaacaacac acagttgggc ctgtctgggg   70080
atgcccggag gggagagcat caggaagact agctaataga tgctgggctt aatacatagg   70140 tgatggggttg atttgtgcag caaaccacca tggcacatgt ttacctatgt cacaaacctg   70200
cacatcctgc acatgtacct tggaacttaa aagttgaaga aaaaaaaatg gggctgcagt   70260
ggacatttcc gtgcatgttt cctgatgcat gggagttcta gttgctccac atcgttgctc   70320
agtacttggt atcattgttt gtttgtattt ttattaatcc tattgtgatt tcatctgcat   70380
ttcaccaata atgaatgaca ttgagcctct tgtcctatgt tgaggctatc tgtagatttg   70440
aggactcctt cctggatgtg gatttatggt ggagaaacca acaaagatgg ctttgagtgt   70500
aggctgaatt actagaaaag taatgatcta gttatccaaa tatgaaacaa aagcatggaa   70560
gcagtttggg gattggagaa tgagattttt aggagcacca taagatgtct atctgactat   70620
attcttgaag agaaaatagt catggcacta caggcatggt ggcacatacc atgttatcag   70680
ctggcactac aggtgtatgc ctccatgacc ttgaggacat atgactttga gttcggtgag   70740
agagatgaac acaaagccta gagagatctg caaatcattt gatttagatt tagaaattgt   70800
gtctggaaaa catttaattt cacacagaaa atcaagcatt aacgcacttt tattatttgc   70860
cagtccttgt gctagcttta gatatgcaga agatgaataa gaagaaaaaa tgcatcacag   70920
gtagggatag ataccttcat gagaatgtaa gctcctagtg ggcaggaact ccttctttac   70980
cccattacgt accctttacct agcatagtga tctttacggg atacttctgt ggtctgaagg   71040
cttgtgtctt tccagaatcc ccatgttgac gttgtaaccc caaagtgatg gtgctaggag   71100
gtagggcctt tggagctgat gagatcatga gggtggatgc cccagaatgg tattaatgac   71160 atttttaaaag ataccccagg gagattcctt gccctttcc ccttttccaa agttataagg    71220
aaaatacagc cctctaggaa gcaggccctc accatacact gaatctacca tgccttgatc   71280
ttggacttcc agcctccaga gctgtgagca atgaatatct gtggtttata agcccccaa    71340 gctatgatat tttgttacag cagcctgaat ggactaagcc aacttctaag ttttggtgtt   71400
gtcttatttc ttttggtcggt gtaggatctt tctgtccaca tagttactc tagaaagatg    71460 tatgccctat tcctcatggt atatttgtct ttcctatctg tggaatatcc tcttatccaa   71520
ttcgtcttgg ctgggcaaca tataagccat taactcttta ccccttgggtt tagtttgggt   71580 tctgctgagg cccctgctga aaattctggt ttctacaatt atggctcatg catgttcctg   71640
```

```
acccattaaa cttcagtgga agaacagaaa tggtgaggga ggtgatggag ttgatacctt   71700
gagctgccat atggtgcaag atcatcttga agatagaaca tttggcatcc tttttttttt   71760
taagagatgg ggtcttgcta atttgcccag gctaaactca aactcctggg ctcaagtgat   71820
gctcctggct cagcctccca attacctggc aatacaggca tgtgccacca tgcctggcca   71880 cattttact ctccaattgc ttaatatata gtaaagataa tggttcaaaa tggtaaattt    71940
tttttgtgtg tataccaata acatttttt ttaccttaaa catattcaat ctttatttga     72000 caattttta aaatttcaac tttttttttt tattcatggg atatatctgc aggatttttt    72060
acctgggtgt attggatggt gctgaggttt gaggtacagt tgattctgcc acacaggtat   72120
ggagtatagc acccaacagg tagtttttct acctttcccc cctccctctc cctgctgtag   72180
tagtcccaag tttgttattg ctttatgtcc atgagtaccc aatgtttagc tcccacttct   72240
aagtgagaac atgtggtatt tgattttctg tttctgcatt aattaactta aaataatggc   72300
ttccagctgc atccatgttg ctgcaaagga catgatttca tttgtttttt tttgtttgtt   72360
tgttttgttt ttttgagacg gagtctcgct ctgttgccca ggctggagtg cagtggcgcg   72420
atcttggctc actgcaagct ccgcctcctg ggttcacgct attctcctgc ctcagcctcc   72480
tgagtagctg ggactacagg tgcccgccac cacgcccagc taattttttg tattttagt    72540 agagatgggg tttcactgtg ttagccagga tggtctcgat ctcctgacct cgtgatccac   72600
ctgcctcggc ctcccaaagt gctgggatta caggcgtgag ccaccgcgcc ggctgatttg   72660
tttttatggc tgcatagtat tccgtggtat atacgcatca catttctttt attcaatcta   72720
ctgttgatgg actcttagat tgattccatg tctttgctat tgtgaatagt gctgtgatga   72780
gcatacatgt gcatgtgtct ttttggtaga acaatttatt ttcctttgta tatatacccca  72840 gtaatgtgat tgctaggtca aatggtagtt cctcttttaa gttccttgag aaatctccat   72900
actgctttac acaatggctg aactaattga cgttctcacc aacggtgtat atagccttct   72960
cttttctctg cagccgcaac agcatctgtt gttttttgat gttttatgaa tagccattct   73020
gactagtgtg agatggtatc tcattgtggt tttgacttgc atttctctgg tgaaaaatgg   73080 tggatttta aatgggattt cattttaga tttaatagaa actgcatagg tgactgtgca     73140
aagaactctt aagatttgac aaaaggcaaa ttagattgta atctccttta tgtaggaggg   73200
gaaataaaaa ccagaatatt aaaatatcta catgtacaaa aatagacaaa gtggcagatt   73260
gctggtgttg gatggatgtt gagcagggat ggaggacttg tgtgtgcatg catgcatggc   73320
catgcgtgga gagtggtcat tcattttggt aacagcatag agctttgggc ttcagaacaa   73380
aagataagcc acatcccact caggtaccct aaaatgttgt ctccactaga cacaaaagaa   73440
aaggaagcca gagatgtctg tagcttatgc agagttttgg gaatagctat tctagacttt   73500
cttagtgaac agtatagaag gattattgta caagcccagt aatttgggca aggatcagat   73560
tctgttgctt ttgtttttctg gatgctccgt aatgaatgtg agatggaagc ggatgtctca   73620
agtgcttctt gttctcagaa acctcctggc agcagacatc tcagtgggcc cagacgttca   73680
gcgtggctgg aagtaaaaca cagggaaggg tgctctttct cagttatcct atttttttt     73740 aaaagcatct acaaagcttc ctgttttcta atatattccc aggcctttga agacaaggc     73800 cataaacacc caggagatgt gactttattc ttttaaggt ccagatacca aaatgcctgt    73860
catcagggct caccttaatt aaaatacgtat cttaaaatta aaccaatctc aatttaagga   73920
atgtatactt tggggagaaa tttattacaa ttttttattca gaacacttta aattctgata   73980
ggcctgaaga gtgtgagcct caccttaatt gcaacctgag tcagaataac tgccctgcag   74040
```

```
agaatcattt aaaatacccca atcaagttat aaattagtca aaatgccatt ctgagatatt   74100
attattttat gcagtctttg cagagaatac atgctatata gcccttcttc actcccaaag   74160
tatatgtata tatttaatga agttttcacc ttttttatta aaattttaa tccattaaca    74220 attttagaat tcattttgta gcatatcctc tttatcttag agatattaaa tatctaccta   74280
tttatgaata actatcaata accacgtttc acccttgtg aaatccttt cagttttga     74340 aactcacatg ggagatcttg ttttttttt tccccacaag gatgtaggtt ggttaaattt    74400
acagtggttc tttaatgatg ataatgcaca tttgattgat atcaataata aatattgata   74460
tcttcaatat caacatttct tgtaatgcta aaaatttaca agttgccaat tttttgaata   74520
tgactatatt ttcacacaca cacacataca cgacagcact aattatattc actaaatata   74580
cctacagata cttaatcatt tacacagcca ctataatttt atacttgatg ccttaaacca   74640
gtaattctcc cttgagggtg gttttggccc ctgggctacc tagcactatc tagagacatt   74700
ttccatagtt aaaactgggt aggaggtgcc actatcatct agtgagtaga ggtcagggat   74760
gctgcaaaat actgtacatt gtacaggcga cgcccccaca acaaagaatt atatggttca   74820
caatgtcatt tatactgaga tgggaaacg ctgggcttta attatagcaa ttttgtgcaa    74880
attagccaaa tttcaaaaaa caagggagtg aaaaaagata gctctcaacc tgtgaatatt   74940
gtgaatgccc aatctagacc tagtaagtgt acagatgccc ttgggcgcgt cttcttaggt   75000
tgctgctgct tcataatcgc tcactgccca tcaggacctt gtgggatgta gatttaggca   75060
gaggagggtt ttgatcatac agctggatca gtcataacca ataagtgact catagtctca   75120
ttcacattga gtttgagaat ttaaggtgtg ggctggaatt ccttatggaa ctaactttat   75180
ataccttgga agaagtccac ccactgaatt ctacatttat tgagctctgt gtttcaggga   75240
atgtgcaata ccttgaggat acatactatc tcatttagtc ccaagtagct tttaaatatt   75300
tgagagtggt tttggccccc aggctgaaag taacagctac ctctggttaa aaatcttcca   75360
ggaaagaagc aaccaaacag gacatcacct ctttgttttt cttgtctgtc tcttaattat   75420
tcagaaatgg gattgctgta tggcagacat ccaaatgttg tctacagtag aattcagaga   75480
tagaagcaaa cacctaaatc agtcattggt gagatgctat ttgtcacttt caaagttata   75540
atccagattt tcagtgcgtt ttcatccaac tctggtgaac ttttcccagg atgtcatgta   75600
ctatggaatt tccccccatt gtattattgt tctgtgataa atccagctcc aatatgtttt   75660
atttaaaaaa aaaagccat gtgatgtatt ctgttcaact gattacttaa atgaaatgga    75720
taattatttt ctgatgcaga tgctctgaat aacccacaaa atccttagaa acacatttgt   75780
atattttgag ttgaagaaca tgctaaaggc accctccttg caacacctag tgaaatattt   75840
tctgttccta ggggatcatt taacaacata atgtccattc ctgcacagca ttcttttatt   75900
gtcacaggag cagcgactta tgtagggata gttatattat ctatgtaaag acaaattgag   75960
gtggtgaccc tttaaaagtt gactccaggc tcaatgggaa agtaactcaa atgcagcctc   76020 agcttttaa atgggctgaa gggtgaagag gatacctctc aaggcatgca gtggcttact    76080
ggaaagtcag gataattgta tcaacacttt taattatgaa tgaagtcttc aagaaactag   76140
cactacagca tgtacttgaa atgcaccatc ttgtatagtg ttttacaagg aaactgagat   76200
tcagagcagt gaagtgtgta gcctaaatat atatgcactt gaccagacca aggagaattt   76260
gtgtccaaag tctacactct tttcatttga tgatgttccc tttgtggcct gataaatatc   76320
cacatcatga tgccagattg acttggatgc atgcttccat ctttctccta ctggaaaact   76380
```

```
tttagagctc catgcatgtc tccttaggaa aatgtgacaa tttccttaaa catttgagaa    76440
acagtgtttt ggaagtaccc atgtattgat aaccagtctg gtaaacaata gcaaaactgg    76500
gaggtgttgt tactataatc tgcataacct gtataactct tgaacatctg tttgatcatt    76560
caacacagat ttgtttagtg ttttctaaat gtcaggcatt gttcatggtg ataggatgta    76620
cagaggaatt aagacaagtg gtggctgcta ggcatggtga ctcatgcctg taatcccaac    76680
actttgaaag gtcgaggggt aggatcccct gaggccagcc tggacaacat agggtgaccc    76740
aatgtctaca aaaaaatcca acgaattagc cggacatagt ggtgcatgct tgtggtccca    76800
gctactcggg agggtgaggc gggaggatgg gttgagccca ggagttggag ctgcagtga    76860 gctatgacag caccactgca ctgcagcttg ggcaatatag caagacacca tctctaaaaa    76920
aaacaaaata aataaagaca ggtgatgttc ttgctgttgc ctactatgtg gagatggcac    76980
tatacacatt tctatacaaa tgaataggaa tttcatagag agatgttgtg gatttcgtgg    77040
aagagccagc cagtgttcta ggtggtcgtt gtgtggcttc attattcttg tctgctttct    77100
tcctctttta ggctgccttg gagttttcat aagaaattgt ccctggaggt gttggatgat    77160
cacagcttcc ttggagcatt gcagttgctg gaatccagtt tcaggattaa gggagggctg    77220
cctccttgca atgggctgcc aagaaaacgg ctgtgcttgt tcttaacctc aggctctgtc    77280
tgtgatcagt ctgagagtct ctcccaggtc tactgctccc tggaaagccc tatctctctg    77340
caggctcgcc tctgggcttt gtctccttgg agccacatca ctgggacagc tgtggatgtg    77400
gatgcagatt tgaaccatgt cacggcccca gggactgcta tggcttcctt tgttgttcac    77460
cccggtctgc gtcatgttaa actccaatgt cctcctgtgg ttaactgctc ttgccatcaa    77520
gttcaccctc attgacagcc aagcacagta tccagttgtc aacacaaatt atggcaaaat    77580
ccggggccta agaacaccgt tacccaatga gatcttgggt ccagtggagc agtacttagg    77640
ggtcccctat gcctcacccc ccactggaga gaggcggttt cagcccccag aaccccgtc     77700 ctcctggact ggcatccgaa atactactca gtttgctgct gtgtgccccc agcacctgga    77760
tgagagatcc ttactgcatg acatgctgcc catctggttt accgccaatt tggatacttt    77820
gatgacctat gttcaagatc aaaatgaaga ctgcctttac ttaaacatct acgtgcccac    77880
ggaagatggt gagtacctca ctggaacaga aaacaatacc tcttgtgcag tgtgtagaga    77940
gatttgctag gagggtttta taatgtctca tgcatgatct cttctataac ccgtttattt    78000 tatttaatt tattttttcat attccaaatg caattcttgc agcaacttac cacatgttcc     78060
acttgtatgt attgggccat ctactgactg gacaaaacta taataataa ctttaattat     78120 tttcatatat tgccttctta acttttata atgcttattt gcagatgaaa ataaatatga    78180
gcatataatt ttgcatgtta tacctgaatc atctgtaaag gaatgaatct atagaaaaat    78240
aatagaatta agtacactat tatgctccag tttgcaaact gaaagataga gaaaatggtt    78300
ctttctgcct taatgactta agatattagc accttttttg agttttcaaa gaaaacttg     78360 attgtttta atatacaagt aggggatagt tcatacaatg gttggatttc attgtttaga    78420
atcggttttc ttaacgtaaa tttggatgtt cttttcttcc aatattcgct gcaatcaagt    78480
ggcaaaatgt aatcagatga ttctagctac attagagatg aatgcgtttg tatttttaaa    78540
aatttccttt tttatataaa acaacaatga aagtctgtag acacaataac gtttaatata    78600
ttaacctaat gttagtaaaa catgaatagt tttatgtctg tatagatttc aaattcagat    78660
ttccttggaa gaataaccag actaaagtat gccataatgg tatcacattt cccagttagc    78720
atttccatat gccgttttta gatgaggaga aagaacaaca gagaataaaa tatacctgga    78780
```

```
aagaaaggaa gttaatttgt gggaatgata gatgtatcta atgtagaaac tagagtgtgt    78840
cctttgtata aagttcttcg tggaaagtgt gataaatttc ttttatggag aaatttcttc    78900
ttcttctttt tttttttttt taaacttcaa tccctggaaa acattttttca gtaagatttg    78960 gctgaaaata gtaaatcaac aacgacgtta atccactgat ctccaaaatt gttttgcatc    79020
tatcagatta ctctttctcc atataaatgc cagatagttt aagtagagtg tcatgaaaaa    79080
ccataccagg gttgtgtgtc actgaggtta caaattgtca ttgagattac aaagaacagc    79140
ccagagaaag aaattaaagg attctgcttc attatattag tggtttctgg catattgccc    79200
ttgtcgttat ggtgacagac ctctcaatta tctcataaag tccaggtctg aatgtgattc    79260
aaggagttaa actgacattt ggacgctgta cttccatggg gtgttctgag ctgtctccgt    79320
gcctaacagt ccctctttgt gtgtgtgtgt gagatgaata agagctctca aaagcaatta    79380
gggttctcat ttgagcagcc acctgggttg agatctttct cataatgaac tattcaaaca    79440 aaaccaaaa agaaaggaag acaaaaatgg ggagaaaacc ccccaaacag dacaaagggt     79500
taaaattgct ttcataatac tttggatgtg ctagagtctg gtgattttgt agagctagcc    79560
ttggcaacaa tgaatgcact tcaaatagaa ggcctcctca tataggagtt ggacagaatg    79620
agaccaccca tgaaaaagaa tcaatagcct ccctgactgc agagccctgt atgtacaatt    79680
gtgtggatgg agaccacaaa cggtgtggcc gtttcattgc aattcggtat tgaattaaaa    79740
tttgaggaat gtaaatatgt gaaaaatgct attcagtgaa aaagtaatcc aaacttcata    79800
ataaacccag ttccacttgt ttagatcttt aggctttttg aagcaatatg tgcatatgat    79860
cttgacaagg gaatcagaaa tctaatagtg actgaaaagg tagaatcgat ctccccacga    79920
tgtgtaaact ttagaatttt gctggtgaga gttcaaagct acagccctgc atgtttgtac    79980
catccacaag tcacagccta tgggttagg agttttatt ttttggttgct tgcttgtttt     80040 cttaactcta tcaacgaaga accagtgcag gccaggcgcg gtggctcacg cctgtaatcc    80100
cagtactttg ggaggccgag gcaggcagat cacgtggtta ggagatcgag accatcctgg    80160
ccaacatggt gaaaccccat ctctactaaa aatacaaaaa ttagctgggc atggtggcgc    80220
gtgtctgtaa tcccagctac tcaggaggct gaggcaggag aattgcttga accaaggagg    80280
tggaggttgc agtgagccac aatcgcgcca ttgcactcca gcctggcaac atagcaagac    80340
tccgtctcaa aaaaaaacaa aaacaaaaaa agaaccaatg cagagcttta gatgtttaat    80400
tattaattat tcactaaatg aatgaactcc gcatccacaa catattgaaa tgttggcatc    80460
atgctgattc tctccaaagg ccttctctta gggagtatct cagttcagat caatgctttt    80520
atttagcagg agagagagca atattattat ttggaattca aaattccact ctgaccagtc    80580
tgacaaagcc agaagacaa atctaaacaa taacaacagc aaaaatctac tttttttgtt    80640
tagctttgtc tttctgcctt gatcagattg gctcaaattt ctatgtttct actttcataa    80700
aatgtgtagg tatattaaaa atacaaaaat agactatttt agatacgtac ttatccttac    80760
atttaagaac taacttgcat gaggaaaagt gttggaaatt tcttcgtagt acaatagttt    80820
atgaaacata tattttttt ctgtagaaaa caatactttt tataattccc tttaaaataa     80880
atcaggtctt gctgaaggtg agtctttttca tttaaactgg catcatgatc tactaaactt    80940
aggcttgggt ctttataact atttcctacc ttacaaattt cttatttaa atttttcatag    81000 gttattaatt tctctctttgtt gttagacaac aggctaatta attaacttga attgcatatt   81060 taacctttttg ataggtgctc aaataaggtc aaagtcagtc aagccagtcg gaagctctag   81120
```

```
taggacacgt gggccattgt tgacaaggaa cagttggaga ccgattgacc gaatctgcat   81180
ggtgtgtgtg tgtgtgtgta tgtgacagag agagagagag agagagatag cagagagagt   81240
gtgactgagt gactactttg aggaagcaat gcagaatatg gcttggtagc ttgattaaac   81300
ataaattgtg aaagtcaagc cgagaagttc cagtctcaca tactaagtcc acttgagttc   81360
atacatgagg ggatggcagt acagttcgtg attcgtcttg gtccccaagg agactgaaca   81420
cagaaagatg agttatggaa acacttaagg ttttttaatga gaaccagtga tactgtttag   81480
aagtgaggtt aaaaagtaag ggaaaaataa aagcacacatt ttgaaggagt tgctcagaca   81540
agatatcata ttaaatataa agcttggagg agaaagagcc acaagtgagt ccagattgcc   81600
ttgggaaatg gacagaccca tggaaccact tcctgagtga cctacacctg tgctttttct   81660
ctggatcctt ggacatacat cttaaggtct tattcttgaa agatttcagg ggcgagaagc   81720
ccttccattc ttcatcatgg gactaaaaat actgggaaat ataaggaaa atataaatga   81780 aagtcattat cgcccaggca cagtggctca tgcctctaat ccgagcactt tgggaggtca   81840
tggtgggtgg atcacttgag gtcaggaatt cgtgaccagc ctggccaata tggtgaaacc   81900
ccgtctttac tacaaataca aaaaattagc tgggcatggt ggtgtgcgcc tgtaatctca   81960
gctacttagg aggctgaggc aggagaatga cctgaactcg agaggtggag ggaggttgca   82020
gtgagccgag atcgcaccac tgcactccag cctgggcaac agagtgagaa tccctctcaa   82080
aacaaaacaa agcaccactc attatcattg tattttcatt gtagcataac agcaaatgcc   82140
attatgattt ctagaaaagt gaaattttgg gttgtttttt ttttttgcta gcaatacaat   82200
tgaaaaagga agatattaaa aaagaacaga ttattggatg caaggtgtcc ctatcatctt   82260
tttcccccaa gatgacacct gactctttga atactatgac ttaagtaagc ttgctatgat   82320
tgttgattga ggacctattt ggtgaaaaca tggagcttta tgatgaaata taaacagaca   82380
cgacatggac aatgacctgt aggagtttgc acagttaata aacctagagg tagataataa   82440
gccagagcat cctagttagg gaacaaagaa agctctgtga cagctcaggg acaggctatt   82500
ttttgaggaa aaacttgatg gaagctgtta agttgttgag ctgtgccatg aagaatatat   82560
gggtgatgga agggattcat ctattaaagc atctgatgaa tggaacattt gaacacagaa   82620
atctatgtta agcagtttgg tgtcaatcgt tgctgttgtt actactttggg tgttaagtgt   82680 ggcgtggtaa cagaagctgt gctttagcat gggctgtttc tggcagtgcc atatcatgaa   82740
agttcttttt ttttttttt tcccttttaga aacaggatct tgctctgtca tccagggtga   82800
agtacaatgg tgcactcata gctccctgca gcctcaacct cctgggctca agggatcctt   82860
ccatctcagc ttcctgagta gctgggacta caggtgcact ccaccatacc tggctaatct   82920
ttttagtttc tgtagagatg gggtgtcact atgttgctct ggctggtctt gggttcaagt   82980
gatcctccca cctcggcctc ccaaaatgct ggcattacca gcataagcca ttgcactggg   83040
cccataaact ttttatgtt atccacagct gctgaccta tactttctag ggtagacaag   83100
ctacctaaga tgaaagggtg gcaggagaac aacagggaaa gaagctggaa agtcaaccag   83160
ctttgctagc gattttacaa aaaaaaaatg tattcgcttc ttttatagat accactggat   83220
ctaattcaag atataattta tagcatggtt ttcatccttg aatagctccc atctttttctg   83280 agggtcttac aaacttttct ggcattctgc attagtcaag agatatttgt gttcaaatgg   83340
tagaaggcaa cctagcctca atctgacttt gagggaaaaa atggaaattt attagaaggg   83400
ctatgggata tccaaactta ctgtaaaagt tgagaaatca gattggcaga atggcaggga   83460
tgcagctaga cttagacac acctggaagc attgaatcca aggacatcac caatcttcat   83520
```

```
atctcgttct ttgcttcttt ctggaaatag gcttgcttta aatggcagta agagggttct    83580
ctgcagtttt tgttagttgc attttgtttt tctcagtacc accagtgagg acaaagttc    83640 cataattcca tactaaaaat cccagggcgg ggttttgatt ggcccacttg actcaggagt    83700
aagaagagat aaaactgggc tgttcttgtg tataccagtt ggcaggggga aaggacagt    83760 tctcaccata aggtgtctgg aatgagcagg cactacttca cttcactgtc caaatatttt    83820
ttgagcatcg attatatgcc agacatgcct tagaggctga gattgtgaga gatacaagca    83880
ttcctaattt tgagagatag gtacttgtag gcagaaaagt catggtccct gagagatgtg    83940
caagcaccgc cctccacccc tacccccccag ccaactcgcc cattcctgga acctgggaat    84000
aggttggagg catggcacct gacttcttca atactctgcc ttaaataatg acttcaaatg    84060
gcaaagggga attaaggttg ccgattgaat taggtttgct aatcagcaga ccttccaata    84120
gggagaatct atcctggatt ctcatatata ttaacagaga ccctccactg tggatgcaga    84180
agactcaaaa ggagatcaga gttggtgtaa agcaacgtga aaagagata cctgacatt     84240 gctggctttg aatatgagag agccaggaga aaggaacgca ggtggcagtc tctagaagcc    84300
ggaagagaca gggaaacaga ttttccttta gagcttccag caaggagccc gacagccctc    84360 ctgataccett gattctagcc ccatggaaga aactctgacc ttagaactgt aaaagaataa    84420
atgtgtgctg ttctaagctt actaagtttg tggagatttg tcttagtggt aatagaaaac    84480
taaggaagag ttttatcacc ctgtaatatt atttgaaatt cataatgaag tattactctg    84540
aaaacaaaag ttcagagtct ctgaagttgt ttggtttcgg gccttctgga cccctctcca    84600
ttctgggatt ctacttccaa gaatttctag ttgaaaacac ccttgggcac ttagagcttt    84660
ctaccttgct caagcatgct aaggagatca tatcaattct tattttaggg cagacatttt    84720
tcagattttt aaaaatgtat ttttaaaaa tttgagagat aggtaccctg tctctgaatg    84780
gggtcttgca ctgtggccca tgctgcagtg cagtgtcaca gtcatagctc actgcagcct    84840
cgaactcctg gccgcaagtg atcccccaac ttcagcctcc tgagtgtctg ggactatagg    84900
ctgagactac tatattgagg ttcagagaag aagcatgtcc aggtgtctgc aaattagaaa    84960
atggtggcag attttttaaa aaagaaacga tgaaaaatta tccctgatta gatttacatt    85020
acaattttca gccaccatga ctggctagtt ttaaatttt taaagagttg gagccttcct    85080
atgttgccca gactggtctg gaaccctagc ctcaagtgat cctttcatct caaactccag    85140
agttctggga ttacaggtgt gagccaccac gcccagtgac attttgcaaa tttgacattt    85200
tgcatcatgt taatatagcc tcatggccaa ttgtcctaaa tggtatattc aaaagataat    85260
actgttttga cacagaaagg taccaaaggg tcatttagaa ttttttcagg aagctataac    85320
agatttccag agtagatggc tttgaatgac atataacaaa ataccgaaat tgttctttcc    85380
tcatctgtct ccacagagtt tcactcaaga tcgcggctgc acctttacat gtcttatttt    85440
cctacttaca aacactgctg acaaaatcct ctgtgttccc cactccttcc ggctacacct    85500
taagctgtgg tctcttctgg gcaaagtgat tctctgacct tttcaagcta caccttgttt    85560
cctcctccaa ccaaaacttg tttgctggag ttgaaatgcc agtttagccc cttagcagat    85620
cagtcattat gggcaagtga cccagcttgc ttgggccaca gtgtccttat gtctaaaata    85680
gaggcggctg agaggtttaa ggttttaatc catataaagt gcttagtagc cagcacgtac    85740
aagcaccctg taatctgatg ttagtgcagc atcattaata acagaaaagg gaacccgaaa    85800
atttcagcaa aattgcatgt gcatagtggg tctggtatgt atattagtct aggcataata    85860
```

```
aatgttgaac gtctgtgaca taactattgt agtagtagag gggtaagctt aagaagtaag    85920
accaataaat agcccatcat ttctggcagt ttctagtatg gttttaacaa aagggaattt    85980
tgggaggaat aacattttta aaaagagccc actattatca ttctgcttta ttcctaactt    86040
tagtcctttt gagcctgtgt tatcaaatgg attttgagca tatgtgaatt agagaaatta    86100
atcactagga aaggattaga attaactttt ttggaaaagt tccttaaacc gtgaaaaggc    86160
agtaacacca ttctttgtgt gtgagattaa agagaaatta attttctttc tcttcttgtc    86220
tagacacaca aagtccaatt gtacgcatac agtcacaaaa tataggtgaa aaacgaaaac    86280
tgtgttaaca cggtgagaca gatgttttaa ccaatcaaca tcaacatgca actaggtgaa    86340
aataattaaa ttactccagt tttcatctgt cagttggatg tttgacattg tgtagacaca    86400
gcttataagt aaagataatt atgaaagatt attaaataaa gatctccctg acacggatta    86460
attgaaaagt atttagtatt ttttgtaagc acagttaaac tggagtggat ttccgatagc    86520
atgtgtctct cccccagctc aaaaagcttt cagcaatttg aatactgagt aataatctta    86580
ttgagggttt agaaattaca tatgtttgga ataaatactat ttagtagtat gaattatgcc    86640
tgtttgaata attaagaaat atcttttcct aacaaagaac attttcccctt atgtacataa    86700 tcttccaata catgaattt aattcaattc aatttgcaat ttagattctt gtcataattt    86760
gaacaaatac agattaccta gaatatatta aaaatcaaat tttcacatag tgcatatcat    86820
aagaattttt ttttagaaat tgtcagagat agaaacttta ggtacaacta gtccactgga    86880
atatttggcc atttaaaaca attagctcat tatttatttg tggagtcttg cttcctaaga    86940
tgttgtagtc ttatttgttg tcaattaata ttgctggttt gaacatggtt atttattttc    87000
cgtactattt tagccaagct attaattttt attatttatt tttttaattt tatttttttt    87060
atgtttgaga cagtcttgct ctgtcaccca ggctggagtg cagtggtatg atctctgctc    87120
actgcagcct ccacctccca ggttcaagtg attctcctgc ctcagcctgc cgagtacctg    87180
ggactatagg tgcccaccac cacacccagg taattttgt atttttagta gagatagggt    87240
ttcaccatgt tagccaggct caaactcctg acctcaggtg atcctcctgc cttggcctcc    87300
caaagtgctg ggattacagg tgtgagccac cgtgcctggc ctagccaagc catttaacct    87360
ttaaatattt agtgtcctca gctattaaaa ataagagtaa tatgattata catcctatga    87420
atttgtttta taattattgt gatttgggag taaacaacta tataagaaat aattataaaa    87480
gagataagat tagtgcatat taagactttg atgtcaggtt aattgaatgt taatcccatg    87540
actttatctt tcattgcaag attctttgcc tgagtgggt actggaagcc attgttgaga    87600
gtagatccga tcttactaga ctgttggctg gttctcctaa aaccaggctg ttttcataat    87660
gagttagttt aacattttgt ctttatgttt aagcacccct ttccttggtg cagtcacagc    87720
caaactgcaa acagaaatcg agaagttgtg agctccagat ttgagagcca cagagagttt    87780
gtgagatcaa aaacatccac tctcagtaaa taaatcagag ctacctaaat cacacagtca    87840
gcttaaaggc aagggaacca gagggaaaaa ctccaaagga gtgatctctt catgcaattg    87900
ctactggtaa aataaagcaa agatgagaca gtgtagtctc caccttatta tttcaatcta    87960
atattctata ttgaggttca gagaagcagg tccagatttc cacaaattag aaagtggtgg    88020
cttgctcttg taatcctagc acttggggag gtctaggtgg gtggattgct tgagcccagg    88080
agttaagacc agcctgggca acatgacaaa accctgtcct taccagaaaa aaaaaaaatt    88140
agctgggcat ggtggtgctg gcctgtagtc ccagctactt gaggggatga ggcgggagga    88200
tcacttgtgc ttgggagatc aaggctatgg tgagctgaga tcacagcagt gcactccagc    88260
```

```
ctgggtgaca cagtgagacc ctgtatctaa aaaagaaata aaagagaaac atttccttgt    88320
tagactttac gtatctgacg atgacttttg atggtgaagg taggcattgg tatgtggtct    88380
gtggtgtgtg tgtgtgtgtg tgtgtgtgtg tgtgtctgtg tgtgaatgct                88440
attgaaggaa acccgtgtagg agaaatatcc acaattcagt taagatcaaa catgttacaa   88500 tttctggga agtgccaagt tttacaacac ctaaactata tcctcttcct ctctgaaacc     88560
ccaaacatcc caaagtctcc ttcaagccag acatcctctt ggtctactgt gcatggtgtc    88620
tgcacggtcc tcaagtttgc ctcagggaaa gtgcctgttg ccatcagaaa gaagaatgc     88680 agcaggtact gatttatctc aggcaaagga gctcttgtgg tgggtttcaa caagatatga    88740
aaattgtagg ttcttgaaca ctcctttct tcttccttaa aatggatgtc tttagctaca     88800
ttctactctc ttctctgtct tttatgacat aatcagtcat tcactcaaca agggaacatc    88860
taatattcac ctaacatccc atttgcctgt cacatatgga ctttagcctc cagtcgggcc    88920
aatgacacta ttgatctcct aattccaatc tagactcttt gggtattttt ttctcttttc    88980
cattccttat tttctttaga ggcatttag ataactcatt taaaaattat tagtaaataa     89040
atcattattt gcaatcagca tagacaaggc cttgggtgag tctaagtgga tatctggaga    89100
gatctaaacc cgctgctgga aaagtgagtg ggaaagcccc attgatatgt gacccaacta    89160
aaccaacgtt tcatcaaaag cagtgtcttc agggactgct ttaggatttc agggaaaaga   89220
aaatggaggc aaatctgaaa gtggatgttt tctatggagg atccttgata gaaaagtttt    89280
cacccagcct tgagtgaata tgcagagcgt aaacacatgt ttgtgcagtg aggaaatgct    89340
gtctatgttt cctaaaatgg aagttcttgt ttattgcttc tttagctgca cggagacata    89400
aaagatgcaa aactgggag aagggagaga taaaactaag acaaaactgg aggagggtgc     89460
aatgatgttg taatttaaca tgcaaaatac tcacttgggt attttttaaa ttgttacatt    89520
gtgacattgg agggttcata aatggaattc catccaaact aattctaatg cctatctttt    89580
ctttttagca gactatagaa taaagttaaa tcaaagaaca tgaggtccca ttcttaccaa    89640
attcaaatat acttttatc acctggtgtt taaatcatta atacaaaagc tttcagtctc     89700
ctccaaattt ctattctagt aaagtacttt cataatttta tattgaaat gtactaatcc     89760 agataactag tatgaaatca agttataata ctattttgca tgtttctaaa atgtttacat    89820
ttaaaaatag agaagtaagc cttagggaga aaacttcagc tttcccaaga atattaaaat    89880
gttaacaaat tatttcattt tgagctaaaa tcagataata atgagaacaa atttccaccat  89940 cgcacattct acagggatct ttgcattta tactttttt tttgttttgc tttataagag      90000 gggatttttgg tatattgaat atcatactgg aaatttacct ggacggaaac gatagagtca   90060
acttagactt taatcacaga atgataacat cttccaagga gaaggagctt tgaggtcat    90120 ttcaccaaaa ctctttcacc atacagtatt ttcccgttca ttaacctttt ggcactctaa    90180
gcagagatga agtatcctcc cctgagttcc tagaagttga atttaatcac cattttacga    90240
gtctgccctc cccagtagat ggtaaaccct ttgaagaccc agagcatttt tgagataaaa    90300
gaatgaatca tatacttcag tacatggaac aaatgaataa acctgtagtg cctggccacc    90360 cagcttttttt tttgaacctg accgataaag acgtttacag cttttttaatt tcattatcag  90420 agaaagggtt ggcaatattt acctgagcac tctctacaaa cagagatgaa gaaatttgga   90480
atgtttcctt tctctcctaa tacatagctt tggaagtctt agaaaacatg ttggtatgtt   90540
ccttctaggt agtctttgc aagcatcctc ttcagtgtca agcatctatt ctcatgcatc    90600
```

```
acattacagg ttatgaatat acccagagtt tatgtgagat cttttttgt caaatgcatt    90660 aaacccttgg cttatatata ttgagctgga agccacaagt ttttgtaata tttaaaagt    90720 aatatatttt ataatatgcc ttagaaatta aaagaaaat agaatacctc cacttcctat    90780
gacaaaatgt cagcatatac agcaaggcaa agccatttgt tgctgaagct cagttttcc    90840 caccggatgc tgaatgcaca caatcacca gccaagccag gagtctgttt actgcacgtt    90900
tccctgaaat gccaagcccc tgaggtgtta caaggaggga aggcagcata catgtgtgat    90960
agaatggcca ataaactaat tggtttatag ttttgagaaa gcagctggtt gcctgttttt    91020
aaatgcagtg gtctataatt tgatagaatg cagaaggaat catttccaag aaattaatta    91080
aagttcatag gttggaaaat aatggagctc atcattaggg aaagcttatt ctaagactta    91140
ggataaaatg agcttcctct tgcatttcat tcaacttaag gttttgtagt tacttgtcat    91200
catcaaaaat atcatcagag tcatcgccat catcattatc taaatttgag tagctatgag    91260
aaggtattgt gaggtcctag ctttagagga atcaatttct ttgagatttg atattgttat    91320
tttaagactg cagagcatag gttagaatct gtgttttaaa aactttgaca ggccacgtca    91380
taggtagtaa agttttctct tggcatgagt tttgagttga cttgtgttat ggttgaattg    91440
tgtctctcaa aaaattgtt tatgtcttaa ctcctggtgc ctaggaattt cacctatt     91500 gaaatagga tttctgcaaa tgtaatcaag gtaagatgag ttcatactgt gttagggaag    91560
atcctaaacc caatataatt ggtgttcttg taagaagaga cacaacaaca aagacagaaa    91620
cagggagaac accatgtgag gatggaagca aacgttgaag tgattcatcc ctaagccagg    91680
gagcactgtt ggaaaccacc aggaaccaag aacaactcaa tccaagacag aagcatgaaa    91740 tggatttct ttaagagcct ctagaaggaa tcatcttaat tttggactct gccccagaac    91800
agtgagacaa tgcgttcttg tttcaagtca ccaagtttgt ggtaattagt tacaaagccc    91860
cagaaatgaa tgcagtctgg attaggtata ttctgcgtac atatgctgcc taagaatgcc    91920
agaagccaga agaggtgatg tctgcatttt tggttcctaa aatcctctct cagtacccac    91980
tgctctgtcc agggcaaagc tcccctgaca cattttagc ctttaggcta tgtcctatct    92040
cccctgctca ccagagaagt aggtcttgga ttccagtctc tcagggctgg cattttccaa    92100
gtgaaagaca ctgcctttgt gtaaatcctt ccccttgag tgtaggcagg acattggatt    92160
tgtttgtgtc tcatggaata tggtagagat aatggaacac cacttccatg attatgttac    92220
ataagcatat aaattgtgtc ttactagtat acccttttg ttgcattctt ggtttccatg    92280
ctttgatgaa agagcagcca tattaaacag gtgcatatgg caagaagctc agagctgcct    92340
ctgaaacaac agccagcaag gaacagaggc tttcagtcca gcagtccaca gggcattgaa    92400
tcctgccaac aaccacataa gtttggaagc gaaccttcct cagttattca gctttaaaat    92460 gagacccag ctcaggccaa caccttcatc agtgagagac ttcaaagcag tggaccctgc    92520
taaggttgtg cctggattcc tgatatgcag aaactcataa aataaataca ttacttgaaa    92580
ctgttaagtt ttggttattt gttacatagc agtcaataac taatgtggca taatatgcaa    92640
aacatggatt tcagctgagc acagtaatcc cagctccttg agaggctgag gtgggaggat    92700
tgcttgaggt caggaggtcg aggctgcagt gagctatgat agcaccattg caatcatagc    92760
tcatggcagc tatgagcctg ggagacagag caagaccttg tttctaaaaa agacatgga    92820 tttcaaattt ggccagattg taacccaact tctacataga tattatgtct ccattggagg    92880
gatatatatt ttgagacttt gcaatcctta attacttagg aacaattagt tagcaagtga    92940
aagaaattca ggttgaattc acttaaggga aaagaagaga ttttcgggtt ccatttacta    93000
```

```
gcggtgcatt tagtttcgaa aatggtgtcc tcaggtctaa tcattgctgt taggaatctg   93060
gcactttggc gccatgtttc ttctttggct ttcttagaga ggcttgtccg tgtgtggtgg   93120
taggcagtca acagcatttc ctagtatgtc atccttttct cagagaagca cattggccta   93180
gcaactatgc gtactggcct aattttagtt gcatgccaac caatgtctat atccagtgga   93240
aagagatact tgaattgata tggactgctt gggttatgta tactcttcag aaatgagaag   93300
agattgggta agtccagtag gcttagggta gatggaagta agattgctcc ccagaggaaa   93360
attgaatgct aggtaagcaa aactcattga tgtccattgt tgcttatatt acaaatagta   93420
ccaaacaaga aagaatggca tggctgcttc atggaagagg agatgaactt ggggcaaaac   93480
cttacctagg atatttcctt ttttcagcta aaaagaggaa cttggacatt cagaaatgag   93540
aaaacttgta tatcagttgc tgttgttgtt ggtttgtaaa cagctgtagc tcttagtgac   93600
atagagagat aaagtgacag gaacagatga ggatatttct attaggatgt tatccaggca   93660
gttctatgtt gggagtcacc ctcctgggac actcctgggt ctggaagctg tcagctggtg   93720
gcaaatcaga gatagtctga gatttaatgc cagatgggaa acgtgacctc aaatgaatga   93780
ggctgtttag gagtgggcgc aacatgctgt gcttgccatc tcttttaaga gttctaactg   93840
aaaggttagg tttactgaag gataagccaa tttggggagc tgatctggtg aacatgaatt   93900
tggccaaact tcagcctaag cgtttagcag ggtgaaagtt tgggaagagt ttcgttgtag   93960
aacattaggc aaatggctga caaaagagct tccagttctc tcacaaggaa ttcttcaaaa   94020
agcaaaggag gtccttctca gtcagcctgc tcttttctgct cagtagactt ctttgtgaga   94080
ctatgctgtg agtgagttct caggctggtg atataacctg gtcttcaatt cttgtgcagc   94140
tctgtaagtc cacgtaggca ccactaaata tccttacgac attaagtgtc attggattgt   94200
ttgctaacat ttgcttccat atgggcccca ggcattagca aacatgtagt ttattcattt   94260
atttattcac tcagtgaata tttattgaac ttattctaat tgtcaggcca ctttgctaaa   94320
tgttgttcca tcactttcct tgcagaacat acaggggaaa atgcacaact aactggaatc   94380
atcatttagt gtaatccatg caatgatgca acaagttggg gagatgtgag aacatctggg   94440
agaagcatgt gtcccagact gagagggtga aaatgcacta aggagaaatt tgaagaatca   94500
gtaactgacc aaaattgctgg gaggagagtc atttcagaca gacagaggag cacgttcaag   94560
gctgaagtcc acagcctgac attaatatcg attctcttag ctaagttttg ttaaagaaac   94620
caaatgacag tgaatttgaa gtcctgcact cagccaaccg tatgaagtgt agtcactgta   94680
tggtcagtta attacagggc agcatccttc agtcatcagt cgagctagag agaatattga   94740
cagatgtgct cttatgaaag ctgagaagct caaccaggac aagtatttag ctaaaagggg   94800
gtctgacctc cttttagaga tgggaagcaa gggtggacaa cataacctgt agactaaatc   94860
tatcacactg ctgttttttgt gaagggttta atggaacaca aataagccct tttatttatg   94920
tattgtctat gtctgctttc acactacaaa gacgaagttg agtagttgca aaagagacca   94980
tatggcctgc aaagtctaca atatgtacta tcttaccctt tattttaaaa agttttctga   95040
cccctgatgt aaaggaccaa cttcatgaag tcgcatgtgg attttctagt taccatatag   95100
acatgaatgg aagagtacag aagttccatg tcagacagca attgttttca aacttgctat   95160
gaattttttc caaatgcaga ttcctgggct ccatccaggc ttccagtgac tcaaaatctg   95220
ggtatagatt ccaacaattt gccttttagt gaccttagag gtgatattga tggcaaaaat   95280
tttatatatg tacatattca tgaaacagaa aattggacgt gaaatatttt taatccacat   95340
```

```
ataaacagat actcctttct gtcattaaaa accaattagg aaaaaatgat aaaagcctga  95400
ttttaaaacc atggtccata tggcttatgc aagataattt tctgaagtga ccttcaagat  95460
gaaatagttg caaagtatat ctgtgttcag ttaaattagg aggtgtgtgt gcaacaagga  95520
attattagcc gtagatcttt aaaatcaaat caatgtaaac aaaacactgt cagcccagtg  95580
gccaaagaac acaatcaatc aaaatatgaa taaatataca caattataca ctactactac  95640
tagatgatga tgatgatggt gatgatgatg gttatgatgg tgatgatgag gatggtgatg  95700
gtgatagtga tgatggtgat aatgatgatg gtggttatcg tgatgacgat ggtgatgatg  95760
gtgatggtga tggttatgat gatgatagca atgaagataa caattattgt gatgataatt  95820
tatggcgata ataatgattg tggtgatggt ctgtttctat gcgtcaatct cagttgctcc  95880
cccagactcc atacaaacag aaccaccttg agatgtttc aaacttacca tgttcgaaac  95940
tcagctgctg cttttgacac aatgaatgcc ctcctgtctc cattttacc atcttaggag  96000 aactcacacc atccctcat cactcagtga gccaagtgtg ctagctgctg atccacatgt  96060
ctgaatggcc gccttgagga attgacatta ccttggggac ctacagggag caatgatgct  96120
ggactggggc aaggatgaat aaaggaggga taagtccaag ttgttggggg aagacagggc  96180
agccaactct atctggagct ctcagatggg tttagcggtt gtggagatat ttccaatggc  96240
attttgaaga cgtggaagaa tgttattagg catagcagag attcttaact aagagcaatt  96300
ttggccccac tgtaagggac atttgacaat gtctagagat attgttggtt gtcacagctg  96360
gggaggtgct actgacatgg agtaggtggt gaccagagat gctgctgaac atggtaaaat  96420
gcagaagaac gactcacaca gcagagaatt atctagtcca aaatatcagt agttctgata  96480
ttgagaaact tggctctgta ttgtgcatgt gtaatcgttt tttacttact gattctagat  96540
tcagctggca agggggtgtc agcaatgtct ggagatattt tggattatcc catctgggca  96600
gtgtgtgctc ctgacatcta gaaggcagag gatgctgcta acatcctac aatgcacagt  96660 acagccctca caacaaacat aatcatccag cccccaaatg cccacagtgc tgatgttgtg  96720
aaaccctgct ctaagtcaaa gcattgtctt actcaatttt taattcctag tgtatatcag  96780
tggttctcaa ctttggggag gggacaggtt tgcttccagt gtacatttgg caatgtggga  96840
agacattttt gtttgttgtg agtatggagt gtgttactgg gaatggaggc aagggatgcc  96900
actagacatc ttaacagtgc ataggacagc ctccacacct cagaatgatc tggcccctaa  96960
tgtgaacagt actgaggtag agaaaacatg aggtagactg tagaagccta tagaagaaga  97020
gaatctgaga aaattgttgt gcttgggaa cactgaagaa tgtggagcaa ttgaacaaat  97080
gcttgtgcag acagattggc accaaattgc aatggagcac caatgggaca gtgaaaaggg  97140
acaagtccta caatgcacag ttcttgacca tccccaaagt gctccaaagc tacagaagtt  97200
ggtgtgcatg tattatctca ttgatcctat ttgggaatta tcatgttgac agctggagtc  97260
ccatgaagga acatttttaa gcagcaaagt gacaagctct gatttgcctt ttgagattaa  97320
tgactcagag actgccagtt atttgttaac ttgcttgatt cagcctaagc agacatctag  97380
agggtgtaat ttgatttatt ctgcagaggg gtgattggcc cctacattat cttggcacac  97440
tgcctgaatt tctgaacacc aaagactat ttatttagtg tatggccatc tcattccaa  97500 gagtcaccaa agaagtgaga atggattaga tagggaacaa gctgaccatt ggattagttt  97560
atcagatgat tagcatgcca tgctaattta tcaagacatg gaacatttaa agaagggag  97620 agtaacatat acagggaaga taggagatct ttgtcccaat tatttctttt tttttaatgc  97680
atgaatagtc ttttggtaaa tatagtttat gtttgtttct gctttctaag ttaggctgca  97740
```

```
aaatattatt tatcggtggt attctttgaa attgattggc atggcaagac tgtaaaagag    97800
tatccatagg tgtatttaaa aataaaagat cgtcttttca tctttgcaga aaacatgta    97860
tttactattg cttggaatag aaagcagaat tttgctgtag ccattaggaa gtgacaaaca    97920
ctacgccata attatagtga gaagaaagca tcaaaaagaa atgttttggt ttttttata     97980
tacagttggc acaaaaatgt ccacatatat gaatactcta agaatgcac cataaaaaga     98040
accttccacc actattaaca ggattaatcc gtgctcatta ccatgggatt ggggatacat    98100
ttttacatgt tcttgattag attcaagagc caaagaataa ggcctaattg atgaaagtgg    98160
gctctaattt tgtgctttta aaataatggc ctctggccaa atatgggcaa agaaacagc     98220
acttgatttg ttactttaca tttgtttctt gcatcctgct cgaaaataga gatgatttac    98280
agttttaata tattttcat gcacaattaa catcattgtt gccagtttta tagaagaggc     98340
aggaaagtgg gccttctatg atttattgtg agtgcatgaa acagaagtaa tgctactagc    98400
aacagagttt tagtaggaaa aagttaaagc acacagtctt aaaaaggaaa ggttggtgtc    98460
aaaattatgt ttgctttagg taagctttat acctccatgg atggcttttt ttatagtaac    98520
aacaacagta actgtattta cattggggcc ttttctctgt ttcagaggct ttcatgtgga    98580
gtgccaaaat ggtaaaatat ataacattgt tatatgaagg agtgagggaa aatccaatca    98640
agattggcat ttttttaaaaa agaaaaggag catggggaat attttaaaga tttgggccaa    98700
agcctcgtgg ctgatgcctg taatcccagt gttttgagag gctgaggaag gagaatcact    98760
tgatccagga gtttgagacc agcctgggca acatagcgag acctccacct ctataaaaaa    98820
gactaaaaag ttagctgagt gtgatggcac gtacctgtag tctcagttac taggaaggct    98880
gaggtgggag gatagcttga gcccaggagg gccaggcttc agtgagctgt aatcacatca    98940
ctgcactcca gcctgggcaa cagagcaaga cgctgtgtct caaagaaaaa aaaaaaaaa    99000
agatttggta tctttctttc ccccacagtt tgcatataca ttgaaaactg tgcatttaag    99060
ccaaaatagt ttttttttt aaacatttca ctataaaaaa ggagtctggc tttcacatgg    99120
gtacatgatt ttgctttggc ttcttcaatt cccacctgcc ctgttgtgag acccatgaag    99180
taagcaaagc attcttttttg ccacggaaat gaaactccta aacatattgt ttattgtcac    99240
ataatggaaa ggagaaacgt ttcaaaaata aggatacatg aagcccttat tgaaaagcaa    99300
tcatacattg gtgaatttaa tgttttggag caaaaactgt tatgttggat acctattagt    99360
cttttagct agtgaaatat gtacaaggca aaatcaagca tcaatagaag ggtctaacta    99420
agcttgtttc tcatatggtt tctctgccag ctcacacctc aagggtgcct cctgcctgca    99480
atgtgtactc tctggtccac acactgattt ccccttttct gtttcatggg gtgacttgct    99540
gaccttctct gtgcatggct agtagtactc tattgactgg caagggttgt gtcttccact    99600
tgggtcttcc aagctgctga agaaagcaac acagaaagta tagctgacaa taattatctg    99660
tcaaatgtat gtgaatcaca gtgtggatgg tcgacctgtt gtttcttttt tctctttgaa    99720
aggaagattt cagttttctc tgcagccatg gtactttata aattatttcc tcttccatct    99780
cttaaaagtc actgttattt accacccat tagctgtgga tggggtgaaa tgcccactca    99840
tgcagcacag gaggatacac agattgtcac acatctttc aggagaccac acagcagtgg     99900
gtagtgtagt attaaataaa tgcctgaaat atgagctggg aatgcattgc acttcaagga    99960
attttatcca taggatgtaa ctgggaaagt gcagaagaat gcatatatat atagttgttc   100020
attgttacat gtttatgat agcaaaaaaa aattaaaaaa tattcaactt tcattttaga   100080
```

-continued

```
cacggatttg caggtttgct acatgggaat actgtgtgat gctgaagttt ggggtataga   100140
tcccattacc caggtagcga acatggtacc caacaggtag tttttcaacc cacatccccc   100200
tgtcttcctc cccttctagt agtccctagt gtggagtgtt cccatattta tgtccatgtg   100260
tactcagtgt ttagccccca cttataagcg agaacatgtg atattttgtt ttgttttcta   100320
ttcctccatt aagtaaccaa aattttaac aatgtagaat ccattacata attagagata    100380
caatacaagc attgaatacc agctgttaaa atggcattac aggataatat ttagtgtat   100440
ggaggaatat tcagagtgta ttatatacaa acattttcat catatcgttt tttactagag   100500
tggactgtca ttttcttgtg ggctcccttg tattatttac tctattgcat ctcagttttg   100560
ttgcatatta tgtaaaatag aagataatga tagcttggcg cattctctgc tgagactatt   100620
tacagtggtg taaaaagatg ttgccagggg tgtgtgcctc agtctgtccc agccttcgta   100680
gggcccatg tttcaactcc ctaatgaccc attgaagaca cacgggcaca caggggagaa    100740
tgctctggtt taaacagtca accataagcc agacacagtg gtgcaacctg tgttgcacct   100800
tgtggtagcc tcttgctacc caagaggctg agacagagga tctcttgagg tcaggagttc   100860
aagaccagcc tgggcaacat agcaaaactc ccattctaaa aaattaaagc aaactcaacc   100920
attttgagtt ttacatgttg taaatatctt ctcccactgg cacccaccca tcattcctgg   100980
ttttgattga aacaaaacca ttagttttaa tgtagcaaaa tgccatcaac atatttttct   101040
ttctaacggt ttctcctacg tagtgcctgt taaagaaatc ctgttctacc ccaacatcac   101100
aaaaacattt tcctataagt atcagaattt cattgttcat acagacagtt tttaatccat   101160
gcagagttta ttttttatata tgaaatgagg tgggaatctc atgttatttt ttccccaat   101220
agggggaacat tgctttgaca catgaaggaa gcaatgtatt ctttttttc ttttgagaca   101280
gagtcttgct ctgtagccca ggctggagtg caatggtgca gcctcagctc actgcaacct   101340
ctccctctca ggttcaagcg attctcctcc ctcagcctcc caagtagctg ggattacagg   101400
cacacgccac cacgcccagc taattttgt aattttagta gagatgggt ttcaccatgt    101460
tggccaggct ggcctcgaac tgctgacctt gtgatccacc ctcggcctcc caaagtactg   101520
ggattacagg catgaaccac tgtgcccagc tacaatgtat tcttcccaa tgatttgtgg    101580
tgtcagccag gaccttgata gggataaatg gcatgcaact tgagaaatgt aattaagatg   101640
gggacaggat agtggagtcc ttatgtgaag ttgctgatgc ccgctgaggt tgaactggac   101700
ctacctacca gggagggaac tggaggtcat atatacaggc cttactcgcc ttctgccctc   101760
cggattacct gctagtgtct tccttggctg aaacccagga gcagccagaa ggcaagagtg   101820
aacctgttta tttaccttcc acaccagaga ggagtggaga tgaggaaaag tcttgaaggg   101880
gacagactcc tccccccaca aaatagtaca agcttttaaa attcatcata tatacatcag   101940
ccaatccaag ggctttatat ttggtcttgt tgatttcctg atccattcct gcaagattaa   102000
agtatgactc aaatagtaca aatgcccata tattttcat cttcaacatt ctcgttgctt    102060
tttgtagaat ttattctttc atatacaata tggaatcaat gtatcaaaat ctgcaacatt   102120
cttctgtctt tgctgggaat tgtatttatt gaaatgttgg tttgaggaaa aataaacatc   102180
ttccaagctc atgttatctc atttgtaaac tggcatagtt cattacttgt tgagatctaa   102240
tcatagcttt attaaagact ttgagcatta tgtgttaatt gattattatt attattttgc   102300
aaatgatatc ttcaattaca ttttctactc ctggtataaa agaatgtcga tcttttttat   102360
acattgatta tatgttcagc catcttttt gattccctat tatttctagt agcttttctg    102420
ttaaattaca tggtttccat aaaaatggtg acattatgta caaataatga ccattttctc   102480
```

-continued

```
tctttccttt caatacttgt aattttcatt tcctttataa cttgtaccat tgtatggccc   102540
actgacgtcc agtgcgagga tgaatactgt tggtacaaac ttttgttccc attcatgatt   102600
ttacaggaaa tgagtctaac atcttttttg taaatgcagc gttgaggaga gattttaaag   102660
catgcagtca ttatcagata atatgaatta cttgcaattc ccagtttttt ctaagttttt   102720
aaaaaatgtt ttcttttgtt cataaatgtt gattatgacc aaataatcaa ctggcatttc   102780
tacagctggt tatatgattc ttctcttata attaatgtgc tctgaaaatt aatatatttt   102840
taaatatata ttcaatttcg ggaataacac attttaatc ttaaaagaaa cattttaaa    102900 atggccatta ttctattata gtggaatata ttgtatatga aaaatagcta ctattctact   102960
aagtttggtt tgtaaatatt ccacttaggt tgtctacatc taccttcata aatgaatttg   103020
atttataatt ttctgatgtt atacactcta tactttgat atgaatgtta aactgtccat    103080
acaaaaggat ttgggtagct ttctttaatt gtatattttc tgaagaaaac ttaaataagt   103140
agaattacta aaattttgt gaaaattatc ttgggtggtg agtttttatg tgggagattt    103200
ttagtgattc tttcattact acttatagct tttagtttat tcatttcttt gcgtaaagtt   103260
gctttgtttg ttttttttcct caaatatttc aatttctttt tttaatacca gggcttatac   103320
tattaaaata gtattttgta tttttttataa ctttgtttat ttgttatttt aaaaatgatt   103380 ttcctctttta aagactattt gttctcatta tttgttgtat attatttgtt gtatattgtt   103440
gtatattatt tgtttcatta tttgttgtat atgttactct tccttggtca gtcttgccag   103500
aagtttgttt atattattaa gcttttcgat aaactagctt tcattttggt aattagctca   103560 actgttttt ctctgtttcg ctaatttctg ctcttacctt gatcatttcc tattttcaga    103620
tttatttgga tttattctgt tttctcttct tcctgtttct tgacttgcct ccatggctcg   103680
tttatttcca attcttcttg ttaccttgta aagatatttg aagttttaat tatccctttt    103740
aagcacttct tcagtcccat ctgacaaatt tcacatgtg acatttgaac tatcactgga    103800
ctctgactgt tttgtgttta tacggtagca taaaggcaca tgcacacata tacatacaca   103860
catagatgtg tgtgtgtata tgtttagtgt tctatcatta ttttgaatgc ttttactat    103920 tgatttctaa ttctgttgac cgatagaata tagtgctgaa tgctgctgtt tctttaaagt   103980 actcttatg aaaggcagat tttgtaaacg ttcggtgtgt gcttgaaagc tatggacaca    104040
tttacacata catagacata ttcacaaata caaatacaga tatacgtgta tatgtgagaa   104100
tgtgtgtttt gaggagcata ggtttccata gatacccacc agatcacatg tatgggttac   104160
ttcagtcttc tatatcttat ttgttttggt gggtggggct agggacagag tctcgctctg   104220
ttgctcaggc tggagtgcag tggcctgatc tcggctcact gcaacctcgg cattctggct   104280
tcaagtggtt ctcctgcctc agccttccaa gtagctggga tcacaggtgc acaccaccac   104340
gcccagctaa cttttgtatt tttagtagag acgcggtttc actttgttgg ccaggctggt   104400
ctccaactcc tggcctcaag tgatccacca gcctcggcct cccaaagtgc tgggattaca   104460
ggcgtgggcc actgcaactg gcctatatcc tcaattacat tttatttcct aagtttatca   104520
ctccaagaat gttgtgtttt attctactgt aacatttat cttttcttat ctgtccttta    104580
tcttatatat ttaatgtata tggatatact atgttatata tatgtagtat gtatatataa   104640
aatgtactta tataccttt acatgttttg aagctgtatt attaggatgt tacatgaaag    104700
tgtcagttac acctttttaa tcttccattc cttttctagt atttattatc catttttgac   104760
atttacaatt tttgtttgat actaaatttg cttcctgtga tatttttca tttatatttt    104820
```

```
gttttatatt taaaatttttt agtgtcttca ttttcaagtt tatgtatcca tttatttttaa   104880 atatatcttt tcaacaatat gttgctaaaa gtattttaat caatatttta tctttattct   104940
aattttattt ctgcagttat cattattata gatttcactt ctgacatttt attttatatt   105000
ttatatttat caatcatgct ttttaaattt tacctttttt ttttttttgct ttacctgact   105060 tccattatat aattttaaaa gtttctttta ctgaccttat tattatattt ttctttcttc   105120 tgttttttt tccttatagt tgggattcat caaatttccc tcttcccatt ttatgctgca   105180
cttatatttt aatgaagatg tatctagtct tattagctat caaacatttc agtatccata   105240
attttcctca aaacaagata ttgatttagc attttctcta ctcttcggca tctctctctc   105300
tcaatcaccc cacactgtgt tagattctaa gagaatctgg gctctagatc atgttaaaaa   105360
tttgatttta gatcattgtt tcttcggaat aattttttgt cgttacctgt attatgttgc   105420
tgtgttctgg gttcctctcc ttgcagaaat atattgtgtc aagatttctg tgatgtaagt   105480
ggatttggat ttaagctatc atttaaatga cagtttcact ggacataaaa tccaggctga   105540 ttttcttttcc cttgtacttg ctgggggtga aagccactg cattttgtat cctacgttgc   105600
tttgcaatta gcctggtttt cattcctttg cacatcgcct gcttttctc cttgaaaaaa   105660 ttagacatat tttgtttaca tttgaggtac tcaaaaattg gaatttgttt ttgctttgtt   105720
ctgttttaaa tcaacgtatt atttactttg tgagtacttt cacttttaag ccttttttt   105780 tctttcattc tgggaaattc tcagcctttc tgtctaatgt agttcttcct agtcttttc   105840 tctttgttct ctttctgggt catttttttt tataggactg gtaacacttc tatttccatc   105900
ttccatactt tagcatttgg aggatgtttt tccaccattt ttcatcccag atccattttg   105960
ggaaaatgta tctctgtctt ttggctccta tgtgcattgt ttgtgggtat ccttccattt   106020
cagtctgttc tttgtgctct ccagttcaac aatttcattt cttctcccg gtatctcgtg   106080 tgacttcctt tgaaaccctt tgttccaact ttatatcgct atcattgtct ctctgtccat   106140
tggagggatc tgcttctttt gaatcccagt ttgtttactt gggtcatttt attattatta   106200
ttttttaaat aggatgttcc ttttctttta agtgctttgc ttttgactg gctcttaaaa   106260 atttcttggg agttctttta ttttcttgag gccggtagag gtcttggaag gtaccaagtg   106320
tccaatgggc aatcaaaagc ccacctctct gcctggcgcg gtggctcaca cctgtaatcc   106380
cagcactttg ggaggccgag gcaggtggat catctgaaga gttcaagacc agcctgacca   106440
atatggtgaa accccatctc tactaaaaat acaaaaatta cctgggcatg gaggcatgtg   106500
cctgtagtcc cagctacttg ggaagctgag gcaggagaat cacttgaacc cgggaggcag   106560
aggttgcagt gagcagagat tgtgccactg cactccagcc taggtgacag agtgtgactg   106620
catctcaaga aaaaaataaa aaacaaaaaa taaaggccca cctctcgatt tcatgcctct   106680
gggtaaattg gagggaaaag agggtccctc tgtgaagagc ccttggaact cgagttctaa   106740
tttctaaacc aagaacttta tattctttcc tccctcccta tcacttccat ccactggctg   106800
gctcttatct gaaaactgtc gtgtgcagtt ataaatactc aacacttagg gaaggagaag   106860
gaattctgag agatttcgcc agcctgattc ttttcattgc cataaaattc cactgcttta   106920 ccagaaaatcc ttggaatgtg ctttcctag ctttgcactg tgaccttctt cattcggaat   106980
aacgaagatg agaaaagcat tgatccgccc agacagtgag gagcgaagag caatacctag   107040
gtggaaagct ctatctcccc tgactgtcct gtgaaatgca cctgagtctc agaggactcc   107100
actgccatct gtctgtccag gaatttccca ttttgtatgg cgacttcaaa gtaggtaaat   107160
actttgatta aaggaataga gaacagaatt tgggtagctt gttcaaaaga tggcatggaa   107220
```

```
aattctgtga ctggagtagt tgtgaagcat cactcttccc gtaagaataa aggaggcatt 107280
tgccagatgt ctgaaaacac acagacacac acacaaagga attacttctg gctgcaagaa 107340
tattctctct cagcatcttc ctgcatctcc atgggcaaac agacccacaa cagcctggga 107400 tttttaatt gccaacagtt ttcattgcat gagagcctga catgtctgtt gcatgatagg 107460
gtgtgttttt attttggct tcctattggt ttcaacatat ccctccttcc atgtcataat 107520
gacaattaca aagacctgag ttgaacctag aacgcttttt ttttgtcaga cacaacaatg 107580
cagtggatgt tagtcatagg gtaattcaaa cagagataat tttgtatatt ctagaatatt 107640
atgttttcaa acgtaggttt tgatgtacca taagatttct tctgccattg aggcgatata 107700
tatgtgtgtg tgtgtgtgtg tgtgtgtgtg tgtatgtata tatgtgtg tattttaaat 107760 ttaaattaga tattttttag aggccttagc ccttaagcag aattccctcc taatttaatg 107820
attttggacg aagctcattg tgaatcattt aaaaacacat tcatgcttct tcaaacagag 107880
gtaacaaagg atacagcacc ttgacttgtt gactaagtgc tgtcatggta gatgttatttt 107940 agcatagaag atgcctgcag ggtcagttct actctctaaa gtttcttgag gctgtgttaa 108000
atgaaatcaa acacctgtgg attttttatt cttgttcacg cttttatac ctctcctttc 108060 ttctccctgg gcaacctgct ttcacactag tgcctacctc tgttttccct tcagaatgtg 108120
atctatgcta cacaatctga ttaacaagct caacagagtt ctactggaca tagaataaag 108180
aaaccagtat agttttctct ctagggacaa ggcagtgagg aagccagttt gaatacaggt 108240
tcttgctctt gtaagcattg acattcagca ggttccttac tttctgaaca ctgcagttat 108300
atgatgggca gacagggact aagaataaca cctacctcaa cggggctgtt gtgaggatta 108360
ctgagataat ttatgtaaat ccctagcaca atgcctgact catgcgagat ctttaattca 108420
tggtagcagt tactaatttc atttatcata atgagctgcc tgagctacca aggagctctg 108480
ccactcccag tactgttcta cagttctttta attcaacaaa gaaattttttc tttagttcca 108540 aataagtgcc aggcatcagg ctaggtgctg ggtgtatgat gatgatcaaa acagtgttcg 108600 tatggggta gtcatcattt tgtcgatggg ccatttttta tgatgtccct cttcattata 108660
ggtcttgatt cttgcctctg ttttgtatac atatgtgttg cggcaggggc ttgctataaa 108720
aatcagaatt gcccaggctg agcgcagtgg tgcaatcatg gctcattgca gcttcgggct 108780
tcagtgatcc tcccacctca gccttcttag tagctgggat tacaggcaca ctccaccaca 108840
cctgcctctg ttttgtgtag ctgtgattac gtagcaattt tctgaatcag tgacaagatg 108900
caatgcatat tttttcagt aggttaatta atttatctaa tctacatttg gagctatttt 108960
ttggagtgtt agtcatcata ataaatatgg tggcactgtc aatagtaata taaatataat 109020
ggtaccttaa ttccataata caaagatcac gtcttcatga ctgatgggcc atttcaaacc 109080
cataggtaca tttgctcgct ctgtaaagta tacaaaagta agaattctgg acatctttaa 109140
aagttgtaaa ttttttacatg aaaacttaca ttcacaccat cttttgaata ttgaaaagat 109200
ttgggaacat ggggcctata tgtgactgtg gatgaggtgt ggctgttccc tttagacaca 109260
gcactcactt tgccatagtc acactcccca ccgctcccta ttgtgtctcc aaccccagg 109320 ctgttgtctg tttcttttcc aacgttatta cccactcata gatggtcaac cttatgatca 109380
ttgttacttt ctttttcctca gaatctttct agtatttgtg atttttttca tgtggttatt 109440
ttgagctttt tgcattaaga atttgggatc acatactcaa aagtttagta tttaccagtt 109500
tgtattattg agcacttcag aaatttattt ctgttgctgt tatcaactca taaaatatct 109560
```

```
gtttaattat ccaactaaag actagatagg atagtgattc ctattttctc caagctcata  109620
tctgtgaact ccttgattgc ccaacatagg cattcaatca ttcattcaac aaatacccat  109680
tgaggaccta ctatgatctg ggcactttc taggtgctga taattgtagt gaaatagtag  109740
accacagtgg acagtgttc tttatggaat ttaagtgaat aaggaagtta ttttggagta  109800
tttcagatcg tgattcctgc tacgaagaaa aataattcag aataaagtag ataaggaata  109860
ataggaatgg acccacacag ttattatttt tattgctgtg gtcatactga tatctgaagc  109920
aagtaagaga agagtttcct atgaggatgg aatagcatgt gcaaagaccc tggagttgta  109980
gaatccttga tgcgtccaag gaatatggag aagaccagtt gggctagagt tgacaaaatg  110040
agggtgaagt gggggtataa aatagagag gtgctggaca gtaggccgtt gagagggctt  110100
tagcttttcc gtgatgaata ttggaaccca caatgtaatt ttgagcatga aaatgagagc  110160
cttgatttac atttttatca gatcaccctg agttctggtt ggagaatgag ctctaaggat  110220
ctgtgggtat atttagggag atacttaggt ggcctttgca ataatacgct caagggagga  110280
tgctggcttc accagagagc tgatagataa gccatggcca gattctggga atattttaaa  110340
ggaagatcca acaaatcgat tattcctaga atgcagaatg aatgagaaag agacaactta  110400
tggccaaccc caattccttt ggccgccgta actggaagaa ttgcgttgcc atgtgctgac  110460
aacagggaga ttgtgagagg agcacttag ggtgagggaa ttaggagact gcttttgttt  110520
aagttaagaa caaccaagga gagatagatg tcttagagac agctgggtac agtagtgtgg  110580
acatgaagag agaggtctac gctggagata caaggtcagg agacatgagc atgtagatga  110640
tatttacagt tgtgagactg aatcgcattt ccaacacaat gaatgtagat agagaggaga  110700
agtaagtgta ctagaagaaa aagaaggatg aagaggagga gagagagaag acagtgagga  110760
agaggaaaga agcagcgtgc atgtgtgcac ttgtatgaga aagagagaga gagagggaga  110820
aagtggaaga tatagataga aggagagaga gagagactgg gggaagaatt acatccaccc  110880
aaaacccaaa ttttaatgac ttacaatatg aaagcttcat ttttttttc tcttatgttg  110940 cacctcactg atggactatc atcagcccca cttctcttcc aagtctttat tccagaatcc  111000
aggctggagg ccatgcctga actgaggaaa tggtgttcat gtacaacagt tctttcagct  111060
tctgctcaga tgtggcattg cacatccact catatgcgat tgtccaaagc attttctat  111120 tctctgggag atacttcaag gggcacaaca gtggctgggg attgaggggg ctgtaatag  111180 actttcagga aaaggatca gctgtgctaa atgctgctga tgagtgcagt aacacaagga  111240
tgagtaactt gagtagcttg tagagaggta taggccattt gtttcatgcc caggaacaag  111300
gcaggaccag gaatcctggt tgagatgctg cagtttgggc tagttggagg tggggcaag  111360 ttttctctc actgctggga cttactcagg ttaacagatg ggacgttgtg gaggagctgg  111420
agacggagga gaaagtgtag aagagttaac taggagatgg attgagagtg tttgatgtga  111480
gaggcagtag agcatgcatt gaacctaggc tgtatggttg gagggtttt ttccagccat  111540 gtcctgtctg ctcaggttca gaggaggtag gaggtagatt gaaccagcca caggtgatgc  111600
tccatgagta aagaagggtt gagagtcagg aattgaggag tccaaggcat taactgaaaa  111660
gatggttcat ggaatttaac aaagatgcgg acaaatatga ggagaggagg cagtcaaggg  111720
agagagaaag agtagggttg ggatacaggg aatgaaagtg agctccttaa gatgaatggc  111780
taatcccaca aaactggcca attcccataa ggtgaacggc taatcccatt agtgcattgt  111840
tgacatgaaa atgtcctcac caaataatga agaaaaattt gatttcctta tgtggaaaaa  111900
gcaggaccaa aagcaatcaa ccaaaatcgt atctactacc tggcagtcca ttagaacaca  111960
```

```
ctaaacacac acataaagag aaaaatgaag tatgttaatt gtgaaacttg tatctccaaa  112020
aactggaaag cttcttggca cttaaaagca cttcttggca cttgggatta cttgcctgta  112080
atcccagcac tttgggaggc tgagacgggc ggatcacttg aggtcaggag ttccagacca  112140
gcctggccaa catggtgaaa ccctgtctct agtgaaaata taaaaattag ccgggcatgg  112200
tggcgcatgc ctatagttcc agctactcgg gaggctgagg cagaagaatc acttgaacct  112260
gggaggcggg ggctgaggta gaagaatcac ttgaacctgg gaggcggggg ctgaggccga  112320
agaatcactt gaacctggga ggcggggggct gaggcagaag aatcacttga acctgggagg  112380
cgggggctgc agtgaactga aatcgtgcca ttgcactcca gcctgggcga cagagtgaga  112440
cgctgtctca aaaaaaaaa aaaaaaaaa aaaaaaaaa aaaaaaaaa agaaagaaag  112500
gttcaatacc tacttgttga atgaaagtgg acgtgtgaat tcaaagtttc cgctctttca  112560
cagtgttttt ttttttttt ttttttttt ttgacagagt ctcggtctgt cgcccaggct  112620
ggagtgcagt ggcacaatct tggctcactg caaactctgc ctcccgggtt cacgccattc  112680
tcctgcctta gcctcccgag tagctgggac tgcaggcgcc caccaccacg cctggctaat  112740
ttttttgtatt ttgagtagag acggggtttc accgtgttag ccaggatggt ctccatctcc  112800
tgacctcctg atgcacccac cttggcctcc caaagtgctg ggattacaga catgagccac  112860
cgcgcccagc ctcattcagt tctttattac atttgtaaag gtaactctaa ctccgtgaga  112920
gcactttctc gctcacctct taattcttga gcaaacagag aagctgtgca tgataaagct  112980
ggagaattgg gtggtgtctt cctattaagc ttacaggaaa gcactgggca tttggaacag  113040
atgttgcatc ttgagagcca cagagtcagg tgtgcacgtt aaaacgatgc ttctaattgt  113100
tgcatagaga cagaagacaa tcacaaagat tctgccttga cctccttacc tctccagttc  113160
taaaaacatt tctcccacta cagaaagcat ccatctatgt gttttttgcc tccacgtggt  113220
cctattcctg aaatgctcct tccaagtctg tacttttcca agagctacta tttctggatc  113280
ttttgcagtt gcttcagcaa gaatcagttc tggcttcctt ggttctacca tgccaacttt  113340
accttctcgt ccctcagtgg gatgctaggg cttgggttaa ttcatctctc tccttcaagg  113400
cgacatgaag cccctgagaa cagggggcata ttttgtgccca gccattacct acaatgatac  113460
aggagtcctg taatattcgt tagagaaatg tgtccactga acatgaattt cctatcctgt  113520
tccttctaaa aaggatgcat gagttatcct atattcccaa ggcacaacat gactttgttc  113580
tgatatgtgc caccgtgatc ctgtagaatt tgttttgttt ccagtcccta agaataaatg  113640
tctcttaaag tattgtagtc attcactcta cattttatg agttattact ggcccaccta  113700
caaccatatt tcctccgaaa ttcatccatc ctcctggaat tacctgattc tgaattatta  113760
agtggttctc ttggccattt gctcaaaaaa agagcacact tattccaaca cacaggcatt  113820
gtttctaaat tattattgtt ttttcttcct agaaaccatt tagagatgaa gatccacttt  113880
agaacatgaa cccatttagt ttagactata acaattgaag atatggtgac tactgtttat  113940
ttctgttagg gatatatttt ttgtagattt cacaaaagac agaacctgct gtgtgacagc  114000
ttatctgcag gacaccgatg gtttgtagga cgatggtgag gctttgtgac aaggcagaaa  114060
tgtggaaggc tggcaagatt gtttactgag cttcccctaa ggatggaata attcaccaat  114120
cccacaactc ctccaccctc agtcactacc aatagctgtg cctcagtgtt ttcttttaa  114180
tgattgtatg tattaagaaa aaatcctca tatgtagtgt ttagtttatc tgattttcgt  114240
tactaaaata ataaaggaga aaagtaaata attcatataa aagtaaactt tcttattcca  114300
```

```
agcaggtgta tgtgtgcatg tttgtgtgtg tgtgtgtgtg tgtgtgtgtg    114360
tttgccactt tgatggaaag aggctgactt tgcagagact attttttgtt aagaactttc    114420
cattaaatta gagctttaag ttataacact gattgcatag gccagggaaa atggtaggat    114480
gtggcttaaa aggcaatctc acaagaagta tgacttttat cttatattat aaacaacagc    114540
acaaccttgg aatttgtccc aataaattcc ataagtataa aataaactaa ataagtaaag    114600
tgactaatat cctactaagt cttttccttc acacatgctt ttttgcctaa agccatttaa    114660
agtctctgag gatttaaatc tatgattctt tcatggagta gaagaaaccc agagaatata    114720
gaaatttaga aaaactttaa gacttattgg tttaacagaa gtaggccggg tgcggtggct    114780
catgcctcta atcccagcac tttgggatgc tgagctgggt ggatcacttg aggtaggagt    114840
tcaataccag cttggccaac atggtgaaac cccctctcta ctaaaaatac aaaaattagc    114900
cgggcgtagt ggtgcacacc tgtagttaca gctacttggg aagctgaggc aagagaatca    114960
cttgaaccca ggagacagag gctgcagtga gctgagattg cgccactgca cttccagcct    115020
gggtgacagg gcaagactcc atctcaaaaa caacagcaac aaacaaaaca aaacaaaaaa    115080
cccagaggta gatctaattc tgcagactgc aatcactcag ttatggatgg ataagtcagt    115140
ccttaagtcc atctgctatt tgtgtatcgt gcatttttt tttttttga aacaagcacg    115200
ttcccacctg gattgaatgt taatattcac tgaaagccag ggcattgcaa cgagcccta    115260
ggatgttata attctgggcc attttacag ttcaggattt cagatttatt gcaatgttgt    115320
aagttttag tttcttgtct ttctctaaca tctagtaagt tccaaaactt aaagaactac    115380
aggttttctt gataaatacc tgtgtcacta ctttttattt ttagattttt cttttttact    115440
acatgatctg agttaaaagt taatatata tgaattattg ttttgaaaaa tattacctat    115500
aatagttttt taaagaaac tttaatttta gatttgtgct aaattggcga agattgtta    115560
gagttttcct tataccccac cctcaaattc cactactaga aacaccttac atcattattg    115620
tacatttgac actattaatg agccaatatg tgtgcaattt tttactaaag cccacccatt    115680
cttctgattt cgttggtatt ttccttctgt ctttttttctt tcctcaaatc ctatccagga    115740
tcccacatta catttagccg tcatgtctcc ttgagctcct cttgactgtg acagttttc    115800
ttcttttgtc tttcatgacc ttaacagttt tgaggagggc tggtcacggg attggtacct    115860
tgtttggttt gtctgatgtt tttctcatgg ttatactggg gggctatgga ttgtgcagag    115920
gaagaccaga ggtgaagtgc cactttcatt acattgtatc aagggcacat actagcacca    115980
tgacattgca gttgatacta accttgatcc catggatgag gtgatgttgg ccagatatct    116040
ccagtatcac gttcgtcctc ctgcacacac actttctata ctgtaccctg tggaaagagg    116100
tcactacgtg cagcctacac ttaagaaagc aggaggccgg gtgtggtggc tcacacctgt    116160
aatcccagct actccagagg ctgaggcagg agaatcactt gaacccggga aaggaaatt    116220
gcagtgagcc gagatcgcgc cattgcactc cagcctgggt gatagagcga actccatct    116280
caaaaaaaca aaatataatt aaaaaaaaaa aaaaagaaa gcggggacta taatcccctc    116340
cttgagggca gagtatctac agaaattatt tgaagttatt ttgcatgaga gatgtgccta    116400
ttctcgccta ctcatttatt tattccctca tttacatata tcagtatgga ctcatggata    116460
tttattttat acctttgggtt gtaatctaat gtgatgttgt ttatctgcat agatttttgtg    116520
tttacgtaac ttttttttcaa attcctgagg gatagctttt tagaaaatcc ctgttttac    116580
tttagatcca aggattacgt ctgcaggtgt gttacaaggg tatcttgtgt gttgctgagg    116640
ttcaggcttc cgttgatccc gtcactaggt tattctgtgc ccagataatg agcacaggaa    116700
```

```
gttttttagt ccttgtcccc cctctgcaac agattgtagg aaataatctg agactgatca   116760
tttttaattt tcaagcactg aacatgcagt tattttatct agaaggtaga ccagcaaaac   116820
aaaattatat ttgacatttt agcatataag tattttctag ttaactttga catacaagaa   116880
gccaggttat gaatgtattt gttcatgact ctagcttgtt tggttaaaat tattctcctg   116940
ccaaccaaat gctttttgc taccctgaat atttaaaaaa ttttacaat atttcatctt     117000 taagagctat aaatgtatgt tttaatatcc cagggtaaga tatagggata ttttttagtc   117060
tgtcgaggct gctataacaa ataccttag actgggtaat ttataaacaa tagacattta    117120
ttgttattat tatcattaag acagggtctc tttctgttgc tcaggctgga gtgcagtggg   117180
ttgatcatgg ttcactgtag ccttgacttc ctgggctcaa ctgatcctcc cacctcagcc   117240
tcctgagtag ctgggaccat acgtgtgtgc caccatccct ggctaatttt tattttttta   117300 attttagta gcgatgagga ctcactacgt tgaccagggt ggttttgaac tcctggcctt    117360
aaacatttct cctgccttga cctcctaaag tgttgggatt acaggtatga gccactttgc   117420
ccagctaaca acacacattt atttctcatg gtcctgggaa gtccaggatc aaggtgctag   117480
cagattcagt gtctagtgag ggcccattcc cccaaatggc atcttcttga tttatcctca   117540
catgttggaa gggacaaggt ggaagggcct gcagcctctt ttataaggac actcatccca   117600
ttcatgaggg tagagttatc atgttgtgta ttggatttca gcatgaat tttgggagga    117660 cactaccatt cagactatat aacaagatac attaggtttg gggtgttctg cacttgagtg   117720
aatctatgta agcccttca catattttta ctttcactga aataaaacta aataaggaaa    117780
ccaatgctat cctatatctt aaaatgagaa tggtttgtaa cagctcattg ccttgcatca   117840
tggtctttta gggttagggt tcgggttagg gttaggatta gcttcgcttt gctgggcaga   117900
gtaggtattt ccgcctcgaa ccacctctaa gggcttcagc tttcagtaac gcacctgtca   117960
cttctaatgc aaaaccttga gtcctctgtc tgtgtgcaga ttcaggaaca ggtttgaggt   118020
ctaagaattt tcttattatt gccttccatt tcaatttcta gttcctccaa agtccttcac   118080
aatgatgacc gagaggagac actcaaaaat ttgttagcca gagtctcaaa gtacatagaa   118140
gctgtttctc ttgggtggat attacaagtg cctctacagg caactgcatt tctttctctt   118200
tccaggattt ttgcttattg tccagatatg ctcctcctag tgagagggac acttctgatt   118260
tttcctgcct ccatgaaaca ggggcttcag agaagaaact ctctacagcc ccttcgttcc   118320
attaataatt tataattaaa tgcatttcca gcatgaaggc tgcctaggag tagagaagca   118380
tattagaaga accaatctgc tgcgtatctg cttatagggt ttgagcccag tcaaggaggg   118440
atgcacagaa actcaggatt ctgacagccc agcccccttg caattgggag ggtcgccaaa   118500
tttctttctt gcaaggggta cttactgtct gtgagtggga gcctcttgtg gataaggagt   118560
gagggcagag agggaacagc agagccctgg gaagttcttt ccacttgact ctgagcgtct   118620
agacagcagc ctgcccccac cccctagatt ggctttgtac ctgtgagcaa gtttctgac    118680 tgtgccatac atctctggaa tacatttagt tgctaatgga gatattacta taattccaca   118740
tatgttttta gtctctcctt ggggctgtgc cctctgtgt ggcttggcag aagagaaagg    118800
agagaaagat tatacatggc agccttgctt tggagggagt gaaacctgtg attttccttt   118860
tctgtgtcag gaaagcgttt ttctgctgct tgactagcca cctcccaggc acattaacca   118920
gtcaggtgat gctgacattt gtaccccta atctggctta tttctgaaac cctccctttg    118980
agccctaact gctataatta ggagactgga tcctaacagg tttggaaaaa ggtttgcaat   119040
```

```
ctcaaaataa agtagtgatt ttgaaagaga aatgtatagt agagttagct atggggtttg    119100
cacattctac atttatgttt gtttgttttt attttttcgc tcagactgct cacagatgca    119160
gtgagcacac ccaaatgcat gtgatcaatg catgtctgac ttctgcagct atggaaggtc    119220
tgggtttgta agatcactgc tgtagaccct tgtttgacct ttttggattg ctggatcaga    119280
aagtgagaga ttgcgaaagt tttcttaaaa gaacaagtca gtgaatcaat tcattaattc    119340
ttttgttcat taggattagt taatatactg ctacagtaaa acctttttgtt attgtctgta    119400
ataataaaag ttggattatg gcatggctaa ccccaatctc catacaatct gctcatagtt    119460
ttgacctcat tctaatataa ccctgtattt cacgtgattg aatgttttgc accatattta    119520
taatattaca tccaggtatt acttggtttc tgaaggttta taaaattgta aatgcagtac    119580
atagggtatt agagattttg ttgttttatt tttttagaga ctgggtcttg ctctatcaac    119640
ccaggctgga gtgcagtggt gcaatcatag ctcactgtaa ccttgaactc ctgggctcaa    119700
acgaccctcc accctcagcc tctggagtag cttgtattat aggtgcatgc caccatatcc    119760
ggctaatttt ttattttgat ttttgtagcg atagcatctc agtgtattgc ccagattggt    119820
ctcaaaatcc tagcctcaag caatcttcct gcattggcct tccaaagtgc tgggattaca    119880
ggtgccagcc actgtgcttg gccattacct agagttttg ttagagataa tgaaataaga    119940
atgagattaa aatgaggtta gtctcatgct gcttaaaaca gtgatatgct taggagcagc    120000
tgcaggaaca tctgatccaa tcttggaggc agcctggagg gcttcccagg ggaagcacaa    120060
tgtagtccaa aacctgagag atgagcaggg attgactaac taaagagcag acctacacac    120120
caaattctgc catcagttcc ttgcatggca tggaaaattg atttctacaa ctacgcagta    120180
tttttcttcc tttttttttg aaacagattc tcgctttgtc acccaggctg gagtgcagta    120240
gagcgatttt ggctcactgc agcctcgacc tcctgggctc aagtgatcct cccacctgag    120300
cttccctagt agagtagctg gtactacata tgcacaccac catgcccagc caattttta    120360
tttatttatt tatttatttt tgtagaaaca gggttttgcc atgttggcca ggctgctctt    120420
gaactcctga gctcaagtga tcagcccacc tcggcctcct aaagtgctgg gattacaggc    120480
atgagccacc attttatttt ggtatgtgtg cattctatagt tattctacaa aaaataatat    120540
ttaataataa ttcacagtat cctgcagatt ccaaaataaa gtaagcttaa gttctgttgg    120600
aaaatgaatt tctgtgagaa ggctttggtg ctttgacttg aagctgacat caacattagt    120660
gttgggcatt tggctacaca cctgtcacat tcaaaagcca attcactttg agtctttatt    120720
ttgttggcag taagggctgc acatttcgat ccactgtgta ttttcctagc ccagattcca    120780
ctcaaagcag aggtttagag aaaacccttg tttattgcaa atattatgcc aaaaatagg    120840
atgaggaacc agcactgtgt tgtgggaagg aacgagaaat aatcactatt tacaatagcc    120900
gagttgtgga atcaacctaa gtgtccatca acagtgcatt ggataaagaa aatgtagtac    120960
atctacaaca cagaatacta ggcagccata aaatagaatg gaatcatgtc ctttgcagca    121020
acatgaatgt ggctggaggc cattatccta ggtgaaataa ctcaaaaaca taaaatcaaa    121080
tatagcatgt tgtcacttat aactgggagc taaacaatgg gtacacatgg atataaagat    121140
ggaaacaatc aacactgggg actcaaacaa gggaaaggct gggaggggt gagggttgaa    121200
aaattaacct atgggtacaa tgttcactct ttgtgtgatt ggaaccctag aagtccatat    121260
gtcaccagtg tgcaatatac ccatgtaaga aacctgcaca tgcacccctg aatccaaatt    121320
aaaatttaaa aacaaacaaa aacacaaaaa agtgtattgg ccacagagga gtgactgctg    121380
cttgacccag tgaggttgtc tgaaaaccct tatgttatgt gtctccagac caccctttacc   121440
```

```
cggtgaaaat ggaggaccca tattcacacc atctttcacc tcttattagt ttactggggg    121500
taacctctcc aggctgcttg gggagtgcta agtaggtttt agtgtgcatc cactgtgagg    121560
catcagagaa acttcaggaa atcaagaaaa aggcaagttt gcaggtatga agtgaggctg    121620
cacctgcgtg aagctggctg aagtctaggc agagcagatc accacaagag cggctggaat    121680
aagccatgtg gccgaatggc atccagcaca acgatcaagt gaaacagagc tcctccagct    121740
gtggtagaac tagggccaaa gtatgtgaaa gtgttcaaag attcttcgca ttgaattcaa    121800
gctcatcatt gtccacaaat caatgagacc atgtctatat tggtaaagaa agaataaagc    121860
ataaattcat atttcaattt ttaggttatc tgaataaatg aatttcaaga gtgcttaagg    121920
tttttgctag atgtttgcag gtttttgcct ggagaggcac aggcagttct ttgtcctatc    121980
attctagcct tccacttgta gggattccct ggaaagttga cataaccgct gattcctagt    122040
tctgttttgt gggaagtatc aagattaaga gaccctctgg gtgaacaaga tgtctttcaa    122100
tagatgaatg ggtaaataaa ctatggtgta ttcagacaat ggaatattat tccatgctat    122160
aaagaaatga gctattaagc catgaaaaga catggaggaa aattaaatgc atattactaa    122220
gtgaaagaag ctgatgggaa aaggctacat acagtatgat tccaactata ggacattctg    122280
gaaaaagcag aactggggga caataaaaaa tccatcattg tcagagtttc ggttggggat    122340
ggggaaagaa aagataaata ggtggatcat agaggatttt tatggcaggg aagatattct    122400
gtgttatact gtaatggtgg atgcaaggag gttcttttttg tctaattaac tgttcacatt    122460
catcataatt gattccatac agtatgcatg gattttcagg gtccaagtgt taaccaactt    122520
cagtggactt aaaccactct gtaaatgggg tgctctttag tgtttgtttt gtttactgtt    122580
ctaggactgg ttaatagaaa tcagaggaca tacagatcca gagtccctta tctacaattt    122640
gaaagtcaaa aacagttcaa aactttacag tgatatcaaa actcatttgg gggcaaaacc    122700
tgatctgaca gatgactatt tgtgttcttt cttttccacc tcagggtgga catttagata    122760
ttttcctgca ggaatattaa tgagtttgat ttgggagtga tgttccatat tcctctgagg    122820
gtgctgcata aaacagatgt aaaaaaatta aaaagttctg agtccccttc ctcttgtcca    122880
caaaagcata ctcattccca agggtttcag atccccattg tggatctgt gatatcaaag    122940
gtctcattga taatgttggt ggtcagtgga aaatagttgt gtggagagag atgtgttagt    123000
ctggacctca tgcaatgact gcagaaataa ttttatgatt tccaaagaac aacagacaat    123060
ctaaccacct cccttacctt taaagactga catctgtgtt gtgttcatgg atgattatgc    123120
aaaatcaagaa aagtggcttc catcaaaata atgtcatttc ttttttggaga aaagagcctg    123180
ggactgagtt gtgttatgtg tgcagtttgc cagctaaact cctggcttaa tgattgggat    123240
gggtttccaa gggctggttc tgagactcag tggcagttag ttaggtggta atttccccat    123300
taacattaat gagaaatgaa ataagttact taagaaaacg tgctagacga tagtctctaa    123360
gtactgaaaa gtaaatgaac ccacctacgt ttgttcacat aaaatttctt agtatatttt    123420
aaatttgcta atctaatgta ctttttttttt tgcttgtgct ttaactttgt taaattatgt    123480
cacgtaaaac attttattcc atattctaaa ttacataaat gtgtcacaca caatgtcatg    123540
aatcaagttt gtctaaagag gagataggcc aaggcaggtg gatcacttga ggtcgggagt    123600
tcaagaccag cctggccaac atggtgaaac cccatctcta ctaaaaatac aaaagttagt    123660
ggggcatggt ggtgcacacc tataatccca gctactcagg aggctgaggc aggagaatgg    123720
cttgaccctg aaaggtggaa gttgcagtga gtcaaaatca tgccactgca ttccagcctg    123780
```

```
ggagacggag tgggactcca tctcaaaaaa aaaaaaggag ataatacact ttcacgtttg    123840
taaaataatg ttgattaaat ggtctaatgt gattttatct tgctaatcca gttaccgtcc    123900
cagtatctga attatgataa cagtttacgc agcatagttt tctaacagtt ttggttccat    123960
ctctgctatt aaattcaggc cactggatct gtttggttca acttggatta gggtgtgagg    124020
ttctgttttc ctacctctaa ctccatatac attgtccgtg ctcctgacct tccatgcagg    124080
aggcttgcag gtatctcctt aatctgtctg tcatctgttt cttctgcca tctcaggac     124140 tcctgatctt tccagactgc ccatcctctc ctgtcccttt gactcttcct tttttgttca    124200
ctttctgtaa ctccagtctg atcatctaaa tagtctgagg ggaagatgag gtactgaagg    124260
cactcttgtg agaatatttc tcaggttcct aggtccaagt ttccgttgca tcttggtttc    124320
tatttcagtc tgagcagaga gagagagaga gagcaaaa aagatcttca ggataaaagt      124380
gagagagaga gaagatggag aaataaatat aaatgaacaa ctgataaatg ccttgagcta    124440
taactctgcc aaatgaacac agaaactcat gtgcagttag atattatcca cctgagaatg    124500
tagttgataa catatttcat cataaataat atcgtctaaa gcccttactt gggaagatta    124560
tgaagcaagc caaatcttat gcagtatgtc cttctgttct cttgacaagc ataagtttct    124620
atttctgtat tgctagaaat ttttagtcac atgcaattcc aacagtgctt taagctggtt    124680
attactaagt agaaggtaaa tgtttgatga tggaagaatt tgcggtggag gtgaaattta    124740
ggataaatat tagcaacttt gaaaagtaag gtgtagatct gtgcggtacc agaaaacatt    124800
taacagattc agaagttagt ttatgtgtac ctatatgtgc acacacatac acacacaatg    124860
catgcacact tatgcaaatc acacacacat gcctcacgca caagtgcaac actcaggtgc    124920
acccaattgc acatacgtat tctattacta ttctttgcaa tgctttgaat gctcatcatg    124980
taccacaaag ttatggtcta attcataata ccataaggtg cgtgtgcttt agagatactg    125040
tgtatttcct ttcaacatcg aactagtgac tattaatgtt ttaaaatcaa atttgataac    125100
attctgaaat aaaatactga tgtattaagt accaatgcgt tgacatcagg tttcataggt    125160
gttgaactgt agcgaggaaa acagttatca ggtgtcctac tgtaactcta cccagcagga    125220
aagctctatg taatgatggt agaatatcca aatgatggtg tccacatctg cacaggtacg    125280
atttgagatt cactgactta tttaggagga ttcagtaaaa tttcgcagat gttgttatgt    125340
agtaatattt ggctcattca tattctgcac tcctagacat tgcagaaaga catgcaactg    125400
tgatttccat ctcatccctt tcaccctatt ttgaaacatt tagttatgtc tactagttac    125460
cctaagttgt attttttacc ctctaaaaag gaacaagaga agttggaatc catcccagct    125520
ttccttccag aaaatggagg ggaggaacaa ttggaatgga gaggaactcc agggagaaaa    125580
agacaaaagg cacatgagtg agtttgtcta ggctgggaga gtgggcgatc acatgagatt    125640
tgtgaactaa ttttgttctc cttctgtttc cactgataag cactttatga gtgccaccag    125700
tgtaagtaaa tattaaacct catctcaatt agtatctact cttttccaaa tatatgctta    125760
tgtcagaaaa tgagcagtag aaagcaacca caggatacca cctgcacacc cacgggctga    125820
gcattgcata ctttcaagga gtgctgttgt gttttcaaac ttagtaattt cccaaaacag    125880
agaattcaca gcttccctaa tcaccttcct cagaaccctg aatcttgtta attgagtcat    125940
ttttctgatg atcatgtact catacaattg actaaatgtc tcactatgcc ttcctgataa    126000
gtagtgtctc tacatgtgaa gtatctattt aatctatcta cccctctctc tctatctaat    126060
ctgttgattt cttatctatc taatttatat ctatcatctc tatgtatcta tgtatgtatg    126120
tatgcatata tgtatgtatc tatatatata tcgatctatc ttatctatat gtatctatca    126180
```

```
tctctatgca tctatgtatc tatctgtcta tgtatgtatg tatgtatgta tgtatgtata 126240
tatctatcaa tcctctctct ctctcttagt tcagcaaatt acttacaggt ttttgttatg 126300
taactgagca aaattatata cacacacata agaaggctgg aagttcaaga tcaaagtgct 126360
tacagattca gtgtctggtg gggacccact tcctgattca tagacagcgc cttctcactg 126420
tgtcctcaca tagtggaaag ggcaagggag ctctgtggga tccctttat aagggcactg 126480
atcccattca tgaaactcca ctgtcatgac ctcattacct ccaaaaggcg cccacctcct 126540
aatactgtcc cgttggggat taagatttat atattttttc ttttaatttt ctaattttg 126600
tgggtacatg gtaggtatat atattttatgg agtacatgag atattttggt gtagacatgc 126660
aatgcataat aatcatatca tagaaaatgg ggtgtccatc tcctcaagca tttatctttt 126720
gtgttacaaa caatcaaatt atattatttt agttatttta aaatgtacaa ttaggccagg 126780
cacggtggct cacgcctgta atcccatcac tttgggaggc tgaggcaggc ggatcacgag 126840
gtcgggagat tgagaccagc ctggctaaca cagtgaaatc ccatctctac taaaaataca 126900
aaaaaattag ctaggtgtgg tggcgggcac ctgtagtccc agctactcag gaggctgagg 126960
caggagaatg gcgtgaacct gggaagcaga ggttgcagtg agccgagatc atgccactgc 127020
actccagcct gggcgacaga gcgagactca gtctcaaaaa aaaaaaagt acaattaaat 127080
tactattgac tatagtattg actatagtca ccctgttgtg ctagcaaata ctaggtctta 127140
tttattcttt ctgactataa tttttgtacc cattaaccac cccacttccc cacatcccac 127200
ccccactacc ctttccagtg cctgataacc ctttttttgac tctctatgca catgagttca 127260
atcttttga tttttagctc ccacaaataa gtgagaacat atgataacag tctttctgtc 127320
cctggcttat ttcacttaac ataatgatct ccagttttat ctatgttgta aatgacagga 127380
tctgattctt ttttatagct gaacaatact ccattgtgta tatgtaccac attttccttt 127440
atccattcac ctgttgatgg acagttagtt tgcttccaaa tcttggctat tgtgaacaaa 127500
gctgcaacaa acatgggggt gtggatatct ctttgatata ctgatttcct ttctttgggg 127560
gtttggatat aaacatatga attttgagag gacagaactt tcagactata gcatactgta 127620
ccatctatct atctgtccat ccatctgttt atctgtctcc cattcctgaa tattgcatgg 127680
catattttgt taattatttc caatgtcata ttgagttta aagtaagatt acatttctga 127740
gaggcctcac gtgggggcat cctgaaaagt acattctctt tatagtttaa atgttttggt 127800
tttttctttt atttttttca tatttaatta tatttctttc aagtgactcc tttgggagac 127860
atgatttcc tacctcctgg gactgccaca attcccctgc ctcttggaat gcaatcgatc 127920
tctagtctgc ctcaagtata aagatgatat tcatgttgat gacattgaga aggatgagga 127980
gaaaggagtt gatcagagat ctatattcat ggtatatatg tttatcgtat atatatttat 128040
ctgcttatcg tcttcagaat ataaactcca agactgtggg tctttgtttt cttcagtact 128100
accttgcaga gtctaggcct atttattcaa agcttaatat ttgtgaagtg catgaatgaa 128160
taaatgaatt ctaatgttat cactgccgtt ggtatggtat ctgtttctct atctgtattg 128220
tcctctctac ttttcattat ttgtttaatt cccactcatt gagacagatt gcagaagatt 128280
cctttgccaa ctacttctgg gtagagataa atttccctcc acggagctcc cactggactc 128340
tacctgcagc tatatgttat cttgtatttt ccaacactca gctgtaccac ataagacttg 128400
attgagtgaa gaccctgact tagctttgca taaaaccaaa gtaaatgctt tccacacata 128460
gccattcaca gacattttca catttttatac agcaactgat gaactaggct agtgttggga 128520
```

```
acaggccccc taaaatctgg ccataaactt gcccccaaac tggccaaaac aaaatctctg   128580
cagcactgtg acatgttcat gatggccatg accccccatgc tggaaggctg tgggtttacc   128640
agaatgaggg caaggaacac ctggcccacc cagggcggaa aaccgcttaa aggtgttctt   128700
aaaccacaaa caatagcatg agcgatctgt gccttaagga catgctcctg ctgcagataa   128760
ctagccagag cccatccctt tatttcagcc catccctttg tttcccataa agaatacttt   128820
tagttatcta taatctataa aaacaatgct tatcactggc ttgctgttaa caaatatgtg   128880
ggtgaactgt ttgaggctct cacctctgaa ggctgtgaga cccctgattt cccactccac   128940
acctctatat ttctgtgtgt ctttaattcc tctagcgctg ctgggttagg gtctcccgga   129000
ccgagctggt cttggcaggc tataaagaca ttttctactg gcttaacaga gaagaaaaac   129060
aaagcttagg gagactgatt atgcagaatt taatttgcaa caagcaaaga caagtctatt   129120
gacttcaaat ggacatcatc acattgtcat ctgataattt ttccagcatc ctttgcctcc   129180
tctgtgttaa attataaatt aatgctgatt tatacagttc agttcagctt cacaaatatt   129240
taatgagcac ttgctgtgta ccaggtatta ttatataagt agttctttat ggtgtaagaa   129300
tggatagtag atactttttt atccattcaa ctttaaaagg ttgatgccta gtcatagata   129360
ccaggaaaca cttaagtgaa tgaggacaag ttttctgctg tcaaagagag agatcagaca   129420
ccaactagag tccaagaaag aacaaagtaa ttttgatcaa caaaactcat agaagaaaat   129480
aagcattctt tgttgttaca tatacttcag agccatttta gtgctcaaag tttgataaga   129540
attgatacac aggacttgct gctctgaatt ggctatccca gaatattcta cgagctacaa   129600
ccagacctga cattaacctg tagttacttg tggtttattc atctatccat ctaaatgtta   129660
tgagcatctc ctatgtactc ttcatggtac tagactttag acattgaata cggagcaaaa   129720
aagacatagt ttcttattta atgtggctta tactctgatg tagcatttct tcaccagggg   129780
taattttgcc tcagggggaca tttggcgatg tctaaggaca gtgtaggttg tcatgactga   129840
gatttgttgc tgatgtctag tgggaagagg ccagaccccc ttcacaataa agaattatct   129900
gaccaaaaaa ggtcagcagt gccaaggttg agaaactctt ccagcagttg aagaaaaata   129960
atcatcagat cacccacaag tataattaca aactgaaata catgttagat gctggtagag   130020
ctggtttcca aagtttctga tccagttgtg aggatacata ttgatattga aacgggcgg   130080
ttgaaggggc agtagtaagt tattagggta agaaggtctt ggtgagcaga gggactttca   130140
tgcgaagact ccagggctcg aaggagccca gtgcagtcag gatctgaagt gacaggtgtg   130200
gcttgagaac agcggcaatg gggagttagg caggaggga agctggaaat gcaggcaggg   130260
gtagacaata aaagtacgca ggccgtttat attatacaat cctgtagact tctttcttct   130320
ttcattcttg atacttttct ataataacat tcaagcattg gatcagcacc ctttgttgtc   130380
ttctgtcatg tagcccaaag gtttaccttg gagacacaaa ggcaactaag acaatggttt   130440
ctgcactagg gagatcatat tctcactcag aagacatttg cagggtgtga ttagtgagtc   130500
tcacatacat gtcaatttct tcctaagacc ttgtgctttt ctagttttta tttttttatt   130560
attatttta tttatgtatt ttatttgaga gagcctcgct ctgccaccca cactggagtg   130620
cagtggtgtg atcatagata gctcactgca gcctccaact cctgggctca agcaatcctc   130680
ttccctcagc ctcccaagta gctagaacta caaacatcca caaccacacc cagcttattt   130740
tatttttgt agaggcaagg ctgtctctac aaattccgtt gcccaggctg gtctcaaatg   130800
cctgggctca agcgatcctc cggcctgggc ctaccaaagt gctgggattc caggtgcgag   130860
ccatcgcgcc ccaccctcta gttttaattt ggttttatttt cttctcatat ttcagttgag   130920
```

```
cattattcat ttattgctgt tgaggtttta cttttttttt tcttcccaaa ggtagattgt    130980
agacagctca cctttgttac caatttgaaa tgctagatgt taattcttaa tgttgtagct    131040
gtaaagggcc atgatttgag gacgtgttat ttttttaagc ctgagtttgg attggtctga    131100
gttgaatgca gttgctaagc catcgaatga gggagtgtcc ctgaactaat gagtgacatg    131160
gaccttttct tataggtgag agtccatttg tgataaaggc attgttttag gatacataag    131220
ggtcatggtg tatattctta gcaagtgtta tgaatacatt cgatctattt cttttgaatt    131280
ttagtgtttc tctactctcc atcttactaa accaggtgtc ccagatttcg ggttcagcac    131340
atttgtgtct gggttcacat agagggacta actaggtgga gtttagggta agggggtatt    131400
cagagtcctg ccctcctgca accacagcaa caccccaag  tctctctcat tagattgtat    131460
ttgttctcct acttatgttc tttggcctct gctataaaca ttttcaaaaa agtatccaat    131520
gaaaacaatg ttgtcaatga ctgtctttag taagtctgta gtcagattca tatctttaaa    131580
atatgtacac tgtgtgaata tttcaaagta tgtatcatga aaacaaataa ggaaaaaaaa    131640
aaaaaagcca agaaagctga gatggctcta ttaatatcag gcaaagatac cttcaagata    131700
aggattattt ccaaaataaa agagagacat ttcataatga tacaaggaag aattcaccta    131760
agagaactaa taatgttaat ttgtgtacac ctaataagag agctgttaat tatacaatta    131820
gcaataaatg caaagaaaga ctcatcaata atgacagttg gagatgttaa gatgttacca    131880
caatagatga aagatgaaga tagaaaacac acacacacac acacacacac acacacgata    131940
tgaaaatttt caacagcacc atcaatgtcc ttggcaactt cgtacttcga gtccaacctc    132000
ccttcacaat ctaatacaga aacaaacaac ccatgatttt tctgcatttc gtggttaggt    132060
tccctgtggc tcaaggcctc tggcgcaaat gatgttgtct tttagatttt catgctaaga    132120
agatactcat gttcgtatgt gtgtgctttt tcctctatag catccttaat gttggcctcc    132180
agatgagagt ctctgacaat ggggctttaa catcaaacag ccaaagtctc tcagcgagtt    132240
aacctctttg gccttaaatt tctcacataa tgacatacaa cagtccgctc ttcttcaagt    132300
ggcctttgag gagtctaggg acacttgtga attcacttcc acaactcagc tgcattgcga    132360
attcaattat tgtgctggga gatgttgtac cattatttt  ttttaaaggt gcatattcta    132420
aaggttaatc ttgaggctat cacattaagg gttaacattt tatcgggggc attatagagt    132480 gcattttga  tggctgtgat ttcagataac aagcttgttg tttctatttt tcagctctag    132540
cttggcctct aatctgtagg gaaggctggt tcctaaatgc aggaaatgag gctcaataga    132600
acatgaaaag ccagtgttaa tacaccattc aatctcaaga aagagtggga ggaagaatga    132660
cagagctgtt ttttgacaga tgagtggtta ggcatccccc tagctctcca agtcaccact    132720
aggatgaact ttcaggatgc agtgtcctgt ggaatttggc tctgaaacat aacttcttca    132780
taaggcagat attgtaacgc agttctggat tttgtaccta cagacagctc tgtgttatgg    132840
taactgtttt ctgttggcac aacaaacaat tagttagctt catgctgtag aatatttcca    132900
gatgccctga tactccaaac cattggtcat tgcagcctcc atattcagat gtagcggcta    132960
taaacaggtg atgcatgcat cctggccagg gaccattttg attttccac  cttttctttt    133020 cccaaattca gggtttgtcc acattagcac tattaaaact ttggggcgc  ttcctgtgcg    133080 ttgtaagatg tttagcagca ctcctggcgt ctacccactc caagtcttta cacctaacg    133140 cccatcctta attgtgacaa ccaaaactac ctgcaggcat tgccaagtgg ctcctgaggg    133200
ggcagcattg tcttcattga gcaccagtat ggtaatccta gcctaatcta ttgtgttacc    133260
```

```
ttattgttcc ttaacatata tggggtagaa tcagaattac aggaacgtga atttctttca    133320
acaattattt ctttacaatt atgtaataaa atcataaaag gtaaaactgt atcttttag    133380 aagccaagaa gcaacagttt atgaaacaaa acctctttta gtatttcata ttaatcaata    133440
gatattgtgg aaaggctagt tcttctttaa ggtaacagtt gcttaagagt tgaagtgcag    133500
cttatgagtt ttacaagccc tgatttatgc acagcttgag gcattgttgt tttgcaacta    133560
ttgttttcca gcagcactgc tatttttaaa aagcatgtat cagcaatagt atagaattgc    133620
atatatgctt cagagtcaat gcaatcatta aatagcatgc aatctgagta gagtctaccc    133680
aaagctggaa ttcagagcgc atatttatgc acttagcaac attgccataa ttacacacac    133740
acacacacac acacacacac acacacacac acacacacac gcacgcacgt acttaaagcc    133800
ttagccattt aaaaatagaa ttcaacaact aaggctcgta cacatggaac tcttttcata    133860
gcaggatttc caatgtgcaa atttgataaa attactcttt ttaaaaaaaa aattgctgca    133920
acgtttttca ttaacaccat aaacatttac acatgattca ccccaaattg caccctagat    133980
gtatttaccc tgacttggca atttcatact tcatgtctct acttcccttc atgcttcaat    134040
acagaaacag acaaccgatg acttttctgt atttctgtgg ctcaagtcct ctggccaacc    134100
tgataaatgg cttaggctat tcgataacct gcagcagatc ctctgagatc ttctttgaaa    134160
atttcctcca agatcctaac tacattcatt tgtagaaata tttgagatgc aatgcatacc    134220
ctgtctagta tcccccacc ccataacaga aatgtgaagt agggtgatct gtcatctttg    134280
tgcaggtcat tgccagctct agcaccagaa tctcctcacc tggggaatat ctcagtccca    134340
ggccaactgg gacttggata ctctaattct aggtgtggtt gaagcatcgg tgggttccta    134400
taacactggc acagggaaaa acattaacag tgggacagaa tagagagtcc agaagccaga    134460
agtgcatatg aatagagaag ctggtcccag ctgggaccag cttttttaacc ttgccaaatc    134520 ttgctattgc atctttagct tttcttcttt ccttttttata ccttcttcct tctactttct    134580
gtttagtttc ttctgttttt ctccactaat ttcttaagtg ggatgattca ctcattactt    134640
tttgcccttg tgtttgttac tgatgtcagt atttatggct ttaaattttc tctactgcta    134700 atttttcctgc ctcctgtaaa ttctaaaaca cagtatttca gtatttgtct attaagtgtt    134760
aagtgagatt tgtgtgacgt tctaataaac agttaatttt taagtgtttt gtgtgtattt    134820
tctaatgatg agatacaaaa ttatgtaatt gtctatcaaa tcatcggtta actgtttatg    134880
gcatctgttt ttcctatttt ttgatctatt aaaattgaaa ataggtttct ttgtatcttc    134940
cattaatgaa tgaatttata aattcttcct ataatactac tgatttgggg tttttttaaag    135000 aacgtatgtg gcataaaata tataacaagt tatctccttg aagaatgaaa tattttacta    135060
tgtaatattc ttgctatctc ttaaaatgct ttctgtttta caatagatat ccaatattag    135120
tagaaatatg cttgtttctt ttttactttt gggttggcta ttgctgagaa tatattttt    135180 atattttcac ctttagtaat ttcagatatt atggttgtat catttcatat gacagatatc    135240
tataatttct ttttttcaat gtgacagttt cagtctagta attgcataac ttatgctatt    135300
tatgagtttg aagatatttg atataattca acgtatttta atcttcggga ttccttttt    135360 tatgcattcc tttaataaaa tgagtttgtt cttttttctgt attttcttct taatttgcca    135420
tttacttgat ttctactttt caagaaaagc ttgcagttgt aaaactcaca tttaagtcat    135480
taaagtctaa aattaagcaa gaccttagct ccattctaga aaataccaat cacctgtctc    135540
cctagttaca ggctattatt atgtatcatg aatatttgtt ataaactctt tcagtttttg    135600
tttgattgaa tacctttgtt ccctgctcat tcctgaaaga taatttttgct tattatgcaa    135660
```

```
atccaggtgg accattattt cacatttcac tgtcttctgg ctatacagat gtcagttggt   135720
tttgagttaa actttatgca caggttgtct ttggcaaggg ctaaaattta agatctcctg   135780 tttattttg  gcattcatca gtttcatgtc aatattgatt ttttttttgc tttatccatt   135840
ctttctatgg tttctgtgcc tttggattca tatatttaat cattatttga agatcttagg   135900
gatcaccttt caaatactga cacttctcca ttcttcctgt tttctcaaat tttgatttga   135960
tatatgagat tctcattttt gcacccatgt ctcctaaatt gacttttata ttattagttt   136020
ctgtcttctg ttttttgtaa gattttccca gacatatctt tttttattgt cttttcttct   136080
gtgtctaatc tctttagcta atccattaat ttctatttat ttcaacaaat acagttttta   136140
tttatttcat ttctatgtgg tcattttca  aatcttcctt gtcctttcca gtaatttcct   136200
gttttttgtt tattgtttcc tgtttcaaac tttatttttt aaatagctat tttaatacca   136260
caagttttgt gtgcagcacc tataatacct cagtgttcat gggcttagtg atctttgact   136320
gtgaactcat gtttgtttga tcttaatctg tgggaatttt ctggcctatg ctggcattct   136380
ttccccaggc aggtaggttc gctttccttc tgatagaagc tagagtgtaa gacttgagcc   136440
ctttcaaggg tccaaattct ccaccttact ggaagccaag cttgggtttc tggccccagc   136500
cccttgtctt acacatctgg ctgcccttcc agctacctgc tccctttgtc tgaggtcagt   136560
gctactatgg gtgtgttaca taagggcaga cttcccttag gtccagtttt ccctttgctc   136620
aggacaccca atatattcttt tgcttacact gttggaggag ctttatgtgg gaaagcttaa   136680
ttttggatat ttctcttact tccttgtgcc cagaagttca ctagcaagtg catcttatca   136740
ggaggtaatt gttttgttca gggaaggtct cccagagtga tgtgttacct gctgatgata   136800
ggagtggaag cttttccttt gagaaggttt caccaatgga aaacaggaa  ggaatgaggg   136860 agggagggag ggaggaaggg gggaagaaag aaaggaagaa aggaaggaag agagagaagg   136920
aaggagtaaa aaaagaaagg gaggaaggga gagagggaag gagtgaaaaa agaacaaagg   136980
aagaaaggaa ggaaggaagt aaagaaggag aggaggaaga agtactgagg aacatcttac   137040
tcaatggtga gacccagttc gtacatgttc ttatcctatg agctaatttt ttctcttttg   137100 ttttttcttaa gagaattggc tgtctcttac tctgtaatac agatctgtga gaaaatagct   137160
tttataaaaa gagattttgt agtattacac acttggcagg aatatagttg tctgttgtaa   137220
taatgaatac taatctagaa taggaggctg agaagaaaaa tataattaaa atggtaatgg   137280 ctttttttt  atgtgaatga aactcatcca gtattggttt tgaaagatat ctaagttcta   137340
ggagcagact gtagcagaat ctcctttaat actctaagga aaggacgctt ttagaaagta   137400
ggcattgcct ccttatgtga aaactgcatt ccttttcatga gggttccatt ttctggaaca   137460
caggatgtaa gacaggagac ataagaaggg atcttgtagc agtgcagatg aatcaagtca   137520
ctgcactttc ttatttgatc ttatttttaaa aagatgcttc cagggaagca ggaccttgga   137580
acccacaaag tctggagcaa gtcattgacc tcgcaaggta ttcacgtcct cacagtaaaa   137640
tggagaataa aattgctagt ttttaaggat actcttagga ataaataact tgttatagca   137700
catatcagac catcagtcat gccagcctgt tttcctttct ctcttactct ctccctctgt   137760 tcatttttctc catcttctct ccaactattc ctccctctct accactgttg ctccctcctt   137820 cctcctcc   cttccttcct tccattttt  ccttccttcc tttctacatc cctccttccc   137880 ctctcttttct tttcctttgc ttccttttct tttcttcct  ctctcttttt cctacaaaac   137940
agtatttgtc aactttggca ctcatgacat gtggagctga tcaccccgtc tttgttgtag   138000
```

```
gaggtgtcct atgcattgta ggaggtttag tttagcagca tgcctgggct ctgcccagta   138060
gatgacagtg gcaccactac cacaagttat gaaaaccaaa aatatctcca gacattgtca   138120
aatattgcct ctgaggcgaa accacccctg gttgtgaacc accactcaaa aatacacttc   138180
atatcaataa aaatcctgct ttatatatat atgtttttg ctcagttcag ggttattaag    138240
attgtaagac actagtgttt ttacaagatt tctagggatg ttctttgatt gagtcttaaa   138300
atcttactgt tgatgaaaaa ttgaaattat gttgttattt ttatattcct tcatatagca   138360
gcataaaact tggtatttta tgggaatgag tatgcatctt gttctgattc tatggtctac   138420 tttatgtgt ctcaaaatga gattcagatc aagaaaatt aaaacgagag caaaagtgaa    138480
tattaaggta aaggtatagc attctgatta tctgctgctt gtccatctca ggtatgcaat   138540
actgacactg tgccactagt agcttcttga cattcttaag atgaaaatag tttagttttt   138600
atctaaatat attaatagag aatatacaat atatatttat tcatatatta atactggaac   138660
aatagagtaa ggttaaacac tcaaaattta gctcaaccct gagattatta tgaagtactt   138720
acaaaaataa aaactaaaaa gacattagta gcgtacttcc cagcttcatc tctgcaggag   138780
gtgttacctt agctcagggc ttggagaata ggacatgtgt ttacgtgatt gactcttgtt   138840
gggattgttc tcagagctct cctgaccttg gtccacacac ttgggagcac atgattccta   138900
atactgataa ccacagtctc atgaatttt ctcattttgc agaggaggga attgaggcac    138960
tagatggtaa tatcttttc atttcacata gttgctggtg gctaagggaa gctggtgctc    139020
agcttgtccc aggccatatc taagacattt gtctggcccc ttgctttcct tcctttcatg   139080
catacagcaa gcatatccaa cttttctatg ctggtctatt tctagaaggt gttatttgac   139140
atggcatcac ctcctttgta gccctctgac tatgagaatg atagaatgac ctctcttta    139200 aacctatctc cttatccgcc ccaacacata cccctttggg gtgggggtcat aaggggggtat 139260 cccttctcca cactaacttt accgacttct ctcttcattg tctctctgca gcagataatg   139320
taagcaagaa aaagattaag ttaattacat gcacctcaag tttcagtagg aatatcccac   139380
aattcctctg tctcttaatt taactgttat ttattgaaca cctgctgtgt tcttgggaaa   139440
attccaggtc ctggatggaa ttagtttatg atgatagcta agacttgcag agacattaat   139500
gtgctgttct tcttcttctt cagaaagtat agccatgtac aaactactaa agggcgatat   139560
caaatgttgg ggagataaat atcaaaatac agagcttcca tacctgtagt tttggttagt   139620
ttaataggcg ttaacattta ctcatttca gctacctaca tttattgagc agtgcctata    139680
ccactcattg taatttaatt gcataataaa ttacactgta tttgctgttt atagaaattt   139740
agaaatttag tttaacgata tgtttataat tttcttacta ctatggataa tacatttaat   139800
gactataatt aaattcttgc aaaatttttg aattgttttt agtaaatttgc caatgatttt   139860 cccaggtatt aatttaatat attgaaattt tgtctttata gcatagaggt ttttatttc    139920 attcatttat ttaacaggca tttatcattc atctgctta tgcaaggaaa aaatggtca    139980 agacaaggat gccaagtctt taacctcagg gaacttacag tttatgtaca gggacacata   140040
cttatcaaat aaacagagaa aggaatgtat attcatatga actcggcatc atatattctt   140100
ctttatgtta tcattaataa catccaaatg tcaacaacac atctattgtt actttggtta   140160
aaaagctaca cagacagtag tagatatggt acttggatga agaaagctga agtttattat   140220
tttctctttc tagtttttaat ccctaagggt cattgataaa agacttacac aaacccccct   140280
ttagtaacct aataatgtat aataatcctg ttccttaaaat ggtgatagag atttgcttgg   140340
tttctactac ataacaccat aataccatat taagacttga atctctttat atcatggaac   140400
```

```
aactcaggta gtgttacaaa ctgctgttac tgaataaatg cggagaagaa caagctctcc   140460
agagcagtgc catgcctgtg tctgatgttt cccaggatag aaaactgcgc agatgttgat   140520
ggtttgtttc aggtgctttg acagcctgat catgggctct agccgtggac catgaaaaat   140580
ggcttctgca ggggcttaag aaagacaatg aagagcttcg cattttctct ggcatttcc    140640 tgctattgtt taaaaggtca catatgcaat ttaaaatgtt ccatgcatgg agcatgacaa   140700
atgccacgta gaaaatgaaa ctgctttcgt tgacattttt ggccaatttc caagggtac    140760 cattttccgc cttttccctt ttgtggattt gcaaatttg gcttgtgcaa aatgcgtgcc    140820
ccacggtgca ctctaggttg ggaagtgcca catgttaggt agaaaatcgt gtgtagatga   140880
gaatggcaca ttcagaataa aagtgagaaa ttaaatgaca tcaaaaaaat agagaaaaat   140940
agagaaaaac ttgtaaatga gtccatcaga actatcagaa gctcaaaaag aaagaaaggc   141000
ttagaactca tcaataacaa tgtccagtct cattcatatg taaagaaagt gaaatcaact   141060
ttattttagt taattttact ttattttatt ttattatcct tttacctagc tgaatggcaa   141120
aactcagttc agttatcttt gggcatggaa aaatgagcac tctcacagtt tgctagttgg   141180
aggaagaatt gaagtagagt tttagaagac attgggtatt atacaacaaa atttagaaag   141240
agacccactt tactcctctg gaagcatttt tgcttccagg aatctatctt acagatatat   141300
acacaaagat atatgtacat aggtgatcat tgcaactgaa attttctca tcaggaagat   141360 gagtgaatta ttttaagcac ttagaatatt aaaactatct ttcccttgaa attgaagagg   141420
cagagcaaaa tgtgaggaca cagagtaata ttcacataaa ctccttaaac ctatgtatgc   141480
acgtatagat acttgtatat atacatagat atgaatgcac aatagtatcc atacacatat   141540
gtgtacatat gtgtgcatgt gggtgaatgc ttatgtgtag atttgtatac aaatgtgtgt   141600
atgttgctgt attaaaaaaa gtcaaaaaat aaacaaatta ttaacaatgt ttgcctctta   141660
gaaggtgact atggtacggt gcccttagag agaggctttg attggcagag aaaatgaaaa   141720
accataactg cacctatatt taagatttta aaaaattctt tgtagtgagt ttgagtaact   141780
tttaaaagta cattgacatt tcatttatgc agatcttcta ggtgtgtata aaaagccatg   141840
agaaaaagat gatttcatgt gatagagaaa actagcacag gttagaattt ggactcagct   141900
gatgagacag tatctgccca aaccaattta atcaaagctt tgttgcatga gccgggtgtg   141960
gtgagtcaca cctgtgactg cagcgctttg ggagaccgag gagtgaggat cacttgaggc   142020
caggagttca agaccaggct gggcaacata atgagatccc ttctctacaa aaagtttaaa   142080
aaatctagcc aggcgtggtg actcaggcct gtggtctcag ctactcagaa gactgaggtg   142140
ggagggttgc atgagcccat gagtttgagg ctgcagtgag ctatgatcac accactacac   142200
tccagcctgg gggacagaac aagacccgt ccttaaaaaa atttgtttta aacacttcat    142260
tgtgtggaag aaagctgtat atttaaacaa atataaccaa acccgtaata ctggggagaa   142320
agattgatgg attgttgaaa ggattatacc cgttaggcca attttgagat gtaggcaagg   142380
aatctcagaa gttccaaaaa gttctgctgt ggttcagtgt tacagggaaa tctactcaag   142440
ggaataatat atggcttgca atcattttgc ttttttgtta catttcctat tattcattgc    142500
ttcattgggc ttgagagaag ccccacagag gaataagaaa taccctacat cattcacatc   142560 ttccttggctt tgaaaatta aattttatat acttaaaagc agccatgaca catgaaaaca   142620 ttttcttct tcctcaaacc atctttacct agcctcaccc aaaccaaact ttaattttta    142680
cattaatttt tcttttccaa agctatgcag ctgacactca tctgctcact tggcataatt   142740
```

```
catttggtat ccagtaagtt taagaaattc tgtctgggct tcatgcaatc ataacctaca   142800
tccaaatagc aacacttata ataacagtaa taatagtatt ttttagtgtt cacatggatt   142860 ttctcccttta attttcatga catctcaaca aaatagacaa aatacatggg cttctcctca   142920
gccctgagct ttgcctatcg ttaaccccctt gaagaaaaat ggcgctgagc tatcagtcag   142980
tcattccctg gcagaaaggg aacagaatca gtatagatgg ctttctgaag acattgactt   143040
gatttctgtc accaacaatg gcatattcag gctgtgctcc atgccaggtg ccgtgtgggc   143100
atggagtcca ccacaccagg ggaattctca gaagcagtat tgaaaacaca taggaaagca   143160
ttacttaagc ctgtataaac ataagctctg tccagacatg gaatacagtg ggagttcttc   143220
ctaggataat cccaaaaact aatacatcag aaagcttacc tataacatga gaattcaagg   143280
caaaggcatt tttggtatgt aagtaaaata ttaggttgaa tccatctctt aatgcggatg   143340
ttgaagaatt aatgttatat ccatgaagcc agtgttgact ggaaggactc aaaaaaatct   143400
gaagaatata aattccttga ccttctttat tgaagacttc agctccatta cacgaccacc   143460
tcacagtcct cattcggttg cctttttgcct gtttctgact tactgaagga caatggtgtg   143520
gagctacgat ttatcaccca gaaaatgatt actaaagtcc gtattctact ctgaatactg   143580
aaaactctga agtaatgacc ctaacctaaa cctcctcttc ttctggctat cacttcttcc   143640
ttcccacttt gatcactctt ccatgaatcc tggcaaacct cctagtactg agtatccttc   143700
cagccaccaa acgtctgaca tagatcgctg gatctgactt taattctctc actaagaccc   143760
tcaatttcct cctctgcttg tggtgggctc accctgttgt ttctcagcta agggtgcatc   143820
cagatatcaa tttcttgtgt cccatagcac tgctagcatt aagtgaatta ctgcatggtt   143880
tggtctcatt agtgtgtggt ttccagaaac acttgagatc ttactgttgg cttgtaatct   143940
gtcttagtcc attttgtgct gctataacag aatacctgaa actgggttgt aaaacatata   144000
aatttatttc tcctagttcc agaggctggc aagtccaaga tcaaggcacc atgatctggc   144060
aagaccttct tgaacatcat caaatggcag aagggcaaag agcttaagag agtgaaccca   144120
ctcctgcaag ccctttttat aattacactc atctgttcat gagggcagag cctttgttac   144180
ctaaacacct gccattgtcc cctctcctgc aacactgtct tactagggtt taataatatt   144240
catgtcaacg catgaattcg gggaacacat tcacaccata ggacaaccca tttacactct   144300
ctcctcatcg gggtcaaagg gcatcaattt aaggttttt gacctttttt gttttcatta   144360
tatctcattt ttatactaac agattcattt gttcgtataa ctctcctgtc ttccagaatc   144420
tgggacagtt ttccacctcc caagtgggat ctaggagtta acccccacca tcaacccaag   144480
tactcctcct gtgtccaatg gccagtcagc ctcaatcctg tcttctcttg agttatgaca   144540
tatttttctc cttccattaa tagtgaccat tactgtaata ggaatttata gttctttgtc   144600
ctccagttct ccaaaactgg ttctctatcc tttcaatttt atgctaacaa atctcattaa   144660
agtatgacca gtgatttcta cattgccaaa acccagtggt gtcttttttag tgatgatcct   144720 atatcaattt gatgggcact ttatcacttg cagaattctt attcctttttc atttatcac   144780 tatgttctgg ttttattcta caattgtgag aagctcttct gtatttttctt ctcttattat   144840 tcttaaatgt tgacttttcc taggatttgt tcttgacttc attctgtata ttgtatgtct   144900
aggtaattca ttgcatcttc ttatcttcaa ctatctgcct ctatgtggat gattctcaag   144960 tcttttatttc cagctcaggc cactagcttc agttacagtg tttgtaattt tagccccctat   145020 tagaaatctc tagttgagtg tcacatagac actccaaaca caacacattc aaatattaag   145080
agatgctctt cctctaaaac ctattcctct ctgcaccctc ctgttagtta aaggtgcccc   145140
```

```
atataccagt gtgtccaaga tacaaactct gttggatttt acttctcttt tctcagcact    145200
tatgtaaatg gatgtctact tctcatttct gccctgcaga acattcctag ctatgtgctg    145260
tcttcctgtg gcccactgtg acagcttcct tatctcagtt tagattgtta tgcagtccat    145320
tactcttctg cctcctacct tcaagctact attggagtca tcttcctgat tctcacatct    145380
gatggctttc agtggctaag tgatgcattc caatctttct tagttcattt tatgctgcta    145440
caacaaaaca cctgaaactg ggttataaaa aatagaaatg tatttctcat agttctagag    145500
gctgggaagt ccaggatcaa ggaccatca tctggcaaga ccattttgca catcatcaaa    145560
tggcacaggg gcaaagagct caagagagtg aacccactcc tgcaagccgt taaaaacgca    145620
tcatgggccg ggcgcggtgg ctcacgcctg taatcccagc actttgggag gctgaggcag    145680
gcggatcatg aggtcaggag atcaagacca tcctggctaa cacggtgaaa ccccgtctct    145740
actaaaaata caaaaaatta gccgggcgag gtggcgggca cctgtagtcc cagctactcg    145800
ggaggctgag gcaggagaat ggcgtgaacc ccaggggcg gagcctgcag tgagccgaga    145860
ttgcgccacc gcactccagc ctgggcgaca gcgagactcc gtctcaaaaa aaaaaaaaaa    145920
aaaaaagaaa aaaacgcatc atggcaaaat ctcttttttt accacctggg aaaacctaag    145980
acccttggga cagcacagaa gactccttaa tctgcccatg tgtccctttc cagtgttagc    146040
ttcttttact ttttcttgta cacctcgtgc ccttgcccct tggaacaaac agctcacagt    146100
tccctcagca cacccaccct tctacctgcc cgggagctgc cttccgataa gttgtatctc    146160
gatgacttcc tccccactct ccatctggga agatcccagt cattcatttg ttaaggccca    146220
gtgaaaaaga tttttatttat tttccttcat ataatatttt tatgtataca tatatatgca    146280
tatgtatgct atctatctat tagatacatc ttgttttggc ttattttat tttttatgtt    146340 ttgagacaga gtctcagtct gtcacccagg ctggattgca gtggcatgat cacagctcac    146400
tgcaacctcg acctcctggg ctcaagcaat cctcccacct cagcctcccg agtatctggg    146460
actacaggtg cataccacca tgcccagcta attttttgtat ttttttttttt gtggagacac    146520 agtcccacta tattgcccag gctgttttg aattcctggg ctcaagcaat ccacctgcgt    146580
cagccttcta tagtgctggg attgcatgcc tgtgcccctg tgtctgacgt tatccttgtt    146640
attttaatgc ctacctcatt tgtctttttc aaataataat caacaaatga tttctggatt    146700
gataaatgca tgaatgaaat gatagtttgc caaaatacag aatattaaaa ccatagggta    146760
accttgagac aatttaggta aaaaataggg gattatttta tattagaaga ttattcaatg    146820
tattattaaa atgtttgttt attgcatgtg ttttaagtgt tgagaattta acagagaacg    146880
agacatgaat ggtctaagtg tttatgcatc ataataaagt tgaagaaatg tagggttccc    146940
atggtgtttc ttttcaaact ttgataataa cacttcttta ttgatcgcaa ctgtacattg    147000
gcagcaccgc ctccagactg gaaaataaga tcgatttctc ctttgtgttt cttttataac    147060
cttgcaattt tattcctctt gggcttactg ttatgagttt ggtttctagt ttctagagca    147120
tgagttctaa gaagtggaaa tcaagatgga aggaagttac tatagtgaga gggtgtcatg    147180
ccctgcaggc taggtatctt agagtctgac tgcaactccc ttgacacagg cagttctttt    147240
tcttgcctgc agccctttcc aaacaaatat caccagcctc atattcccct ccctttata    147300 gatggagccc ctttgtcaag caggccagtt tactgggaaa aggcccttct cagacatgct    147360
ttctcatcct gatgctttgc ctttaccagg agtgaggcca gaaccttcag catgcattta    147420
tatcaaaaaa gagagatgtg ctgttttcat ttaaattccg catttccact gggcatagtg    147480
```

```
gctcatgcct gtaatcccag cactttggga ggctagggca ggaaaatcgc ttgagaccag    147540
gagatcatga ccagcccagg caacataatg agacccgtc tctacaattt tttttgagaa    147600
agggtctcag tctgtcaccc aggctggatt gcagtggcat gtccacagct ccctgcagcc    147660
tcaacctcct aggctcaagc aatcctccca cctcagcctc tggagtagct tggaccacag    147720
gtgtgcacca ccatgcctgg ataattttg ttttttggta gagacagggt tttgccatgt     147780
tggtcaggtt ggtcttgaac tcctgacctc aggtgatctg cctgccttgg cctcccaaag    147840
tgctgggatt acaggtgcga atcactgcgc tcagcctcta aatttttt tttttaatta      147900 gtgtgctagt agtctcagct acttagaagg ctgaagcaga aggattgcct gagcccagga    147960
gtttgaggat acaatgagcc atgatcacat tccaccctgg gtgacatagt gagacgctgt    148020
ctctattaaa aaaataaata aacaaattat aaattttcac atagtcgtaa acctctgaag    148080
atgtggatac ttcatttgtc acatttaggt ctttaataca ctaataccett ctcttgggaa    148140 acagtgtttc tcagtctctc ccgtattgat aatgtttcca cttttgccctt gaagattttg    148200 tgggttatgg ggaaacagtt tatggggtgt ctttcagcag aaccacaacc cttttagga    148260 agaagctaat tatggtgtga aagggacagg tgctcttatt aggtagtgat agtaagagtt    148320
aaaacccagt tctcttgagc tgttacttgg attcttcaac tgagggtgat tttgcatctt    148380
tggcactaga tgtcattcaa ctgacagtca tggactccca ggggaccccc aaactctatg    148440
tcacctttat gagtaggcga gaatggattt ttccttggaga ggagtgtctc ctcaaagaag    148500
tctgtgacct agaagaaaag atgaaaaatc tctgctttgg attcggaatg tcaggactgt    148560
tcacttggaa cttaaggaga gtttcttcct agtatatacg agactgaacc ttatgggtt     148620 gccattttct tagacccaaa gctttcaaat acagtcattt tcatatgact tctacttaga    148680
caataagatc atcatgtatt ccttttttcc tctttcagca tctggcattt ttctcctctt    148740
gggcttgttg ttctggtttt tttttttttt ctggtttcta gaccataagc attcatgcat    148800
tcacattatg ttgcctccta agttgtaagc tctccaaaga gagggaatat agctgcttta    148860
tgtcttcacc caactttgag tagagatgat ggcaggaaac agagagcatt tcacagaga    148920 agatggagtc catttgagtc aggggatctt gtttgaaatc ttacctgtgt gatctggggt    148980
gaattaatac agctgtctgg aaaatttaga acagagacct cagaggattg cagtaaggag    149040
tcctagaagt taggatctcc tcagtaaata taaatactta ttctcttggg taatgaagct    149100
gacccacagg atgatgccaa ttatttcctt ggtattataa gcacataaac aatagttcac    149160
atttattgag tgcttactat gtgtaagata caattatgtg ctttgggata tgggttcaca    149220
catgaaacaa gtgtttattt agtgcctact ctgtgcccaa cactggagat gcagctgtca    149280
tgagcactaa caccatccca atatcatggt gctcatgtac ccatgtggga aaagtaaag    149340 acaggctcaa gcatataaaa tagggaaggt ggtcttagga taattcaagc tggattggga    149400
tcagtagtga ttgaagggct agattaaatg aggagtttag gacatgcatc tctgcaagat    149460
ggcatttgag caagaaacat aggcaagact tatctacttt aattttcaca gtagggtcat    149520
gagattacac tgtttattaa ctctgttaca gagatgtgga aactgagatt aggatgattg    149580
aataacagcc agattagtaa tagggctggt agtcttaat gcaagtctca tgggctatgc     149640
tgcacacagt cttaacaact tgccaccttc cgtggtataa gagaggaacc aacccaattc    149700
ccgttgcctg ccttccctgc tatattagtc tattcttaca ctgctataaa aaatacctga    149760
gactgggtaa tttataaagg aagaggttta attgactcac agttccgcat agctgggaag    149820
gcctcaggaa atttacaatc atggcaaaag gtgaaaggga aggaaagcac cttcttcaca    149880
```

```
gggcagcagg aaggagagaa gtgctgagca aggaggaaga accccatata aaaccatcag   149940
atctcatgag aactcactcg ctatcatgag aacatcgtgg gggaactgtc ctcatgatct   150000
aatcaccccc catgaggtcc ctcccccaac acgtggggat tacaatttgg attacaattc   150060
aagatgagat ttgggtggag acacagagcc agaccatatc acttgccatc taattacctt   150120
gatcaactac cctgcaacca ttccttagtg agtaataggg ccacactcag gaatggtttt   150180
aatagaattt aaaagttatc agtattgtag tttaattgta attttaaaaa tggtgaacct   150240
cacatcagtg gctaggatca gcacatgata tgctgcatct tggggtcaat aattgccgca   150300
agcacattat tagagttgct gttaatagtc atggaaacca ccctgtacct tcttccccca   150360
gtgcaaccaa cctggcagtg attgacctac tcggtagcga gttgctagac atcaggagaa   150420
gtcagaagta agtggaagaa ggccaggtgt ctagaagacc cccccactac ccatagcagt   150480
agcaacacat atgcatagga ataggttaaa tgagtcttca ctcattgatc cattcattca   150540
tctttcatcc atgaattaac tattcatgac ccattgttgt tgactctgaa gatacgatag   150600
caaacaggat gcacaaattg tcctgctgtt actttagtta tggggacaga agataaagca   150660
gtgatcaaat gcatgaagga cagaattgct gatggtgatc atagctttga gggaaatgaa   150720
gcaacgataa catctaatgt gggttatgag gatctttgag atggagtggc cagggcatgt   150780
ctttatgagg gtgaggaatt taagcatccc agacacaagt tctgactcaa acatcagcct   150840
tttaattatg tgaaagggtc tcgcaaaatt taataaactt agtggtagga gttcaggtaa   150900
cactacaaga aaccaagctt tctttgtgaa tggtgaggtt agaagggggtt tgttgctgaa   150960 aatcccattt gcaggttcta aggctgggga tgaagtagaa ggaacaatct cttgtcattt   151020
gccaatcaaa gaacaatccc tgtatctggc aaaagagaca tacctttcta tgaatcctgg   151080
ttttggtcat aagccaaact tctatattag ttttcccttt ttggttgagt tagtgaacaa   151140
ttggatgatt agctaaatgt tgctgaaata ggaggaaggc agattaaaaa tacagaaagt   151200
aactcttatt taatgatttg aaaaaatgag gttaatccga caaaatttta aggaaaagtg   151260
agataatttt ggtgtataaa actatgaaat tttaggctgg gcatggtggc tgacacctgt   151320
agtcatagca ctttgggaag ctgaggcagg aggattgctt gaccccagga gttcgagacc   151380
agcctgggca acatagtgaa accccgtctc tacaaaaatt acagaaatta gctaggcatc   151440
ctggtgtgtg cctatggtcc cagctatgag ggaggctgag gcaaggagaa ttgcttgaac   151500
ctgagagttc aaggcctcgg tgcactctgt cctggcttgt agagtgagac cctgtcacac   151560
acacacacac accacacaca cacacagaca cacacacaca cacacacaca caaaataaaa   151620
ttttggaatg taataacatt gatgctgaag tgaattgtgg aaaaatatca tataaaatat   151680
attttaatca catagtataa atttctctct gtgcattagt taccaaaatt tgaacataaa   151740 catttttcaaa tacacacttg tgcaaatgtc agggatagca ggtggtatat cacttttttat   151800 atttaaaatg catgtaggaa tgaaaggaaa aaggtaaaaa tatgttaagt gtagaattct   151860
aatgaaagaa catattggaa ctatgaaaac attatggagg actttgttca tttatggtct   151920
gagcacagat gatgctaaac atggtccttc aactttagct ggcagccatt tgaaatgaac   151980
acactaaaca ccatgagaag caactgcatg aaaagcaaag agagttatcc aagtgaactt   152040
catatctcat catttgcctg tgtttatgta atagtaaaga cccaaggaat tggtctaatt   152100
aattggtatt ttatttttagt gatgaaataa tgagtgcggt tgagcatgcc agatgtattc   152160
atctgataca ttcttccagt cacatggtag gctgcattag gtgataatgc ttcaccctgc   152220
```

-continued

```
attcatttat aagttagtga agggaagtcc acaactctgg tctcagagca tttatcccat  152280
tgttgatcag ctaagctgtt gctcttactt agctgctaag gaatgaagct aattggacca  152340
ttccagcatg taaaatatgt aaaatatgtc ctttcatgga actctgaaac aaacaatgag  152400
aacaaccaga aaaattgcca gagtcataca aaagctgtct atttctaaat gatcattcct  152460
caagctcttg tcatctactg ggagcccta gatggatgta tagttgttgc tgttgtggct  152520
gattttgata ggactaacat aggaccagtg tatggagctg tttattaaga tgcttttgtt  152580
gctgagtatt tacattttgg gtgttctcgg ataacatacg ttaattccta ctgcagtatt  152640
taataaagtg taactagtgc ctgtctcacc tgtctgaaga cattcaaata tggagcgttt  152700
gtttctttct ctagtgcaga tactaaatat catattgtaa ttagagctat acagagattt  152760
agcatatagg actggcaagt cttggaggcc aatttttatg atgtgggaag aggggggcgt  152820
gatttagagt ggacaaataa agtgtgggaa aattttgtgt ttctggcttg agtgaccagc  152880
tcttacctct cctccccata ttctcttcct tgcctcagtg caaattcaca ctgtcttcat  152940
tttgtatgat caccctctgt cttagtccat ttagttttgc aattaaggaa tctctgagac  153000
tgggtgacat atagaggaaa gagatttatt tggctatgat tctgcaggct gtacatgaat  153060
cacggcatca ggatctgctt ctggtgaggg tgtcaggaag cttccactca tggtggaagg  153120
tgaagaagag ctggtgtatg caaagatcac gtggcaagag aagaagcaag agaatggggg  153180
gaaggaggtg ctaggctctt ttaaacagtc agctcttggg ggaatgaaca gagcaagaat  153240
tcagtcatta ctgcaaggct ggcaccaagc tgctcatgag ggatccacct ccatgactca  153300
aacacctccc actaggcttc atctccaaca ttgggaatca aatgtcagct tgatacttgg  153360
agaggacaaa catccaaact atagcactct gtctccttag gtgcaccttt cttcttcagt  153420
gactaatcta gagttctctt tggaaaatgc aaatgtagtt atgtttcttt tttgcttta  153480 tgccttactg gttccctgtt ctttatagca tcaggttgca tcttcatcaa ctggggaacc  153540
agttgatgaa gagaagatca gcatcctgaa gtatcttgta acttcttgaa gtatcttgaa  153600
gtatcttcaa gattcagaat gcatgttacc ttctctgcaa agtgctcttt gcaccttgtc  153660
cagtgtagct gtgttaactc cagtgcacct tcctgatgat cttcctaagg ctcttacctt  153720
cttgtcatta gtcgtttctg tgaccatctt gcctatagga atgtgggcta ctgtgggcaa  153780
gtacaatgcc tggcatgcag caggctttcc agaaatgctt gtttggcttc tagttctc  153840 tttgctgtta ccacatccat cccttatca tccttttttc cctagtcatc tttcctctgt  153900
acctttgccg ttggttcttt ctccatgaat caatataaat aatacaagct tgtgcatag  153960 cagaccttca ctcttgtctc atgatttcat ttctttcttc ggcatactga aaggcaagta  154020
cctttctctc tctgactctc aatttactca tctgtataat tttgatggtt ctttcaattg  154080
tctgctattg ctgatgatgg cacgaactca gatatgcaaa gtatcagact ttcactcttg  154140
tctcatgatt tcattgcttt cttctgcata cttaaaggcc attaccttcc tctctatgac  154200
tctcaagttc ctcatctgta taattttgat agttgtttct actgcctgcc attgctacga  154260
caatggcaca aactcagata tgcaaagtac ctctgggtta aatgtgaaca aaaccttcaa  154320
cctgctgcaa gataatctga cctctgcttg actgtctagc tctgtttttcc tggcagttgg  154380 atgaagaaca tggcaacaat attcttggcc acattgctta caatacaaac gatccctat  154440 ttgtaaatag catcatgacc aggagaaaacc ataaagacct gaaagaacct agtggtaata  154500
ccaccccacc tcaggcttcc cggagggcaa gttttggagt cactttgcag ctgctctgtt  154560
cactctagga accatggaaa ctctgctcat ggagtattta cagggaatat tggctgctgt  154620
```

```
gaaggctggg acttcaatgc caaggaatac ccaattcccg tggatatgga ccttgtaggg    154680
atctttgcat ctcagctgtc ctttgtggag cagatggttc ccatatgcct gctgcagcct    154740
tcctgatgag ctgagcttct tgtctgtatt gttttgagtc ggttggcacc atggtaactt    154800 tggggggggtc ttgtgattct gcatgtttaa tggaacctga aagacccctt actgggcatt    154860
aaagaacaaa gacaaatgtc cctgtgacag aatactggct caacaattgg ttttctctct    154920
gatgcctctt ccctgcttgg aaagcccttt tcttttatcc ttcataatca cttcttacat    154980
ctggcacagc cttcagcttt gcattattcc ttcattatct tttctcatcc cacattaaaa    155040
aaaattcttt aaattgtggc caaatgaaca tgacataaaa tgtaccattt tcacatgtgc    155100
agttcaagag tattaagtac attcacattg ttgtgcaaac atgcttttt tcactctgtg    155160 ccctcatttt gctctttcct ggtttccaat gcagtatctt atatatgatc taataaatgt    155220
gtcctgggca tctcagtctt gtatattttg gtcctctgtt atatcaggta caccttaagg    155280
atagacattg tgccctacta atcttcctcc ttcatcacat gaaatattgt gcttgcatag    155340
tacattttct tcactcccct ccctgttatt ttttatgtat atcatgacac ttatttgcca    155400
aggatggctt tggccctcta tgcaaaatgt caccaatggg aacaatgcta aagtctgcat    155460
aaatcttaag tttaattcta attttaaata tttgaatata gtgctagtgt tgtcattcta    155520
taggattcat taattcatcc catcaacaaa cacttattga gttccaaatt tgttcaaaac    155580
atggccgtat gtgctgctgt agaaaaaatg taaaaagtca gtttctagtg taagggaaat    155640
aaaatatgga tatcattaag tcctggagaa ggcaggggggt gactgatttc aggcttgtac    155700
catagggatt cccaggagga ataagtaggt tgcagcattt aagaagggat catgaaagac    155760
atgccacttt aactagttcc aaatggaatt ttggaagcag agccattgga tgttatagct    155820
gaagtaatat tttaagcaag gtgtcagaac aggattgagg cataatttca gaagaacatg    155880
aagtccttgt ttactaatgc agaatatgtt ttatgatagg ctggaaagtg aatctgtgac    155940
tagatttggg agtgattcag tgtacaatga atatggcagt aaagagcttg gacttaattc    156000
gggctgctgg tctggtcagc ccttgtgttt ggagagatga gtaacatttg caaaggtgga    156060
gagaaggaat tggagattct agttaggtgc tttgggcata tgttcagtga gggatgaggc    156120
attaatgttc atcaaggcag cattcacaag ggctatggcg gcactgaatg ggagagcaga    156180
cagacacagg tgtcatccca gaggtggact ccgtatggca cagcggcaag ggagtgtgaa    156240
gggttatgac agatgctgag taggtgctag caacatattt tttaaaatag tggcaaaatg    156300
tatgtaagat ctataatttt tgcatgtaca gtttagggat attaacaata ttcacactgt    156360
tgtgcaaaca tgcttttttc actctgtcct cattttactc tttcctcatt tacagtgcag    156420
tatcttatat atgatctaat aactgtcccc taagcatctc agtcttgtat attttggccc    156480
actgttctat cacgtacact ttgagggggc attttcagat aattccaggt aaaacgtaaa    156540
cctcacgatg gcagctaaga aaacaggggc gttctctgca ttggttagtt gcagggctat    156600
tagtcaaaat tccaaatctc atatgcagaa ggccaggatc tgcagtctta agtagttcag    156660 tttgttttcac ggaggtaaat aaaagaaaaa aggcatgctg aagatacata tccctggcct    156720
ctagataatc agacagtaag atctctccca cacaccagag aaatctattt ccagcttttct    156780 gttgcagtcc atgaaaatga cagaaaatac atgccctgct tggaccacag cctagctcat    156840
gggaaaaaaa aggaaaataa aaaagaaccc gagcttgctg tggatggttc ctatggagtg    156900 ttttttggcac tgtcagagtg cacactctga caggctgggc atggtggctg acacctgtag    156960
```

```
tcgtagcact ccatggcact gaatttacgg tggaaggatc acattggcaa gtcaaatcct   157020
tgggctacag gaaagactcc catgtgctgc ttttatgctc cccagcagcc aggctgtcgt   157080
tcacaaagca ctctccaagc atcttcattt aatgttgttg ggcacaaggc cctggtgacc   157140
ccgttaaaat ttaaatcttg ctcatacaaa gtgagggcag gttttcagtt gacatttgga   157200
ggtttctcca gccatgttag aaacaaaatg catttaagtg atgagccctt gatacataag   157260
aaggtgtaga gccagctgga tttctccggg accatgaggg gatccatctg attagggctt   157320
ctgaagccga aggaaactac agagagatgt aacttggctg actctcagtt cattatttc   157380 tcttggtaag agcacttctc atattggaca atcttttctt cactgattta gatattattt   157440
tagatgcacc ttttcttttt gttatggaag ctttatttta aataaagtt aacctaaaat   157500 gggcgtatta ctctcccccc gccccaccgc taatgattta aacatgaaa ataatccaca   157560 agaccatggg tgctgtcttc agctacaatt actactttct taattgtcat ggaaacatga   157620
tttattattg gatggttttt tactgtctta tgcaaagatt tcatatgagc cgcaatacac   157680
actgtttcat atgggtaagt ctcaatatta tctgacaaag agagcttctc tgcccaagtt   157740
tatgaaaagt acatttttt ttaagtcact gtcttgccca ggctgcagtg cagtggtacc   157800
atcatagctc actgcagcct caacctcctg ggctcaagca gtccgctcac ctcagcttcc   157860
ttagtagcta ggtgttttgg tttggctttt tatccccact tgaatatcat cttgaattgt   157920
aatccccaga tgttgaggga ggaatctggc gggagatgat tggatcatgg gggtggtctc   157980
ccttattctg ttctaatgat agtgagtgag ttctcacgag atctgatggt tttaaaagtg   158040
tctggcaggt tcctccttcg cacattcttc tctctcttcc caccatgtga aaaaggtcct   158100
tgcttccatc ccgccacctt ctgccatgct tgtaagtttc ctgaggcccc ccatgccatg   158160
cggaggtcaa ttaaacctct ttccttctta aattacccag tctcgggtat ttatttatag   158220
aagtgtgaaa acaaactagg acactaggac tacaggcaca tgccatcacg gccagctagt   158280
ttatgtttat ttttaatttt ttgtagagat ggggtctcac tatgttgctc aggctagtct   158340
caaacttttg gccttgagca gtctttccac ctagacctcc caagtgttg ggattacagg   158400 catgatccac tgcacctggc tgaaaagttt ctattgaatg gaaagaacaa tgctgtgaaa   158460
atatatttta ttaatgttca ggaaattgtg gaacttgaaa aactctagct ttttagcagt   158520
tttaatggct actatgtgct tctaaaattt gtacctgctt ttttgaagtg ttatatgcat   158580
ttttgtttgt tgatggtggt gatgttttg ccgttgatct cacctgctaa cgtggaaaca   158640
tttcaagaag tggaaaaatg tcttatttta gtacatacta tggtgtcagc tacattaaaa   158700 aaaaagcct taagaatgt agcttgaatt gagggttgct atgactttt gttgtagtag   158760 atttatgaat tgtgtatcat catttccctt cagtggaaaa ttcagtaact agtatgttac   158820
tggttcctgg attccaaggg aggagaacat gaaacattgc aatggaatta aactccaatg   158880
agcttgaccc agctacgatg ttgaagtgag ggaatacata aagacttggg tgtatgtgtg   158940
tgatctgttg gtattaaagt gccaggatta caacattcta tgaaaatggc taatcatatt   159000
caatatttat ttgagacgct taagatgcat ggtttgggtg gaactagggt taggggctg   159060 ctgttttgaa cagccaaact agaattctgc tcaattatct cacacaggca cacttctgag   159120
gcatttttta catgatgcct caagaaagct ttgctccatt ttgtatttca gcatgaatac   159180 aaattttga aatttccaca gtaaagtgtt tagacttacc aaaaggtagg ccttgttata   159240
ataacaccag taggaccgat gtagtcattt ctaaaatgat tcaagcactt tatgtttctg   159300
gatgagctat tagatcttac cttatgtgtc tggataagct attagatcat tacatatttt   159360
```

```
aaagtgaatt tttgaaattg ttggttcatt gtttaaattt tcaattttgt ttctgttgca    159420
ttaatctctg agatttgaaa atgagaaaag aaaaaagatg gatacacatt aatgcttta      159480 taccttcctt tgtaacagca attgattgtg cacttgcttt tggctgtagt tagtcctttt   159540
cttaaattag tttctggtat ggatgtctac ttttatttaa ttttttttt tttttgagac    159600 ggagtcttgc tctgtcaccc tggctagagt gcagtggcgc gatctcggct cactgcaagc   159660 tccaccccg aggttcaagc aattctcctg cctcagccag ctgagtagct gggactacag    159720
gcacctgcca ccacgccagg ctaacttttg tattttagt aaagacgggg tttcactgtg     159780
ttagccagga tggtctcaat ctcctgacct cttgatccac ccgcctcagt ctcccaaagt   159840
gctgggatta caggcgtgag ccaccgtacc cggccccact tttatttaat ttttattcaa   159900
ttttacattt tatatgcctt gttacttcat ttcttagcac cagaactaca agtttaattc   159960
ttcagacatc ttctctagca cctcataagg tattctttgt tacttggtga tagagaacta   160020
tgtaatttga ttttcttctt ttgcaatgga gtgttcaaat acgtcgttgc ttttaggtga   160080
gggatgtgat taattagaaa aatgagtgga tcttagctca atgaaattta atcagcagaa   160140
tggaattttc cattcagagc aaatgagttc ctaggactgg acacacctag atctgctgac   160200
ccaaacccct ttatagattt catttctgaa tgagctatta gatcattgta tattttcagg   160260 tgaatttta caattgttga ttcatcgttt aatttttagt tttatttct gttgcattaa     160320 tctctgagat ttgacatata aagaaactc tcatgccagc cccaaacgct ttccctatct    160380
cctcctccca tgccttcctg gagtggaggg aacgtcaggc ataagcagag cccaggagac   160440
actcatagac attctgagaa agcttttctc tgtagaaggg accaacacat cttgcaccct   160500
ctccctctct tgccccctgc ctgcatgtgg gtgcaggtgc ttttgtcagg accccactgc   160560
ttatctcagg tcaggagctg gcaaacctat gaacaagatg gaaacccaac tgctgaccag   160620
ggtggtgttc tgacaggaga gaagacttga gcccttatag acactgttga atcactaagc   160680
tgtaaacaat tttctttggt cttcttgtct ggtaaaatca attctctttc atccttttta   160740
aagacctcag tttgggcttt agaatccata ctggcaaatg cttcctcact aatattgtga   160800
gatttaatta gagatagcat tttatgtgct cacctaaaac tatacggtag acacaaagga   160860
gtctgggtct cagatcccaa cacgtggatt atagagaagg cagaatgcta taatgccttg   160920
agggtgagcc atccattatt tggggatttg aaaaaggaca atttctgttt tatgtttctg   160980
tcctcctaaa tggagttgag agacagcttc ttttctcctt agcatttggg caagaacaga   161040
atccagtaaa accactgagg aaggtcatca ttgcagcgtt tatttaacat gagtaattct   161100
agcatgagct ggcatgccat ttacatccat ctgtttaag tgtttgcaag cagaatggta    161160
ataagaaact ggggtaagtg ttaaaaataa ttatatggaa tatagattgc cccagatgca   161220
ctatctaatg ctgatgggaa aggagagagc aggggtacc tggaacctgg acttctcctt    161280
ggaaacatgc catgacccggg tatgttactg gattgcatag gtgcagaaca tggaacattg   161340
cagtggaatt gaactccaat gagctcagcc caactacgat attggagtga ggaatgcatg   161400
aagacaaaac ctttattata agtctgtgtg tgtgtgtgtg tgatctgttg ggattaaagt   161460
gccaggatta cagcattcta tgaaaatggt agtggagaaa aggaaggta gaggaaaaga    161520 gaaaaccaa agcaagagga aaccactgg aagaaaagaa gatgggaagg agaaagggca     161580
tctctgaaga atgtaaggag tacaagatcc cttacaggca gtgaacacat aagaaggcat   161640
cattcaccag aaagtcatac cagtttatgt attaaaactg ggaatggcaa tgataggcat   161700
```

```
tagttagaga ttatgcttta aattgtatgc atttgcatat ttttatatgt tttatttaat   161760
tttgttttgg ggggggggact gtatctcact ctgttgccca ggctgatgtg cagtggtaca   161820
atcctagttt actgcaacct tgaactcctg ggcttaagtg accctctcac ctcagcctcc   161880
caagtagctg ggactacagg catgtgctac tatgtccaac taattttgtt attttttgt    161940 agagacaggg tctcaatgta ttgcccaggc tggtctggaa ctcctgggct caagtgatcc   162000
tcctgccttg gcctcccaaa gtgctgggat tacaggcgtg agccactgtg accagccctt   162060
ttgcatattt attgtttttg tttgtttgtt tgtttttga dacagagtct cactctgtca    162120
cccaggctgg agtgcaatga cgcgatcttg gctcactgca acctctgcct gctgcgttca   162180
cgcgattctc ctgcctcagc ctcccaagta gctgggatta caggtgccca ccaccaaacc   162240
cggctaattt tttgtatttt tagtagagac aggatttcac tatgttgggc agactggtct   162300
cgaactcctg acctcatgat ccgcctgcct catcctccca aagggctggg attacaggtg   162360
tgagccactg tgaccagccc atttgcacat ttagtgttta ttttcttaat cagtatcgaa   162420
actgtgaaag gaatgttaa aacggtggag ccaggtgaaa aagaaaatcc aagagtcaga    162480
agagagcatc caaagaagaa ggcagaggca ataacaagta gactctgaga ctgaaattaa   162540
actgtatggc tagaagatgg gctagcatag gacaagatga ggtaacatgc taacatggaa   162600
gattgagaag aattgcaaat gagaaatcac ggataaaaca ctgaccgcct aataggataa   162660
aagcagagga tgttcataag cagctgtcat caccaaggaa gaggaaaaca tgggaaaggt   162720
tttgccctct gagcagaaca atcctgcatg tcaaggggga gcctcatata ccatgtaacc   162780
tcatgttaaa ccataaatac ttaccaatac ctcttacagt gtgacaggac acaaactatt   162840
aaacctgatg cagataatgc cttttaaaat gagtattata tttgattatt atttctaata   162900
atgttataac tatgtttaaa ccatccactt tattccctag atgaaatata attgaattaa   162960
atgttaaaca tatttgacat gcatttctcg gggcttttga tttaacattt taaaatatgc   163020
aatttagcta ttttaaaaaa cagtcttaaa aaataacata gtatatcaag ataggcagaa   163080
ggaaaattta ggcaccaaat aatagagtac atgtttccta ttatgtgttt tggttgggag   163140
atgatctttg gaaagtgctg attctgtttt tgtttccata aaacaaaatt tccagagatt   163200
atatattgga ttctgcttga aagagttcag tagacattgc acttctatca cactgatagc   163260
ccaggaggaa tttaactat gtaattattt aaccgcaaaa ttttccacct tctcccctta    163320
aacatttggc ggataaatta tgataaaagc agtcatgata tgcagttcgg tttcatagtt   163380
tcctttctct tcctttttgc tatatttcct aaagttctat tatggagaga taccagtttt   163440
aaatgtcaag caatgttaac atctttgcat ctttatcttt tcctatccac tcttctctct   163500 tttctttct ttttttttt aagggccaga gagtgacact tagccaatac ttaaccagta    163560
ctctctttct gtttgtttgt gggaatttta tatctatttt ttcttttca attttatt     163620 taggttcaga gggtacatgt gcaggtttgt tacatgggta aattgggtgt cgctggggtt   163680
tggtgtacag atgattttgt cacgcaggta gtgagcatag tacctgatag gtagtttttt   163740
gaccctcagc ctttcccac ccaccacttt gaagtagacc cttgtgttta ttgttcccct    163800
ttttgggccc gtgcgtcctc aatgtttaga tcccacttgt aagtgagaat atgcagtact   163860
tgcttttctg tttctgcatt agttctctta agataatggc ctccagctgc actcttgttg   163920
cttcaaagaa catgattttg ttctttttat ggctatatag tattccatga tgtatattac   163980
accacatttt ctttatccag ttcaccgttg atggccatct aggtggattc catgtctttg   164040
ctgttgtgaa tagtgctgtg ctgaacatgc aggtgcatgt gtctgtttgg tagaatgatt   164100
```

```
tatattcctt tggatagata tccagtaatg agaatgctgg gtcgaatggt agcgacttgt  164160
ctcttaatag tttttacttt gcctcgatct cctgattctc tcccttttt tcctggccat  164220 tcccgctgca cttgcctcat ttgctattga tgacatgctt gtccctgct tccatagatg  164280 tgtccacaaa tgcatgtgca cacgtgcttc agctaaagat tcctcagcta aagattctcc  164340
ctctccatca gggtttctct ctttagctca cctgcccttc tctacatggt tttaaagtga  164400
gatgattgta aatgtgtttt tcacaatgga aattctccca gcgggcgggg aggaaaaaag  164460
acatcttgaa atattttctg agaactatga ggaccggcag agtttgacat gttttgagg  164520 cgataaagtc atgtgtccat ctgtgaaaga caggcattgg ctttatccac atccacacag  164580
ccttccccgc tgtgtggctt cattattgat ttgctgtcat gtagagtcga taatgagaaa  164640
acctaggtag ccttgaaccc aactttgcaa gaaccttta ggactctggg acttctaacc  164700
ctctaggaag gtggagttaa ggggatatag gcacagaatg gggcagaagg gaaagacatt  164760
aagagacagc ctttagcaga ccagagaata catgccgttt atcaaattgt tagatgtctg  164820
tgcaccagga atgttgattc aattatggta tctaaaaata ggacagaaat aaggaggaaa  164880
taaaaggaaa tgaaatagca gtttacctct ggcaaaaaca aagagcccaa tcagaaaaac  164940
tagacaaagc cacctgtagg actggaagaa accatgtgag ttaggtatca ctaaccttgg  165000
aaggacaagg acttcctagt attttttgtat tttgtgaagc actttctctg cattttctta  165060
atttgtcctt aagtgattat ctctcaacca accccaaaat ttgactcttc aaatcattta  165120
ttctctaaga ttttaagca ttcaactgta atggcttatg tatcagcata gtcttatata  165180
attctaaaac aacattcata gcatggtatc ttgtaatatt tgactttcac tattaattct  165240
ttcagttatt atttgagtgc ctgtcacatg ccaggtattg ttctaagctt cagggatgca  165300
tccatgtaca aaataaataa aatttcctcc cttgtgccac tgatattcta taggtggatg  165360
gaaaacaaac ttaagagtta aataaattag gttttattta aagacagggt cttgccctgt  165420
cattcaggct gggtgcagtg tttaatcata gctcaccgta ctctccaact cccgggctca  165480
agcagtactc tcacatcagc ctcccaagta cctaggacta caggtgttgc caccatgccc  165540
agctatttat tttctgtatg tttttctttt tgtagagatt gggtcttgct atgttgccca  165600
agctggtctg gaactcctag gttcaagcaa ccctccctcc ttggccccct aaattactag  165660
gatcacagac atgagccacc atacgtggcc aaagttttgt attattttat aaggtgatga  165720
gtgctgtgaa gaaaactaga agaggataag tggaattaga attgctaggg aagttgcagt  165780 atttaagta gggtggtcaa tgacaacctc aatgaaaagg ggatgtggga gtagagaatt  165840
gaaatagcta agggaaaaag ccatgatgat atatgagaag gatgttccag gcagagggaa  165900
cagccagtgc caaggctctg gggtaggaac atccctgttc tgtttagggc agagcagtgt  165960
attagtctgt tctcaagctg ccaataaaga tatgctcaag acttgggaat ttataaagga  166020
aagagtttta gtggactcac agttccacat ggttggggag gccttacaat catagcagag  166080
ggcaaggagg agcaaagtca tgtcttacat ggatggcagc aggcaagaga gagcgtgtgc  166140 agtccccttta caaaaccatc aggttttgtg atacttactc actatcacca gaacagcatg  166200
ggaaagacac accccccatga ttcagttacc tcccatcagg tccctcccac gattatgaga  166260
gctacaattt aagatgagat ttgggtgggg acacagccaa accatatcaa gcagtaagat  166320 ccacattct agagtatcag agtatgccat cagaatggca ggtatcagag tagggtggtg  166380
ctatcgagaa ctttgtaatt ctgagaacca gggagaacaa atggaaggat ttcaacagat  166440
```

```
aattcatgtg tcaaggtgtg tttaaagga gcactttgct tagctgaggc ttgtctgtag  166500
gggcaaaggt ggaatgtggg agaccagtta gaaggctgat gtaagagtca agataagaac  166560
ctacagctgg gaggtgagaa gtggttggag tttttttatac atttgaagta agatttgcta  166620
gttatatgga tgtggagtgt gggagatcga aggaagtcca gagttttttgg cctaaacact  166680 ggaaaaggta gaggtggtca caggtgacat tggaggatgg gctagtagag acattcttaa  166740
gttatcatca aagtttaaat gtttgagttt gaaatgtcta tgagacatca aacggaagat  166800
atcccataag gagatggatg tcagagtctg aagttcaagg cagaaatctg tgctgaagag  166860
aaaaaatgtc agcctagata gtgtcgatgg tatctaaagc tatgaggcgg aataaaatta  166920
tcaagagagt tctgtggaca gagaagagaa aggaccaagg ctggagcttg ccaacaattt  166980
gagattggta ataatacgag gaacctggaa aggaaatgaa cataattgtc cagggtgtaa  167040
aagaaagtct ggtaatgtgg aagtgaaggg gggaaaaagg catttcaatg acagagaggt  167100
agtcaactgg gtgtaattca aataggtcat aaaatgcaca tctgctgcta tggtttccac  167160
tacagatgca aggaaaaagt gtcctcgtcc ttttgtctgt ctgattgtgg cagttgagat  167220
tgaatagagg tagacagagg ggaaaaaaga atgaggaaaa ttgagaacat agcaatgcaa  167280
atgtcatttt tgacctttag tagaaaagta ataattttgg tggagtgttg ggggtaaaag  167340
ccccaattgg ggcaggtttc agagagaata agagcaataa aattggaatc aatatcaata  167400
aatattttca aggatatttt cagaaaagga acaatataga cacactttttt tttttaagat  167460 gagaaaattg ttttattgct tttaagatgg aaaatctaac cacatttctg tgtgctgtag  167520
ggttgatcta gaggcgtggt gttatcaatc agtacagtgt atagtgtgct acattaacaa  167580
atatccctaa aatggcagcg acatccacag ccactaaagt tgatttctcg ctcatgttca  167640
aagttcgcta agggttgact gtggctgttt tctgtgtatt cttaattctg ggacccgggc  167700
tgatggagaa gactcatttta ttcttattat tactaattat ttttgttatt ttagcaaagg  167760
gggaaaatgg gcagaaccac attatagctc ttaaggtttt cgcttggaag tagccccact  167820
aatttctgtt catgtttcat ctgccaaagc aagtcaatta gctataactg aagtcatgga  167880
agtgagtcag tgaaattctt tcgagttagg gacagggaaa gtcttgcaag tgtgtatttg  167940
tccccttgag aggtgtggac agtttttttac acaataatac aacatacaag aggaagacaa  168000
ttctgaggat atagcaagag caaggtgttc tattgttggg ttgtcaagag ttgatggagt  168060
ttgatgggtg agagtcagcc ttatattggg ttcctatcat tattctctta tgaaaagagg  168120
aggcacaaaa gatggggcca ttattgtcac atgggtaaat gggttagtgg tggtttgtgc  168180
atgtttcctt gagatagaat ttcttcagtg tagtaagaag ccaggtcata ttctaacagt  168240
gaagatggag cacagggat tgggattag aagaggaaga agaaggtgct atttagcaga  168300
gcctttaagg gaattcatca gagaaattta gtatgatata caggcatctc gattaaccta  168360
ctggaggttt gtgttcatga atttaatgtg agataagtca gcatgattaa atatcttctt  168420
tcatctgtgc tgatcagtaa aggtgaggcg gatgcatgct gggtggggag gtggatttca  168480
ccagggttgg agttttgcca aggaagaatc aagaattaag gctggattag aattgagggt  168540
gtctaaagga tcgtggatct gctatgactc cacaactcta agaaaagaag attcggtacc  168600
accatcctca ttatggaaat aacaaacgaa tgaaacaaaa ccatttgtca ctttctacaa  168660
gattcagagg gcttgtatgt ctatgatctc aggcctcaaa aagagtaaat cagttaccttt  168720 tttcccacat aactctgtgt gtgtgttagt acaattttgt atgtttgccc tagaatgtga  168780
accatgaatt tgtgaaatga aagcagtgaa taggaaaaaa ggtaaagata cagttttgta  168840
```

```
ttatctgtag caaaaatatt accacagcta tgtaatccac aaaaatggaa gaaatttatt 168900
aggtatttaa tttttatcca agagtagtaa aatgaaggca gctatataat tatgtaggtg 168960
actgttaaaa tattagactt tttgttgaaa ttttttggct cagaaaacag gtttcatgcc 169020
atgctgaaaa attacttagt ttgatgaaaa agtaaacaag acatgacagt gaaatcatac 169080
agtgttgaaa caggaaatag ctaaaatgta ttttctcag taaataagtg gctggcataa 169140
gttgtcctca ttttgggtc aagatcttat tttggtgtct cagctgaaga tgacctcttc 169200
acaatccatt aggtattgtg acactgatta attattatca agcagaaagt atttttga 169260 agtactttgc actaggcagg taaggcagtc gctaccacag gggcacaggt ttcgaagcag 169320
ttcaggagga gccaacgtct tgctgagaaa cccaaggcag acagcaatta gaggataaga 169380
taatgtataa ttaactgcca ccgtgtgtgg ggtagacaat tagagaacaa ggcaacacag 169440
atgttgtaag gtgctgatta tgggttttaa caataatgaa aaatggaaga caacatcatc 169500
agcgtgggct gacgctgtca ggggtggtgt gttttctcat gtgctgttac cctctaatca 169560
gtgttgagtt ggatagtatt cccaggaatg gctgtttggc ttcgcttctc ttaccagaga 169620
attgctctgc cttataaatg tagagactga catgtagaca cacttggatc atgaatttcc 169680
attctactct acaagaagta cagctgcaaa gaaaatcaaa tcatgttcag taccttctg 169740 gaattttccc aagtactcag tagtcattct agctcacatc ttaactctgc tagggttcaa 169800
taagtatacc aaatgcatat ttttttttag ctaattccaa aatctaattc actttgatca 169860
atagtcatct cctatgaatt ccttgtgttt tcttcactat aaaatatttt tgtgattcat 169920
ctttcagtag acgaaaggtg aggtactttg agattatatt tctactaaat catgaatgat 169980
tcattatttt actgaaagta aacacatcca tcatattaaa tccatatcat gttctgttgt 170040
atattgtcac ttaagtgttt ttattatttt taaacaggtt gtataattgc atagagcttc 170100
aggctatcta catagacaaa atatctgaat aaaagtacaa cgatcatatt ttatcttgtc 170160
agtttaaatt atgtttaatg atttttaattc cagggaaaac tctaatgtac caagttacca 170220
actgaaatgt gcccagtatc aatcctttat ttttaaatat aacattgtaa gttgttaagt 170280
aagttgttaa ctcttatccc taaaaagaca taatgttccc ttttcttatc atatgctaaa 170340
ataaaaattt ctaacaatga atgtgccatt tttataagcc agcaaactat gcaagtaagg 170400
atctcaatag aagatttaaa caaaataatt attttgctcc atattctgtt gcttttgttt 170460
tttgatgaga taattaattt tcatggaatt ttaaatgatc aatttgtagt aaattttggg 170520 aaaatatgtcc attatttaat cacagattta gtatcttaaa cacattgaca acgtcaaact 170580
tgtctgcagc aaatggttac tgttaaaaat ttgccatagg ggtgagaact gcaatttata 170640
ctatttctaa gctatcaatg cttcaattat tacatgtgtt tatatatata tgtgtgtatg 170700
aacatgtgtg tgtgtgtgtg catgtataca caaatttaa agtaatggct tactgaaagg 170760 ccttttttc tcttcatatg actaagatat ctgaaattct gcccaaaatt gctaagatta 170820
tatacccttc tgaaaaattg caatgtgttt atgacgtatt tttatgatat ttcagtaccg 170880
gatatgttca ttaccccatg tatgaagtct tatcttgtga tgatgagttg atcagaccta 170940
ttacattgag aatattttta ggtataaact ttatatagtc tctgatggtg agtgtgtagg 171000
taaattgctt tgggctcacc tgattgtatt tcattgttg ttgactttca ttatttcact 171060
aatttgggag caagggcttc tttttttatgg tctatttcta gatcatcttc ccttagatta 171120
catcatgtaa tgaactggca gaagatatta agtgatcttc attcaaacaa gaactttgaa 171180
```

```
cctaaatgga gatttatcaa gctaaattag cctaattgtc tgtaacaatg accacagcat  171240
attaataaaa cctgtgaccc ttacatatat acatgtgcat tttaatgttc ttccactatg  171300
aaaggcattt tgtgatttaa tctgcttgat gaacgattaa tatgatattc actaattttt  171360
actcatctta ttcttaattc atctaattta tctaattctt agtaatctaa atgattcaag  171420
cctcttacag atttttatct ctacccagtt tttcatccag ctgtccgtgt ggtcatctct  171480
gccttggtgt gcttgagaat tatttctgat tctatgacac caatgcactt tgcagtcttt  171540
gaacttgaat tggcagaatc aagcttcctc tagacaaatc actgaatctc ttttctcacg  171600
ttaaggtttg taggaaccct attctcaaag ctgccaaaac actactgctt agtctatgca  171660
aatcaacaac tacaaatgca cgtcactcaa tcaacattat gaaactcctt tttggaatga  171720
ttgatgatca caaatgtga tcttgtgaca atatgatata ttcatttaag ccacattgag  171780
gtttcaaatt ggcaccattg acaacgtacc tctttcatgc taagtgtaat aatttgttgc  171840
ctctcatttt cctatgctgc ttcacttcat taaatctgaa taattaaaaa ttttcgtagc  171900
atcgccaaag tcacttccca ggagctaggg aatgtgtcga tctgtacact gatccagttc  171960
ctgctgacgt ttgcttggat gcagaggcca tccatcgctt tccattgatt tttgtcaatt  172020
gatgcttttc ttccttcttt cctggtgact taggaaatgt tctgaaactg tgcattcaag  172080
tcaacacatg ttagattcat aactaggatt caccttcaca gtggactggt cccaatttgc  172140
tgtatttta ttcagcctgt caactcacac tatctgacta aaagacgcta atgcagtgtt  172200
ggccagtccc ctgtcatctc tttctaattg tttggtctca agcaatggt gcatgttaca  172260
catatccatt taactgtcca attaacgcat gtttctagac aattctgata gaaagggtct  172320
cttttcttcc ttcagcccaa acaaagcaaa acaaaacaaa agggcactta cacgatgttg  172380
atctatgttt tatctttttt ttttttgag atggaatctc cctctatcac cctggctgga  172440
gtgcagtggc gcgatccccg ctccctacaa cctccgcctc ccaggttcaa acagttctcc  172500
tgcctcagcc ttccgagtag ctgggactac aggcatgcac caccacaccc ggctaagttt  172560
tgtattttta atagagatgg ggttttgcca tgttggccag gctggtctca actcctgac  172620
ctcaagtgat ccacacacct tggcctccca aaatgctggg attacaggtg tgagccacca  172680
cccctggcct gttttgttt tatcttaaat ctcttaggct gagactcata tggtcccact  172740
tacccatctt tttacagcat gaaattgtcc agttaaaatt acagctcttt attaatggcc  172800
ttaagactct tcattttgaa tggataaaat agtaataggc tgtgagcacc aacagtatta  172860
atgtatcatt catgcatgat atagtagtgt tgacatcttt cttttccttt tctgtttta  172920
aatgaagttc aggaaaccaa tatgaaaggt aagaaattgc caacatcttg gactatcaaa  172980
tcatggcaga caatgaatta aagaattcaa caaatctttg gcagcatcag tttcaaaggt  173040
atttagatac aaccaccgtg taattctaca caattaatt aaatcattta tcaaatcctc  173100
tacaacttga ataatttaac tgatatcaga ataatccatt tttcagataa ttatttttat  173160
atttaatgtg ttaaatataa aaatatgaca cttctcttgc ataatttgca gaatgttatt  173220
tatttcatta ttttattatt atttttaaaa tttcaacttt tatttgatac atgtacagat  173280
ttattaaatg gaaatattgc ctgatgctgg ggtttgcagg aaggatcctg tcacccaggt  173340
agtgagcata acatccaata ggtagttttg taagcccccc cacaaccagc accctatagt  173400
agttctcagt gtcttgctct tttgcccagg tgcaatcaaa gctcaccaca gcctccaact  173460
cctggactca agtgatcctc ctgcctcagc ttcctgagta aataggacta cagatgccac  173520
catggccaac taatttttta attttacttt tgtagagatg gagtattgct atgttgacta  173580
```

-continued

```
ggatgatcat ccactcctgg cctcaaatga tcctcccggc taggccttcc aatgtgccag   173640
gattagaagt gtgagccacc tcgcccagcc ccaatgcttg atctttaaga gcttcaggca   173700
gttgaagggt tttgtctgcc tgccacagcc ttccatcttt ttgagatgtg tttacctgag   173760
acagctaagt aggtgacaac ctgaactacg gttgctggca attggaaaac agaagattgc   173820
tctgttgatc cattgggaga agtacagtag tctgtagagg aacagaatcc cagggttttt   173880
ttctggcatg gaatcactct agagagccac attaaaaatt taattcctgc tgagcacagt   173940
ggcttacgcc tgtaatccca gcactttggg aggccgagga gggcggatca tgaggtcagg   174000
agttcgagac tagcctgacc aacatggtga acgctgtct ctactaaaaa tacaaaaatt    174060
agctgggtgt ggtggcgtgc acctgtaatc ccagctactc gggaggctga ggcaggagaa   174120
ttgcttgaac ccgggagatg gaggttgcag tgagccaagt ttacaccatt gcactccacc    174180
ttgggcaaaa caagcaaaaa actccatctc aaaaaaaaat taattcccct ttgactgttg    174240
attttattta tttattatta ttttttttaga gacagggtct tgctctgtct ttcagattgg   174300
agtggtatga tcatagctca ctgcaacctt gaaatcctga ggtcaagtga tcctcccacc    174360
tcagcttccc aagtagcttg gttgacaggc atgcaccact acacctagct aatttttcta   174420
tttttatttt tgtagaaaca gggtctcgct ctgctgccca gtctggtctt gaactcctgg    174480
cctcatacga tcctcccacc tagttcttcc gaagtgctgg gtttataggt gtgatagtgc   174540
cgagccattt ggctgctgtt tttacattta taccattatc ttcatcctaa ataggaattc   174600
tgatagtatt gttggcagaa tagggtcaac tggaacacac attttttgttc tctaggtaaa   174660 gatgatgaaa cttaaaatgt agctaatgtt attcctgcaa tgaatatgtc aatttctaat    174720
ctggggacaa aaataaataa aaaaaaagtt gcacgtatta aacaccttct tgactaagtg    174780
gcagctgtaa tgatttcact tggggatagc cattgcttct taactcatgc taacagtgca    174840
ttaaagctat tgattttttag tggctgctgt gctttcgtga ttgtagatca tttctctctt   174900
tggaaactct atttgatgac aaagctggct ctgttgcaga gtaatgataa aagaaaggac   174960
ctaccagaat ttcaagtgaa atgtataaca tatgtgataa tgcatggtga ctgcaatgat   175020
tatttcccga tgttgctgtt taatagccat gaaagcatcc tactgaaata gagtatttct   175080
gctttgaatg gcttagttag ctcaaaaatt ttgaaagctt tctcagtaaa gcatggtgcc    175140
aggcactgaa agattccttt tggaggagcc agagtcaatt tggatgatgt ttataaaatg   175200
ctgctggaaa attgggtggt gttttctaaa tgatcttcct agtaatgatt tatgctgtaa   175260
atcagaaagg ttgccatctc tctggatgga aatgcatagt catatgcccg taaatgcagg    175320
gatttgacct cctataaaaa agctctctct tccccctcat ttatgtgatg attgtatacc    175380
atctgagcgc tgagaaaccc attggccatc ttccacttgt gtgtggctgg aggtgcttgc   175440
tgcagctctg tgatgccctg agccagcatg ctcgtggagt tccagtctgc tgcatgaaca    175500
agtggagaaa catgatcttc ctaaactgct cacaagctgc taaatgagtg atttgtgttc    175560
cctttgaatt catgctgtaa atggaaatgc ttgctccttc ccgggttatt actctgtgta    175620
cacgccattt gaggatgcag ataattgttg catcttcact gaagcatccc atcttagtcc   175680
agatttccgt tttcacagac caaaagggca aagtcagact tggcagacag cgcagcttca    175740
gtctcatggg gggatttctt tgtctcatca gcctcagtca tgggctttcc agccattata   175800
atttcacatg taatatggtg ggtgtccatc tgagcaagtg tggtgcctca gtagggttgg    175860
aggaggcact tggagctgat gtagagaaag gagagtgaat taaaagtgga aggaggcaaa   175920
```

```
ttaaaagaag cgaggaaaca ttcttttca caccagagaa acgttttcaa aacaccaggg   175980
aagcctcaga accaatccag gtactgcttt tatttctgaa ctctgttata atttgtgatg   176040
tcagaagctt ctatggaatc tactgatatg tgcagaaata atgtgctgct gtgcccattc   176100
tgtgttatac atttagaagc agttgcggta tcatgggata cataatattc tttaatccca   176160
atagggcttt caattctaaa tataacaaaa acagttggga aaggcacaca tacacaggtt   176220
ggcctgtaga gatggaggtg gccaatttgg tgtgttttga acagacgggg atgctctctg   176280
cgtactgccc ccacaccaca ggacagctga caggcagccc aaatgcccgt gcagactgct   176340
gaactccaga tggcttgctg gtgctggctg gcacgccttc aagtcctgcc tttcttgggt   176400
ccctaacaga attcacatta cctgaaattt cagggaattt gtggggctgg ctaaacagat   176460
tccttacata actggtgatg tgcggtcaga aagagaatag atgagtaaga ttgcattggc   176520
tgcctgtgtg tattagtttt cttttgctgc atattgaatt actgcaaact cagtggctta   176580
aaatcacaca catttattat gtcacaattt ctgtggtcag gcgtctgggc atgtctgagc   176640
tggatttcct cctcagtgcc acacagagat gctatcaagg tgtcggctgg gcagcatgac   176700
tctcgggagg ctcatggtcc ttttccaagg tcactcaggt attggcagaa tctggtttat   176760
tttggttgta ggattgaggt cccctctttc ttggtggatg tcagcagggg tcgatgtcag   176820
ctcctagagg tcccccaggc agcttcttgc catgaagcca tctcagggac tgtctcccaa   176880
tacggcgaca cgtatcttca agtccagcag gagaatctct tacttccagt cggctaataa   176940
aataatctta gataacataa cctaatcaag gcaatggcat cccatcctat ttcctaggta   177000
atgtaataca ctcaagggat gacttctatc aacctcatag gtccggctca aattcaactt   177060
cctgggatta cgggagggca tggcttatta ggtccttctg agtcataaat gctctaatgt   177120
ataaacttcc tagggtttct ataatatatt aacactgggt ggtaaatggt gtaaactggg   177180
tgacttacaa caacagaaat atattctctc ccggttctgg aggccagaag accaaaatca   177240
aggtgttggc atggttggtt tcttctggag cctccgaggg agaatttgtt ccttgtctct   177300
ctcctacttt ctgggggct gccggttaac ttttggcttt tcttggaagc gtcacttcaa   177360
tgtctgtctt catctttaca aggccttctt ctctccatat gtttctggat cctctcctct   177420
tcttaaaagg atactagtca ttgggtctag ggaccactgc aaatctgtga tgattttatc   177480
tccaaagaaa ttacgtgatc acatctgcaa agaccctgca gtagtacctt tttatccatg   177540
gttttgcttt ccagggtttc agttccctgt gatcatttaa tctctaggct tagtcagtta   177600
actcttgaga tattaagagt taatctcttg ctgtgtataa tttataaatt aaactttatc   177660
atagacatta atacatagga gacaacatag tatctataca atttgatact agctgcagtt   177720
tcaggccttg aaacatatcc tcatagataa ggatgtgggg tgttatatat ttccacatag   177780
gaacacattc tgagattctg gtggatgtga atttttggga cattattcaa cacagtacac   177840
cccgtcaagc tttgcccatg acctgacact gcccaatcct ctggtctcat cttgtgggga   177900
ctctccttca cctttctgg aatatttcct tacaacttcc tttctaactc cttaactcct   177960
aattcagatc atcttgggct aggagtaata ttcagtactc aatcattaga gaagatgggg   178020
tcaccaggag ataaataggt aagcagatag gtaggttgat agatatagat agttagatag   178080
atagatagat agatagatag atagatggac agacagacag acatgggtga atagatgatg   178140
gagatggata gatagaaagg tagatagatg atatatgtgt aagaatagat agataaatag   178200
atagatatga ataggtggat agatgataga tcgatggata gatacatgga tagagatgat   178260
agatataggt agatagagat ggatagataa atgatagaaa ggcagataga tacatagatg   178320
```

```
catagacaga tatggataca tggatagatg atagatagag atgggtagac aggtagatat 178380
atggtagata taaagatgtt agagatggat agatgataga gatggataga taggtaggta 178440
aataagtaga tataaattta gatagagatg aatagacagg tagataggta aatagacaga 178500
caggtaggta ggtagaggac agagatggat agatagacag gtagatgata gatggtagag 178560
atggatagat agacctctta atccctatgt atcaatccat ctctatagct atctgtaatc 178620
acacatgtat atgtctacat gctcattaat aacattttca cagcaggaat tcagtgattt 178680
agtgattatt gaattaattg ttgcataagg ctccctgagg gcaacactgg gtcttcttgt 178740
tcactatcct cagtgctatc attttacagt gggaggaagc ttaccttcct accaaaagca 178800
ttctgtggct ctgaagtggg agaaagatag attctctgcc acctttccca aaccagggat 178860
cctggttcca acatcaggat ttacctggcg ctgaaaggat tcattccatt gcattaattg 178920
tattcatgca catgagtatt ttctgagcat ctctgaggaa ggcaacagtt tctatggtga 178980
acggtgtgga gagcacagtc actcctcatt acagcactgg aagtaatcac aatgatgata 179040
acatacctg cattctatcc agagccattt ttaagattta aaaaatttac ttggcattat 179100
tttcttcatt tgagtagctc tttaaggtat tttgtgaccg ccccccccc ccattttatt 179160
tttccttttg tagagaaggc ataattttac tttcaccctc ttaagagttt tttctgatgg 179220
tcctgagaat taaatggaca aaggacagat cagcaggaga aaaacataca aacccatgta 179280
atttaaggtt tctgtgacat gagaaaaccc tcagatggaa acgaagactc aaagaagtgg 179340
cgacacttca gtgcttttag agaaggttga acaaagacag acgatgatgg aaaagtagct 179400
aacctatgtg gaggctaaag aaatatgtgg tttatttaa catggtcttt tagtacacaa 179460
ttctcttatt tcagcctccc cttctcaatg acaagaatgc ttttccttc tggtataggg 179520
agggcacagt ccatacagga gtttcatctc ttgctttcag aaaggaaaac aggatcagag 179580
cagctttctt gtacctgctg tttttttcct cccctcccct ccctccct ccctccct 179640
ccctccct ccctttcct ggcctggagc ttaaatgacc atacaccaac atagcatttc 179700
tggggtggca gattctgcca gccttttcact ttacatcctc ctgttatcat ctgaattttt 179760
gaattatcac tcacaacttt tgtacatggt ttcttaatat tttacaaata tctatatgca 179820
aaataatgt tcatttggca taccttatt ctttttaaa attttatttt attttatttt 179880
atttttaagtt ctgggatcca tgtgcaggac atgcaggtgt gttgcatagg taaacgtgtg 179940
ccatggggt ttgctgcccc taccaatcca tcacctaggt attaagcccc gcatccatta 180000
gctatttatg ctaatgctct cccttccccc cgccctccct gacagaccct agtgtgtgtt 180060
gtttccctcc ctgtgtccat gtgttccaat tgttcagctc ccacttatac gtgagaacat 180120
gtggtgttg gttctctgtt cctgcattag tttgctgagg ataatggctt ccacctccat 180180
ccatgtctct gcaaaggaca tgatcttgtt ctgttttatg gctgcatagt attccatggt 180240
gtatatgtac cacatttgct ttatccagtc aatcattgat gggcatttgg ttgattcca 180300
tgtctttgcg attgtgaata gcgctgcaat gaacatacac ttgcatgtcc acattgagaa 180360
accatctcac gcaagtcaga atggcgatta ttagaaaact catattcttt aataacatct 180420
ttgaaatgat gattcttcag tcttgaatca tcagtgcttc caggccatac cttcccatt 180480
cttaacttga atcctgactt cattcttgag cttgttggag ttgccctgag cttgatttct 180540
tagagtgaat tatcctgtga ttttactct atgcctaagt tagatggact ttcttagcat 180600
gctaatctct aaaaatacct tttcaaagga gagattggga aaggttttgt accaaaacat 180660
```

```
ggtagatctt gttccattat caactgcgtc tcgtgtcaga gagttctaag gtgagtgaaa    180720
ttgtgcgtgt ttgtagcgtg gtcataaaga catttcacag agtggatcgc aaacaaacca    180780
acagagcaca gagggcttga gagcaatggc agctggtgga agcacaggac agggcacagc    180840
gggaatttca tgggaccacg aaccaagaac agaacccatg accaggctgt ttttccttcc    180900
aggggcccag gctttctcag ctcagccttc acttgcatgc tgctttgagc atgtttggct    180960
tctttgagaa aatgagccac ccaagaggcc tacatccaag tcacctgcac tcagatccca    181020
gccaggagta tggagggccc atgtggggtg gagtggtgca cgtcctcacc accttagaca    181080
cagggaccac ctacctcatt ttagatggag tgggcagata tctgcacac ataccctccaa    181140 aggtgtcctc tattgtagag acaccttttg ttttctccc tcaatcctgg acattttgtt    181200 tgttttctt tatttcacta attttacaat aaactgccag gatatgtctc catgtctagc    181260 tcttttgtg aattattctg gaataacag cctctgcaag gctgctaaag tgacaaaggt    181320
atttttcaat cgcgtctgat ccttttcaga tatttccatc ttcctactcc atcatccatc    181380 tcttttaaa aattttgttt tgttttgag acaaggcctt gctctgtcac ccagattgga    181440
gtgcagtagc atgatcgtag ctcgctgcag ccttggtccc gggcttaggt gatcctccca    181500
cctcagcgcc cccaagtagc tgggactgca ggtgcacacc ccacgaccag ctaattttg    181560 tgttgttagt agatactggg ttttaccatg ttgcccaggc tggtctcgaa ctccggggct    181620
caagtgatcc gcctgcctca gccttcatgt tttctttacc agttggttcc ctctctttcc    181680
cacacttgct aagaccacta ctggttcact gtcacgatgt cacttacttt tttgactacc    181740
ttcagtgatc tttcttttct gatttatgta tatatttcct gagtaatgtc attctttatt    181800
aaaaatgtat atgtatatat gtgtacacaa agtatacat atatgtgtat atatcctaaa    181860
tgattctatt atttattgaa ataaataatg tatgtataat tatatattta tatataagtgt    181920 aagcattagt atataatgta tattatggat acattatata tacattttat acacaattag    181980
gttctgtgta tactatatat gtatgtatac agacatgtgt atatatatat gtgtttataa    182040
tatatacaaa tgattgtaac agtgtgtgta tatatgtgtt tatgtgtata tatagtatat    182100
atataacatt aatgtgataa aagtgtatgt gcatatatgt gtatttgtgt ttttgtacat    182160
actcatgacc acatttaaag aataccattg taaaagctga ccatataatc gtctatgcgc    182220
atatatatat gcagcaaaaa tgccatcatc ttcattaata aatgccttct ttattaataa    182280
atatacattg gttcacaata tcaacctcag cattatatac atttcaacaa acatgctcat    182340
tgttttaagc atacattatt aattcatatt tattttgttt taagttgaga ttgttataac    182400
tccctctttt ttcaaatttt tagctaatgg tacttttaa aaagaatgac tttattgtat    182460
tcaaattatc actagtggga taaataatgt aatgatggga aaaagcttcc tttgttccag    182520
ctataattat ctgtagttgt ttatttgttt tattcaactt aacattcatg ttttattcaa    182580
atcatcaata tataatgatt ttgttctgtt accaaagatc ttattgggaa ttctaaagta    182640
ataaattatt ttgaagaggt atcgatacta ttacactctt gattatacc tggatcaatg    182700 aatgttttta aatatgtaag cgttcttta tgtttcttgt tattttatat attttatgta    182760
acatgtgctg tacacttctt agagttattg ctagaacatt tatcatgaat gtgcaaagaa    182820 tttttcaaa tatatttatg tgcatatata tgacaaatca ttttgtgtta attttataca    182880
attctaaata ataagtgact cattctaaat tatttagctg attctctaga ttctcttct    182940 cttgttggat agtcatatgc aggagtgact ttattttgtc tccttctttc tgatatttc    183000 agttctcaat acttttaat aaaaacatat aggcttcgag tctgtagaag tatcttgaaa    183060
```

```
tatgatggtg atgatgaaca tcattgccct gtttatactt ttagtgaaaa ttcacttagt 183120
gcaacatttc ttttcctatt tgttgataag attaaaaagg atttcctgcc aaaataaata 183180
ttccatgtac tctacttttt aaattaaata cattaatagt accagatact atttgccatc 183240
tttcaaatag ctttttctc ctttgatctt tccctcagct atcacctgac ttctttcctt 183300
caactgtgaa tgagacaaag caaaacaccc tacttcttcc cattgaacca tcttactgta 183360
tttgtagagt caacctaatt ccttattagg tcactgcata gttttttttt aatttaatat 183420
tttacgctat ttattataat gatcattgga ggaataatca gaacgtgtta agattcttta 183480
caagtaactt ttacatttta gtgttcttgg cctttgaact gcgttttgga tgaagaactt 183540
ttaggatttt ctgtgcttgg gggtgctaaa ggtgtttaca cctgagtgaa tgcccagaat 183600
ttgatcatat agatttttct attgacagtc tcaccttctt atggttattc tcttgtaaat 183660
tatctttacc tcaagaccaa gatttgcaaa tatattgatt ttcagtagat gcagtgttca 183720
catagtatct cctgaaacaa tcacttttg cagtgtcttt tgtatatcac tggttgcgtc 183780
cctttactca gatctaaggt acatctgttt ctgtattttt ccttatgagt ggtctggatt 183840
ttaattcttt caatacactt tatattttat tggagtatgc tttgccaacg catccttttt 183900
atctcagact gttcttatgt ctctgtaata aagaaactgc atcttatttt actccatgaa 183960
aaatcacaaa tgattcccta agtgttcctt tagagtgttc ctgagaggac tgtggttgtc 184020
ttttattcta cattgtgtgt ctttttttaag actttattag cgcagtttta ggttcacaac 184080
aaaatagagg ggaacgtaca gagagttctc atatatcccc tgcccccata catggacggt 184140
cttccctatt ttccacatca cccaccagag gggtgtgttt gttacaatcc atgaacttac 184200
actgacatct tcatcaccca aagtccgtcc tttacagtag gctacagtct tggtggtggt 184260
gtacattctg tgggttcaga caaatccgta ataacataaa tccaccatta cagtatcaca 184320
cagtatagtt ctgcaaccct aaaaatcttc cataaaaaaa cctccacaat tttagcagtt 184380
tgtaacaaca aaggcttatt tccttttct gaagttcatg tcggttgtgg gtggacttgc 184440
ttgttactta ggtagactga tattagaagg tgggaaaaga ataataccct ccaggaaag 184500
gataggaact attttgaacc aataatacag ctcactacac aaaatgagtg aacacagtca 184560
cactgaaaga gagatgagtg acatatgctt aagttatgct tatgttgaca aggtctcact 184620
cacctaaact ggagtgcagt gccacaatta tagctcactg cagcctgcaa tccctggact 184680
caagcagtcc tcccacctca gcctcctgag cagctgggac tacaggcaca cacctgtgtg 184740
attttgttat ttatttattt attttatttat ttatttttaa tagaaacagg ttctcattat 184800
gttcctagac tggtctcaaa cttcagcgtt caagcagtcc tcttgccttg gcctctcaga 184860
gtgctggaat tacaggcatg agccactgcg cccagcctcc tttagtgttt aactgaacag 184920
aataaagaac ctcttcatta tggtgaattg gctaagttca aaagagtagc aaaagccttc 184980
gtgggcagta ataattactc tatcttccaa atacttgagt gacctatgc ttcttaaaat 185040
atatatttta gggctcttaa ttgaaatcaa ttgcctttat agcctctatt acagcatact 185100
cagaaattga agagcgggat gattttgtat aaatctagac taattttgtt tttctggaat 185160
gactagaacc atttaccatg tcaggtacac acacaagaaa cgctaagggc gagttgtgaa 185220
tgatttgact aggaacaata gttgggctgc ttttagatgt ctccttttgc tacatagaca 185280
gcaaaaggag aattcaccaa aggtgccagc ccttcagaat ccttgtccca caccaccaaa 185340
aagtcctgtg acagaaattc cacctattaa tcagctgctg tgtcctgact acggagaaaa 185400
```

```
gtatgatgca acagaacgca aacttttcca caatctcata acaaggaaaa aatatatgta  185460
tgtataatat gtgtacatat ataagaaaat gtatattaca tatatagtaa atacatacaa  185520
atacacgtat gtgtgtatgt atatatacac acatattttg ttttgttagg tatttttat   185580 gactatttat ttaaaaaagt cacattgaaa ataaaattga cttttatttg ccctaagtta  185640
cctcttgaaa tattgtgtta aaacctaat aacttctgac aggtatatat atacctgtag   185700
aggttaatat atatacgtgt gtttgtgtgt gtgtgtgtgt gtgtgtgtat gcgcgtgcat  185760
agaagttatt aggttttgtt tgtttgatgg ttttgttgtt gttttttgag atggaatctc  185820
actctgtcgt gcaggctaga gtgcagtggc gtgatcttgg ctcactgcag cctccgcctc  185880
ctggattcta gtgattcttg tgcctcagtc tcccaagtag ctgtgattac aggcatgtga  185940
caccatgtct ggctattttt tgtattttta gtaaagatgg gatttcacca tgttggccag  186000
acttgtcttg aactcctggc ctcaggtgat ctgcctgccc tggcctccca aagtgccagg  186060
attacaggcg tgagccactg cgccaggcat tattaggttt ctagtacaac atttcaagag  186120
ttatatgtat agatatgtgt acgtgtgtgt gtatatatat atatatatat atatatatat  186180
atatatatat atatataaaa cctctatggg tatgttaggt ttttaataca acatttcaac  186240
aagcatctta ggacaaatga aagtcaatta tgttctcaac atgacttttc ttaataaaca  186300
tacatttaaa aataccctagc aaaatacatt atttagtacc tattttaaaa cacactgtgg  186360
tttaatctca agctcataga ttcttcgaga taatattgtc tatcagctga aaattctaaa  186420
aaaaaaatgg gaaaggctca tgtaaatata ataggatttg tatttcattt ctgaggacag  186480
aaacatttca atagtaaaat ttgcaacaaa aagtgcttat ggaaagttag acaatgctct  186540
aggactctaa tagtaagcac aggaatatgt cagagaccca taaaatcttt agatttattt  186600
tgattcctac ctgtaaaagt gtgaaatcaa ttattgctaa atccagcaaa acagcaaagg  186660
aaaattacta ttcaccttt tctctcagtc tgtcttccaa agctactaag agaaaaacaa   186720
gaaaaataca gaaaatccta cttccattat tacaatgaag catttttgag ctagtagaaa  186780
attagaatta gaccttgctt ttactggcat cacaaaagca tttcatcctg ttttttgaaa  186840
tgacaaatgg cagaattctt atatacaata tgctaaccaa aatcatgtta ttgccacgtc  186900
atgaattata atttaatttc tactctcaaa gttaaataag aagatacaat attgcatttc  186960
cctgcttgaa gaggagaatt agttacactt gttacgtaaa ggctgtattc atcactggtt  187020
gtcatagctg ttatgactgt gactcttata atagaggtgg gcttgcagcc aaaaatatat  187080
gattcatcca aaagatattt accatgtaac ttatattata tgtgctgaat attttggtag  187140
tcattgcaaa ttaaggaata tggtgttgaa aaatcacagg taacaccttt ttcttgttgc  187200
taacaatcta acagggagac cttatttaac aagatatcat attacacatt acaattcatc  187260
ttgtgaagaa aaatgccaac tacagtgaat aattgaggaa cccaagttca tttacgaatg  187320
gaaggttggg atgaacaggg aatgccttc tgaggaaatg gaatttaagc tgatcagtaa   187380
aaatgaatct tccaggagca tatgggcttt gcagatggga gaaacagcag agaatgccca  187440
aaagttctaa aggaaacctg atgatgaaat gagttaagcc atgttcctgg tagtgtatca  187500
gttagctttt gctacataag gaaccatctc aaagccgagc atctcaaacc acctttattt  187560
agctaagcat ctcaaacaac ctctatttag gttatgattc ttggctggac atctgggctg  187620
tgctcagctg ggaggctctt cagtctagag tcagcttcca ggtctgttgg gtgctcattg  187680
gccaagcact atcttaacag ggtgcttgac agtgctccat gtggaatatc atcctctaac  187740
aggctagtat agactcttca tggaagcttg tcagggttgc atgtaggtgt gttcaagtcc  187800
```

```
tcttataatg aaagctaaga ataaggacag tgtgtcaccc cccacatccg gaatgtccaa  187860
ataagcaaat ccagaaagac acagatgaat gggtagtttc caggggctga gagtgaccac  187920
taaatggtac catatttttt tgggggggat catgaaaatg ttctgccatt agatattgtc  187980
aattattgca cagatccatg aatatattaa aaaccattgg attgcatact ttgacacggt  188040
gatgtgtatg gtatattaat tatatctcaa ttaagcaatt atatctgtct atcatttatc  188100
tgtaaaccag ataaaataag acaggctagg tatatagaaa aatagaacag aacaaggtag  188160
gcagaaacag aatctagcag atataaaact tggcatgtaa gtaaagagct gtaatacctt  188220
tgtagctgaa aatggaactg ttctctaagg aaataattaa aataatctct atgctctagc  188280
atccagataa ataaattcca ggtgagttat gacccagatg tgaaataaaa ccttaaaact  188340
gttaggagaa tatgtaagca aataaaatgt ctttatgttt ctggattaag taatccttt   188400 tttttaaaaa aagcagaaat tatagagaaa atagtgataa attataatac ttatgcattt  188460
taaagcatta gtttagataa ttaaaaatca ataaaatggt taaagacaac agactagata  188520
tcaccaatgc tcaactgtgt aaacttgggc aaattattta atatctgtat acctaatttt  188580
cctcagctat aaaatgatat tagttacaca tctcataagg tatttatgaa gattgcatat  188640
tcggagctgg acacagtggc tcacacctgt aatacagcac tttgggaggc tgaggtggga  188700
gacttgcttg aggccaagag ttcaagacta gcctgcacaa catagtgaga ctttatctct  188760
acaagaaata gaacaaaatt aaccaggtgt ggtggtgcac acctgtagtc ccagctactc  188820
gggaggctga ggtcgaagaa tcactggagc ccttgagttg gaggctgcgg taagctacag  188880
ttgtgtgact gcactccagc ctgtgtgaca gagcaagact ttgtctctaa aaacaaaca   188940 aacaaaatgc atattcaaca tgcataaagc ccttagaacc atacgcagca ctgctatgca  189000
ctgttaaatg tttgctttta catgctcaaa aagaggccag catccatgaa tataaagatt  189060
tcctacaaat caataacaga cattcagcca gtcaaaaatt ggattgctat tcaagatggg  189120
aatttagaat gggaatatag aaatgcatct gtactagttt taaggaacat gcaaattgaa  189180
atataaactg ttaatatttt atactcatca aagtggcaaa tgtattgtct gataatgtca  189240
agtgttggca cagggtaag  ggccaggaaa ttttcttacc tgctagtggg tgtatagcat  189300
aatacaactt gtttggaaag aaatatgcca gtatctactg aagataaaat tagtattacc  189360
ctatgtatca gttagctact gctgcataac aaaggactct aaaagtcaat gccttaagac  189420
aataagcgcc tattactgct tatgagcctc tgcatcttgt tagctggaaa tttattttgg  189480
tcttggctgg gctcattcat gtgtatgcat tgttgatttg gagtgagttc tcttaggtaa  189540
ttgggggttg ctggaggtaa ttttgcctag gttagggcca atgggttctt ctctatgaga  189600
tcttttgttg tgcaacctgc tagtctgatt tttcacagga cagtggcaga atttcaagag  189660
agtaagaata ggtacagggg atttgagtcc cagtcttgga aacagcacat cattatattt  189720
tttcttttga aaaatgcaa  tcttaaagcc actcaagatt caaggggtga aagtacagac  189780
tctctatgta tgaggaatag taaattcatg gggaggattg tagaactggg aacctttgc   189840 ctgtcagtgg actacaccct gtaattcaac aattgtctat ctagtagtta tgtgccctgg  189900
aactggggtc ttcaaactgg cagatgtctt ttcaaaattt tcaaagtat  gactctgctg  189960 atgattttaa agaaactaat tttcaggtac tcagccccca gatgttctcc tttctaagcc  190020
ttcctggtca ccaaaagctt cttcccacat cacaaaagga tgaccttcag taggcatgac  190080
actttgttac caacctttc  tgccagggtt tataatacaa gaaatatctt tttgaatgct  190140
```

```
gctttctgga aagccccttt gctgaaggct ccataaaata agcctcctat cttatacata 190200
tttccattaa gagtgaagtt tggtcctgtt caggtgttct gatttcagaa aaagaaaaaa 190260
gaagccatag gtcagctatg gcagttcttt caaatgcaga aactgaactt ttctgttgct 190320
aaccaatttt tcaaggtgca tatacattgg gtgaagccca tcggtaaatg atccaatccg 190380
aaaatcatct gaaggtcatc tttcaaattc attgtggtag tgttattcaa gtggaggctc 190440
aaatatattt caagtgtatg catggaatat tttccccagc tagagtctgt tctccaggtg 190500
tatggaggaa agaggagttg tccaggttgt gtacctgttc ttctcatctt tctgggcta 190560 ttcatgtcct ttctgtgccc tcagcctcca acccatgctt ctgctcagag cagcctgttt 190620
tctttgctcc cataaatgta ttcctggccc cagatcttct gtgcatattt agaagcccta 190680
acccacttcc tcaccagcca cccctctatc cccagactct cctaccagga acagcagagg 190740
atcctaaatt catgcatgca ttttcctgcc ccgttggaat gatctgtgtg catgtctgtc 190800
tctgatgttc atctccttct tcagtgtggg tgtgtcatta cctcttttag ccaggactgc 190860
atggcattac ctgtcttagt cgggactgca tgttaaaagg gtcaacacat atttgtagaa 190920
ggaattggct tctgagtgaa tgaacccatg tgtcatgggc agtctgtgag gacataccag 190980
tcacttcctt gctgccgaga gctggggata ttgcattgga ttagaagatt aagcccatat 191040
tactctatgg ccaagtgaca aaataatcaa tcacatccac atctgtgata gccaggaaaa 191100
catttctttc cgtgcccctc ccccaccccc cgccgtatgc aactttccct gtgtggaaat 191160
aatgtactta gcttaaaaag tctctttctc tacttaacaa gactaagttg aaaattaacc 191220
ttgcccactt aaaagaaaac gaatatgcag taaactatga actactaata cagttcaata 191280
tgatatctca tgcagaacaa taatgctgaa ggttcttttt ggttctatta tttccttata 191340
ttcttgctta gataagatca catttgtatc tattgacttt ctatgatgat ttagatacat 191400
aagtggcaat aattaatata tattaaaaat acagatttaa attgttttc tgacttgtaa 191460 tgttaacagc agtatatgtg actgtgaggt tttcctttga tgttaatttt cactttgaca 191520
atagtcttcg ttttccaatt tttttaatt tttttatttt tattttatt tttttttgtg 191580 ataaggtctg gctgtttcac ccaggctgga gtgcagcagg gcgatctcag ctcactgcaa 191640
cctccacctc ccaggctcaa gtgatcctgc cacctcagtc tcccgaatag ctgggactac 191700
aggcatgcac caccatgtct ggctaatttt ttgtaatttt catacagaag aggtttcacc 191760
atgttggtca gtctgttcca gaactcctga cctccgccca cctcgacgtc ccaaagtgtt 191820
gggattacag gcatgagcca ccgcgcccat atcattttcc aaattcttta caaagttttt 191880
ctcttacatt cataacataa agtgctattt taaatagact aactttgaa aataacatag 191940 ataaagcact aaatggggac atcagaggaa caggctaaaa aaagctgga atattcttca 192000 ggattaggga cattgagatt ttatttataa aatgatattt aaattttaat aatagaattg 192060
ttgtactttt gcttggagta tttaaatctt ctctttaata tttaaagcca gttctgcaca 192120
gaggttttac ggagatgcta attgttgtat gaaaaggaat attattctgg aattttgagg 192180
aagggtagac atagagaaga taaaggaaac tcacagccta cctaggtttt atttgggctg 192240
tgtgtgtgtg tgtgtgtgtg tgtgtgtgtg tgcgccagcc acaagctggg tttattcttg 192300
aataaactgt agacaaattg ttttttcctga atcttctaaa acctgcattt acatagtcca 192360
tggttgtgtc taaactagat actcaagaga acttggtttg ttttaaaggc atttaattag 192420
ttatatttac atggacaaat agagcagcag tttattaaaa aagaatgaaa ggataaacaa 192480
attaaatata cgtagaacag gaaagacagc atctaattat gtttctgggt caggctctga 192540
```

```
tatacaagat taatttaaaa ttgggatttg gcaagtaatt tctatcgaaa tctcagcagg 192600 agttttatt gcaactaaca agctgatttg gaaagtttca tggaaaggca aaggatctag 192660
agcaatcaaa aagaccttgg aaaagggaa gaaagttgga gggcttccat ttctctattt 192720
taaaaggtac tataaagata tagtaatcaa gatagcaggc aactcacatg gtataaatt 192780 tagaccaatg aaatataatt aattacagtt ggcccttgaa caacgtgaag gttagaaccc 192840
ctgcacagtc gaaaattcac ttaaaacttt ttaccccccc aacacttaac aaccaatagt 192900
ctactgttga ctggaagcct taccaataac ataaacagct aattatcaca tcttttgtat 192960
gttatatata caatgcactg tattctcaca ataaactaag ttagagaaaa gaaaatacca 193020
ttaagaaaat cataaggaag agaacatata tttaccactc attaaataga agtggatctt 193080
cttaaagatc ttcatcctca tcttcaggtt gaataggctg aggaggacga gggagaggag 193140
aggttggtct tgcagtctca ggggtggcag aggcagaaga aaatccacat ataagtggat 193200
ctgcacagtt cagaactgtg ttgttcaagc gtcaattata agggtttaga aataaatcct 193260
tcaatttgta gtcaatagat ttttaacaat ggtgccaaaa caattaaagg aggcaaggat 193320
agtcttttca ataaatggtg ctgagacaat tggatattca tatgtaaaaa gatcaatttc 193380
aactcttacc tcttattgta cccaaaaatt aactcgaacg acaggtggca atataagaat 193440
taaagctctt aaacttttag gaaacttcag caacacagga gaaggtcttc agggccatgg 193500
attgggaaag atttcataaa tatgacctca aaagtacaat ccttaaaaga attgatcaag 193560
tgaaactcat caaaattaaa aacttttaca cttcaaaagg cactattgag aacataaagt 193620
gctatttgtt gagaaaacca aaagacaagc cataaactgg gagaggagat ttgccaacca 193680
tattcccaat aaaagacttt tatttagaaa atatgtaaac aaaccactta ctattcaata 193740
ataagaagga agaaattat ttttaatgg gcaaaaataa attaatagac atttctgcaa 193800
agacagtgta catgagaaga tatttaatat cattagttac taaacattag ctaaatgcaa 193860
atgaaaacta caatgaggcc aggtgcagtg gctcatgctt gtaatcccag cactttagga 193920
ggccaagatg agtggatcgc ttgaggcagg agttcaagac caacctggcc aacagggcaa 193980
gacccatgtc tactaaaaat acaaaaatta aacaggaata gtggtgcatg cctgtagtcc 194040
cagccacttg agaggctgag gcacgagaat tgcttaaacc caggaggtgg aggttgtcgt 194100
gagccgagat cgtaccactg cactctagcc tgggcaacag agcaagactt tgaaaaaaaa 194160
aaaaaaaaaa cctatgatga gacaccattt cacatccatt agtatggtta acaaaaaaa 194220 ggatattagc aagtgttggc taggtattag agaaatagac accctttata ccaccgttgg 194280
tgagaatgcc aggtattgca gctgatttgg aaaatagtct gtcagtttat taaaacatta 194340
agcataaatt tgccttatga aacagcaatt tcacccctag gtatctatgc aatagagatg 194400
aaaacatata tccatgcaaa aaatagtaca caaatgttca tagcagcttt attaataata 194460
atcaacaagt agaaataaac caaatgtcac tcaacaaata aatggattta aaagatgtgg 194520
tatacccata caatggaaaa taatttagcc ataaaaagga atgaagtatt gatgcatgct 194580
acagtatgaa aggacattga aaacatatgc taagtaaaag aaaccagaca caaaataccg 194640
catattatat gagttcattt atatgaaatg cctagagaag gcaaatctta taaagacaga 194700
aagtggatca gcaaggctat cacacccacg caccacccag gtctggtttt aaaaggtatt 194760
aagcccccat gaaatggaca ttacttgact tttgtttgat atatgaaac agcattatca 194820 agtcttggtt tcaaaatatg tttaagctct tctgagttat gtagaacaga ggagtgtttt 194880
```

```
ccattcacaa gtgttggaga tgacagtatt ttcccttgc cttaatccgc ttatcctaga    194940
accctatagg aaggcaaaga ctgtcttgat tgattgacgc agttaaagtt attgatagtg    195000
ggatatgcac atatgggctg catctgtcta tgagaaggaa gcaatggagc caattaatta    195060
attcaagcaa aattaaatgt tcacacctt taaatgtgga aactataaaa accaaaatgg    195120
tgctctgtgc actaagagca taagctagtt ttttgctatc cttaagggcc tcttcctgca    195180
ttttgcctat attaaaattc ctatgcagat cttattgagg tgatcaaggt agatgacttc    195240
gatttttatt ttcttcaaca aattcacgta ccaataactt tcaaatgata tttagtaact    195300 atttaaaca cagaggacat gatcttcaaa cgatatttaa tagctatttt acacacagag    195360
ggcataactt tcaaatgata tttaataact attttaaaca cataggacat ggtctataat    195420
gttttgtcct gacttaaata tttattgcat gtagtagatt ttaatagaag aaaacaagag    195480
tgaatagtgg gtagtgcttc tctaaacaca gagtagaggt aaatcttagt gatttaaatt    195540
agtcacaatt ctgactttt gagattgcat gtttataagt ttttaatgca tgaaattaat    195600
gtcaattata taatatttg aataaagtcc ttccatgttt actgtgtttt tgcttgcctt    195660
atgaaaattt ctaaccataa tgtgtcagta acatttcaaa aatttattta aattacaaca    195720
tgttaacatc agaggaccat tgaatacgcc ataagcattt ctttaaagaa tgtgggaaat    195780
gtcttttcta ataatttaat ttttttctttt tttaaaacaa ctcacgttag catttttttt    195840
tttgcagtag catcatttta accccaact gcatattcac aggatatcta atatttttg    195900 caagtaacat tttgaatttg ttcttcttga catctttatg tttatatgca ttttgcattt    195960
ccctatctca tttttttgaa atccaaatgt aacaaatttc aacttttgt gttacattct    196020 tttctttttt tctttttctg ggtagcatct ctctcttttc tgaatttttt gaaaacctgt    196080 tgttttgaa ttctcttttt tccctttatt ttccttctca atatgacccc aggagccaac    196140 acaagaaaa acgcagatga tataacgagt aatgaccgtg gtgaagacga aggtattttt    196200
tgttttttca aagctcaacc ccagtgcatg attttatatc tatctatctc tcttttttttt   196260 tttcatttca atctgttttt tctcccctta tttaaaacta gtacactttg gtgtgcttcc    196320
ttaattattt tcttcttgta tagaaaccac tgtcattttt taatcccagt taccatgtac    196380
aggaaacaaa tcactgtgag aagtataaac attgtttcta aacatgaaaa gagtaatgaa    196440
ctactgttta cagagaagcc ctttttttt tttttttggc ttggtcgcaa gaagagaaaa    196500 tggaattta aaacatgcat gtatagtcta ttttctccct tccaaatgtt attttgtaag    196560
ttaatatact acttggagc tttggtcttc ttaattattt ttatgaacta caaaactgta    196620 cagcaccta gaagaatttt ttttggggg gggggggctg aaatatcagt ttttttttc    196680 ttcacaaaca tattgattcc aacatagatt tctgataatc tgctcacagt gaagtacacc    196740
aaaaagtgtt ttaatgagat gctgttgtta acgagccctg atgcattcag gactgccttt    196800
tacagcattt aagggggggt ggggaagata agagtatctc agaactgaaa aaggacaaaa    196860
agctagctat gttcatcttt cttttcacac cacggctttt ttgaaaacgt ttttctcctt    196920
aaaatgtttt gttgctgtga agtttcttct taaggctacc aaattgctca acacattgtc    196980
taccagaagt gaaaggattt tttttaaaa gatggtaggt ctgaggtact catgcagaca    197040
actcgcatgc tgtttttctg cccttctgc acaagaaatg attttttttt tttttaaaga    197100
ggagaagcaa caaaaaagt actcaagcaa gcccttcttc attggtaagg ctctatagga    197160
ttagctaaaa gcacattttt cccatctggg tagcaaaatg catggaactc cattaaggtc    197220
ctggctggac ctttgggtct ctgtctgaaa ggcaatttaa agcccaaaag tgagtcctga    197280
```

```
attatccttg ctggtcaagc ccaacgtcca tgacagggtc ttttgaccaa ttcttgtagt    197340
tgctcccctc cttgcttatc ttcataaatc aactgttctc caagaaaaga aatcttgcca    197400
acacccttgc tgtgcccagt cttcccttaa cattttgagt attgttactt ttactgagct    197460
catagagctg tcactgtctc aagtagctct ctgagagatc tccattctga tggccatagg    197520
agatcaaaat ctacacctgc ttcaggtagc cccttctttg ataagggctt ctgaatgcct    197580
gacattttat cagtattgag caaatacata aaaatgaaat aaacttttgt ctcatatctt    197640
atactgctct aatttgtatc ctgtttggcc ttctcttttt aatacatttc ctctcgataa    197700
ttagaatctg ttttcacagt gttcccagtg aatcttatt accattaaaa tgccatctaa      197760
ttttcatttc atattgttaa gttatgattt tttgactttg cattaatata acagctggtt    197820
attacttcca caagttcaag agagtcttgt tctatatttt atgaaaggta agagatgtta    197880
atctcacata ttttccaagg gagcacttta aagcagccct tcaaaatctc tacttactct    197940
tttttccaca atttactagg caaccgctgg taatggtaaa agaaatgagg ccaaaaacag    198000
caaattagga accagaaaga agcagtggat catgagaaaa gccatttctt attcatatag    198060
cagaagacat ttcccgtagt gtatgatgaa taaatgatta atagaagatt tttacttcat    198120
atttgaattt tatatgagaa aacaaaagac acttttctgc cgtggattaa atatctgcaa    198180
ataaatactt gggtaacttg acactctttt gtgtgcttta ctgtgaccaa tgggtatgtc    198240
gtgtcttctg tatgcaccca gtaaaattgt gatcataatt cattcaaatt ggagccacca    198300
tccaaacgat ggtaattcat atcctcagaa ttcctttgtg gtatttcaaa agtgtccctg    198360
tggattatga ggaaaaaaaa actttattga tgaagaaatt gaaataaat atgcataaat      198420 acttgagttt tcttttagtt acaaagatat ttaaattgta cacacacaca cacacacaca    198480
cacacacata tctgtatcca gaaatattta tacgtgaggt cagtcttcca aagattaaat    198540
gcagccctaa tggctgatta atgttataaa acaggtcttt ttcacaaagc aggccctaca    198600
gatggtctcc aactttctat catcacagat cattgttttt acatcattgt taatttaaat    198660
aataaagtaa attaccaaga ggaatcattg gttgcaagtc acaatgggag tttatattcc    198720
ctgtgaaaat ataaagcatt taaatagttt ggattctttt gccattttt attacatctc      198780 ttttatttt gtcacctaag tatgttagta tgttactgta atcactggaa caaagacatt       198840
tgcttggaca tcttttcttt tttttcccta tttctgttca gttaataatt tttaactgtt    198900
gattttgctt tcttgtcatt atctgtccct tattgatagt ttatagcttc actactactt    198960
ttatgttttt attgttaaat tgaagatgaa tctgtacact cacctgcgaa ttaagatgca    199020
actatattaa aattaattat aattttgaag ttgattttat acttaattag aagataaaat    199080
atatttcatc aagggtccca tgtgtttatt caatttaaat cacattttag ggtttgagca    199140
aaatttagga aatgtgtact ttacctaaaa ccatttcttt tagtgcttta gatatatata    199200
gaagcttaga tgagcagagt acgctaaatg tctgtatgct tcttaaaata ccatttccat    199260
aaatagaaaa cgtaatagca ttgatcattt tccttagaca ctcttatcaa gggtcatatc    199320
atccataaaa ataaatgtgc ttaattcaag tcaaaatagg gaaatcagtg aatctccttt    199380
tttcttaatt tagcattggt gagtcagtgt gattcttat tgtgtttcct tacttggctt       199440 tttttttccag atattcatga tcagaacagt aagaagcccg tcatggtcta tatccatggg    199500
ggatcttaca tggagggcac cggcaacatg attgacggca gcattttggc aagctacgga    199560
aacgtcatcg tgatcaccat taactaccgt ctgggaatac taggtaagtg atttcatcat    199620
```

```
gtgaatgact gagcaagagg aaacatgaaa agtccacttc tcgttttgac ggggctcgtg    199680
gatttgaatc ctgttattcc agttcctggt taattccact tcacggtatt tactttatgt    199740
gattggatat gtttattcct tttactacct tgtgcaaca tggtcatgaa tcccttctca    199800
aaccaatgca gactttaaga tcttaaagat gaaatgaaat tttatttata gcatgtttct    199860
cccttggagt tcaatgaatg tatgtttgtc tacatagacc tgtacaatga acacatattt    199920
ggtgatatta tagttgggaa tggccataga tcttagcttt cttttctgat tgtgtcattg    199980
tatgaatcag tatattgtgt ggaggaaaag attttatcca attctctaac tgattatgtt    200040
gagcctttgg aagatctgtt gttttggttc cattgcattt gcatgcaggg aaacttagct    200100
gttagttgac ttttgtccat tgatgatcta cgattaaagg ctaaatacat ggaaattcaa    200160
gtttagttcc tccttgtttt gatgtttcat ttcttttctt tctttctttt tttttttttt    200220
ctttgagatg gaatctcact ctgtcgccca ggctggagtg cagtggtgcg atcttggctc    200280
actacaacct ctgcctcccg ggttcaagtg attcttctgc ctcagcctcc caagtagctg    200340
ggactacagg cgcatgccac cacactcagc taattttgt gttttaata gagacagggt    200400 ttcaccatat tgaccaggct ggtctcgaac tcctgacctc gtgatccgcc tgcctcggcc    200460
ttccaaagtg ctgggattac aggtgtgagc cactacgccc ggccatcatt catcttcttc    200520
taattgtagg ttggaaaatt atacatcttc agagtcagat ttcagtacct tctgagatgg    200580
cctttcctgg tgttggttag tttgtgaata atattcctaa gacctatgta aaaacatttg    200640
ttttccaggc aaaaatgcat taaaatggta tagaagataa agttttttaac aagttagcca    200700 tgagagagat gtgtatattg gttccagtgt gattatgata caatatgaaa tacaaaacaa    200760
aatgaaggcc aggtgtggtg gctctcgcct ataatcccag cactttggga ggcccaggca    200820
ggcagatcac ttgaggtcag gaattagaaa acagcctgac caaagtggtg aaaccctgtc    200880
tctactaaaa atacaaaaat taactgggcc tgatggcagg cgcctgtaat cccagctact    200940
caggaggctg aggcgggaga atctctggaa cccagtaggt cgaggttgca atgagcgag    201000 atagcgccat tgcactccag cctgggtgac cgagtgagac ttttctcaaa aaaaaaaaa    201060 taataataat actagtaata aattaattaa aataaaaagc aaaataagat ggactaaagg    201120
aggtctgtca aacaagaaat atgactgaaa atgttttctt caaatatggc caagaatatt    201180
ttcttttcaa tcagatgact tcatttcatt ttgagtgggt tttttttttt cctatgtgaa    201240
aacattaacc tgtaagaagc cctaaaaggt ggtgaattgc tgagaaaccc taagaggtgt    201300
tgtaagaaac cctaagagaa atgcatttct tactttgaaa tgcaaatcag tcacaggtgt    201360
tgctaaagtt gtatcttttg aaacattgat aaagaactca aaattccagg ttggtttctg    201420
cattaaagaa aataaacacc accaaaaaac cttttagtgt caaaaaactt attatgtcgt    201480
tggctttatt tcctatattt tttgtagttt tctgtgagcc acatcttggc ggaataatgt    201540
ctctgaactt ttgcatagca gtaattgcac gcttcactga atagttttca gaggcgctgg    201600
atagttgctt tggctactag tgttggaaac aggaaattgt gcttcttgat gttttacaaa    201660
aggttcattc tgacaaagag gtggaaggag gaaagtatgt gtgagggcat tgcacaggcc    201720
ctcttcaaag ggagcagtgt gtgcactgcc tgtagcacgg ccacacgaaa gaaagcttgg    201780
gcatgctttt ctgagggaag cagtgggcat caagaaaatt cttgctttgc tggaaccaca    201840
caatattctg ttgcatgcgt gatgaattga tgtgtctgat aagatagagt ttcaaaataa    201900
attgatctcc ttttcccct aaagctcagt tgtatcaagc aactctacac tatgattttt    201960
tttttatcag ttttgtccct tcgtgaatca attgcacatc ttgcaaatta gcctggaaag    202020
```

-continued

```
tatacacact ttttttagag gaaaaaaaaa ctaattgaaa aattgttaag tctactttt    202080
gttatggaga gtttttaaaa gtcataagat aacagagagc tgtaaaattg gtggggaaga   202140
aataaaagaa gcgatttagc atctctatgc cggtctattt acattcctcc aatgagctag   202200
tgtggaacag ccaagcacac tacagaccc ctttcatttg atggaatgaa atgtgccaag    202260
tttgccgatt ttacaggacg atagagactt taaaatgtga ctgcgttggt ttttatcatg   202320
gatcttgcat ttactattgt cctcttgaaa acagctaggc ggcatttact ttttgcttgc   202380
aggaaactcc tattatcggt cttgaaaaaa tgttttaaa cctttggcat ccagatattt    202440
aaaaagatga tcaaataaaa tacacagcag gcactgcaat gatcatttca gtgagtgcat   202500
ttcatacaag tagatacaat tttaggcaaa aagttgaaat attctttgag ttcttttct    202560
tccagtaaaa gtcataaatg cataaatgtt atcttcctac ctgaggaatg gaaaatatt    202620
gttttaagat ttttttttt taatggagta acaaatgcta ttctctgtta cccaaaagag    202680
aggattaaaa agatgaaaca tgcccataat ggaagcggaa tgctggcatt ggaagaatg    202740
tagatcgcag ccagagacag acaggagcta acaactttcc tctacctctg ccttgagaaa   202800
gtcagctagc gtttcctcag actctttcct tagatgtaga aggcagtggt ctctcccttg   202860
caaggttgtt gtacagtata aaagttccat ggttcaaaat accacacttt acctcattaa   202920
tatataatct gcttgtcaat aaaaaaataa ctttttttct ttcttttttt tttttttga    202980
gatggagtct cgctttat gcccaggctg gagggcagtg gcatgatctc ggctcactgc     203040
aacctctgcc tcccgggtcc aagcgcttct cctgcctcag cctccgcagt agctgggatt   203100
acaggcgcct gccaccacgc cccgctaatt tttgtatttt tagtagagac ggggttttgc   203160
cattttggcc aggctggtct caactcctg acctcaggag atccacctgc cttggcctcc    203220
caaagtgctg ggattatcag catgagctac tgtgcctggc caaaaaataa cctttaaaa    203280
aagatttaat ggactcatgt agatgaagtt tcataggctc tcagcagcaa ccattatacc   203340
cagtcacact acaatttcta gtgttattaa taccattatg cattgtatta atactactgt   203400
ttatccacag taagaattgt agctgaccca acctgtaatg gctaactaat atctatcaaa   203460
tattggcatc cagactgaac catgttaatt taaaataaca ttacaagaca cttgtagaca   203520
ttaaataaat cagaagatca tcatgtttgc tatttttaa aaaataatca gaactgtgct    203580
acacaatctt gctagccatt ggccatataa tttatgatcc aatccaggac atgtttgaga   203640
gttgctcatg tgctatgaat aaactgggat tgtcccaggc aaattgagat gtatcattat   203700
agctataaag taattattta tatctacatg aagtgtcttc tgattgaatt ggtgttcagt   203760
ttgtttttaa agaagctgca cttctataaa cagatttcct atgtgttctg ctatacaccc   203820
ttgtcactag gaaggtgtat atgttaccag aaagggatcc taatccagac cctaagagag   203880
ggttcttgat tctcgtgcaa gaaggaattg gaggcaaatc cgtaaagtga agtaagttt    203940
attaggaaag taaggaata aagaatgact gctccataag cagagcagcc cgagggctgc    204000
tagttggcta tttttatgat tatttcttga ttatatgcta agcaagggt tggttattca    204060
tgagatttcc gggaaagggg tggcaattat tggaactaag ggttcctccc cttttagac    204120
catataggt aacttcctga cattgtcatg gcatttgtaa gctgtcatgg tgcttgtgga    204180
agggtctttt agcatgctaa tgcattgtaa ttagtgtata attagcgtat aatgagtagt   204240
gaggatgacc agacatcact ctagttgcca tcttggtttt ggtgggtttc ggctgttttt   204300
ttttactgca tccttttatc agcaaggtct ttgtggcctg tatcttgtgc tgacctcctg   204360
```

```
tctcatcctg tggctaagaa tgcctaactt cttgggaatg cagcccagta ggtcccagcc 204420
ttacgttacc cagcccttat tcaagatgga ggtgctctgg ttcaaacgtc tctgacatat 204480
atattcaaga atttggaaaa cctcaagttc accaatgcct ctcagattag tcattgccag 204540
ggtgtgtggt gttcctatct gctcagaagc cagaagccag caaaatcctt gctgagctgt 204600
acgtgccagg gcatttgcct ggtctcacct acccacttga gtacctatgc cctatcaccc 204660
attcacctca caacatccat acgtatcatt taccctaag aagattagac attaatccag 204720
gtaataaact ttcagaacaa tcacctccag acagaaactg cagaggataa tctgataaat 204780
ctgaatccct gtaaggccat tactgaatca ataaatactc ttttctccat cttagttcct 204840
tactttagta taacttgagt tctccccaat ctgttttttt tttgttgttg ttgttcatga 204900
tagtccaaag accttcgatg taaaagagaa tgcatcttgc tcatgctttt tgatggaaat 204960
acctggaact tatttattcc ttcccctttc cagttgtctc caagtgcaag tctgtctgta 205020
cctgcagtgg atttcatcta cctccattta aatatgtatt tccgtttagc tcacatggta 205080
ctatcacctt tttggtgatc ctatgacttc atgcttcatg tatgctgaaa ttaattgttg 205140
cttcaaaaga gtcccaacta tgtaacatca actcattgtg tgcctctatg tggctggcag 205200
atattacttc atttaatctt cgtaaactcc cttggaagag ttaaccttat gtcctaccta 205260
tgaggagatg aatgctttga ggtaatggga tttactcatg gcatcacacc ttctagcagt 205320
cagagcaggg actgaaaccc gggtgtaact gaagccagag ctctgactta ccactcagaa 205380
ctcatccaca gccttcttaa ttaatgtcaa gtatgaatta gtaaaccatg aatgagtga 205440 agaaattgag tatcacttta gcatcagatg tagcttttat cattatgcaa aaagttctt 205500 actgctgatc aagatacaca attgtgataa gatgcttaca gtgtattttt aagttcctca 205560
aagtgggtcc ttgaaggctg attcatttcc attcaatcga tactggtttg ctttggttca 205620
cggtgatggt ggcattaacc acaacaatgg catttgtcac atcaaagctc ttcggtgcag 205680
tagaactagt gtttcatcag gaaatttggt gtcctacccc cagttcccat gtcattgctg 205740
gcttgctgtg tcgtgtgcat aaattgagtc aaatgatcat ttcggtgcat ttcttacaat 205800 cttttcacata ttatagctat cctgaaaatt ttcatctgag ggtagattgc gtcatggtct 205860
tctgaagttg tctttctctt taagaccatt cattgaataa acctattaga cgctttggag 205920
tcataattga atataagaca gaaatggttt gatataaaag caaccaacat gcatagcaga 205980
aacagcattt gtagtcataa tttgggtgac ttaacccata tgcacgtgct cagcctaata 206040
atgtggtcac tttccctgtt ctggtgtccc ttgtagggtt ttcctctgaa attgagggag 206100
ggtgggctga gctctgaagc attcttgcaa catcggccag agtggtctca cctttatgct 206160
tttgtgatat gtgtgagcca tgtaatattc cactcaacaa aagaagcctg gaaatcatta 206220
gaagagagga ccaatacgtt cttcccaaga gttacagcct caattccatg ggtgtgcatt 206280
tatgtgacat gcatctgaca ttagtgggag ttcaatgggt cactataatt tccctgaagc 206340
acacctgctg aaaaatgtca agctatctta taaatgacct gtatgttctt ctcccctttg 206400
gaagttagag gagttgctct attttggta catttgctat tttatttctt ttttctaac 206460 aatatttctt ttctttaatg ctttatgaag gatttttatt gaaatgataa atggaacaca 206520
tcttatgtat caagtcaaaa gttcataagc gtatatatta aaaagaaag catcatttcc 206580 tttttcgaga atcaacacac cttgatgcca gtcctggt ttcattagaa tccctctctt 206640
ctcttcctct aaccaaaatg tctcagattc ccccgatttg atttctgtaa atggcctact 206700
ttgactggaa gaattgcctc tctctgtcta aaacaggacc caggcgttac taaaacaaaa 206760
```

```
cactgcaaaa agttaaatga ggagaaagga aagttaagca ttgtacttag tgagaaatac  206820
ataaacaaaa gtagagacgt aaaagaagca tgagagaagg gtgagaaagt gaaatcctga  206880
gacaagatga atggtgtgtg agcactcaaa cccaggaagt agcaaaaggt ggaaggaaga  206940
atgggagcct ttagaataag attctttgtg ggctgggtgg cagatgttat cggtaaagcc  207000
agcctgggga gttggcaggg gtccatgcag tagataacac agcaatagag tgaacacatt  207060
gcagaagata gggcaacctc taatccagaa attatcagat aaagaaaaac caagacactt  207120
tgcaaaacaa aaaaaaaaac aaacaaaaaa acacaacaca atgtcttgtt tttcatcatc  207180
atcttcttta taatgaggtt tccatgcatt gaatacacac ttggaaacac tgtaatccca  207240
tggttgttgt ggctgcagat tgataggtgt ggacaggtct ttggtggggc aaacaaaacc  207300
aggatcatgt ttttgctct cagaatgatc gtttgcttgg acttcctct tctgcctcct  207360 agtggctcaa aatgcccact gcattcattg gatttattca ggatgtgaag aaggtcaggg  207420
gaaattaagg atgagtgctt tgtcattagg acctgagagg caaatggagc agagatgggg  207480
acgactgcag tgggataagg actctctcac caggaaggtg ccattgatgt aatagttgat  207540
gggaacagca gagcaaagag gctccctcgt cctcagctga ctcaacaaca agcgagacat  207600
cagatggaac ggtatttatt gggcaaggaa aatcagggga aggctaggtg cagtggctct  207660
cacctgtaat cccagcactg tgggaggcca aggtgggagg attccttgag gccaggagtt  207720
ccagatcagc ctggacaacc tagtgagacc ctgtctcaga aagaaagaaa gaaagagaga  207780 gggagaggg gagagagaga gagggaggg gaggagggga ggaagggagg gagggagaga  207840
gagagagaga gagagagaga gagagagaga gagagagaga aaagaaggaa ggaaaaagaa  207900
aaaattagcc agatgtggtg atgtatgcct ggtgtctcag ctacttgaaa agctgaggca  207960
ggaggattgc ttgagcctag gagttcgagg ctgcagtgtg ctgtgattgc actccagtct  208020
cagcaacaga gtgaaatcct gtctcaaatt tttaaaaaag actcaaaaga aaatcaaggg  208080
agggagtgga gacaaggtag aaaagaattt tttttatttt gtgctttttt ccctaatgta  208140
ttcatttaat catcaaataa aaattgaata tattgatcat gtacaaagtg atgttttgaa  208200
atatgtatcc attgagaaat ggctaaatcg agctaattca caagtgcatt acttcaaatg  208260 cttattttc tggtgcaaac acttaaaatc tactttctta gagatgttca aatattcaat  208320
tccttgtgat tcaactttgt ttgccatatt gaacagatct tttgaacttt ttcctgccaa  208380
ctgaaacttt gtaacctttg gccaacatct cccgtttcct ctccacctcc agcttcaagt  208440
tctgtaagag aacattctac tctctgcttc tgtaagcttg actttttttt agattccaca  208500
tataagtaag aacatgtgat atttgtcttt ctgtgtctgg cttgtatcac ttaacataat  208560
gtcctctggt tcatccatgt agtcccaaat gacacaactt cttcctttt ttttgaggta  208620 gaataatagt cccttgtgtg tataaacccc attttcttta ttcattcatc taatgatgga  208680
cattcaggtt gattccatat ttcagctgtt gtgattagtg ctgcaatgaa catgggagtg  208740
cagatttctc ttcaaagact tctttttcc aatcccaaat acacaaaatt atcatctggc  208800
atctgtcatg ctatggagac tctccttgat ctatttataa acgattcagg atttctttaa  208860
agaagctgaa atttattttt tacatgcata accatatta gaaatcaaaa tattcaaaca  208920
gaaatcacag aagaatctat tccatcaata tataattccc agttaattga ttatataatg  208980
tcatttaagc atgagttagt agtcacagag aatatgcctt aaaaatgttc tgtctttgaa  209040
agttttacat tcaaaacagt ctcttaagat tattaattct aaaagacacc atcccttct  209100
```

```
ctcttcagcc tgttttcttc attttgcttc tcatccagta tgtgaaaggt tgatgatttt    209160
tagttgatga ggttgacgtg ccctctttct ccttggggac agaaggacat aagttgtgct    209220
ttaaatgaaa ataagagtat gatgagtatc ccaagggatg atggaaagtt ccagggagaa    209280
gcattgaaat tgagagccaa attcaagtac attggaatta gggttctggt gataattctg    209340
tcagtatcta catatattca aggaaattag tcctttcgag taggataatg gaaaaatctc    209400
taaaaggcaa tctgagcggg atgtttaaag actacgtgat tattatgcag tgcatgcctg    209460
taccaaaaca tctcaagtac cccacaaatg tatacactta ctatgtaccc ataaagttta    209520
aaaaaatgta agactactac acatattctg gcctgcagct ttttttcccc tgacatttgc    209580
ctacccgcct gtaatagcac aggcaattct acaagaagca tgaatatgca catatgtaca    209640
tgcatgacag cagtgataca aagacagatg tgttgtgttc tagtataatt gtcttatttt    209700
tgtccattcc aacgttaata agtcattagc tttatggaaa tgaaccctag gggatgaaac    209760
atacaggtgc aaagtaaatt tcctagggac taaattataa ccaaattatg gcaggtacac    209820
cctgcattta gcgatataaa tatatgtttc aaataaaatt gtaacatatt gattggcacg    209880
tccagccata ttcttaagat actttatcct tggactaaaa ataataataa tcgctttttt    209940
gaatgaagtg tttaattttc agtgtaaaaa gtcaggaata ttttagaatg ctcaacgcaa    210000
cattgcttca atgagctagg gcctttatga agataagtca ctagaaagtc tgtgttgatt    210060
cggttaatta tttgagattg tatgcactga ttttcactgt gttaagtata gtggcattta    210120
ttagaggctc agatgttata gagagaaggc tgtgtccagt tatagggctg tagtcataaa    210180
cagatgggta aaatcaacac atcattgtaa atcataaaca ggcaggtatg ataaacacat    210240
aatgataagc atttcagcac tgggtgcagt gttgcatgcc tgtagtctca gctactcgcg    210300
aggctgacga tctttggagc ttaggagttc aagagcagcc tgggcaacat agtgagaacc    210360
catctttaaa cattaaaaag aacaacaaaa aaacatcatt tcagtgtaga caggcataac    210420
atgatctcac agagaaacac tacgatttgt acacaagaaa actaagcttt gcactggtgt    210480
tgggagaaca ttttggaatg ataaactatt tcctgtttgt tttaagaaat atttggtaag    210540
gtttaaagta gtgtctgcct ctttactaaa atattccagt atctgtttag atgtcccagt    210600
tggtcttaga tacttggtgg taaacatata tatacacata tatagcgcat atatgtgtat    210660
atatgtgggt gtgggtgcat atgggtgtgt ataatctatg tgtgtataca tacatatatg    210720
tgtacataca tacatatgtg tgtatacata tacatgtatc agttgtttgc ccttgtgatg    210780
cacacacaga tctatatgtg tgtatatata tgtgtctata tatgtataca tgctaatgtg    210840
tatgtataca tatataaaat atgttccttg attcacagtg ggattatatc ccaataaacc    210900
cgttgtaaat gtaagatgtc attagttgaa aatgcatcaa tacatctaac ctaccaaaca    210960
tcatagctta gcttggctga cattgaacat acttataaca cttacattag cctacagttg    211020
ggtgacatca tctaacacaa atcctatttt ataaataaag tgttgaatgt ttcatgtaca    211080
ctgcagagta gcagttgttt gcccttgtga ttgtgtggct gactgggagc tacagaccgc    211140
tgcctggcat ccaaagagac tatggtactg catattgcta gcttgggaat atatcaaaat    211200
tcaaaatatg atttctactg actgaatatc attttttgtat catcttaaga tcaaaaatca    211260
taaatcaaac cattgtaagt ccgggaatgt ctgtgtaata atttggctat agtcttaaac    211320
aggtgggtag aataaacaca ttattataaa tccatcctgt gcttttgaac acatggaggc    211380 tacccccacca aaatgcctgt gttcaatata ttgcgaacct ctaggtatct ttttccttca    211440
ttgctgttta attttttcctt ctaagcatga acttacaaga ttacttagga atagcattca    211500
```

```
tccttcttca ttcctctttg tttaaaacat gcttagcatt tctcatcttg aaagaaatga 211560
gtagctttct tcttttcaat catatttcat cagaactatt ctcttgaggg ccacagaaat 211620
gtcataagca ttttctctgg cacttctgat acttttaatg gcttttgata catcttcatg 211680
tttcttaatc ttccttgtgat ccttaccatg taagtgaccc gttgagctta tctccaactc 211740 ctattttca ttgtctcctt cctttatttg aaacaactta catccagcgt gcacgtttga 211800
agtgtgcaat tcaatggcct ttagtatatg cacaacattg tgacaccagc aacaccatct 211860 aattttgaa cattgacgtc attccaaaga gaaatcccat acctcttctc tcccaggtcc 211920
ccaggagata ggcttccact aactatctac ctgtctatat agatttgcct tttgggggca 211980
tttcatgtaa attaaatcat ataatacatg ctttttgtg tgtctgactt cattcccta 212040 atgttttga ggctcatcca tgttgtagca tgcatctcta ctcttttatt ttttatggtt 212100
cggtaatatt tcattttatg gatataccac actttgttta tccatccatc tgttgctaga 212160
cattgggatc atttccagtt tctggctgtt ctcaataatt gtgccatgaa cgttcatgtg 212220 caagttttg tatggacata tatttcattt tcttgattg gggatatagg agccgaatcg 212280
ataggtcata tcatgaactc tgtgtttaaa tatttgagaa tctttcaaat tattttccaa 212340
aataggtgta ccattttaca ttttcaccat caatgcacaa aagttttaac ttctccacat 212400
cctcactcac acttgttctc atctgtcttt ttaattatag ccatcctaat gggtgtaaag 212460
tgatatcatg tttggggtt tattttgaa tatttacatc attccaaaaa gaagtcccgt 212520
atctcttctc tcctacatcc ccaaaaagta ggcaagaggt aatctactca agaaatgata 212580
ccagcttaaa ccagggcagt accagtgaga atgcaaagaa aataaaaaag aagaggttgt 212640
tctgcgtgtc ttacagatgc aacaggattt gctgatggat tggatgcaag gtggcagaga 212700
atgagaatgc atttttcctg atgactaatg atgttgaaca cctattcatg tgcttattgg 212760
acatgtgtgt aaatcctttg gaaaaatatc tattcagatc cttttgcctat tttaattgga 212820 ttatcttttc attactgagg tttaggaggg gtacttttaa gtagtataat gtggatacat 212880
gttccttacc acatgtggga ttcacaaaca ctcccattct gtgtcttcca cctccacttt 212940
cttgatggca cattcttatt actcatgttt ctgaaaacat aatcttcagc ctcattgacc 213000
aatgactctg aatattgact catatatgtt taagcaggct tgtccactta ctatatctca 213060
caagtcccat ggttatcgtg acagtccact gctatcccgt cccttgtggc tgtctcatca 213120
ttgtatggag acaatataag gatgccggga cagataaagg gtattaggat agagtgccat 213180
caatgtgtct gtgaagaagg gttcgtttca atcagttcac catgactggg gatttgattc 213240
tgtcaattgc tgactcagga atgtaaatgc tgagtaaggc aggacttgat cagtctattg 213300
ggggaaggca tcattgacca aagtgcagtg caaatttatt cattgactat gaggcatata 213360
actctttata actgtcaata gaaaatggac aaggcatccc tccgttcctt acaaggtttt 213420
gtaatgagcc ctggatttaa aaaaatacta gtaataataa gagaaagaga gggagacaga 213480
gagagagaga gtgagataga gtttctagtt taagtgaagt taaaatgttt tttctatata 213540
tacaaaacta gctttgccaa ggaagatgta gtagtggttt tcattcattc attcttcttt 213600
cattcaagaa acagatattg acaacctgct gtttgacaca tggtataaca acttccattg 213660
aaaatggagt agcaaacaaa acagagaaaa aatccccaat cctacagcat ttctatccag 213720 tagggaaaa aacaacgaca gacaagtatc gtaaaataca cagtagaata tgatatcaca 213780
agtgctatgg agaaatattt agtagagaag ggtgctaaat tagaaatttt gtgccaaaat 213840
```

```
tttgactaag gtggttatgg aaagtttcac agataaggca aaactgatgt gagggagtga   213900
tccatacagt tacctggagg aacagcatct tgggctaagg aaagatccag tgcaaaggcc   213960
ctgtggccac agagtccctg agaatatcag tgcagctgga aagtagtggt gaagggata    214020 gtagcacctg atttcagaga tgtcagcatg agccacattt tatatgcctt taaaggacta   214080
gtgtattgtt cttagtgaga aaggaaatgg ctgtctatgt aaaggggcat taggttagaa   214140
ggttgttgca taatccaccc aagaaataaa aggcatttcg atcagaattt agctcttcta   214200
ctccatgaaa ctacttatca gttccattaa tgccttccac tctgcactct cagggttcga   214260
ttttctggaa aattttgaat tttgattttg attttccaga acatttagag ttctcgatga   214320
ctctctcctt cacgaaaaac attccttact tggtatctat atttgtttct ttcctattgc   214380
tgctaaaaca aggtatcaca acttgttata actctaatgt taactctagg gaattaaaag   214440
caatgcagat ttattatctc acagttctgg gtgctaaaag tcccaaatgt gttcacattc   214500
aaagagagaa tccatttcct tggtttgtct gtttgtcttc ttttgaagac tggctacata   214560
tcttagatct cattctctgt ttctaacctt ccatttaaa aaacaaacaa acaaaaaaca    214620
ttatgattac ctagattcat ccagatgaac cgggttaagt tctcatctta agatcctcac   214680
tttttttttt ttttctctct ctgagatgga gtcttgctct gttgccaggc tggagtgcaa   214740
tggcgcgatc tcagctcact gcaacctccc cctcccgggt tcaagtgatt cccttgcctc   214800
agcctcccga gtagctggga ctacaggccc gcaccaccat gctggctaa tttttttgta    214860 ttttactaga cgggttttt caccatgttg gccaggatgg tgttgatctc ctgacctcgt    214920
gatccgctct ccttggcctc ttaaagtgct gggattacag gcgtgagtca ccgtgcctgg   214980
ccaggatgtt cactttttaa aattgattta ttcttatttt attttagaga tgaggttttg   215040
ctctctcaga taggttggag tgcagtgtca taatcatagc tcactgaagt cccagcctct   215100
tgggtcaatt gatcctccta tctcaccctc ctgagaagct gggactacag acatgcacca   215160
ccacgcccag ctaagtttta tatttgttta cagaggggg ttcaccatgt tgcccaggct    215220
ggtcgtgaac ccctaggctc aagtgatcca ccggcctcag cctcccaaaa tgctgggatt   215280
ataggtgtgc ttcctgacac cagtttctga ggtccttgac ggctgtggtc atagctcata   215340
ctacctctct ctccctagtg tctaccggac aataagcagt ttctgaatga ttagccgttg   215400
cagggttttt gactccaaat tgcaaaatgc aagctaatta aaaaaggagt gaatctattt    215460
actcattttt ttttttttt agtttgagtg aactgattct caaaatcagt gaatgcccag    215520
tttcatgtaa accgtgttta tttccactgt ttacactcag cagctgtttc tttttcacaa   215580
acactggaga ttccatgttc cccgaaatat ctatgtatac ctgtatcata attcattaca   215640
cataggttag ctggaatgga gatattttat atttgtggca tgcatttgat cttgaattga   215700
aacctgtagt ttagaaaaat ctacatatct ttatattttt aacagatttt gagaattata   215760
aaagcaaaac agtagagctc tacggtagaa ttttttttc tttaggtctt tccatgggta    215820
ttttaaatgt ctcattatga aaagaccata aaccatggtt ttctaagagt tctgctgaat   215880
tttgcaattg gctggcacat tttctaaatg atcctgtaat ctccatgtat tagttttcta   215940
gagcggccat aacaaatgac cacaaatgtg atggctttaa aagagagaaa tttactctt    216000 ctcatagttt gggaaccag atgttcaaaa taaacgtgtt ggcagggctg cctttccctg    216060
ggtggttcca gaaaaagatc cttccttgcc ttttcagctc tggtggcctc ggtgtttgtc   216120
tctatcttcc caaggctgtc ttccctctat tgtatgtgtc gtctccttt cttataaga    216180 taccagtcat tggatttagg gttataccct caattcagga taatttatc tgcagatcct    216240
```

```
taactaatta tatctgcaaa gaccctattt tcaaataggg tcacattctg agtttccagg   216300
tggacatgta tttttggagg atattacgca acccactcca cccaacacat cattattgca   216360
atatatatgt atgaatatag gtgtttcaga tatttacact acacatgtgt gtacaaccaa   216420
tgtattcagg atgccacctg gctttctcct tactaggcca cactctggca agaagatcta   216480
aggacaatct gggattcttc atctccttct tgcatcctct ttgcttccaa ataatgtagt   216540
catgcagtat ctgaaagttt atttcctgag cctttaaaac ttctccatca gtttgacaag   216600
gagtaaaagc gttttttcccc gttggccaca aaacttgtgc ttttgctcca gcaatacgca   216660
aagctatatt tcacacttcc ttcttaaatt acaggctata aatataaagc aaaacctttt   216720
accttggata ttctttctgt cttttccctc tgtgattaaa tctgattaca aatgctcatt   216780
aatgctctgc cttggaattg caatttgggc atgtgccatg tgaaaatgga ggttcctaaa   216840
aattaaaatc aaagattaat gcaggtttta aaaagggtc ttattcaaat atatctcaag    216900
ttttaaaacg actcatggac ttttaatgaa atcaatggcc ttgtaatgcc tcattttttt   216960
tttcaaactc aactgtttca tagccttctc tttagaacat atctgattta ccagaaccca   217020
agatttgtga gatggtgtta ttttttatct ttactttttc ctcacccac ggtaccatga     217080
agagatcgtg taacatcctt tcctggtttt aaagacaggt gagtaacgat tacataacgt   217140
tcaaacaagt caggtgttct ccagaagatg gtgttaatgg tgtctgattc acagatgctg   217200
ccttgacccc tggcggtggt aggacctata ttctggtgaa agccaatttt aggccatgga   217260
ttataggacc tagatggaga aaaacgatac ctaaacctca tgagatctta attcactgat   217320
cggtggagag atattttttct ttcagatggt atcatcttat tgcatctcca gcagagtgtt   217380
tggccggtga aaataaaaat ggccattata agaagttct ttagacttttt aaaaatttta   217440
ctaggatcat gccagaaatt cctgctgtag aagtagatat gtatgtgtgt atacatatat   217500
atatatatat atatatttct gaatttgaga tgttgggtat tggtagagat tcattcattt   217560
gaatggaaat acgcttgctt tactttttggc cagcatgaat gctctcattt gccacaggtt   217620
ggcaagctta ttggtttaaa tataaaggat cttgtgggta agactaacag caggttttca   217680
tagtgccaac atttctttct ttttattat catatttagg aaagtctctt gactctgaga    217740
tactttatat tgtgaaataa tagttctggt gcaagtatag attaatagat tattaaacac   217800
tttaagatat ggatggaaga gtacaactag gatattatta atgagtccca tttactattc   217860
tttaatttgc agtggaattt tcatttaact tttgaatata ccaatgatag gaagttagta   217920
gtgtttgcct gtaattatc ctgagctcat ttatttgaag ttcaaatttg aaagcttcct    217980
tttgttgttt ggtaaataga gattattgtg attcaaaatg agtaatccct aaattgatgt   218040
agaaaaagat atttgaggct gggcacagtg actcacgcct gttatcccag cacgttggga   218100
ggctatggga ggtggatcac ttgaccagga gtttgagacc agcctggcca acatggcaat   218160
accccgtctc tactatgaat acaaaaatta gctgggcatg gtctcacaaa catgtaatcc   218220
cagctacttg ggaggctgag acccaagaat cgctggagcc tgggaggcgg aggttgtaat   218280
gagctgagat tgtaccactg cactccaccc tgggcgacag agcaagactt cgtctaaaat   218340
aataataata ataataataa taataataaa ataaaaagaa ctttgagata ttcatattgt   218400
ccaaaaagta taattcaaat acttaatgca gaaggcagta ggatcactaa actacagact   218460
cattcatcaa ttataacaga tggaagggtc tttgttagag tcctggaggc tgattgagca   218520
ttttaaatgg caggttcata ggggagatcc aggaggtcta aaggtgaggg tctacaagca   218580
```

```
ggaagcaccc ccactcccac ccccaaattc atgacaacaa cactaactag gcagcaaagg 218640
gatatttcct gatgtcagca gtcagcagaa tggtactgaa ggttgctaga taaatgcaag 218700
ttttgtagtc actcacctgc aagttatagg caagatattt atctgtactc ctacaggaaa 218760
ttagccctaa ttgactgctc ttaatcagaa caagacattc taacctctta ttcatggtta 218820
gcagtatatc ccacttgctt cactttgtga ttctccatca cattggaata actggacgtg 218880
ggatacattt ggaattgagt ctcaaattca aatcgccata gaacctgaaa agaaaatgta 218940
agaagagaca aaacagaaga aaaatgcagg atagagagtt atgatttaga tgtgttcatt 219000
ctgtgaacag agagcagatt ctcttggatc tggctgaaac aggggccccc tgtgttgtga 219060
aagtggtgta tgtcttcata cgtgttccca cgggcctgga caaccaacca catttgaaaa 219120
atgaagaaat gaaagcttgt ggtcagggtc acaaaacttg acagtggcag aagtggatcc 219180
aatttccagt caaatctatg actcgttcca tcttggccac aattatactg caactcaatt 219240
gcttttcttc cagtcagtac ccacccaccg aaatgtcagc tcttcaaggg cattaattgt 219300
tgtttgtttc attcattgtt gagtcttagg agcctgggac agtacattga aaatctcaat 219360
tgttgacatt ctcaataata cacaagaaat catgttttca gatcatggaa atcatatcca 219420
ttaggatggc tgttaataaa gtaaacgtaa aataagaagt tgtaatggag atgtggagaa 219480
actggaactc tttcacattg ctggtgggaa tgtaagatgg tacagtcatt gtggaaaact 219540 cttttggctgt tcctcaaaaa agtaaacatg gaactaccat atgtgatcca acaattctac 219600
ctccgggtat atactccaat tctacctctg ggtatatact caaaagaatt gaaagcagga 219660
attccaggag atatttgtat acgcagtcct taaccatgtt attcacaata gctaaaaact 219720
gaacttttga actagccaac tatccattga tggatgaatg gataaacaag tgatatatat 219780
gtatatattt atgcgtgtac acacacacac acacactgct gaaatggaat attattcagc 219840
ccttaaaaga aaggaaattc tgatacatgc tacaacataa ataaaccttg aggacatcat 219900
tctaagagaa ataagctaca tgctagtcac aaaaggacaa aagctgtatg attttaccaa 219960
tatgaggtac gtagagttgt caaattcaca gaggcaaaaa gttgaatggt gtttgtgtgc 220020
ggctgagagc cggagagaat ggaaaattat ttcctaatgg atagagtttc agtttggaaa 220080
ggtacaaaat gttctgaaga tagatggtgg ggacagttgg acaataatgt gactgttctt 220140
aaggccactc aattatacac caaaaaatag tttaaatgat caatttcata ttctctatat 220200
cacagtaaaa taaaacatta tggtatctgt gatttaattg actatttgta atcatcacca 220260
tgttagagca tgttcagtat ctcatatcct gcaatattgg aatggacatg gtaatttttg 220320
agtggtagaa aataaagtaa ctttaaaaaa cccatctcta tgtattcaca taatcttaca 220380
tttcatataa gtgaaatcat acactctata tctcatttct ttctcctaat aaaatgttta 220440
caaggtttac aaggttcatc cacattgtag catgtatcaa tcagtaccgc atgctggttt 220500
atggctggat actattccat tgtatgatag accgcattct gttatgttta tctatttttc 220560
atttgatgga tatttggatt caattcatag agacagaaag tagattagtg gttgctggtg 220620
cttggaagag gactataggg aattagcgtg tcatggttac agagtttcag tttgcgaaca 220680
tgaaaaattt ctagagatag attcacaaaa atgcaaatat actaaatgac attgaacaga 220740
acagtacact ttaaaatggt tcactttatg ttacgtgaat ttcctcttaa atagaagaaa 220800
aataaagtct gaagttgtca tatccttcac tgggatgctc tctttaaaag tgtagaaagg 220860
tcctgaaagg agcatataaa caaactaaac aacaatcaaa caaaacatgt catcgtaccc 220920
cacagcatcc tgacatggaa gactaaaaac tgtcccaggg ctctcttctt ccttatctgt 220980
```

```
tactttcagg ggcatttag cttaggattt aatttgacta ttgacaaccc cagtgtctcc   221040
atttgatctc agagcaaact tgaattgata attaaatttc catgcttttg accagggaaa   221100
gactttagga aatgtctttg aaactgtgaa cttgcagaaa ggagaaaatt ttatatgtat   221160
ctagcttcta tccattccat ttgtcatatg gtcagaactt acatgatgca agcaggccat   221220
ttacagggcc ctgggctgac agctacatgc tatattttgt atttgcttcc actattttgt   221280
tagcaaatgt atgtacttac taacaaaata cgtgttttaa gaaataaaat tattttaaga   221340
acaaaataat acaatgtttt aagaaaacct gcttttattt gcttttattt ttttatttaa   221400
aaatgtttat aaatttatgg gtgttacaaa ttcagttttg ttatatgggt atattcatag   221460
tggtgatgtc ggggcttta gtgtactcat cacccgaata gtggaacctt tatccagtag   221520
gtagtatttc atccttcatg ccccttcctc ctccttccac ctcctgacac tttatagtct   221580
ccagtgtcta ttattctacc ctgtatgtta atgtgcacct gttgtttagc tcccacttat   221640
aagtaaaaac atgcagtgtt ggactttctg agttatttca cttaggataa tggcctccac   221700
ccagtttcat acatgttgct gcaaaagaca taatttcatt cttttttatg actactactg   221760
agttgtattc catggatata taaaccatgg tatatataaa catttatata tccagtcatc   221820
tgttgatgga cacttaagtt gatttcatga ctttgctgtt gtgaatagtg tagtgataaa   221880
catatgagtg gaggtgtctt tttgatagaa ccatttcttt tcctttgagt agaaacccac   221940
aagtgggatt gctgggccaa atgatacttc tatcttaagt catttgggaa atctccatac   222000
tattttccat agaggttgta ttaatttacc ttcccaccaa cagtgtataa ctgtacccctt  222060
ttctcagcat ctttgccaac atgtgctgct ttttgacgtt tttcaaaatg tcattcattt   222120
tcatttttat tataattact taaaaatgat gacttttaac agagaaggga aaaataaagt   222180
tggtaatctt ttgtagtgcc atataattc tagttacaag accacagata agtcccatgc    222240
tgaagagagg tgggtaaaat agctcgtttg aaatgaagca catttgggaa gataaaattg   222300
tttttaggat gataacgatg tttgatgtct aacttttggtc tagttttct aatgttaagt    222360
gtattcttaa catctgccca aattattcac tctttaaacc acatgccaaa acattactta   222420
catttacttg gttataata aaatttggga ctattagtgg atgatattta ctgcaagaat    222480
tgttaatctg gcgttggat ctagtattta gattacttta tattttcagc tgcatatgca    222540
actattagat atctgcccac acttttcct tcccactgtg gaaatacac actgtattaa     222600
ggtgacaggt ttcctatttt tcaccccta gacttgagtt atttttctcat cattattaac   222660
tcatagaacc tgtgctttgt tcctggcttc agcttgagca ctgtgcaaaa atttatctta   222720
taagatttgg tcaaaactgt tggctgtgta ggcacttccc ctagtagaaa cttccccttt   222780
cccctctgag ggtcactga aaaatcaact taaaaaggca gattaattga agaaaaggca    222840
tgcaaatttc ctttaatgtg gatagcttgg caggaaggat taggagactg attacccaat   222900
atcttaatgg agtagatatg cttatatact ctacttccta gaggaaaggg aggtgaggac   222960
tcctggatga tacttagggg gatagtaaat gattttagg ggaattaagt gggcttgaag    223020
aacatacagt ggcttagaac aaagtctgtt gggcttgcag agcagacagt ggtttgtcac   223080
aaaagtctgt ccaggtgtgt tgacagactt cattctttct tcctgcgata tgagtccagt   223140
tactagaatc tcggggaagg gaccagaggt cattgttttc ttctttgatg ggtccagact   223200
ttaggcagat aaacaacttc agaaaacaac ttcctcctgt gctttgggg tcacagaggg    223260
ttgagagaca agagggagtg ggagaagatg agagagacgt tgaggcttct tcttcagttc   223320
```

```
agcacatcaa agtgccatat tttgctgtat gggtttatga gtcccaacaa ctgggtagtg   223380
aagacaaccc agggctgtgt gttgatggtt ccgctgcaga cagtcaaggc tcacttctct   223440
gggaggaagc taaatgccac tcagagacac atccccatct cagatgtctt tgttatattg   223500
atgacagttg gcacccagat ggcatgtatc ccttgtggtt tcaaccattg gttgacatga   223560
ccttaaaggc ccaaggtatg tattcgttgg tccattttt ggaggaatgc cattttactt   223620
ccacaatgca gcatagctgt taaccattca tcatgccagt aagagaatcc ccgggatctg   223680
cattgggaca gaatccccat tcactgcctt gtctcacttt tgtagtttgt tttgttttgt   223740
ttgaatttgt tttagttttt aacaaataat ctgaaggtaa aatacaattg aaagaagcac   223800
ttatcttatg atatcaggat aagtaaacta gtgcagtttc agaaacatct aaccaagtgt   223860
tgttttcttg ctggattgca atattgatag gcacatggga taatatctca tgtaaattct   223920
gaaacatcta attgcatctt gatccttcat cttgaccctc ttctcagtgg gctgcattta   223980
tccctaaaca gcaacattct gtcaattctt aggaacgtga aacgttacag tctgcagagc   224040
aaattaccag caggagaaaa tattactgaa tattcaaaag catgcctttt gtgtgaatga   224100
tcttgaagcc ccagggaatg ggggaaacag ggttgggagt acataagcca agaaccttat   224160
ttgatccagc agtttccggc ttctaaaacc ctacccatgc agttccaaga agaaaataac   224220
aaattggcat cacttaatgt ttagtgatag aagaagaaaa gcatgccttt gttcattttc   224280
tactcttctc atttcctgct tcaccattcc tatcaaatga aacatttcgt tttcatttcc   224340
tctctataac ttgtactatt tctgtgaata gatgatgtgc ttaacatatt gatgtttgtg   224400
agtaaagata ctcttgctat catcaaaaga aatagtatcc atttgagaag catctagtat   224460
atgaggaaaa gttttgtttt cattttccc ttatgttgtt ttttatattt taaatgtagt   224520
tgtaaaatga cagaacatgg gatcacaaag aaacacaaaa ttcgtaatta ataaatgtga   224580
ttttgtatttt attttaggta tgcaaggggc acgtttgtgt gggagttcaa aagcatttaa   224640
atattttaaa tctcctttca ttcatttaat aagtgtcttt tgaggtcaga gtaaacagaa   224700
caacttgtta cacatgtttc ttgtttttag ggaacttcca ccccaacatg ggaaataaac   224760
agagaccta ctagttcttt aacagtttct taatgaaaca ggatatttcc ctgacccctt   224820
cacaggtggg aactggagtg cactggtgct ggaactagcc ggctgcttcc aggccagcgg   224880
gggtgaaccc tgctcactcg ctgctctacc ccttgtggga gggaagcac aggtgagcag   224940
gtacaggagc cagggcgaac aattttgggc accagcaaga atgaactcca taccagcccc   225000
acggcagcat ctagtagagg gtagcccgca accctgaag acccagagga agtgttacac   225060
tgcctgtttg gctttgccat ccgcagagac cgtaagtgtt aacagctcag tggagggtca   225120
atgtgacagc cttttgcacc cacactcatg gcacgcaagt ttttgtcctg aggtgggaaa   225180
ttaaagaaaa ataaaatcaa aaagaaagag aaataagttt tcctgtatta ggctgacttt   225240
tcccagaggc agcaacaggc acagcccaga cccaggaaaa gtcttgataa tattatctaa   225300
tgtgctctgg agactctccc agcactccct aacatagggg agaaggaaaa caaattttcg   225360
tttgtttat ggaatgagtt tatagattcc tgttctctgt aactaatgac ttcaagtatt   225420
ctgtttatc taaaaagtac aacgaaggtc atgagaagcc tgattaggcc tgaactacag   225480
ctgcttgggc accatagtga aggttatgaa ataaccagt gcaaggcact ttagagcaaa   225540
acctaggtaa cagacatctg gattgcttgg caatggtcat atgcggtcct gagtttgtcc   225600
tgcctctgta tccctgcttt cacgccactg taagcttact tcaagctagc ccaccccctt   225660
ttgttaagtg tgtatgaaag acaagtgctg tctttgttcc gggcccagtc gttggacgtt   225720
```

```
gagtctgctg ggtctgagtg cactcaataa taaagatatc ctcctgtata caccccgagg  225780
tctctctctg gtcctcctga tcccgcaaca gactgacgtc caggagcaat caggtcacac  225840
gaacaaattg aagatggtaa atgcagggga ttttttattg ctggttgaaa gtagctctca  225900
gcaggaaggg gaactgaaaa cgggatggag caggaagata atcttcccca ggagtcccgt  225960
catccccggc cagaatcttc tccaaagcta tgccatcaag ctgtccctct gaagtcaagc  226020
cacttctctc tgatgtccaa ctataatttc cgatgtccag ctgcttctcc cctttccaag  226080
ctatgcctgg agtttttatg ggcacaggat gtggtgcagg gcaggccatg ggtggttttg  226140
gaaaaggcag cagtcgagtg ggaaaacagg aatgtaaatt ctcactttgg gccctggttg  226200
cttttttggct tgagggtggg gcacttaccg ggaacccgct ctcttctgcc cagaatttcc  226260
ctgccttctg tccctatcgg ttttgtattt attttaggta tgcaagaggc acgtttgtgt  226320
ggaagttcaa aaacgtttaa ttatttaaaa tctcctttta ttaatttaat gaatgtcttt  226380
tgagctcaga gtgtaaacagg caagtacagc ttatagctgc agtgaatgct gagaatgaag  226440
tactcaaaca attccagctg aacggggcgg ggaacagctc ttctgagaga gtgctgcccc  226500
aagatccatc cacctgaata tttattgaga gagcttgttt aaactacagt tcagatgaac  226560
aaaagacatc caccaggtgg ctctttgcgg ttgggtcatg aggcacatat gaccttgtaa  226620
aaaacactca aaccacattc ttaggaggct gtgttcagca ctccttatca cacatactac  226680
tccctgtcct gttttcaggg acaaggagtt ctagtctcat gcacaaacaa catgcacaca  226740
gtgcctcagt attttttccat gcctcgacct cacgtgtctt ctacattagc ttgaatatgt  226800
tgccatgcac cccccacagg aagtcattac acatgtttcc tgattttagg ggagcttcta  226860
ccctaacatg ggaattaaag agagatccta ctagttcttt caagtgtctt aggtaaccaa  226920
ttagatatat tctacacccc ttagtggcaa gtgctcatgt tgtcaaattt gcatttgttt  226980
tcaaatgaga ttaaaacaca acaacaacaa tgtttaaatg tttctactat tagaaaataa  227040
aatcaatgta ttctatcttg gattttttcct ttatttcttt atagagttct ggtttgcaac  227100
aaagttttat cagtagctta tttaccttcc caagagctcg ggcaggattt gatggtgaat  227160
gtacatttag tggtttccat atttaaaaaa aaaaaaaaat gactctgaat aagctcccag  227220
gctctcagtt tcttctagtt cttttctgaaa tggtccacaa catgattgtt ttgaaattga  227280
aaaattaaat gcttttattt caaaccccac cgatctaaaa ccagtaggtg tacctttcat  227340
gagcacactt cattctgcag gtgaaaaatt ttcttccaac aattgtctat gatagtgatt  227400
tataagtcag caatttgctc taaagaatgt gtctctttct aagcatcaca agaagtaatt  227460
taaattatgc tgtttcttag taagcatgtt gattgaacct cacatatttc cactgattct  227520
acactaaaca cagactctct tttagttgta ctccatttga cttggtttat acagttcaca  227580
tagtcacttt tgtatgtcta aacttgcctg accatttac tagatggcat ggtgatatgg  227640
tttggctttg tcctcacccca aatgtcatct tgaactgtag ttcccataat ccccatgtgt  227700
catgggaggg agccagtggg aagtaattga atcctgtggt ggttaccctc atgatgttct  227760
catgatagtg agttctcatg agatcagagg attgtgtaag gggcttttcc tccttttgct  227820
cagcacttct ccttgctacc accatgtgat gaaggacata tttgcttccc cttccgccat  227880
gattgtaagt ttcctgagga ctccccagcc atgctgaact gtgagtcaaa cttttttcct  227940
ttatacatta cccactctcg ggtatgtctt taatagcagc atgataatgg aaattgctac  228000
tgagagtggg gtgctgctgt gaagatacccc aaaaatgtgg aagtgacttt ggaactgggt  228060
```

```
aacaggcaga aattggaaca gtttgaaggg ctcagaagac agggagatgt gggaaagttt   228120
ggaactttct agagacttgt tgaatggcct tgaccaaaat gctgatagtg atatggacaa   228180
tgaagtccag gctgaggtgg tctcagattg atatgggtaa cttgttagga actagaataa   228240
aggtgactct tgctatgttt taccaaagag actggaggca ttttgcctgg cgttgttgtt   228300
ccatgatttt ttttttatg ttcaacagga cgatggcaca acctagctgc aaggcacaga    228360
ccaactccca gcattgccag ggcttagggt acattaccag gtcagctgct gaccagcagg   228420
ggctgctttt ctcttttgtg agtaactgag aattaaataa actaagtaac atgcctcaaa   228480
tcctgcagag ggttggagat aatactggag tctcaacata gactatatgg gaaagtctag   228540
cccattaatc tccaggcttt tttctaagaa accaaacgcc aatatttat ttgttgcaga    228600 aaagggacat cctgtggtca acacaatctt cagtgggagt taattttaat caggttcttt   228660
agaattcagg aaagctggaa aaagaggag ttgtgtaact cacatactgg gaggcatctt    228720
ctgtggccag tcagcagata ccatctccat tggagagatg caggcatctt aaggatggga   228780
gaattccatt tatagcctag acttttgtc catgggcctg gcttggatag ggatggccca    228840
tattaatgtc tttgactctt ggttttattg ttacattctg tatggctgat tcagatttgt   228900
ccacactgat atatttgttc tctgattctg atcattgtgg ccatcttttc ctagaacaaa   228960
gggcttaggt taattttgc ggagtaatga cattttctgt ggcagccaaa ctccgtagaa    229020
caatattgct cctacttctt gttttcttcc aatggtaatt gaacgtgcaa gccacattca   229080
ggagtagggt ctgaaattcc caagagcta gccagcgata atagtgcaaa tctaatacat    229140
gcccttgaaa caccaaggga taaactcatg tgcatttgtt cttttggggt ttgaagaacc   229200
agatgacatg caaagaaaa atattgacaa aagatatctc atcgtttact ttcaattatt    229260
gagtttgatt ttcatgcatt caaccttagt ttttttaaga ggtaagtgat tctagtttgt   229320
gagagccaga agcatgcaca aataaacctt atttaacaaa ttaatctcat attttcttgg   229380
ttctgatgat tgcatactgc ttattttaaa aaggttgtga gcaagccaaa gttatcatac   229440
ttatttttaa agtgacagca tggctgagct ttcaaaatat gtttaaagat tctaagagaa   229500
acaggttaga aaacaagatg attgacagct ttttgggtta ttagatacag aaaattatac   229560
ttagatttat ttaggttgaa aattaatcct acagcattta aaccagctgg gagagcttgt   229620
gcatgcacaa gagtgttcaa gctgcaactt aaggccattg gcaacagta gaaagaaaaa    229680 aatggttatt tcttctcttt cagaaccaac tgtgactgat taaccacaaa agatcagtgg   229740
gggtattcag gcctaggtcg tcttggtggc aactgggtt ttagtttgct ttcaggctca    229800
ttgctggaaa aggctgttca gaagcttcct ctacaacaag ggagatgaca gtgcgtgagt   229860
acaaagcaga gaggtgcagt gctttctaca gcaccgagtg ggcaaattgt gcagatttt    229920 cagtagaatc tacttaacac caatccatgc atttgcattt tattaaaatg aaactgtgat   229980
catttcaact gcacattgca gacatgcct ataaaatgtt tgaagtcctg ttttggacaa    230040
aagttttgaa aacatgcacc ccgtatcaat ttctctactt atattttgta tttaatttgt   230100
ctaaagaatg ccacattttc aaagcaagca ggccaagaga atgatctttt tttcctcttt   230160 tttttccca gtgtttaaaa tgcaactgcc atgggctgt gccattttag ctgttggaaa     230220
aaataatcta ctatgccttg gttgtatgtc tgagtcatca gagcttctgg gaatgattct   230280
ttggcacatt ctaccaacaa tttaacatga cacaaaatca ttttcatatc ttgtgatagt   230340
gtcagccaag tgtttcatac acatggtgct aggtgctgaa aaaggtgtct gaataaaatt   230400
gttttcttaa aggaaccata ggggacatga taaaaagatg cacaattata tatcttttttt  230460
```

```
tttttttttt ttgagaagga gtttccctct tgtcgcctag gttggagtgc aatggtgcaa    230520
tcttggctca ctgcaacctc tgcctcccag gttcaagtga ttctcctgcc tcagcctccc    230580
gagtagctgg gattacagga gcctgccacc acacccagct aattttttgta ttttttagtag  230640
agacgaggtt tcaccatgtt ggcctggctg tcttgaact cctgacttca ggtgatccac     230700
ccgcctcggc ctcccaaagt gttgggatta caggtgtgag ccactgcgcc cggcctaaag    230760
atgcacaatt acatttcata aattgagaga gtttcctaaa caagagagag catacctgga   230820
aatatcagag aaaaatacaa agggcttaaa gatgttgtat taagcaaagt tagactaagg   230880
cagcttggat gtgcatctcc tccactttat gtttatacct aagtagagat taaaagcaga   230940
ggaatttcaa tttccacatg acttgtatat gagcaacaga tgggagttct aactactgac   231000
cacattggca catcacacaa tgttttcttt caggtttctc tacctatggc aaaaccagtg   231060
ctgtattaga gcctcgtgag ctgtgtgttg ttgattaatt gacttaaccct ctctgggcct  231120
catttttctc acctttaaaa taaatgagtc ttatggtgtt ttgaggatca aaagagttac   231180
tgtacaaaca gtgctagtaa gagtccctgc cacatggaaa ggctattata tatatatata  231240
tatacgtgtg tatatatata tatatatgtg tatatatata tgtgtatata tatatacaca   231300
cacacacaca cacacatgta attttatata ttaaatgtgt ataatttata aattttgta    231360
ttataaatgt aaatctgtga tatatattaa aactatgaaa tacagatcat gtaatatata   231420
ctacctattg ttttttttttt aatttgtaac catattttga aaattttatt ttgcttatag  231480
gtcttgaaag tcattcccca atcaaccttt attaaaatcc ctttgattca ttggagaata   231540
tcaatacata tgaggtatta atatataata catatgtaac tcttctgagt ttataaatgt   231600
atgtataaaa cataaaaatt actaactctt catatatatg tttgtatcta tataataattt  231660
atatatatag atatatatac atatttgtat tacatatgaa taatcatcac agtgtgtctg   231720
catttgttaa tctaacctcc tccaaccccca cccccaaaaa agcagaaact aaaaatagag  231780
gaattttaag ttccacatga tttatatagg agcaacaaat ggaactacta acttccgacc   231840
gcattagcta atcatacaat ttttttcttt cgtgcttttg ttgtaaatat gattttatt   231900
taagagggta ttattgatta tctacgcaag aattagccat gttctccata cttctacttc   231960
agtttttaa aaaggatga ggatagaccg ggcataagtg gctcatgcct gtaatcccag    232020
cactttggga ggccgaggcc ggcggatcac ttgagggaag gagtacaagt ggcctggcca   232080
acatggtgaa accccatctc tactaaaagt acaaaagtta gctgggcatg gtggcgcatc   232140
cctgtaatcc cagctacttg ggaggctgag gcaggagaat tcctgaaacc gggaggcag   232200
aggttgcagt gagccaagat cacgccactg tactccagcc tgggtgacag agcaagactc   232260
tgtctcaaaa aaaaaaaaaa aggtgaaaag ggtgaggatt gttatttctg tgggcaggcc   232320
cacacagcat cagattcctc agaaactgca ccggtaaatg ggaaagtctt tgagtccctc   232380
tgacagagct tcaaggggct ggctgttcat tatcccacag cctcctttgc tctgtgtaag   232440
tggaggctct gtgcctctgt tatcttgcag tccctaggtg accccggcag ggagaaaaat   232500
cagtggaatc aaactcggta gcacagaaaa acgccccaaa ggcaaggatg agaggaaagt   232560
tgtgatccca catatcaaag tcggactctt atctagatgg gcacacctga gccacaggct   232620
ggcaggctga gattctgcaa aggctctgga ccccagataa gcttgactga ttgcattgtg   232680
atctcttctt ttcatcaggg gaggcgctgc tttgaatgac taagctggat ctgactttcc   232740
agggaatcct ttcagggact gtgaccatcc agctatcttt ggatggcttt gatgccctaa   232800
```

```
ttatttttca cttggttgag gatacttta ggtatctgtt catgtgtcat cttgtacaga 232860
aatgtgtgtt ctgggcttat aaaaaaagtt taattgtaag acaaagggct ctaggtttca 232920
tatttattca cagtctgatg aatggcactt atggatacgt acgtgtatac agtaagtgct 232980
cactgaattt ctcttgagtg ataaactggg atacaaaatg tcagaaaaga aagagtgagg 233040
atgggcactg gatccagatg tcagtgaact ctgagggtct cttgctggtt aaaagaacag 233100
ggtactttta ttttcattct aaaccctgcc tgacccttgc ccttatatca gtgaatcacc 233160
atctcgatgg cccctcaaac atggcatctt tgaagtagag cctcattgag aaggactcct 233220
tagaagtctg tcatggctac taaaattcat atctgtgctt tgtgcctgag cactagtaca 233280
tgtgtcagct gtttcttaag cctacattga accattaggt aaagcccagt gtgctcccag 233340
ttcctaaaat ctggtcaagt cttgatgttg gtcaacatct tgcctggccc cagtcagatg 233400
tctccagcta tctgtaacag gactcagtgt cttgtttaca aaatgcatta gtcatatggc 233460
ttcgttgctg gctttgctgt ataggtcagg aataagtcag aaataaccaa aatgctccaa 233520
atcaagttct agctgttttg ataccaacat cttccatcaa cttcgcttct ccctgactca 233580
tctgtctgtc tgttcctgtg ctcttcgcac acagaggcaa ttttgtgtat aaagctcccc 233640
aagggaagaa gaggacagtg ccttcatggg aaactccttt ctcttaaata ggatttgcat 233700
acttaaccag agcatttgct tcagttaacc aagtgagagg tggagaaatt cttgcaaaac 233760
tatagctaca ttgagaggga ttattaaaag tattgactca ttcattagag gagctgttac 233820
aaagattgta gcaaccaaag caaaataaaa atattgcca aaagtattct caaacgtatt 233880
ttaaaatgtc caaatattg ggcaagacta acatcaaaga aggtatatgt tttgacattg 233940
atttactaac tacttatcag tgtaagtaaa tacaccttca agcacttatt taggattaag 234000
gtagtcaagt tatatgagtt gtatgagtat gtgcaggcca caagggttgc aaaacatagt 234060
gaattcaata tccctctgcc atattgaata tccttctgcc gaacttctgc atcacagttg 234120
tggcctgcaa acaggtaaca gttgtctgcc aatcccttag ggatcactgc attctatagg 234180
gcttgaccag gaagtaagag gctcttccca ataagcgata tcgttatggt ccttgtggtt 234240
ctgctaagaa tctcagagaa gaaatgaaag atacatgaaa ttgtttgcat gctactagct 234300
ctagtgggta ggttggtagc gtagttcttc atggcaaaag acagaatata tccaaaattt 234360
tcaccatttt gccctggtt tgagggatgc atattccttt agaccattat gttgaaaaga 234420
aagttaaaaa taacataaga agagacctcc taagttgttt aatccaagcc ctcaatctta 234480
gcaagtgcct ggtgtaaaat gtctcattag gtaattaccc atctcctgtc tacccactaa 234540
gaggttctag taaagtacat actggctgga ttcaataaag cacaaatagg cagcaaatgc 234600
ttcttacatc tcaatctaat cggtagcctt ctttatcctc acccttggct gactaacgtg 234660
cataaagcat aggaattctg gccactcaag gatcttaacc atccagttca gtctgttgca 234720
atttctcctc cattacaaat ttttttcact ttcctttcct gggaaagcca cagacaggac 234780
aaccattcag tgagaaagga gtgtgaagct gacgtctttc ctcactaaga ggagagggc 234840
catgagagga aaaggcaact tcttgcgtgg ctggtggtag agttaaagtc tgatgctact 234900
gtcttctggg agcagcagct gtacacagtt gaacttact ttggaggcat atatgatttc 234960
cagggtttct gtggcaagtt ccacccactg cagttcattt gacttgggtt gaatctcttt 235020
cctccctcca tcacttcagc tgaacctctt ctgtgatcct cacctgttct ctagaggtga 235080
gaccagggca cagtcccttt ctagatgacc aaagagcact tctttctatg tggttcacat 235140
ttggctccat caccatcgta gctgacaggg ccaaccctcc ggcatcttca tccttcacca 235200
```

```
ctgtctttgc tgtgccccat aaggcctgaa caaggctgat gggccaagta tggtgtggcc    235260
agccccacag tctgttacta ggccttgctt tggtagacac acttcttgat ttagaaccat    235320
ggctctcagt catgggcagt tgtgccctgc ttggcaatgt aaggagacat ttccagttgt    235380
cagagtgagt ttgaagggtg ttaatgcact tagttggtgg agaccacggt tactgttcaa    235440
catcctacaa ttcgtaggac actcatccat aacaatgatc tgattccaaa tgtcattgat    235500
gctgacatta ataaaccctg ctctaagtta atgttttttt cttactcata tttaaaatgc    235560
ttcctctagc taaaccatta gccccagtg aggtataagt tttcctctcc aagggacatt     235620
tgactatgca tgtacatact tcgggttgtt acagctggag attggtgatg cttctggcat    235680
ctaatggata taagtccaag atgttgctca atatactgca atgcagagga cagcccacga    235740
gaacaaggaa ttatcccatt cataatgcca ctagtattaa ggttgaaaaa ccttggttta    235800
gaatatgggg atacttattg gtgctcccta aggtgctatc tgaaagcagc tttgaagaca    235860
agcagaggct ttgaagacat actcacaggg tatgatatag tttggatatt tgtcttctcc    235920
aaatctcacg ttgaaaactg atccccagtg ttggaggtgt gacttggtgg gaggcatttg    235980
ggtcattggc cggatccctc atgaatgact tggtgcagtc ttccaggtga tgcctgagtt    236040
cttgctctat tatttctcag gagatcaggt tgttaaaaag agcctggcac cttcctctcc    236100
tctctctctt gcttcctctc tcaccatatg atctgcgcac acagcagctc cccttcctct    236160
tccaccataa gtggaagctc cctgaggcct caccagaagc agatgctggt accatgcttc    236220
ttgtacaccc cgaagaactg tgagccaaat aaacctcttt tcttttcttt tttatttttc    236280
taattagaga caaggtcttg ctctgttaga ctggagtaca gtggtgcaat catagctcac    236340
tgcagcctca aactcctagg ctcaagccac cctcccacct caacctcccg agtagctagg    236400
actacaggtg catgcctcca tgcccagtta attaaaaaaa ttgtagggac agtcttgctg    236460
agtttcccag gctggtctca aactcctgac ctcaagcggt cctcctgctt cagcctccta    236520
aagtgctggg attacagatg tgagccacca tgcctggacc gtcttttctt tataaattgc    236580
tcagcttcag gtattccgtt atagcaatgc atatggagta agacattgta caagtcccac    236640
tttgggcacg tctagatctg tctgtgatcc tagacaagtt atgtaatctc tctttgtgtc    236700
taaacctgtt gtttgtttct gtctttattc ctcattaggt ccaactctaa agatagtaaa    236760
attataggta taaatggagt taagagggggt gccttaccaa gagtaaaccc tccaggagtg    236820
ttattctgtc agtatgactt ggttttttagc tttgaaactt ttagcatgaa actaacatgg    236880
caggaaaagg cctaaattag aattcttcac acacaaaact ccttctatca ggaggcagcc    236940
catctgttgt caaataatcc tactcgtaga aatgtattaa attttttcttt tccttcccctt   237000 ttcccccttc attaaatgga attagattgt gacactatga ggaaattaaa gtgaaggtaa    237060
aataaaacaa acaggaagaa gtctgtcttc agattggata tgcaattatc ctgtctttac    237120
tgctgatttc aattataact cattggtgtt accagcccac gatagatgtc ccctgcctat    237180
gtggtgttta aatcaagtgt tggcatcatt cacacttgtt tactgttatt agcactgatg    237240
gatgtaatct tcatgtcttc ctctgaacac tgcatgctga gaaagggggcc ttatttcctc    237300 gtggattttc taggcaagag aatgtcaggc cctcacctgt cctatttcca tctcactcag    237360
cagaaaacac actggctcat ggaaactgca agcatcgttg tcagctgcac ctgcaggcac    237420 catgggggttg caagtcagca tccccttttca gaaatgagga tggaattaga ggtggaaaga   237480
aaattctcca cagtcctctc acttctctgg gcttagacag ggaggtttct gctatgtttt    237540
```

```
cattgattat gctgtggggg aagggagag gaggaatccc ctaagaagaa caatgtctca    237600
ttggatattg ttcctttggg ggaaaaaaaa aaaggaaagg aaatattttc attttttctt    237660 acttttcta  ccctagaatc tcaatgccac cttcaaacat ttgaatctca cagggagaag    237720
gcggccacat atttcacccc caaatgctag gccatgtctt ctcatgtcag aaatgcccta    237780
ttgtgcgtgt gtccttgttg caagccatct tagacttgtt gtttcaggga tagggaaacc    237840
attctgcaat ccaaataagg ttgcatttct tgcaattcaa aataaaaggt gtgcatgcac    237900
acacgcatgt gctggtatta ttgtacagct tgcgtggtgc aaggctgaag gctaagggac    237960
taatggaggc tgaaatttag ccctagatac actctgcaag ctgagtacct gtggggccgt    238020
attacctggc tagaggtgtg cctatttctc atgcatccag tatcaggtac ttttctgact    238080
tagagggtcc ctcaaccctc tcctccttcc cctccaccta tcgtacttag catactgtat    238140
atttgccctt agtctgtttc atccaacttg atcacttggt agcctgtctt tatccccact    238200
gtctaaatca gtatttggaa tgtagtaggg acacaaaaaa aattagttga ataaaggaat    238260
aaatgggtga aatagtgaat gcatgaaaaa ggaaaaaatg aatattttgg ctgctgtgta    238320
ttcttgtatt gttgttatat ataattcttc tgcctgtctt tcttcataca tacctcatta    238380
ttagtataaa ctaccagcat tcgtgatatg caggtctttg cttttgcaga gagccatggg    238440
tttctctaaa aggcatcttg cagcctcccg cccagggtgt ctctgtgcag ctaacctggt    238500
tgctaatctc tgcaagctcg tacttttct gcagcacgtg attctgttct catttactct    238560
tgtaatcctt ctgtttcctt ctgaccagct tgagcttctg tatctagtgc cttgacgttc    238620 tcttctttc ttggtctttt taacattatt atgtcagtta taatgttttt cagttgcttt    238680
tagtattcag aaaattcttg aagccttctt attgcccact ggtattttgt cttcgccgct    238740
tgttgtttgg gtggatttag atatagcaga gagagagaga gagagagaga gagagagaga    238800
gagaggaaaa tagagacaga gatatgtaat ccccccaacc aaccccgtt atctgtgatt    238860 tccattaccc atggttaggt tagtacagta cagtgatatt ttgagagaga gaaagagaca    238920
tcacattcac gtaacgtttt attagagtat atattgttac agttgtattt tattttaatt    238980
gttgttaatc tcttactgtg cctaatttat aaaataaacg ttatcatggg catgcaggta    239040
taggaaaaaa cattgcatat atagagtttg gtactgtcca cagcttgagg catccaatgg    239100
gggtcttgga aagcatccct cactgcccct ggtaaggagg agctactcca gttttgagag    239160
gagaaactaa acagatatga aaaacataca agttgtaacc taataggaaa attttaaag    239220 tgttattaaa aaccatatct tatatatctc atatattaaa ggacttcaca atggacttta    239280
ggaaattaag atggaagttg caatagcaaa agtttagcaa tgcgtattct tacatatgaa    239340
aatcaaaatt aacctagcag tgttctgagc aacttcactt taagaagtaa aactagtgaa    239400
atgataaagg tatatgggtg ctgactgtta cgtaattagg ctgatataat ttagcaagga    239460
tatcagaaat catatacccca aaatgagctt tattatattc aaattagtca cttcagaggc    239520
agtacactaa ttacaataag gtaagactgc tggaaacttc tttatttctc ctcactttaa    239580
aacgtttcag agcccatagt aatttatttt taatatcttg ctgaggcaag tcttaatcct    239640
taaggaggca tttatatttg gatacagcca gggttctgtt gagtaaggtc agtgaccaca    239700
ttgtataaca caattttaat tcaaagacaa ggaacagcta taaataaagg tgagcttgtt    239760
tcaactaact ctttttttatt tttttttta ttttttttat ttttgagac    239820 agagtctcgc tctgtcgccc aagctggagt gcagtggcat gatcacggct cactataacc    239880
tccacctcac aggttcaagc gattctcctg cctcaacctc ccaagtagcc agaaatacag    239940
```

```
gcacgtgcca ccacgcccag ctgattttg tattttttt agtagggacg gagtttcacc 240000
atgttagcca ggctggtctc gaactcttgg cttcaagtgt tctgcccgcc ttggcctccc 240060
aaagtgctgg gattacaggc gggagccaat gcgcccagcc tcaactaaac cttaaggcac 240120
attgaaaaga aaatcaaaat gcattgagct aaatgccagg catatgcctt tccaaatgga 240180
cttgccatga aggatgtcat tcctgtgcag ccaggtgttg tcttctatgt attttagaa 240240 tgcccatcat atagtctcac cttttaaagt ctgtttagtg gaatgttttc taactttccc 240300
atgtacctcc catgtcattt tttgccagtt ctgccttccc taataaccaa tgaaggtact 240360
tgcttcatgt taaattctag gtaatctggt ttctactgaa ttagaacatt cccacccgcc 240420
aatgtctttg aataattaaa ggttttataa tgtggtttcc atacaactaa ctgaatattt 240480
catgtggcta gataaatagg taaattgcag tacagtagca attggtgtag acacttagag 240540
ggtcctaata aattattgca cacgccaatg tgcaatcaga aagaataact gtagtgttaa 240600
gcctcagaca atgctataga cctgaggatg ggcctgtgat ggacggatca atggctcagt 240660
tcctattgga gtttcacatc taggaataag tgaattcacg actattcatc agctgctgct 240720
actgtacgga agtgtgtcca ttgagaagtt gcagaagggg ctgggagatt ggataaggct 240780
tttgcagtac ccctcctttt taaaaaagca gacagggtgt aactctattg caggctggag 240840
tgcagcgttg tgaccatggc tcaccgcagc ctccaactcc tgggctcaag tgatcctcct 240900
gcctcagcct cctgagtagc taggactaca actaggcacc accataccaa gctaattttt 240960
ttaaataaat tcactgagac agagtcttac tatgttgccc aggtgggtct caaactcctg 241020
gcctgaagca gtcctcccat ctcagcctcc cagagtgctg ggagaacagg cgtgagccac 241080
ggtgcccagc ctcaatacct tttaaattaa caggaagtgg aaaacagaaa ttctgcagca 241140
tgtttttctc attagcatga atcactctct ggtgatgtgt tcatggtttc taatggtatt 241200
ttcaagatgg acaatataaa gacaaccatt agaaaccaca aataatagggg ccatatgaaa 241260 caatataata gatgcatgag gttaactggt caacatttat gctgaactta gatttacact 241320
gattaaaaaa aataatccat ttgaagtgta acacacagaa accaaagttc tgtgtgttct 241380
gttatcttat attatcaatg ctccatgcaa tgtgaaagct taaggcaagt gtttctataa 241440
ccaacaccca tgtgaagaaa tatagttttcc atcttcaaag cagtgcatgc tcttttccca 241500
ttctatctcc ttatcctcct ccgtgataac cattattccc ttttactact catttccatg 241560
cttttcttta tattttccca atgataaagg catccctgaa tcacataatt aaattttgct 241620
tgtttggaga ctctaaatga atgcaacttt ctattacttt ctggtgtgtt ttttcatgc 241680 ataatactgt tttataaatt tcatatgtgt tgctgtgtat acatccattc cactcatttt 241740
aattgttgta tagtgttcta aagtctgaac ataccacagt ccctatgtcc attttattcc 241800
taatagatat ggttattatt ttgagtttga ggttattata aattcgtgtt attaacattc 241860 ttttcaggc accctccttt ctcacaagca ttggttttct gagacatata ccattatgga 241920
attgctggtt caaatcttca actgtatagt ttatataagg atgaactgtt ttccagtaca 241980
gaaatgcctg ttttcaccag gagtgtgcaa tcttcaacat gtggcagtat aaaagttcta 242040
ttttattttt ctgatctagc gtgtgtacat ggaaacccat tgtgtgttca ctgtgtttac 242100
tctgaggttg agacatttcc atatatctct tggccattca tatgtcctgt ttggtgaagc 242160
gtctgttttt gatctgtttt tctactgggt tgtgtgtctt attgctgtat ttcgattaga 242220
gtgcttcact gattatatat gttgcaaata tcttctgatt ttccttccat gttttaatg 242280
```

```
atttatttaa ataagctaaa gttcttaatg ttagtttata gactttacaa tattttcttt   242340
cagattagtg ctttggaatt tttgtttagg atatcttttc ctaccaagag atatgaagat   242400
ttccttttat tttatctgaa aaaagcttaa tattttatct ttcatattga aaccacacag   242460
ggaatatatt tattgcattc tgtaagaggt ctagtttatt tttccttaga atatcacaat   242520
acaatttatt ttaaacagtt tgatccatgt cactaaagtt caagtgatct ctttgtctac   242580
ctctgtgcca atcatcacat ttttatcttc atgattttat aataatccgc aatttatatt   242640
tttatacttt gtttatttct tgccaatatg cattgcatcc ctgagaaaag tgtttatttt   242700
gcgatggttg gtgcaatgtg ctatatgtct aatatctcaa actgttgaag tatgttgttc   242760
acatactcta tatagttttc caggtggtag tttacatatt ctttcagtaa ctaaaatagg   242820
tctattaaat tttcccacga tgtttatgga tgttttaaaa tcttttcgta tattttttcca  242880
aaatttagtt tcttgcattt tatatgctta tgaatttag tggatacagt ctagaatttt    242940
tattgcattg tggcaaatta aggttcttct cattataaag tgatcctctg taagtctgtg   243000
gtgcttcatg ccttaatgtc tgtttagttt gacgttaaca ttcctttgt tttgttagta    243060
atccaattgt gtatagttcc catgtgttta cttcaggcct ttctgttgac tcaggttttg   243120
agtcttttct acatagcgtc tatttgggtc tcataatctt tgattttcaa ccgcagatcc   243180
actgatattt acttttattt ttgatatatt tgtgtttaag tcttctatcc taaattgtgc   243240
tactaatatc ccacttctac atcttgcttg aattgctttt taaaaaatca ttcaggccaa   243300
gcacagtggc tcacacctgt aatcctagca ctttgggaga ccaaggcagg aggatcactt   243360
tagaatcctc caggagttca agaccagcct gaggaacata gcaagacctc atctctatga   243420
aacataaaaa aaaataaata aataaaaaaa ataaattagc caggtgtggt ggtgtgcacc   243480
tgtagtccta ggtactccag agataagagt tgacaggaga gtctgatccc atgagttcaa   243540
ggctgcagtg acctatgatg gcaccactgc actgcaacct ggatgacaga acaagatcct   243600
gtctcagaaa ataagaaat aaaagacaaa taacattact ccatttcctt cactcccact    243660
tctccctcta cactagatgt taaaagactg tactagtttt agtaaataac cctagaaatt   243720
acaacacaga tccttaatat aatcactaat tttaattaat acattttcca cttctctgaa   243780
aatacccagt agtcagtgta ttttagctcc atgtttatga cctaacctac ttgctgttag   243840
tacctttcaa tgttttgtgt tttttaggaa tctttttcag atatgattgc ttatcttatt   243900
atttcaatat taattttgat tttctgatga ttacactatt ttatttatgt ttcattactt   243960
tttgtacctc ctactttat ctgtgattat tgtcttaaaa gaatctatcg gtgatctaaa    244020
atatattttc agagctaaca agctgttgga aactctgttt gcatggctaa atgtgtcttt   244080
atgcatcct cttcttgaac aatattctca ttgaattta atttgcaatt acttctttca     244140
gccatctgag aaatcattct cctattctct ggattccatt attggtatgg agaatttagc   244200
tgtcagttta agtgttgctc ctttaaaaat aatatatttt ctgcagatag tttgtctata   244260
tcccctgat acctttaaga tagttttctt ttgagtttct gccgtttcac tgtgatacca    244320
ttaggggttt attaatctga ttggaattcc ttgatgacct tgaaatttgc aatcgtggtt   244380
tcttccattc tgaaaatagt cattacctct tcaaattttg gtgctgtttc tcttgttttc   244440
actctgtttg cacataattt agattttctc cctctggctc cttttttagt cttttttttt   244500
ttgtattttg tattaaattt tactttcaag cttcattctg gattacttt tctcaagacc    244560
tataatctat ttcattaatt ctcttttcta ctgtatctaa tgcatggtta aaccaatgca   244620
tcaaatcttt atgtttgata tatattttca ttacatttca aggattaatt ttagtttctt   244680
```

```
cttatagttt ccacattttc gaagttctca attttatatt ttctggaatg cattcttcct    244740
agttatttta aagtctgcat tttgtatttc tattttttc aatcaccctt ttgtttcttt     244800
ctcttttttg cttttggtt tcattgacta atatcttcat ggtctaagta ttataattat     244860
gcatatatta gatattctca tattgttttc cttatttcta actctctatt ttatatttt     244920 tgtatatgac agctccctgt gttgcccagg ctggagaggt tgtgctctgt gcccagtggc    244980
acaatcatag ctcactgtag cttcgatctc ttgggctcat gtgattctcc tgcctcagcc    245040
tcctgagtag ctgggactac agtcacatgc caccatgcct agctactatt ttatacttta    245100
aaattttttt agagactagg tcttgctttg ttgcccaggc tgttctctaa ttcctggcct    245160
caagcaatcc ttctaactca gtcttttgaa tagttgggat tacaggtgtg gccactgca     245220 cccggtttcc cagcttttt cagatttcca cgatactctc tggatcgttt cttctcacct     245280
cttctcaagt ttgtccattt ttctcttcag ctttgtttaa tctgcccta  ggtggaccca    245340 ttcattttct cattttgttt atttctctga tctagaagtt tgatttgatt tttattttt     245400 cattttaat  actttcttat tccctgcaga tgttttccaa cttttgtttt tcaagctttt    245460
tgaacattct tcaaaaaatt ggttatcatg tatatttt  catggcatct taattccttt     245520 gggattctg  ctggctcttg ttggtgactt cttgtttctt tcttcatggg cttggtaatc    245580
attgtgaatt ggccattgta tttgcaaatg gattagtggc atctttctcc aaagcagata    245640
acccatgggt agcgaaattc taggttcttt catccatggg gccatgctct tccctgaatt    245700
gttcatagat gttatgaagg tagactgcaa gcacttgcaa gactgaattt agttttgttt    245760
catgtttgcc ttgagggtga aacccatgaa ggtaggaaaa tgttaaaggc aagtatatta    245820
gattgggacc ttcaggcgtg actagggtct gagagttgcc ccattacatg gtgatgctgc    245880
aagaactccc acagtttctt ccagattgga acagtgcact agggcaaagg ctgctttgtg    245940
tgctgggcat ctagctggat catcatttgg tcgtcagtgt gtttttgttt gtttctttgt    246000
tttttgtttg tttgtattgt gttttgagac agggtcttac tgtgtcatcc aggctggagt    246060
gcagtggcac gaacagggtt cactgcagcc tcgaactcct gggctgaaga cttcctccca    246120
cctcaccctc cccagtagct gggaccacgg gtgtgtgcca ctacgcctgg ccacttttta    246180 aaaaatttt  tgtagagaca aggttttcacc atgttgccca ggctgtgata atcagttttg    246240
aagctgtaat cttaaatatg atttttagcac taaaatgttt ttaagagact taaaaaaatc    246300
acacatatta caatccattt tcaataagaa ggttggtttg aataatctac tctgttactg    246360
ctagatgtag gcttctgatt tattctaata tattacagaa atgagtaggt ggaacatgag    246420
tttataaaga taatgcaaat attttattag cactgtattc tcttaagagc agttcagagt    246480
tcaaagaatt gtgactttat ttcacaggca ttaaaataaa ttaaatcagc aatctccattc   246540 ctaacaactc aaacttcaaa gaatttcag acagttaatc atcacctgac accacagcct     246600
atgcaacttg ggtttaatta ggatttatgt tactggtagc attgtggttg aaaagatatt    246660
ttcattaaca tttctctctg aagcactgag tcatactctt gtttattcgc aagtttcttt    246720
acacttttca atcaatattt gagtgttcct tgggaaatgt atgttttggct attttggtgt   246780 ttttgagagt gtttgatctt tgaaaatgca tgattaaaag ccattttaga aataaacatg    246840
agtgttttaa atacaaatta ctaaagccac tgttttgttt caaatttagg gatttaatttt   246900 ttttaatgaa aatgctcctg tttatatatg catgaggtta tgtaaggtca tcaacttaaa    246960
gattgatgat ggatttagtg ccagctgttg attagtatgt ctgcaatcaa tctacaacat    247020
```

```
agcaataacg ctagctacct tgagagtta ctgggagaaa taaataagac acaatgtatg    247080
taattggcct agcaaacttc tttgtatact ataattattc agtaaataat acccttgtga    247140
ttatttatct atcaatcagt cttagagcag tgaatttacc tttaaaatct agacacatta    247200
ggaaagaata atggtagatt ttaagacaaa attaaaattt cttggtgtac tcaaaaatat    247260
atattttctg ttaatgcaaa ttaggctttt atatttatta tttttaatat ttgactctgg    247320
aatgttttca aaatttagtt gagtagatct taatgcaagt ctacttttaa aaaatctcat    247380
tatctagtag gctttactag taattaattt gaatttggta gacatgaaac acaccaattt    247440
cttgtacaca atcataaatc ctgtatacta tgtatactct gtatgcctgt atcttggtga    247500
agtgggaatt aaactttatc aaatttccat tgaaaactg aagagcaaac taagatgtaa    247560
tcagaatgtt aataaatatt gtagaaatgg aaaagtttca gaatgtttag atttctcaag    247620
gaaatctcaa agcatgacac ttttcattgg tctgtcatgg ataattaggt cttttgctat    247680
ttttatttat ttatttccaa tccgtcacaa acgtactttg gttgatgcat atatcaacta    247740
tagagtagta aatctgacaa agtctatgca ctgaaaacta tactctgtca ctgagggaca    247800
ctgatgaagg cttaagcaac tgggagacag actgtgttca caaacacaac ccctcctga    247860 gaagatacaa tattgttaag atatttattt tgtacaaatt aatctacaga ctctttgcaa    247920
tcccaaataa aataacagta gactttaga aaatacataa attaacaaga taaatttaaa    247980
attttaatga aaatacaaaa gatctacaat aaccaaaaca tttttgtagc agtagaacat    248040
acttggaggg ctcctgctac ctgagctcaa gacttagtat agagctatat taattgaaac    248100
agcgtattat tgcataaaag atgtaaaacc tgatcaatat catagactag agacaccaca    248160
tagaactgta catatatgga caatgaattt tccaaggaga ttcaaaggta attctatgca    248220
ggaatgattt ttttttcaag aaatggtgtt ggaaacatta agtatccata tacaaaagaa    248280
aagaaaaagt aaacaaaaag ctttgatcta taactcacaa tttgtacaaa aaacaactga    248340
aaagtgagtc aaatacctag atgtaaagct taaaattgta aaacttccag agaaaaaaaa    248400
aaaaaaagaa aaattttgtg actttagatt ttggcaaata tttcttactt aaaacaagaa    248460
gcttgatttt taaaggaacc aattaataca ttggactaca tcaaaactta aaaaaatgct    248520
tatgctacat gaaagacatt gctaagggaa tgtaaagaga attcacaaac tgggaggtaa    248580
gataggcaaa ttaaatatcg gatgaaggta ttgtaccagt ataaatgtat gcatacatac    248640
atatatatga tgcagtttcc tataaatata tagtatatat ggtattagac atatatgtat    248700
agacacgtac tggtacaatt atatactata tatacaatat tcatatatag tatatatgat    248760
acagtattgt atactatata taaaatatat catatatttta ccatacagta tactacacat    248820
atgtatatat atgatatact gagtatcact attactaaaa attacagaat gtgaactatg    248880
aaaatgtaaa agcctattta aataaaataa atatttaaaa tactgtgttt tttatatata    248940
tagcacatgt agtatactaa attgtataca gtatagtata tatagtatac tgtatcatat    249000
atattgtcaa tatagtatat aatttacccc tgtgtgtgta tagatgtgtg tatatgtgtg    249060
tatatataca catatatatg tatgtgtgta tatatacaca tatatatgta tgtgtgtata    249120
tatacacata tatgtgtatg tgtgtatata tacacacata tatatattct aaaaggagaa    249180
ttaaaaagaa accaccccat aacaattgga cagaaaattg aacaggcagt tcacctagga    249240
aaacatacat atgaccaata gcccaatgaa aatgtgctca gcatcattag tcattggata    249300
aatgcacaaa tgaaaccaca gtgaaatacc actacacatc tgagaatggc tgaagccaca    249360
agactcgcta tgccagggct tggtgaggat ttggaggagc tagagtccac cccaagctgc    249420
```

```
tggtggggaa gtgatatgaa accaggactt ttgagaagag tttggcaatt tttttgttgt   249480
taaacctaca agtaccatgt ggttcagcca tttaactcct aggtatttac acaagaaaaa   249540
gaggagcata tgtccatacc aagaccaaga acctgaatgt attcataggc tggaatgctt   249600
ctgagcagta aaaatgaatg aactgttggt gcatgctaca acctgcatga atattaaaat   249660
gattatgcca agcctaagag gccaagcaat gaagagaccg taattctgtt acttcgcttt   249720
taatattttg gaagctgtaa ttcataatgc ctgtctgtaa gcagtaact gtttgcctga    249780 gatgaggagg aggagcaaga gatatagatt ataaagggat atgggtaaac tttggggtgt   249840
gatatatata tatgtacatg tatatatatg tgtgtgtgta tatgtgtata aaatacacat   249900
atatgtatat tttaaacaga gtctcactct atcacccagg gtgaagtgca gtggcacaac   249960
ctcggctcac tacaacctcc acctcctggg ttcaagcagt tctcctgcct cagcctcccc   250020
agtagctggg actacaggtg catgccacca cgccctgcta tgtgtgattg atatttctgt   250080
caccttgact gtggtgatgg cttcataact gtatacataa gtcaacattt attatactgt   250140
atactttatg tacagtttat acttttacaa ctataacttc agaaacccac taccctattt   250200
taaaaaagtt aataattact ctcagccact gtgagacctc actgtttcct tatgctcatt   250260 tttccctta acaacaatgg ggaactagta ttttatcaga taaaaataat gtttgatagg    250320
attttgtgca aagtctgttt tgcctactaa ttctgcctta tggcatctca gacatgtaaa   250380
ttagacaaga gccttcagta tgtctgatct gttgtcacgt tattttccac tagtttgtgt   250440
gatttagatt attttaaag agctgataaa ggaaaggaaa ggaagagaga gatagaagaa    250500 agaaagaga gaagaaagag aaagaaagag aaggaaggga aagaaagaaa gaaagaaaga    250560
aagaaagaaa gaaagaaaga aagaaagaaa gaaagaaaga aagaaagaaa aaagagacg    250620 cctgtcttt taattccagt tggaagcagc tttagttata aaatttccac tctctagaat    250680
attcttgggg aaaaaatgaa gtgtcaatta aattgatttt tttaacttgc atcctatgtc   250740
tctgaacatg attcttttc aatcaggcat gtagttattg aggacccatt tatgagctgt    250800
gcatacatcc catccaattc catccaattc cgtccaatcc tgtccacaga catgttgaaa   250860
gcatgagctt cctgcaagag caatgcacca gccgttttcc tagagatggg tcttcaaaga   250920
gagggttctt tctcggagca cctgctcagg gaacaagact gactttaaac cagtgttagc   250980
aatatgcatg gtacactgaa ccatctgctg gaggacctcc ttgtgtccaa cacagtcctt   251040
ctgttgaatg tcatggaaaa gactgagggt tgaagcaaat cattttatgc agtgaggaga   251100
agaccgtgct catctttcag ttttttgagcc acatctacct aatttatagt caggtttggt   251160
agcctcagca ctactgatat ttgctgcata aatctatgct ttgttggggt tgtcctgtgc   251220
attttaaggt attgaatagc atccccagtt cacacccacc agataccagt atataaatat   251280
ataccgtttt tgccaattaa aatgaataag aaaaaaatca ttgttacaga ttaataataa   251340
taataataat taataataag tggctggaca cagtggctca tgcctgtaat cctggcattt   251400
gggaaggcca aggcaggagg atcccatgag cctgggaatt tgaggccagt ctgggtaaca   251460
tagtgagacc ccatctctaa aaaaaaaatg aaaaattagc caggcatggt gatatgtgcc   251520
tgtagtccaa gctactcagg agactgaggc aataggatca cttgagccca ggtgtttgag   251580
gctccagtga gctagctatt gatggttcca ctgcactcca gcctaggcga cagagcaaga   251640
cctggtctct aaaaaataaa aataagtaaa taagctaaat gctcttgaac tgaaaaaaag   251700
aatgtattct atgagagata cctgataatc acctactttg accatgtttt tatccttcaa   251760
```

```
ggatttcaaa ctgttacaac aaacttctaa acgtgtatct ctttagttca gcttccttac 251820
atgaatttaa tgctccagta tgtgagacca attattgatt taaaaaaggg tagatctgtt 251880
ttaaaattcc tttaccaata ttcctcatgc tcatgagaaa gatatgaggc agtgctgttg 251940
actgcatttg tatttagtta ataccacgag caagtgggaa aaattcagaa gtgacactga 252000
gttggtcatc tctcaattat catcatgaga agtacgcaca atgtgaacat tctgccatag 252060
ggcttgtctc tgtaaactgc tggtcaaggg gcatggacag attctactat ttttaaaaac 252120
atctttctga acagataacg gaggcttaat tgtagtgtaa acacactgat gtacaaatct 252180
cgaaaaacat aaaataaagt gtgttgagat tggaggtgct ctgttcaact ttcgagggat 252240
agaaaatatg cctatcagct gtaaaagcgg tgcatttatt ttcatttttt gagaccaaca 252300
ctagagcaga aagacacatt aacaaaaggg taagagtctt cagagcagat tactcccact 252360
tgaaaaatga gttaagtgat ttcacagcgg gagagaggga tatttgcagc aagaagtttc 252420
attagtcact gaatgaggtt tctctgacat atattttcac agaatgagaa gcatgatctt 252480
tagaagcaag agccataacc tttctatatt tttcttctgt ttattcattt tgctggaaga 252540
ttcccttccc tagccttctg gaaatttcag ccttctagtc tgatttggtg acctttgttc 252600
actaggaaga acatagtccg tttctctttg ccaaaaggta gttgcatgca tttgcaattt 252660
aaacaaggaa catccaaaaa aattagaatg tgtgtttgtt gaaatattg tgattattaa 252720
agtcagaaga gatagctaaa acagaagatg cccatacttt gaaatcagat gattattaat 252780
agatgctgct ttgtgttgac tggagtttaa ctgccagtcc tttcttttgc caagatattt 252840
tcccaaaaga aacatttcag ttgtaggctc aataaggaga ctggaatctg ctttgtgaat 252900
tggtggcaaa aggaaaaggt ggggaaggta ggagaagaaa agagagatgg agccttcagg 252960
taggagacta ctttttcttc ctttggtgtc tcatcttaat atttaaaaaa ttaaattgaa 253020
gactcagcta aggtatagaa aatatcaggc ttttctttt tgacatataa ccaacattat 253080
ctcttgtcaa gcaatttatt ttttatttt attttttaa ttttctaata agactaggtt 253140
tattcagtac cctagtaaaa gttttattta taagtatcca acagtataaa aagtacaaaa 253200
cagacctgta gatttctaat atattaatac aaagtgctta ttttttaaac tgcttttttt 253260
tttttttttt gaaacggagt cttgctttgt cgcccaggct ggagtgcagt ggcgccatct 253320
cagctcactg caacctccat ctcccgggtt caagcaattc tcctgcctca gcctcctgag 253380
tagctgggat tacaggcacc caccactatg cctggctaat ttttttgtat tttagtaga 253440
gatgaggttt caccaagttg gccagcctgc tctcaaactc ctaaactcaa gtgatccacc 253500
cacctctgcc tcccaaagtg ctaggattac aggtacatgt caccacgccc agctaatttt 253560
tgtacttta gtagagacag gttttacca tgttggccag gttggtctac atgatgactt 253620
cctaaacaag tgcataactt cgattctaca aaagatgaca gaattcatta gtactactcg 253680
tttgtcctca gttatacttt ctgcagtttc agttatctac ggtcaaccat ggtctgcaga 253740
aaattccaga aataaacaat gcatcagttt tacattgccc ttggttgtga gtagcatgat 253800
gaagtctcca gcagtcctgc tccctcccaa tccatcctgc ccaagaggtg aatcctccct 253860
ctgtctggca ttttcatgct gtagagactg cctgacccct agtcacttag tagtctgctc 253920
agtgaccaga tcatctgtca tggtactgca gtgtttgttc tcaagtaacc cttatttcag 253980
ttaacaatgg ccccaaagtg caagagtagt gatgctggca tagtgttata attcttctat 254040
tgtattatta gctattattg ttaatttcct gtgactaatt gataaattaa gctttatcat 254100
aggcatctat gtataagaaa atgcacagca catataaggt tcagtactat ctgtgttttc 254160
```

```
aggtaaccac tacaggtctt ggtacgtgtc ccccgtgggt aacggaggac tcctattgtc  254220
tgtgttttat ttgaagggat tttgattcat ttgtgatctg tttcacgccc tcttcctttt  254280
ctcctctggc aaatttgagt tggcatgccc tccacttaat cttttaaatg cttgatccat  254340
tctattctgc agaagaatgt taaattttc attatgtcag tcaatatgct tttggaaaaa  254400
gggacactcc tgtttgtgtt tcctctttaa attcatggtt tagagttttc tcctcttcct  254460
ttcgcttgag cctccccaac tgcagtgtct cctcagtcct ctaactccat gactgtggat  254520
gaaactccat cttgtttttc ttcaatgtgc tatttctcaa gtttacatct acaaatgtgc  254580
tgcaaatatc tggtactgaa tgatgtttca tttcagtgaa gcgtttgttt ttgtttgttt  254640
tgaaagttaa ttgtgcatgt ggtttaaaaa atccaatata acaaaaggca tacagggaca  254700
ccatttgacc atgccattcc ccaccccttc attcagttgt ttcagcgacc acctttcttt  254760
gttgtggctt gagaatcctt ccagagacgt gactaaacag ccatggaaat gccagtgcaa  254820
cagagcattc tttacatctt gcttttttcca cttaataaca taactttgag gttgtcctat  254880
tttgacacat agacatccac ctcattcttc aggaagcctc tgtcacaggc acatatatgg  254940
acctaccata attcattgat tggactgcca tggttggaca cgaagattgt ttccaaatac  255000
ttgctaccat aaaccctagt gcagtgaaac ttccttcaca cacctttttt tttctttttt  255060
gagagggagt ctagctatgt cacccaggct ggagtgcagt ggcacgatct cggctcactg  255120
caagctccgc ctcccgggtt cacgccattc cctgcctca gcctcccgag tagctgggac  255180
tacaggtgcc cgccaccaca cccggctaat tttttttgtat ttttagtaga cgggggtttt  255240
cgccgtggta gccaggatgg tctccatctc ctgaccttgt gatctgcctg ccttggcctc  255300
ccaaagtgct gggattacag gcatgagccc ttcacacacc tttgagtggg ggtaggattc  255360
catatctatt ttaaatgtat atagatgtta ttgagttta gaggactaaa caatttagct  255420
tccaagcata acctataaat gcatcttggc cactttcttg ccaacagagt gtgttataaa  255480
gcatgtcatt tttgtctgtc tcaggtcagt gaaactcctg taaggacca gatagtaaat  255540 gtgagccaca tggtttctgt cctgactact caaatctgcc cttgcagtgt gagagcagca  255600
atagatgatt tgtccatgag tggtgtggct ctcttccaat aaatctgtat ttacaaaagg  255660
aggtcctggc caggtttgct tcctggatca tagtttgctg accctggtc tatctaataa  255720 caacaataat aatcttttagt ttgtttcttt tgtatgagtt aggctgttca tctgtttaaa  255780
aatctactta ggtatttttt tcctgttaat tacatccgtt gctcattttg cataatgcag  255840
tttaactttc tcttgttggt ttattaaaag caatctatat atttgaaact taattacttt  255900
tatatattct gaaaaataat tgatctgtta gctgttgcaa cagttggctt tctgataaat  255960
ttctatttga catagaacca agtaaaaatt atgttacctt gggttgtaac agttactctt  256020
aaaaacattt agatctgcaa ggcacagtgt ctcatgcctg taatcccagc actcttgaag  256080
ctcctggctt caagagacat cccgccccc acccgcccc cgccccac cttgtcttcc  256140 caaagtgttg ggattatagt tgtaaaccag caggcctgac cttgtgtaga catggtaatt  256200
gacaagaatc ttgtagtcac attttcatag actatgcagt agatgcaata gactaacttc  256260
tgtatgaatc ttttttcattt tgtattaatt ataatcattt gccaagtttg cttcattcat  256320
ttgtttagta aaagagtatg tgtaaggaat ttggtaggca attttttagaa cttttagtga  256380 caactttgtt tttgattgtt tcttagtgaa agaaggatta caataagaac ttagccacaa  256440
aatacaagtt tccatgagtc actgcaaaat aacagggata gtttggaaag gcaaggagta  256500
```

```
accagaagct ttggggcata gttttcctta gttaaatcag tataataaat ggggtacaca   256560
ttgcaaatta tttattcata gtttggtagt ttgcattggt atgtcttaaa cctgaatact   256620
ttagagtgaa tgaagtaaat aggatgagat gatggggaat gcacacacac ccacacacat   256680
gcacacacaa acacacatgc atgcatgcat acatacatgc acacacacat atacatatgt   256740
gtgtgtgcct gtgtgtgcac atgtgtgtgt atgtatgtta cgtttacatt atttctgcat   256800
attaaacact ttcccctttc gttagatatt ctttattgag aaaatgcact acactagatt   256860
accattactt aaaagttgct ctcgcagcac aaatcaattc attatcttta aggataagcc   256920
catgtctgga ggtagggaaa tcatttttta aaaattaaag tttctgtctt gaaatattgt   256980
catccttcac tttttctatg cactaggatg ctctttgctt tcaggaaaac acgttatgac   257040
tcatttaata ctgttgtccc tcttatccag aacagaacat accgtggttg cctaacagga   257100
aggctgcata taaacccag ttttgtctag tatcattttc cccaagtcca ttatgtgtgt   257160
tattgtgcag tgcatgtcca aatgaggatt tgagcagtag agaagaaatt cattaaagaa   257220
atgtgtcatc tccttgcaaa aaggaaagta ttgttgagga aattgttact gataagacaa   257280
aagtggtgaa tgaacatcta ccatttgaag gcatttctct gaagtgaaaa ttaccttgaa   257340
ttgtcttggg atcagttgtg acttgatcct tctattagga gctgtttcaa actcagaaa    257400
ggggtgatga ttcacactga tgactgaagg tttcttggag ctggtgtgaa taagaaggga   257460
aaagtattgc aaatgcatca ttgtggcttt cactgagact cagtgqacag aattcatcat   257520
gatcttcctg ggctccagaa acacaggctt gaaatttagt agccagtctg ccaagcatgg   257580
agttaggcac agatgggatc tgagttagag aactctcctg ggactggtac ccaggggagg   257640
taatgtaggg tgaaatgtca ttgttcaaca tgcttattat tcacctgaac atgggtgaca   257700
ttcctttcct gagaaactct ggtctgacaa atgggttctt acaattattt ctgaaaatag   257760
aaaatgtatt tccaataatt attagttata tctatttatt atttctagtc atattattcc   257820
taataattga gctctatggc tattgggtga ggttcctcag ggaacagcgg attctctgtt   257880
actgaaggag tttaaacagt atctataccg agagtagtca agacatgcag agatgatttc   257940
catattataa gagaagttgg attgaattaa gtctgtgatt ccctgccatt ctgagatttt   258000
aaaagtccag gcctttaatg taccaattcc ctgtcatcat tagtctaatt attggcaact   258060
acattgaatt atacagtata gtatcagttg atgaatatag tatcaattga ttggtacaac   258120
actgtatcag gttgaattta actgagttaa ggtatggccc taccttctaa gagcttacca   258180
gttgacaata aaagcacatg ggtaggcaag agacacccac attattagat ataactgtgt   258240
tattcatgtt acctaaagtt ggagagtaag aagaatgaat ttcttgaggt agggatgaaa   258300
gtatatcccc attccaacag tttagatcca gagaagaaaa aatgtttcag agaggagata   258360
tgattttaaa aattgcttca gaggaaaaat tcagattggt aatggcagcc tagaaagatg   258420
ctaaatgagg aattctaagt caaaggcctt gcagaaagct aggaatgaac atgtcactgg   258480
ttctcatgga aaatgcttag agtcctgcag ggaataaatt ccttttttt tcttttctt    258540
ttattattat actttaagtt ctagggtaca tgtgcacaac gtgcaggttt gttacatatg   258600
tatacatgtg ccatgttggt gtgctgcacc cattaactcg tcatttacat taggttatct   258660
cctttttttt aaatcattat tactattgta tttatttatt tattttttat tatacttta    258720
tgttttaggg tacatgtgca caatgtgcag gttagttaca tatgtataca tgtgccattt   258780
tggtgtgctg cacccagtaa ctcgtcaatt aacattaggt atatctccaa atgctatccc   258840
tcccccctcc ccccaccccca caacaggccc cggtgtgtga tgttcccatt cctgtgtcca   258900
```

```
tgtgttctca ctgttcaatt cccacctatg agtgagaaca tgcggtgttt ggttgttttt    258960
ccttgtgata gtttgctgag aatgatggtt tccagcttca tccatgtccc tacaaaggac    259020
acgaactcat catttttatg gctgcatagt attccatggt gtatatgtgc cacattttct    259080
taatccagtc tatcattgtt ggacatttgg gttggttcca agtctttgct attacgaata    259140
gtgacgcaat aaacatacgt gtgcatgtgt ctttatagca gcatgattta taatcctttg    259200
ggtatatgat cagtagtggg atggctgggt caaatggtat ttctagttct agatccctga    259260
gaaatcgcca cactgacttc cacaatggtt gaactagttt acagtcccgc caacagtgta    259320
aaagcattcc tatttctcca catcctctcc agcacccgtt gtttcctgac ttttttaatga    259380 ttgccattct aactggtgtg acatggtatc tcattgtggt tttgatttgc atttctctgg    259440
tggccagtga tgatgagcat tttttcatgt gtcttttggc tgcataaatg tcttcttttg    259500
agaagtgtct gttcatatcc tttgcccact ttttgatggg gttgttttgt tttttcttgg    259560
aaatttgttg gagttaattg tagattctgg atgttagccc tttgtcagat gagtagattg    259620 caaaatttt ctcccatttt gtaggttgcc tgttcactct gatggtagtt tcttttgctg    259680
tgcagaagct ctttagttta attagatccc atttgtcaat tttggctttt gttgccattg    259740
cttttggtgt tttagacatg aagtccttgc ccatgcctat gtcctgaatg gtattgccta    259800
ggttttcttc tagggttttt atggttttag gtctaacatt taagtcttta atccatttg    259860 aattaatttt tgtgtaaggt gtaaggaagt tgagactggt agaagactaa gcttcttcca    259920
gactttaatc attgttatct ggaaaggaat tgaaaatagt tttttctga atcattgtaa    259980 tcatgtgaaa tcactaaatg tcagtgttga attgaccaca aggaccaagc taattatgga    260040
agaaataggt gggggagaca ttgaacacag caatccacag gagtttgagt aagtctggag    260100
tgttgaactg gtgaaagtcc tccctgcaac agctccatcg gggcaattct gttaagtcaa    260160
gactcaagca ctggacggtg aatggtccag aaaaactatg tcattaaaaa tgcacatttg    260220
tttaaaataa ctaactgctc tttcgtggat gattggtact aagattttat aaactgttta    260280
gggaccacca tgattcctca cacacattaa ttaattcatg agagttgatt ttcttttcaa    260340
acacattgat acattattag tagatagcac cccaacacac acacacacac acacacacac    260400
acacacacac acacacacac acacagagag agagagagag agaggggtac ttacaatcaa    260460
agacagccat actagatcca attggtagca acaaagtgag aaaagtacca gaacacacag    260520
gcaaattgaa aatacacaaa gccacatcca cagcatgccc tttaatggag gaagtgggaa    260580
gaaggttcca ttttccactc tgctcatttt cttccccacc acccattaag agtgtcaatt    260640
ctcattcaca ttccttttag agaagaacga accatcgaaa agggagctga gagttgtaat    260700
aaaaatattg cattacggat ttctccagtt tcctttcagt atgaagtatt tgttacttca    260760
ttgaaaaaag tagaagtatt gatcagccgc ttagcttgtg gcttctgctc tcaaggagtc    260820
agcacatagt ctgatgtgga ggaaaatcta taaatggatt tctgcaatct gcaggtaagc    260880
atgggatgaa atgttccttg acatccaacc caggttagaa atcagttttc aagactctaa    260940
atttgaggac ccctaggagc tcaaatgata aagagaagaa ggtttatagt ccatgatggg    261000
ggagggactg cacactacct gcagggtgag cagaaaggat gcaggggctt ggtatcacag    261060
gaccagcatt gtaaatatta caggaagtaa ccttttcctgt gtgtccttca tgtgcttttc    261120
tttgtgcata ttcttgaggc ttaaaggaaa gggagccagt ctgtgtccat acttctctcc    261180
cgtgcacatc atcccggcat ggcactgctg atgcaaatta aaaaaataac ctttgactag    261240
```

```
aagcattttc ccagctacca gtttccttct ccccagtgca agacaatgtg acagcaaagg 261300
ttcatgcaca gaagcagaaa ggtagtggaa tgactcagct tctaactaaa ttccttccac 261360
cttccttagc tttgtggtct caggatttta aagaggtct ctcatgtgct gctacagaac 261420
cagcaggaaa aatcagacag ggccaagaca gagagaaaag agaccttt ctcctatatt 261480 gccctacct agggctccta tccaaagcat gttctagttc ctagatggtt gattccaata 261540
aaataacata aaaataaact gtgcaataaa aatttaaagg gagttgcgct gaccatcatt 261600
tttgaaatat ttaaaaatga gtcctcagta aattttggtg tgaacattag tattttgtca 261660
tggatagagg cacaagaaag gagtaaatgt gagacctaca ttgcatccaa tgcctgcatc 261720
agtagaatct aatctcttcc ccccatgata aaatggcctc attctgtcaa ctacaggctt 261780
tgctagcttt ttctcagaca acagaccaaa tttatcccca gcctgataag gatctttatt 261840
gcatttgctc ccaccccacc tactgtattt agggtaatgg tgaaaatgt acattgatgc 261900 tgaattttat agaaatagta gaatggaaa tgatcttaca gagttgtcat ctactatctg 261960
gtgtaggttt ggttacaaag ctgtatttcc tcttccaagt tttaagtaat caagtttcaa 262020
aacaatcttt cctgacatcc agtttgtgtt aaagccaatt tcccaaatga ttttcatttg 262080
cattctggaa atgcagtgaa gccttgacat tttacaaaat gacctatctt ctactcaagt 262140
caatgaaact acagtaaaca ttttatgtgt agttgcaatg cttgtatctc cctcaagatt 262200
aaacacagaa aagcatcttt ggggaggata tttaaatacg atattaaagc atataacatg 262260
tgtctgtatt ttttcagttt taagtatact tactaataat aacaggcaaa gtggtacgag 262320
gtaaaacact acttttcatt gttcagttta cagtagtcat tgactattct acatatgcgc 262380
ttagcataat atttacagac tatgtaatac aaatcacact ctgtgaattc tcatgtcctg 262440
tgagacacag gaacagaaga gctttgtaaa aaaacagcaa agtacaactt gaaaagttaa 262500
gccatatgag taagaaatca aagtgatgaa tttactaagt gtttattaat atttaagcta 262560
agtttacaca tgactcaaca tcatattcat actcatagtc tgttactgta ctttgccaaa 262620
ctgtctgtac tattttgtga gaggatatta tctttaatat tgctctcact gcaatgaagc 262680
ataaataaag tatatgtcat gttctacctt ttcaggagct ccaatgaaca catgctatgg 262740
tttttaatga ctgtaaagaa aatttcaaag ccatatctta tctgtttcta tggagaagtt 262800
gatcaatgat caataccatt tgcaaggacc ccgatgtgtg acttgtttct ctttatactg 262860
tgacatgttt ccctgaaggt ggaacgtcaa tgagacattc attttctact aaatgaaaat 262920
gatgttaaag ttgcagtcta gtgataaagt taccaagatc tgcttcttgg attttttatg 262980
gggtttgggc aacacataaa gaaactttcc tctcattcaa gttgaacata tccaaccact 263040
tatatatatg ttgcccagtg aggtcagtgt tacatgaagt tgtagaacat ttactttgaa 263100
atgaggtttt ctcatttaat aaaagtgtca ccttgtgtca gtggcttagc tagttccagc 263160
ttctatttta tctcttatcc aatgagaata tgcctatcac ataaggagtg tggctgggaa 263220
gaatggtggt ctgtccttat ctcctgggtt ctctggtttc agaacctgca cagcggacag 263280
ttccaaacac tgcattccac catcatttca tcagcattcc tcttggaata aatgtgtctt 263340
gacagtctct cttagaagtg cttttctctga agctactgag gaccatgcca tgtgtaggca 263400
taactgaagc gtgcacattc tatagagtgc ctcgaagatg tgcacattct atagagtgcc 263460
tccaaggttt tcaagaagaa tggagcccaa cttggccaca ttggttacac acttgtgcat 263520
ggtccattta ttgactatcc caccttccaa gtaatttacc tgcacccgac ttcttgtctc 263580
atgtggggcc tttagagtaa ctccaaataa gaccaggtgg atgtgcagat gaaacgtttg 263640
```

```
atgcttgcat gtgcttgcct gattatgact gttaatcacc aggtgtgtca aactactcta    263700
gatgctcatt gtgtgtgtat gacaggtttt ggtgctcttt ctgcttttga taagccattc    263760
aatttaatag ggtgttctct gaatgcccag cttttcttta aacttagcat gtatattcac    263820
taccccacga tccacctaag acagttgcgt atcatttctt tatgcctgtt ccgtgttcta    263880
tgtatattag atgatttcat atagataagg agggaaagct catattttat acattttaac    263940
tattatgatg aaaaccttat ctagaagagg ttctcttctt tttgaagttg catagcatta    264000
gtaaagctat aggagctatc tcttgtatct gactagaaac gatacacatt taagataaaa    264060
agcatgggcc agtggtggc atatgcctgt aatcccagta cttttggagg ccaaggcagg    264120
aggatcattt gaggccagga gttcaagact agcttggacc acatagcaag ccctccctcc    264180
ccaccctgtc tctacaaaaa gtgaaaaaat tagccagtca tggtggcatg tgcctatagt    264240
cacagctgct cgagaggcta agttgggagg attgctggag tccaggagtt caaagatacg    264300
ctgagctatg atcatgccac tgcagttcag cctgggtgac agagtgagac catgtttcag    264360
aaaacaagtg agtaaaataa aataaaaagc aataacaaga ttgcattatg ctttgagggc    264420
attaattttc aaatttaact ttacttgcat ttttttcctg tcattctttc tgtgtcggct    264480
agttcttatt ttagttgtaa tcttttttta gaatacttat gaatagaata ataccactg    264540
tattcacata gtatatttac tattattttt gtctccttgc attgtatttt aattatctat    264600
gtcagacact ttcctcagtc aaatgtacta ctagccatct aaatggagaa tttatcttag    264660
gaggagaatt cttctcattt attttttgcat acccagcaaa ttattcggga gtgagtgcac    264720
tgtttcatcc tgttgatagt cttccctgaa catttataac ccaccctga ctggctccag    264780
tctttacacc ttcctcaaga cctaacttaa atacactgaa ctgcctgaag tcgtctttga    264840
attttacatc ctttctctta actctcatac actttgcatt gttttcccat acaggggcat    264900
caagaaatag accatattat aatgaatgta caataaagta ctaagagtaa taaaagtaaa    264960
tatattccga agcaggaaag agcaaatgct tgggtttttt atagaaggag agaaacgata    265020
atttgagaat gtttcatgga aactcttgca tttgagcaga actttacaaa ttaggcttag    265080
gcttcaatag ttaaaaatta gtgaagagaa catctctgca aagttgaatg ttctggtctc    265140
ctttctgttt gtttagtgag cagaattgat aatcgacatg caagtggctt ttaaactttt    265200
ccaaggacca gtcattgggg aattagtgtg gttcctctga acctttctag taatcccagg    265260
atttgagtat taagaacagt tagttgtgtt agccttaaga tgaaattctc ctaccttgtt    265320
gtttgaaga tgttacttag agggaaggag atgttttggt ctgttcgggc tgctaataca    265380
tcttttttctt ctcaaatttt actttaagca gtcaggagga accaagccat tccttcaaca    265440
cttttcttag aaatagcttc agctaaatct acttttatca ctcacacgat ctgccttcca    265500
caaattacta aaacatgaac acagttcagc caagttcttt gccactttgt agcaaagatc    265560
acctttcttt cattgtgcaa tggcatattt ctcatttgcc tctgacagct cataaaaatg    265620
gagcttcctg tccatatttc tagtgtcatt ctgttcaaaa ttgcatagat tttccctaag    265680
atgattgagg ctttctgtac agctcttctc ttttttttt tgagccctcc cctcactaga    265740
atcaccttca aggtctatt catggcaacg taggctgtgt ctagcataca cttcaaaact    265800
tttctggctt ctacttatta cccagttcca gagctgcttc tgcattttta ggtatttgtt    265860
atcttaacac cacactctca gtaccaattt ctgtcttagt ccactcagac tgctataaca    265920
aaataccata gtctgggggt gggggtgggg gggggtaata aacaacagac atttatttct    265980
```

```
cacagttctg gaggctggaa gcccaagatc aaggcagcag aagattcagt ctctgttgac   266040
aacccacttc ctggtccaca gacagtgact tctccctgtg tcctcacatg gaaaagggg    266100 gagggagctc tttgagatct tttcttgaag gacactaacc tcattcacga gtactccatc  266160
ctcatgatct aacaacctct aaagatgcc acctcctaat accatctcct gggggaaggg    266220
agtttaggat ttcaaggttg aattttggga gaatgccaac attcagccca taaaaggaga  266280
tagtatagga aaactacaga aatcaataaa ctcttctact gttttgatta aaatatagca  266340
agtgcatttt tggtgtacat attttacttt atctttgtta ttattcatct agaaaacaaa  266400
cgtacatagt gatagttaat tcttccatga cttttttgca aaagtgttgg tatgcattgg   266460
ctataagtct cctctctgac ttcataagac cttggaaagc tgccaaatat ctcagaactt   266520
gttgtcttga gtcttaaagt gactaaaatg accttagctc tacctgcctt ataggatgct   266580
ctgcccaatg atgcatgcag tatgcatgtt ctttaacaga gtatgttttg agactgcagg   266640
tttaggcgtt attagaatcc atttgactcc atagccctt  ttatggaaac atacatacat    266700
acttaatgtc aaatagttta tatctttta ctagctaata tggataagta ctgtctcttc    266760
ccatttgact gtgtgtaact gccttctctt agaactcaac acaaaatgag ctttatgatt   266820
cacatttaca gtaacatgga gacagaacca cctcattcaa aacaggaaaa agcaggtata   266880
agatgccatg aagggaaatg agactgaatg tgttcaattt ttctttgttt ggcttatcac   266940
atatcgtaga gagatgtcct cttacatgca gtagaaataa gaacatcctt gaaaactcgg   267000
tttgagcagt tcaaaatcat atattttta atgttgtatg agtttcaggt gataaatcct    267060
cttcaggata ccctcaggggt tcgcaaaaat gtaaaaatat gtttaaagtt tgaaatgact  267120
cacatttttt agtatccacg gcaaagaact gcttttccaa ccttaatagg atttcaaatt   267180
gacattgaca ttttagtaaa tcagaattag ctttttcttt ttaagctcct gtgtcttatg   267240
taaatggctg tgctgacttt tatggaattg aatattccag aaaatgtcat ggaacctaat   267300
ataaaacaag ttaacattct cattttaga tcttaaaggg atatggtgtt aaaatatagc     267360
ttttgatacc catccaacct gtgcaaggtt ttctgtgtat atgcgaattt caaatttgag   267420
aacttagcat gtcgatgaag gcaaatctat atacctgttg aaaacaaaat tgaaattctg   267480
aaggaattat tgtaatttac ttaaataaga actgtaagaa gtcagactgt taatggagtg   267540
tcaatagatt tcttctgaga gcttcaaaat cttttcactg cctttattac aagtctacca   267600
aaatatctgt tagattctga aagccaatct ctcattacaa aaagcattat tcacaatttt   267660
aacttatttc cacaatgaac attctacaga attattgtat ctttgtttaa agataaaaaa   267720
ttctccctcg ggaggctgag gcaggagaat ggcgtgaacc cgggaaggcg gagcttgcag   267780
tgagccgaga tcgcgccact gcactccagc ctgggcgaca gagggagact ccgtctcaaa   267840
taaataaata aataaataaa aataaaataa agtaaataaa taagtaaatg aataaataaa   267900 ttctccccc gaggtctgaa atttattatt aatgtgaata ttttaagcat ttttagaaga    267960
aaataatttt gtaaaaaata ttgtaagtta tggaaaatat ggtggtgaag tataacattc   268020
acgaacttgc tagaaccttg ccctaaaaat gaactaatta ttggatcata tggcaaactg   268080
attaagaaga ataaggaact actttatatc atgaaaaaat acatgactat ccacctgcct   268140
tcctaaaact tcttcctctc atgtgccgct attttactta gagttttctt tcgggttaag   268200
gaacaatatc tttagaaggc tattcattaa agtactaatt agaaaaggta gttaattaag   268260
cttgtcacac acaatttata tattttctta tgatgtgtaa gagaaaacag cataaaaaag   268320
ataaattatt tattttcagt caaaataggg cacttttttt gctttcctgc agctcattat   268380
```

```
acctaaattc ctttgtgaaa gtatttaagt aagttctttg aaatattgct tttaaaatat 268440
gtttactctt taaagtttta aaaataagga aatgtataat atagtgaaat ttccccatca 268500
gtgtgttctg tgtattttct ccagctcttt cttgaattac aaacagcagt tctacaactt 268560
taccacccac acacacacat ttattcattt gcacatattt cttttagtg ttttttttttt 268620
tttgcaaaat tggcatcata ttaattatac tactctgcaa cttgctttat ttactgtttt 268680
taatatggaa attgactgaa gttaattttc aagcagttgt gtaatattga ttgaacttaa 268740
ttgatatact ataactgatt aaactacctc actgttattt ggaacactta tcgacaacac 268800
tgcagtgtaa aaccctcttt ctacttttgc agctttatga taattctata aataatcaga 268860
caccgattgt gatgcaatcg tatcacaaat tcaaagacac attataatgt cagtggaata 268920
agttagacat acagtgccaa ttaactcagg gttccagggg taattctttt cgtattgatg 268980
aaacgcaaat gcatcttact cattcagagt tgccagggcc ctggtgtaga aatctaaatc 269040
ataaccaaaa caaacagcat caccacgaag aaatcaacaa aaacaatttc atgagggttt 269100
tgagtatttg aataatattt cagtaattaa attttaaagc aagaactgac aggtttgccc 269160
accccatcca tcctgtgatg tcaaatgcac ggtatgtatc tggctgacag ggaaattgag 269220
gtaggaaaat agaatagata atatgctatt atgtacctgc gcttcagttt gaggaggata 269280
aaattgtttt aaccttatgt ccacattcct ggagtggttt gctagacctg catcagaaaa 269340
tccacatctt agttcttcag ctgttcacat ctcaatccac acagccttt gtcattagca 269400
tgccagaaat gcactacatt catgaaagga attactagtt acatcatggt gaatgttagc 269460
atgaactctc attggcccat aacattaaaa tattcaaaac atacaaattg gctaaaatcg 269520
tttagagaaa atgttcacaa tggcatgatg aaggtataaa aatccagaaa tgcctatgcc 269580
tttgacctgc tccagtgccc ataacttgaa gtctctttag tcctacgctc agccatggac 269640
taaggaaaat ttctcattac ctgatgctga ctgagaaaga taaaagaaca ccacttgttt 269700
tgtccttaaa gacttgagag gcaaagagct acatgataga agttgtacct ctcacaagtt 269760
tatggaagga gacatatgaa ctgttttctg tctgctgtgg aagtcagatg aatgactgcc 269820
tatatgtgta acacatttgg gcctgagaca cacatgatga ggggaggaat tacaaactat 269880
cactggtctc cttctttttc tgcgattact gttaccttac ctaacagtag gtaactgtaa 269940
tctaaaatga acctaaaaat tgtgcatgaa caaattagct caggtagctt gcaacattga 270000
ctttacagtt tgacctaggg gagccccacg ggctgaacct aatgaaactc agccaggtta 270060
tattaaaact gcgatagcct gtatctctac attttctgca acctggtttc tacataggga 270120
aatgctgctt gtgtttgctg taggcaaatc ttaaataaac catgactcag caagaagaag 270180
agaatgatgt gcagagatat tttagggaag ggataagatg gcagttttga atgggagccc 270240
acatggtaca agtactcata ttccattacc aacttcagga gcttttact ttggaaaacc 270300
atttttcacc ttatttcagt aatatgtcaa gcatttcagg tggtctgcaa aagccacata 270360
gctcagaggc ttagcaaacc tcctcagaca tcaggcagaa acactttcta aaccccttaa 270420
tgagtgtcaa gcaggaaatt gtgagtatat agtattaagg agatggactt gctattctta 270480
aatttacaga aaaaaattct ggattttctt cctcagtctc cacttaatga cagatttttt 270540
tttaacaaaa agatgcatga cagtacctat ttaaacttac tctgataaat ttgatgaaat 270600
attctttttt taatccagac atctctatga gtttcagaat tattacccctt gtcaaattca 270660
tctatgcttt ttttgtggaa atgttcaact tttgttctca ctgctccctg ccttccccca 270720
```

```
tcaacaaacc ctgaatatct gggaatttct caccagctat tatttaactc cattccacat   270780
gtccatcaga tgtcctacac aagattggtt aaatagaagt ttgttcgctg ggagaagatg   270840
acaacttttt atattaaatg cataaaaatt ttctcaatac tgcagggtga taaagacaaa   270900
gaaaaggcca atttaaaagg aagtctttag aaaaaataca ataaagcaga aatgcttcac   270960
tttcctacac aatagggaaa aaattttaat gcttttgcaa aaattaaact ctaatgatgg   271020
aacaaagttt atttttatact gggtaaattt atgttaggca tgaaactaca taaaaatatg   271080
tggacaacaa agagtgattc agggctgctt aatcgctgtt gctcttggtg tggtttttag   271140
gggattgcat aattggtgag ttccttacac gttgatttct cagattcacc aggcaataca   271200
taccagctgt cttggtaaat gcatgaaatg ttgcaatctt gcaagtcct gcaattttac   271260 ttcaccagta actttccctg gtcaactaac agtatctaga gatcaggcag agggtgacca   271320
atggctgctc tgacgtacac atggagatac tgaaagatgt ggagttaagg atatttgaat   271380
aaatatttca tataatgaca actgtctttg ttagcaagca gaaatatcca ctgtgatgca   271440
aaggcatatc cttatgtcat atatatttgc tgtgaaaggt actgattcgt gcttatgtga   271500
aaacctctta aatcccgaat ctggggtctc ctctccccgt ttttctgga actcagatgc   271560 taaagttgat acaggaggag tggactgtcc caaataaagc agtcgggaa aggaggatcc   271620 attgcaaata aagggtaaaa aaggtacata tgaatagtat atctatttgc acgtaatgca   271680
ggttattctg gagggtatta aatatctatc agtaactatc atttgttaaa aaccaggat   271740 tcccaaggat gttagtggat gtatgagaaa gagtttctgg agatatatgt ttgggtgtcc   271800
actacgattg ttgcatttct tttcttcttt gtctctctct gtctctgact gtctctctct   271860
ctcagtttgc ttctctttcc ctttaaacac acacaaacac acacacacac acacacagac   271920
accacacaga atattcccaa cttcttaaca cacaacacca ataaaaatg ccaataatca   271980 gattgtaaaa ctggcagttc ttttctttca atgtggcttt ctattctatt gtctctcaca   272040
tatcaaagaa acaagaggac aacagatcag gatacatttt gtcatgttta cattatgtag   272100
taacctgaaa caaatgccca gtgagtggag ggtttcttag cttctgtca gttttcaaat   272160 gttttccctc ctcctgcctc cctggctttg ggttggtgat gcacgtgctg gtgctcagag   272220
atgccgtgcg ccctgacaag agattttgaa ctggggcata gatgattgtc cccaaagtga   272280
tctgctcagt tcccataatt ctacacattt caggcaatgg aaacacaatg agagagatag   272340
tttgggtggt ttttggattg caaacttagg cagccacagt ttcaaccagc aatactgatt   272400
tttctcagcc tttccatttc tacccagtgc ataacttata taattttct tccaaaactt   272460 cacaattaaa ctattcctta ttttatgaag ttatcaatgt gtgtatgtct tagaatataa   272520
ttggtgtcat acaaaccagt ttatgcctct ttaactttag tgctatgatc ttaaaaattt   272580
tgactcccag gcaaatatag atataaatat aaatatacat gcatttttt cttgagagtc   272640 aaaattatat atttatatat atgtgtgtat attatatata tgtgtgtata tacacacata   272700
tagattaaat atatatattt catattatat attacagatt aaatatatat tatctatatt   272760
taatttcatt agtcatattg ttttctacag tttgatttcc agttttgcag gactttgtat   272820
tcatattcct gatatcagga aagggtgcat attgacacta cagctcaggt ggaatattta   272880
gaagacacat ggttgtaatt agttacttgc atttttcctg aatgcttttt atggtgttga   272940
ctgtttaaga atatcttgca ttgctttcca aacaaatata ctacacaagc agcatttctt   273000
gaatctcgtt gatctgtgtg gtgtgttggt gtggtcttat acaggatttt gtctttttt   273060 ttttttttagt gtggttgttt ctccttttttt cctttaatct aacaaatatt gaagtacttt   273120
```

```
aaaattttta atactggttt ttatggagaa tgagagtttc ctatcatttt cctggggtaa  273180
tgtcatacaa tgcatttctg aaaaaaaaat acttcttaaa ttttgttaat gttctgatta  273240
tttttctgtc attattttgc cactttgtat tatgttacat tactattcca taacctcctt  273300
tgattccagc attgggaatt ggttttcatt tccatggact cattactgag gtccttgttt  273360
ctttcgagat attaaacctg accctgaatt tttttcttc cctgtgagag tggaaattat  273420
aattcttttc tactggttca ggaaaaaaag aaacttact ttctaaagaa tatatttctt  273480
tttatggtca gatacgtttt aaataaaacg aaagctttca atatctgtct gtaaaagagc  273540
agggtttgga attctcattg gtgatggata tgtttatttt cttacctgac acgtcagcta  273600
ctgcagctaa agccagtgaa ctatttctat atcacttact gatgaagaaa taagggctc   273660
tctcatgata ctaagtgtat tgctgttcca ccatccggat attttggct taaacctga   273720
ggtgttacca gatggtaagg attttagaaa tgctaaaatg ataatagtag ggactacttt  273780
cgatattgtg aagtcagata tatcattgca agttttaaaa aaatggaata ttttataattt 273840
ttaagtatct gatttacctt aataaacact ttcatcaatt tcaagagcat ctacatgcta  273900
cattctggtc ctgaatttc atggttaaaa taaagcccca cccagagact agctaataac   273960
tatggtgatc aacagtggac agaaattcag agatactagt tatggtaaca tcctttaatg  274020
ctggagcctt actgtcatag aaacatgtga atgtcaaact aaaagtttaa agccagata   274080
tttcaaaaga gtggggagtg ggagagtata aattaccccc aaggaccctg gaagtgctag  274140
attctgggca agatccagat attgcaatt tgtttaactc ccagttgacc atctgagaaa  274200
tattgagcaa gagagacaga gagagagaga gagagagaga gagagagaca gagacagaga  274260
gagacagaga cagagacaga gacagagatt gccagggacc aagggatgat gctagtgaac  274320
catttagcta caaagtgtca atgtatgagg ctggcgtggt ggctcatccc tgtaatccca  274380
gcacttttgg gaggtcgagg caggaggatt acttgagccc aggactttga gaccagcctg  274440
ggcaacatag tgagacctca tctcttaaaa aaaaaaaaaa aaaaaaaaaa agttagccaa  274500
gcatgctggt gcctgcctgt agtcccagct acttgagagg ctgaggctgg aggatcattg  274560
agtcctgcag ttggaggctg aaatgagctg tgattgcacc actgcactcc agcctggtg   274620
acagaacaag accctgtctc taaataaata aataagtact atgtatatgc tgactctcca  274680
gccttgccta gtccccagaa gccttgcaac cttccaaaac ttgattgttt ttctcctaaa  274740
tttctcagat aattgagggg aaaatagagc tcagaatttg acaacagctg tccacatctc  274800
ctggaatccc tggcagaatg ctggtgctgt ctcttctctg ggtttcacag ggcgggcata  274860
aattataact ttattaggtt gagcacatat ggcctttagc cccaggagac cctccatggg  274920
gctagtctgt tggcagaggc agcttctgca ctttcattca aattcacaat ccataaggaa  274980
aaagaggcct tcaaggctgc agcctgcctt gggcttccgt ggggcatctc ctatcattgc  275040
caataatgct gtggtgaaac ccaggccaaa tattccaaca tctttttgct gcttgtatga  275100
acacgatgca tattgcagtt caaaactagg aaaaagaag agcatattac aggcgaacac   275160
gaatgcatca gaatatggta cctttaaatt aaaagagaag gctcttgatt ttgaattctc  275220
aagtgtttct cttcaaatac acacaatgat gtctttcact ttaattttaa ctattatgga  275280
tacataatag atgtatatat gtatggggca catgcagtgt tttcctacag gcatacaatg  275340
tgtaataatc aagttagggt aattggggca ttcatcacct caagtattta tcccttctct  275400
gtgttaagaa cattccaaat ccactctttg gttattttaa aatatacaac agattatttt  275460
```

```
tgactatagt cactctggtg tgctatcaaa tagtagattt ttttttcgag gcagggtctt    275520
gctttgttac ccaggctgga gtgcagtttt gtgatgatag ctcactgccg cctcaatctc    275580
ctgggctcaa gcaatcctcc cacctcagcc tcctgagtag ctgaggccac aggcacatgc    275640
taccacagct ggctaattat tattttttta attttgtgta gattaggtct cactgtgttg    275700
cccaggctgg tctcaaactc ccgagctcaa atgatccccc tgccttgtcc tcccacagtg    275760
caacgattac aggtgtgaac ctgtgcccgg ctgataggaa ttttgatgg agtttcccaa     275820
tatctgggct ttcaaagatt ttggatagtg aacgagatac tgcaaagatc tctctaaata   275880
tcaccagcct gaccagggac cttgtgttac ctatatgaat acactgaggt tgctgtctgt    275940
ttctctgtta atgtataagc agagaaagtt acattgatgc tcatcagatt ttcagtttaa   276000
tatcagagca ttgcaaatta aaatataagg tgcgggacat gtacaatttt actgcgggc    276060
atgcaaaacc tgagggcccc caaagcagaa gaaggcattc ggcctctagt ctgcatttcc   276120
tccctcctga gttgccagcc agccagccag cctgtcttac agattccaga cttgccagct   276180
cccacattgc atgagccaat tccttaaaat agatcaattt aataaattta acctatattg    276240
gtgaacaaat ttagcagaga actttgatat acattagtac cacttattat ttttagaaaa   276300
attggaattc gaataactaa cactaaagtc taattcgtca tctggtgtgt atgttataaa   276360
tgcacaccca ctcaccgaga cctattcaca gccacagcct catataaaaa taggcaatag   276420
atacaggaaa tgagaagcag ccatagaggg tcttacgtaa gaaacccat ccttctcaca     276480
cctactcaag aacgttgttc ccaacatcta catcttttgt agtttatatc cactgggcgc    276540
acctaacatc acatccacat tcttttgttt atcccgtttg gaaatacgtg cctgaccttc   276600
actttctctg cctgatgtgg ctgcatgttt ttgtttctct ggcaaccatc tcctcgtctt   276660
ccaagagtcc tcaccgatca catctcaact cctctccacc tatcctttct taaattcact    276720
ccaatcagta tatagcctca ccacttcacc agactcctct tgccaattat accattgcat   276780
cctaggcccc acaaaagtgg agttgctatt cctaatgttt ctaaaaaatg gccattctgc   276840
attttccctc gaatctccac tgcctctatt tttggaaaag agtttcatct ttgaaaaagc   276900
atttaagacc aactttttc ccactctgga gggaaatgaa atattgctga atgcagagga     276960
tatctccaag gcttcatact acttgctctg gcaatatttc cagatcctta tcctgcagca    277020
tttgcggtag ttgtcccct agaaatcata gttgaaacct actcctcaac tgtgtaggta    277080
tttggaagtg gggctttgga aggtatttgg agagtggagc ctcatgagtg gaattcctac   277140
cattataaaa gggaccccag agggcaccct cgtccctttt atcatgtgag gacacagcaa   277200
gaaggcgctg tctatgaccc agaaagtggg tcctcaccag ccactgaatc tgccatgcct   277260
tgatcttgga cttccggtct ccagaactgt gagcaatttt ttttacaagc cgtgggtct     277320
gcagtctttt gttttagcag ccaaaagagg taagataggg catgttggga aggaatggag   277380
atgtccacaa acaccctgaa tcatatactg ctcccccaacc ccccgtcctc ccagcagaga   277440
gagcaggaaa gagaaggctt acttcctcca ggttcgatgc tcttctacac acagttatga   277500
cagacagatt gccttatatt tttattcttt ttagttcatc tgaccaattg tcaaattgct    277560
caaatgtcag aaaatggct caagggccg ctatggattt ctgcagtaga aaagaaaag      277620
acagaagact agatcccaat gtgttcctgg actggaagaa agttcttatt ttatggagcc   277680
ataaataaat atgacatttc ttgtgcctga gaatttgagg caggtagtac tcctgtgaag   277740
taagataatg tcttctgtaa aagaataaat tcattaaaaa ccatgggaat cattgtaagt   277800
ttcattgtca agaaagaaac agacatgatt ttggatgtag gtgaatgtta attattgaag   277860
```

```
atgattattg ttctcagaac aagtttattc tgattcgtag ccacagcagt tcaagagaaa   277920
agcaataaag gaaccacaac catatgaccc ttcttataat catgttgtgg tggggatgtt   277980
tcttctccgt cctacttcct gagaatgaca gaagggtttt gcaagagtga aggcagctgg   278040
gaatatattc cagccgcttc catagttcat gctgtggtaa ggagtttcaa ggtcacagtg   278100
aggcaaggag tttcaaggtc acagtgattg aacactagaa cttgtgcctc tgttctctgc   278160
tgaacgtctt ccatgactgc tacatcaggg cttggggttc ccactgacgt ggtgtttaag   278220
taacatttag agtccttatg gttatacact ttcatctcct tgtacagaaa gtttctggaa   278280 actgccccact attatatgac acatattaac ctgttgaatt tggttatttta tgtgaggaaa   278340 ccacagaaaa ccataacaaa tcaaaatacc taagagccac aaatttcctc cagtgcagcc   278400
acatcccata gacaggtaat gtgcactaca tgtgtaattt taagttttct agtagttgca   278460
ttcaagagtg cccgaagaaa ccattgatac caattttaaa aatacattta atgtatccca   278520
atatttataa agtactaagt cagcagacaa tagagacaaa atatagtttg catatttttt   278580
actacatatt tgatattcag agtacatttt acacttacaa cacatctcgg tttgaacaag   278640
ccacatttta tgtgctcaat agccacatgt ggttattggc tagcattttg gaaaacacag   278700
tgctagaaaa tgcattcttc ctgccatgat caaccattgt ctctcactta ctcctgggca   278760
actgtgttct aattgatttc cgggcattga ttattgcctt tcaggagaa caactgatca    278820 ccgtattata gtaggtcatt cctacacatg gccttcaggt cccaaacccg tctgatttgc   278880
taagccgttt ttccctcttg tcatgccatc ttcccttcat ttgctacatt ccaggttttc   278940
tagtctaatg cagtcactcc aggcactctg tacttgtact cagcatttac tgggtggtgt   279000
atatctgtcg taggctgttg gttgtaagtt tcatgacagc atacactatg cctcccttt    279060 tccacatgca ccaatccatc aaacctcatt gaggacataa aacacagcat ataaagcact   279120
ccatcgattg aattgaatta atgtgtgaac aattgcacct gcaagtgtaa ctgagggctc    279180
acgtggttgt catgtatcat ttttaaaatg tttaaataat gcgagttttc atctatattc   279240
ttattacttc tgtagaaatt aatctataat atttcaacag taacatggtt gaaattgagg   279300
ccttatgtaa tgtttgaaca caaatgataa cttgattctg aatcaacact gtatgtgcga    279360
tttgatgtct gatgtatgat ttggggcagt ttgagggtca gtcatttatt tgtactgagc   279420
ctctcaaatt ccctgtatgt gaagggaaca gttgagaata agtgtcttca gtggataaga   279480
cagtcgtctt tatccctgga aggcatcacc aactgatcac agcagtctgt ttttctgagt   279540
caagaggcaa cttcccctct atgtaggata ctacttttag tgtagtgtgc tcttccatat   279600
ctattggaat cattacacct gatcaatcag gtttaagata aagggtgtga tagatagaaa   279660
tggatgcaga tgctcttgca aattgagttg aaccctttgt ctttgcatct tgtgctggcc   279720
tcagtgactg tcttcttgaa tagaatgttc tgggagtaaa gcactgggac ttccagggct   279780
ggatcataag aagctattaa gcttccattt agggcacttg gagtactgac cctcagggca   279840
ttctctcttg gaaaccacat ctcatgttgc aaagtgttca agccccatgg agaggctatg   279900
catggtgctc cagtcagtag ctttagcttc actcccggtt gacaaccatt agtaccgcca   279960
tgtgagtcac ccattgtgga catcccagct gattgaggac tcctgtctct tcctatccct   280020
tagctgacta aggagatctc aagagagaac ttctcagcta agcccagtca gctcacagaa   280080
tcatgggaga tcctcataaa aggttgtttg aagccccaca ttatgggcat gtttgttaca   280140
caacattagc taaccagagc aggcactgaa actggaagtg aggttctgtt tcaacagaaa   280200
```

```
cctaaagtac atggtgttgg tgttggaccc tccatagggc aagactaaag gcttgaagaa   280260
caagggaaga aaattggagg ctggggaaat ggaatggaca aagagaactc tttgaatgac   280320
tcactcacag ccttacagga cgagaagtaa cttttagcac tgtgcaactg caagcaaact   280380
ggattttgtc ctttaaaata gaaagatggc atctcaaaga acacatttgt catgagtagt   280440
tcctaataag cataatactt aacataaagt tcactggcgt atgttattta taatcttact   280500
atagtataat ttccattgga tagcaaaagg tcaaggatat aattacagaa atatattctt   280560
ttaaaatttc ttttggttac acttaaatgt aaattgtgaa caccatttta ttttctattg   280620
tatcccatga cttttctatt gtttgggtca tattaaatct attttttacag tataaatttt   280680 gcagcatata ttcccacagg aaagaacaaa ttataaaaca cacagtttgt atatgtcttt   280740
cctttaaaag tgaaatttta actagttttt ctttttttc tgttactatg tctttccatt   280800
ctttggttca atacattccc acctactctt gaacgttttt tggaaagttg gcaatgaccc   280860
tttaaattct tttcagtctc tatctgccta acatatattt aggttccgta tatttata   280920 tcatttccta cttaaataca catatttcca tttttgtgct catgctattc tgcaaatgcc   280980
tgcattttaa ggatgagaca tacatttaaa aagggcatct atgccttctt tcagaatttt   281040
ttttctaaat atctattact ttgatatttg aaattttgta cccacaaaca tacacataca   281100
cccatgtgtg cataatatac atctcacaga aatgccagcc atgtcgggaa aatgacagct   281160
ccatcagaaa tgtctttaca tccacgtaat atatcttatt tccttgtata aggcacagat   281220
cctctgttac caatatcaac ttatccccag gctctaaatc acttgaagct acttttgatt   281280
ctctggagaa tttcagaata tattttttc ctcaaaattt catgaacttg tatgcatttt   281340
gtgcctcaga ctttgaacgc cttggacaaa ttcctttatc cctgtgaatt tttaacgaat   281400
tctaaacaaa atacctgact ccactttccc cccaaatttc ctgaccttgc gtgcattttg   281460
aactgcagac ttgaaaacac ttgtgcaaac gttccttcat ccctatgaat ctttaatcct   281520
aaacaaaatg cctgtatcaa tgctggcaag gttgtggaga aaagggaatc cttatacact   281580
attggtggaa gtgtaaattg gttcagccat tgtggaaagc agtgtggcca ttccgtaaaa   281640
agctaaaagc agaactacca ttagacccag caatcccatc cattactggg tatatactca   281700
aaggattata agttgttcca tcataaagac acatgcgcac atatgttcat tgtagcacta   281760
ttcacaatag caaagacaca gagtcaactt aaatgtccct cagtggtaga ctggataaag   281820
aaaatgtggt acatatacag aatggaaaac tatgcagcca taaaaagag caagatcatg   281880 tcttttgcag gaacatgaat agagctggag gccattatgc ttaaccaact atgtcggtaa   281940
cagagaatca aatactgcat gttctcactt ataagtggga gctaaagatg agaacacatg   282000
atcacatagt agggaacaac agacactggg gcctgctgga gggtggaggg taggagaggg   282060
agaggatcag gaaaaataac tattgagtac ttggcttagt acctgggtca tgaaataatc   282120
tgtacaacaa accccatga cactagttta cctgcataac aaacctgcac atgcacccct   282180
gaacctaaaa taaagttttt aaagaatgcc agtatccact acatttatgg gcggtctttc   282240
tgagtttcac ctcagagaaa cactcctaaa attcaagtta tgactattta gactatttgt   282300
taatgatagc tctgtgtgtg tgtcttagcc ccctctctgt ttcctatgtg ttctacttga   282360
ttttaaaata aactatagga gctccacata ctaatttgat tctctacata aaatggtgcc   282420
atattctctt attttccctt taggatttgt acagagactg tacaaaatat tttttgagtt   282480
gtgtaatggt atccaatatg gacaataaat gataagtaaa ttttggaaaa atcagttaaa   282540
agaagtgtaa tagatacata ggtgtcttaa ttgttttccg tcctcaagta tggacgtttt   282600
```

```
tgcaaagaca cgagctttt  acttcaggag acatttgtcg acgtctggaa aaaattttgg  282660
ttgccacagc tagatcatgg gggtgggtat cacttgcatc tagaggacag aggccaggga  282720
tgcttttaag ggacccacaa ggcacagaac agccccccat gacaaagagt ctttcatcta  282780
catgtgtcaa tatcgatgag attgagcaac ccaggtatag agtaatactg atgagcacaa  282840
agtatagctt gaagcctctt tttccatatg gctgtgatag attgttttaa atgatcattg  282900
gaagaaataa acccttggtt ctatggaagt catgaggaat attctgccca tgtgcttgtg  282960
aaacctcagc ttggagcaaa gaggcgaata tcatgcaagt ggcttcctag aatcatgggg  283020
ttttgtacag attatttcat catccaggta ttgagccaag tacgcattag ttatttttt   283080
gatcctctcc ctaccccac  ccttcaccct caagtaggcc ccagtgtgtg ttgttcccct  283140
ctatgtgtgc atgtgttctc atactttagc ttccgtttat aagagaggac acgcagtatt  283200
tggttttctg agctggaggc cattatcctt agaatcttct atgttaaaaa caacagagca  283260
cctcctggct ttcctgggaa tccttgtttc ctgattccag acaagcgcca tggctgtgaa  283320
atcatgtatt tatgtgtatg ctgttggatt ttaatgtgaa ataccttttc actgcgccaa  283380
gttcgcttcc aaatgtgatc ccgccaggct gaccaacaag gcattcagtc agcctacttt  283440
cttatgccgg gacctttcac aaaatgaatc atatgtcact tttcttttca gaagcatatg  283500
ccattttatt ttattctggg agtttgaatc acaccatgca tctgttttag tgttgttttt  283560
agtaagttca ctatcagtgc ttcctgagca tggtttctcg tatggggtac tcactgacct  283620
gtcccatcca tcttttcttc ctataaagcc tttactgcta tacttgtcta cttgcagaac  283680
ctccacactt tttatgagct cccattttc  tctcttcttg gtatttatca ttacttattg  283740
tgactcttgc atattggatg gtcaaaagag atccccagtg gttacactac aacaagataa  283800
atgtaggtat acttttctta attgttatta gtgttactta ttatttgtt  ttattagaca  283860
ctactttcaa aggctttaca gcactgggta tgtgttctac cttttctctt cattttatcc  283920
tccacaacag ttctgtgatg aaagtactat tattaacttc atagtttaca cgacaaagca  283980
tggtttcata acttgtcagg atttcttagc cattatttga taaaattagg gatctaaatt  284040
ctgtcttcta gctccaaaca gatggttctt tccatgctat ttgctattat cttgtcaaaa  284100
gtaatgacaa aatagaactc aaatagtatt tttcttttgg ctgatttctt ctttcagacc  284160
agagaggttt ccaaggttaa agtagttcat taatttcaat tcttcttct  ttttttttt   284220
tttttttttt ttgagacaga gtcttctggt tcttttgccc aggttgaagc acagtgacac  284280
catcatagca cactgcagcc ttggcctcct aggctcaagc agtcctcctc tcttggcctc  284340
ccaaagtgct ggaatacagg ggtatgccac catgtcaggc tacttttat  ttttattttt  284400
ttaagagaca gtcttgatct gttgcccatg ctggtctcga actcctgggc ttgaacattc  284460
ctccctcctt gacttcccaa agtgctgaga ttacagacat gggccaccat gcctggcctt  284520
aatttgggta tcttctaatt gatgtggact cttatgccct attcatttgt gttttgaagt  284580
gaactgactc tgaatgtcag tgatagggca ctgcttagtg ttgggggtgg ttaggaagat  284640
atgcaagttt cttagagaat aaagcagctt gctgttcaca gcagagggg  tgtaactgtt  284700
tcaagaattt tagaatacta ctgtctgtga gttctgcaag aagttaggga agcctccac   284760
tcctggttag actggcagca acttttgca  ttataacaca acagacattt catgtccaag  284820
ccaggtaatc tgagctaccc ttgttcattc cagatccagg gttggtgagg caaaaggggt  284880
gtccccaaaa tagatgggtc tctttattga acttctgggt tatctccatc atgtacagag  284940
```

```
atacagaatc atgcatttat aaactttatg gttgaagatg gcacccacag ttacagtttc  285000
ctcccaaacc tccctggcct atctcagttc ttaaagatgt ctggggattc ccagttaggc  285060
atagagtaac aaggcagctc tatccttaaa tgatcatggc aagctgccat atggctggta  285120
ttcatcctca gttaatgtgg atattctagt aggagggcac agtgacatag gaagaaatgg  285180
tcactctgtg ttcaaattat ccctttaact tagaaggcaa gtttaccacc ctgtgggtac  285240
tgagcattgc agacttcatg taagcatatt tttgagcatt ttctacaaac cctcatttct  285300
ccaaatccca tcctttgcaa cctcaagttt atccagggga ttcacactgc ctgcatgtcc  285360
ttgtatgcgt ttcttattgt tcctgtaaca aattatccaa cctgtagtgg cttaaaacac  285420
acgcatttgt tatctcacca ttctgaagct ctgaagtgtg agtagctcgg atggtttctc  285480
ttcatcatca cccaagggtg atttctgtgt gttggcagaa aggctgtgtt tcttcctcca  285540
gactccaggg atgcatccac ttccaggaac atttggttg atggctacat ccagttccat  285600
ggggttgagg ttcctgcttc cttgcaggct attggctgag ggcaaatttt ggcttcttga  285660
gaaccgtagc attccttgac tcctggcctc cttcctcccc cttcaaagcc agcagtggca  285720
gcttctaatg cactgaatct ctccgacttc cttttctacc tcttgtctcc tttcccaagt  285780
tgcatggctt gtctggactg attgttccat taccattttc ctgcttctca gtatcatgga  285840
cccacttgga tattctagga taatcagctt atcttgacat cagctgccta gtaaccttaa  285900
ttatatctgc aaagacaatt cacaacagta cctagattca tgtttgattt aataaccagg  285960
ggaacgagaa tcttgggtgg atgactttat aattctgctt accacattcc tgtctataaa  286020
ctaatcttaa ggttggtgga caggcccctt acaactgact tgagtacccc agaacactgg  286080
cttcctatct ttactcaacc agtgggctcc tccaggaaaa gcccaatcaa ggaagataac  286140
gccattattc tcatgctttt ccttccccct tccctcccct tctctcccct ccctcttcct  286200
ccccttttcct ttccttctct ttcattttga cacagagtct ttctctgtct cccaggcagg  286260
agtgcagtgg catgatctcg gcccaatgca acctctgcct cagcttcccg agtagctgag  286320
actacaggac catgccacca caccacctaa ttttctatt tttagtagag acgaggtttc  286380
gccatgttgg ccaggctggt ctaacctcag gtgatccacc tgcctcagcc tcccaaagtg  286440
ctgggattcc aggcatgaat caccatgccc agcatgtcat gccctttcga agtctgggta  286500
ataatcctca gatggtagtg cacatagtta tggagaatta tgaaccact cctccctgat  286560
gtggctcgcc cccactgcaa ataatttgtc tatttttatt tttattttta tttatttatt  286620
cttttttgag acagggtctt actctgtcgc ccagtcttga atgcagtggt gcaatcatag  286680
cccactgcag cctctacctc ccaggctcac gtgatcctcc cacctcagcc tcccgagtag  286740
ctgggactac aggtgcatgt cacctcgcat gactaatttt taaattttt gttgacgcag  286800
gatgttgtta tgctgcccag gctggtctta aacttttagg ctcaagcagt tctcccacct  286860
aagcctccca aagtgctgaa attaacaggt gtgagccacc cagcctggcc tatttgtcct  286920
ttttaattta aaagactcaa catgtagaaa ccatttttacc ccttcacctt gtgcattaag  286980
agcttccttt ttcttaacat cctgctcctt gaaatcaacc cactctactt gtatggcagt  287040
tgttatttta atatttctaa ttaagataca gttttcattt taccttacag agacagtgag  287100
cgggtgctct tgaattccag tctggctttc tccattcctt tgggtaatca caggttaact  287160
ttttccttc atcagttttc agcagtcagt gaaaggtgca ttcattttca taaatcagcc  287220
atttggcaac atttgaatgt ttaatcagtt tgcgatcaca tcaaagaaca agggaagttc  287280
ttgggagatt tattacctcc tttggaatct gtgttcttag ctacaaaggt gcaatgactt  287340
```

```
tttctagttc tctgcccag atgtctgaac tgttaatatt tacagtgctc ctttcctgaa    287400
attcagagtc agcacctcat tttatcctat ttgtatccca acttacttta ttcaaagaga   287460
ttttacaacc tgagatagct ccgtaggaag agttcagttg tcagaagcaa tctgatccat   287520
ggaaattttc tggtgtttgt ttttccttga attaatttgc aggtttaaat tcttgcttag   287580
gccactctag gacttttaat tgctatttct taggaaatat tccttagaac atgaagcagt   287640
ctgtctttca acacacacac acacacacac acacacacac acacacacac acacacacac   287700
accccctagc atacgatcca gaacaacgtt ttatctttt tttttttttt tgtaggaggg    287760
agtgtctcac tctgtcaccc acgctggagt gcagtggtgc cctcatagct cactgcagcc   287820
tcgacctcct gaacccaagt gatcctccag cctcagcttc ccaagtagct gggactagag   287880
gcacacacca tcacccag ctaatttaat tttgaaaaaa cttttttttt tgtggagaca     287940
aggtctccat gttgctttgg ttggtcttga attcctgggc tcaagtgatt cttctgcttc   288000
agcctcccaa agtgctgaga tttctggcgt gagccaccac acccagccct aacatttat    288060
tcttttactg actgtgagat tttcattgac ttacgctatg tcaggcagac ttttcaagcc   288120
ataacctggc tttggtgatt tattattta gctcttcatg ttttaacagc ttctctgcta    288180
ccatgatagg ttataataag tgatagaaga aaggcatttt aaagtaattt atgaatgtgg   288240
atctcattt gcttagctaa aaaaaaaaaa gtttttttt tttctagaga atagaaccaa     288300
acagtgttca ctgtatcaca tattccttt agtgtattga gcattaatgg ggtatttgt     288360
cagcatcaga tcttcacaag gctggggttc atcagcagca cagtagctat taggtgattt   288420
tactcaaggc agcaaaattc gtttcttata acacagtctc tattgaagac acactctaag   288480
gcagtttgcc tcatctattt agcttttccaa aattctctct taaattgcag tttaatgaat   288540
agactaaaac acaaatttta agaaaaatgt agttataaga tatgaagtgt cttttaaatc   288600
tgccagtggt ttaagggata gtatacattt aaaataaagt tataggcact gatttagtcc   288660
tggaaaataa tggcttat tcaataagcc agtatcagaa attagttttt gttttctttt     288720
ttttttcccg tgatgaaatg tggtttctag tactggataa gaaatgcatg agaaataatg   288780
tatcccagca tatttaatat gcaacagtgt gatctcagta gccttgcaga tggctgagct   288840
gaggcactaa aagtgatgag atgacatttt gtattttcc acacgttctt gcccattctc    288900
aggtgagtct gggctctcat cagtatttaa atgctgtttt accttggcaa gacatttagg   288960
tccagaaaat agtttaaaaa attaacatct acgcagaaag aacctccagg tagttaaaaa   289020
tagggcaatt tgcggataca ccacatcctg aagacttagt gttgctaagt aaaccacatt   289080
attttaggtg tttcttcctg acatttttat ttttttcttg tgttatttta attctggaac   289140
ataactggga actgagaata ctacatggga cccttatctc ttttctttgt tatgactgaa   289200
aatcataatt tgaaagatgc ttggaaaagg gaaagcttaa tatcttacac atattttat    289260
aagacaaaaa tatggaaaga tatgaaccat aaaatcagtt tagaatggga aggttagta    289320
aaacattttt tttgagcaga aaaggaatca tggaatggac actttataat atagtaattc   289380
agccaattta tttgatggaa ttcaaatgtc atgtcctctt tgtagctaag agtgcacatt   289440
agcattaacc ctaaaccaga ccacttggag ccaaagagat gtgtatgtgt gtgtgtgcat   289500
ctgcttctgt gtgtgtgtgt ttgccccatc tgagtgattt gattttcac catctctcta    289560
ttttttccact tccaaaattt aagcatttag acatttatta tattaaatat gtttgcattc  289620
tccctccctc cacatgcagt gttttacaaa tttcctatca gactgttccc atcctgcaaa   289680
```

```
cccccagagc tctatggctg aggtactcct ctttctgttc ccttctccat gcagatggaa    289740
tgtctgctgg gaactatctt caatctatat gtttcccatt cgtagaggtg gctaaatctg    289800
tgacatgcat ccatcctcat ccaatagtgt ctccacatga gtgagctgga taatgcaaaa    289860
ccaagcttcg acatcagtgg tatgaagtac acacacacac acacacacac acacgcac     289920 acacacaaat acaaacacac ataatctctg tagctcagat tgggattgtc tagggttaat    289980
atcttttgtg ctaaaaatat ccctgtgcca cattgaagct tattataata attattaatt    290040
actgatatat ttcaactgtt atgtctccta aaaatatgca tagattatta agttttccct    290100
tctccttgtg ttttttctgat tatgattttc tatcataaag gtgaaagtga taagggtccc    290160
atgtagtgtt ctaactctaa acctaatact gaccctaaac agaattgaac gctttaaact    290220
aacccatggc ctttgaccat tgcttcttga ccgttgagtt aacccataac cctgaacaga    290280
gaatgagaaa ttgaacccaa atttgaaccc aaaccctaac tagtgactgg atatgaaacc    290340
taatcctacc caactttgaa aaagaactca attctaaact caaaagcaaa gccaaccgaa    290400
cacctaatct aactttaatg taaaccttg  aacttaccct taacttttgc cagtagccct    290460
tgactcttga ccctgatct gaacactgaa ggcatccccc aaattctccg acccatggcc    290520
tttgatccta atcttgactt tgatcactg tccctaataa tgaatataat cccttgatca    290580
taacattgaa ctttgctcct accctgacat tcaattagtg atctaaccat accacaacct    290640
gaacttgaac ccaaatccta acatgaacct tcctccatac ctgaaagcta tcctaaccct    290700
tgacctttga tctttatttt tctccttgac tcctgactgt gagatcccag cctggactaa    290760
aatgtataca cacactcaaa atcttttttg ttctgaatcg ttacccaaac ctgaacttga    290820
acccaaaccc tgaccctacc caattacaaa tctgaataca aaacctatcc ctattctaaa    290880 gttgggggatt tgagtctctt agtcccgtag ggtagatgtg gtgtttgcag ccctgcagcc    290940
actatggaca ccacagactt ggacaaaatc tccaacgtat ttttgggaaa aaaggatgca    291000
accattagag aacaagatgt tgaaactttc atccataatc tctgtttgta cagacttcag    291060
ggtgaaatac atgtggttgg aattgtgata tttccagcca caaaattgta ttatgttgag    291120
ataatgtggg tttccctatc cctgaaaatg tgttcatcca accaatagtt acttgtacca    291180
gcagtgcacc agggaccatt ttgggttcct ggaggcagcc gtaagcaaaa gcatcccaga    291240
tccctgcttc tggaatccct gactatgaa ttggcatcct cataatgaat gtaataaga    291300 aataaggtaa ataagaaat aatctagact caaatgtgaa ctttagtcgc tctggaagtc    291360
caaaccctgt ccaaacatgt ccgccgatta cttttcagagg atgggtgatg actcaggtta    291420
atatggttat ttttggagcc cgtcttacct attgtccttt atagatgatg tgttttccac    291480
ctcagatatc aacatgaaag actgggtcac ttctcaattc agaaatccac tcaaggttag    291540
gcactttggg aggtcgaagt gggaggatcg cttgagccca ggtgttcaag accagcctgg    291600
ccaaatggtt aaatcctgtc tctacaaaaa atagaaaaaa attagctggg tgtggtacca    291660
cctgcctgta gtcctggctg cttgggaggc tgaggctgga ggatacctga tcccaggagt    291720
ttgaggctgc agtgagctgt gatcatgcca ctacactcca gcctgggcaa cagagtgaga    291780
ccctgcttaa aaaaaaaatt cattcaacta tgtgtaagag agagagagag gtgtttatta    291840
gatttaactg aggatttggg gagaaacttg ggggcatttt atcctatggg ataagaggga    291900
aaaataaacc ttttaaatta aacatctcgc ccttttgctg actaccttt ggctatccta    291960 acatgaaata ttcttctgga tgctacaact ctcagctcca ctgatcggct agagcagatt    292020
caccatcact tcttgttttt ggatttcacc ctctgccact cgtgatttaa caaataattc    292080
```

```
tctgaaaggc agttctcttt tgaaaaagag ttttgcttct ctgtgttaaa ataatgtgtg  292140
ctgctgttaa aatagttttg tatacacgag ggaactcctt tagaagcttt atcacgtctc  292200
ttagctgtgc gtgcaatttg agtaattact atgtaccaat tccagtaaca tagccaatac  292260
atcagaactc tcaggggacg tagctgggaa ctttcttgca aaacaactcc cacgtgttca  292320
ttcctgtctg gaaaccacca gtaaaattta aatcagtaa taatttctcc aggcacagca  292380
actgagaatg gtagaacatt agttttaaaa accattttaa taaaatgcct ttataaatat  292440
tgagacttaa ttatttagat taatttgttc cagttaatga aagatctctt agcacaagac  292500
tgggaaaaat tagaacacgt ataattttct tcattccaga taaacaatta ttttaatgtt  292560
tatctggtat ttgaccacaa acttaaattc ctgggtttcg taggattaga aattttaagg  292620
ttagtaatca ctcccgttgt taaactgctg gattttacct aaaattactg caaggatgta  292680
tcatttttttt atacctcaag ctgttttgtg cagttctgct tccaacttcc atagacaatt  292740
ttaatcattt attttttgttt tttcttatca gataatgttt cataacatgg atgtgaagaa  292800
ttaaatgaac atccttctgt gcacaaatta agattagaac acgaagattt tgggattccc  292860
ctcagttcct tttataaatt gtatttcttt ggacctgtcc taaggataac cacttttgtg  292920
aatctgattc attatttcct tcttttatta agttttattt ctgcaaaatt gtcatgacca  292980
gcataaccca agaatatat tgttcgctct gcttttgatc ttttataaat aggatcatcc  293040
tatgttcttc ttgacctggc atttcccttt tcattgaata gtatgttttt gattttaacc  293100
atgaagatgc ttggagctgt agtttatttg tgttcactga tatatggaac ctcacccgat  293160
ggttatacca caagatattt aactctttca gaagctggaa atttgaattg gccttatgta  293220
aagagttcag ctattaggat tctgtgcgtg tctcttgttg aaaaaaaatg cagaagtttc  293280
tccaactaga aatgtattta ctggaccata ttttatgtgc atatttggat atacactctc  293340
aggttaaaaa ctgtttaagt ggttggacag ttttattcac ccaagaacag tatcagagtt  293400
ccctgtcctc tctgcattca ctgcactgaa tccaaaattg aatagaaatg aaattagctg  293460
tctttgattt gttctctctt tagacaaaag gcttccaatg ttgtatcatt atgtataatg  293520
tttgaagtaa gatataaata aactaccatt ttcagataaa gaaatgttta tttctttcct  293580
taatttgata acatacaatc ataaattggt tcaaggcatt tttctttatc ttgtaagatt  293640
atccttgctt tgcatttaat ttttttcatgt agcaaattaa ataacttaac tttcaaatgt  293700
taaacttagc ttgatattca gtatcttctt taatactgtt tttgtatttg ttgttagata  293760
ttaatcattt ttttctatct ctgtacaaaa caagatagac tataatttttt ctttgttgag  293820
cttccctggt tttagcatcg actaatagta gctgtgtaga aagagtaaga gaacatttgt  293880
ttatgctttc tgggagagtt catataaaaa cacaaattat tcattcatta ataggtggta  293940
gacttgccat tcagtccacc ttggacagat tatttctttg ttgtacttaa aaccatcatt  294000
tatttcctcc ttgatttgtg gactacatta catattgact tcttgtatat atgaagaaaa  294060
acatgtttgt atgtctgcac atgtctgtta tcactctatt atgttcccctt tctgcatttg  294120
tctgtctgct atatacattt tgctaaactg tcataacaaa ttatgagaaa tttagcagca  294180
taaacgaata gccatttatt acatcaggga tctgtaggtc agaaatcctg gtgcagtgga  294240
gcctagcttg gtcctcttct tagggtctcc catggctgaa atcaagagat tggcagggct  294300
gcattccttt ctgggtgctg tagggatgaa tatatcacaa catatagatt tttaaaatct  294360
aattatttgc actaacttct gatttttacca cattagattc atagggtgaa ttcctgtcat  294420
```

```
attgatcatt cgagtcttat ggaagctttc tttctatctt acaacatcgt cagattgtta    294480
caggttttca tatgtattta ttcttatgct ttaaacaagg ggttttctct gttttatgta    294540
aagtttgacc taatattttc atcatatctg tgttatactt gagatgtata ttgtgaatat    294600
ataagcacac acaatgaact attcttcagc cttaaaaaag aaggaaataa gaaggaattc    294660
atgtaatttg tgacaagatg gatgtacctg gaggacatta tgttaagtga aataagccag    294720
gcacagaaag gtaaacactg catgatctca attatatgtg gaatctaaag aagtcaaact    294780
cagagaaaca gagagtagac tcatggttgt cagggactgg aagttgggtt catggggaa     294840 ttttggtcaa gaggcataga catctttctt cttcttataa tattatgttc ctatgttcta    294900 gttttttgagc tattaggatt tccatatcag cattttaggt cttatttatg cttgcatttt    294960
ttatattctt gataatttta gtctttctat atcttttggg tttaaatttg tctcttgagt    295020
tggatgcatt cttcatctta ggttttgtta caaacatgag attgtctgga aatttttta    295080 aattcatgag tttaaaccat ttatgtttgt tgaacgttaa ttttaccgat gcttatttct    295140
gccatcttgt tttatatgtt caatttagtt acttcaggat aagcgtaact gtacattttg    295200
tttttgaaaa cataagtttc tacctgtcat ttaatagata tttaaataca tagttatttta   295260 aaactctgtt atctatttt tatccttact atggttaacc ataactgatc acagggaatg    295320 ctgtttatttt tcccagttg ttttttataaa tttaacaaca taatattggt ttataccaat   295380
tttgttcaat ttctatatga aaatcaaaaa tatatagaat acatcaagga attcattgac    295440
agatctggga atttctaaca agataaactt ttttcaaaca tgcatctttt ttagtcccac    295500
ccctagtgct atttaagtag atatttccaa gaatttaagt tctgggctat tatccatata    295560 tgattttttgt cttcctttt ctacccattt tagccaaata gaaattatag ttattggttg    295620
tgcttgcatt tcatatattt ttcagaattc ttaccaaatt agttatattc tttgataagt    295680
attttctcaa agataatttt cagtctttaa atctttgctt agcaaaatga ttgaatctct    295740
ttttgatctt ttttttttaac ttggcctata gtattaaatt ttttttaaatt cagagttatt  295800 tttcttcaaa ctttcaaata tgactcctgt gtctgctaat gtcttgtgct atgactggga    295860
agtttgatgt caatctgatt cctattcatt catagctcac ccatttttct ctctgaaggc    295920
tattagaatt ttctgtttgt ctttgatgtt cttaaatttc ttagtaatat atctattcag    295980
ggcactcttt gagcccattc aaaataaggt ttttgttctt tttgtttgtt tcaagtgtat    296040
tttcattctt tcatcaactt agttcttcct ctgtattttt ttttctcttt ctgttacctg    296100
atcctggtat ctctaacaaa gtcatccatt ttttccaagga tgccttttctc tcctttattc   296160 tttcctgatg ctttctggga atttcttcca tctgatcttc caatttggta attcattcta    296220
tgatttatct taactattag gttcttgttc atctttacta ttatttattc tatacctact    296280
atatttacca agttctcttt tacttcttat tataatctcc tatttgaaat atattccctt    296340
aggtgatcga atatatttat tttgtctatt gtaatttctt cattgatctg ttccaatcat    296400
tatatttaac gtagaagaat ttttttttct gttgagagag agcgtttggt accttttgtaa   296460 atgttcaggt atatagctct ttgttaaaca tttagcctgt gttctcctta ggtgagtgga    296520
aactcatcca tcactctggt ttgtaattac gcatgtgatg ggacctaagg gcagaccaa     296580 gtctatgttt cttctatgag attaacattc aacaaacact tttagatcac tctggcgcac    296640
tgaagaagtt tgaaatttga gatttggctt taaactctct aaaggagcca gcattaggaa    296700
gaaacagcct ctttagcttc attcctgggg gtgtggaggg gaaggggggtg aaacaggaaa   296760 agcccatagt ggccataagt gactggtggc cctgaaagtt tttaaccagc tcctcaacgc    296820
```

```
agctgagttt tccgtgggct tgccagagtc ccactacctg atggctgccc tcgagttcta 296880
agttgtatgg agaagagaag atgggaggga gattagacaa tgattaactc aaggcattct 296940
ttataagaga caagagtgaa cttaatactt tgttttttaaa ccagcatctt tctattacca 297000
cttccaccct ctgccagaag gtgcagccac tcccattcac catatataca tgattcatca 297060
gcttgtaatc tcctcgggat ggcttatagc ttactgattt catgttctat tattgctctt 297120
tccgcagatt gatgcctcgt cttatcctct gtagttttc aaaagtagat ttctgtggag 297180 gaagggcat tatgttctat tcaccatctc aaaagaagca taactctctt tcttggatat 297240
attactattt ttcccacgtt gtgtatgctt ctcattaaag gtaggattct aaaccatcca 297300
aatgaatctg tgccaccacc tgccctgga ctttggactg aagaggattg agaaatggtg 297360
aaatacttaa ctatttgata gcttccttca ttcccacaga ccacatcaga tgtagttagc 297420
taatatacca attaacaaaa ttacccagga aatgcaacat atatacttat ttcattactt 297480
gtcaaaactt tctaaatggc tttcatctat ttctaaaaag aatcccaaat gttccaggaa 297540
caatttccta atgttctggt tttgaatatc acagctcatt tatcagcgta tatcatagct 297600
atgactatag acgccaaaat attaagtaat tcataatgac aatttggaca atgaagggta 297660
tattagaact tctttgagta tttttttattg caatatgaat ttttaaccaa agacttgtat 297720
gagctccaga gagcaaatcc actacatttc cccactctgc ctcccaaccc atcactatat 297780
agatccattg tggagctttt ttacttcttt gtggtgtatt aaaacaaagg ataataatc 297840 ccctgattat ggatgaaagt gatggaacat ttactgccat gagagtccct tatgataagt 297900
ggtagctgaa ctggaagttt aaagaactgt ggcagacagg atgggtaaa tcaataggat 297960 ccaggaccta ggaatgcatc aggaaagaca gcaacaggga aggatgagct agagcaattg 298020
aaagggtgat acatatattt ggagccaatt ctttttatgc tatcatcaag ataaaaccag 298080
tattcctcac ctggtagata tttctctttg caaaggtgga tattccacag ttcacttcca 298140
cagacctcat gcaaatgtca gattcagcgg ggagagggag caccccagtt tctttggcag 298200
cacagaatat aatgcatcat gtttatttgc aagcctggag atattcttgc atacatattt 298260
tatctagcag atgacactgg atccaattaa ttggtggctt tgaaatatat ttattggaat 298320
tcattatttt gggttatagt tgtttctgtg atccatgcaa tctaccagga tactcttcat 298380
gcttttgcat ttaaaagaat gacaccaagg gcttgtgaaa ggcacattct ggggtccatc 298440
ccccacaatt tgtgttctgt tgctttaggg gagggtgtga ggatttgtgc atctacctgc 298500
tttccacaaa gtagggtccc tgctggtata agggcacacc gtttaagtgc tactgcacag 298560
aagcatcaga tgtcattaag attgtgtgtt atctacattt cttattgttg ctcaactgcc 298620
agttactctt ttcataaaat atgtatctgt cctatatagg gctaagaatt aatttatccc 298680
agtctataac tacagagaga agcctactta atgagcattc ttgatggggc ataccaccca 298740
taaatatggc accttagcat ttgaaaaaac agaagaagca ggaaagttct ctctgacctt 298800
ctccccatcc ttctccccta aagccaggtc ataagaccct cctatgagag gtgactctct 298860
ataccaagag gaatagaaca ttcttatctc tgaggacaaa aggacacaga ggagaatctg 298920
aacacacagg ccttgctaag ttctccccag tttttttccca ttagataata aacattttta 298980
cttcaatcat actttccaat gactgtccac tctttatcaa acctaagtat ctaagcacaa 299040
aaatccacag gtttccctgt ttcttttggg tcttcattgc cttatgaagg ctcctgtgtc 299100
atataaaact gttattaaat gaagtgcact ctttgcttaa tctgtctttt gtcataggg 299160
```

```
cctcagccat gaaactaaga taggaagaaa agatatttct tttcccttat attattcaac  299220
aatattctag ttatacatgt aagcttaacc aaaagcttct agaatatcaa agtaataagt  299280
gtgaaatatg tgtgtgtgca cacatgtgtg catgcatata tatacacaca ctacattgta  299340
ggtgtgtata tatatgtata tacatataca catatatatt ttataagatg cgtatacaca  299400
tatacatttt tgtatgtgtg tgtgtgtgac agagtcttgc tctgttgtcc aggctggact  299460
gcagtggcgc tcactgcaac ctccacctcc tgggttcaag tgattctcct gtctcagcct  299520
ctggagtagc tgagattaca gccatgtgcc accatgcccg gctaattttt gtattttctt  299580
ttagtagaga tggggtttca ccatgttggc caggctggtc tcgaactcct gacctcaggt  299640
gatcttccca cctcggcctc ccaaagtgct gggattacag aggtgagcca ccacgccaag  299700
ccggcacata atacatcttg taaaatatat ttagcaaagt ctatttaaaa ataattaata  299760
gtttattaaa tcttatgtag atttttttttt caaaatgaac aagcttctgt ctttccaaca  299820
aagctttgga ataataatc attgcatttt cctctaacag gttaatcagc agatcaacta  299880
aaaccaaaat gagtctttct ctgggcacgg tggtgcatgt ctatagtccc agctactcag  299940
gagactgagg caggaggatc acttgagccc aggagttcaa ggaccagctt gggcaacata  300000
gcaagatacc atctctaaaa aaaaactaaa aattaaaaaa aaaataagt ctttctataa    300060
ctgtatgaca gggctaaggt gattttattt gacagaggaa ttaaatttca atgtaccaag  300120
ttctatccgt atgatatctt ttctgatggt tggaagggca ccaagggct tccatgaagc    300180
tcagtgacag catttttcaca tggaagtcac tgcagcggaa agtagggtac acattcttgg  300240
taaataatat atgattgcac tattgatgaa tagcatttca aaagctctgc tatttattgt  300300
ctattgaaag ataaatgaat ccagcaagta aactgcctaa atatttgta cactgttata    300360
aaatgtaaac acctctatca tactataaat ctccctcccc tccgctggaa aagacttcaa  300420
gctgagatca tcctcgtcct catcacatga ttgcttggaa tagagttgtc cctgaggcca  300480
cctgtcacct aagaggactt gtattcattt attcagtgtc catgtaatga agaataaga    300540
cagacatact gtgaatataa gaacacagag ttcaaaagac tattctgatt gagcagaagg  300600
aagatactaa acaaatatta gatgaacaaa gcttgtgtgt atggctttgg aagataagcc  300660
taggatctta atcttgttta taacacaa ctattaaacc ttcctgcgta aaatacattt      300720
taattgagac ttagcatgaa gatagaacac caagtctggg cattctgaaa agtttagacg  300780
cagaggaata actggcaggc agtgatttaa agtggataca gattttttgcc ctggagttgc  300840
agatgcgtgt aggaatgaaa aggaagtaat gggtgtgata accgatttaa acactaatca  300900
gtgagcccca atattaacc atatactggg attctacaaa gagatgccat ggtaaaaata    300960
tgaattcaag tgttttaacc tgtatagctg gatacattct tgtgatatta acacgggaaa  301020
taagaaaaga gacgagtttg aatgagaaaa agatgtttag ctcaatatag cacacactga  301080
gctttaggct cgaataagac atctgagtgg tggaagactt agtcaagcat gggagaagtt  301140
agagctgaaa cccaggtaaa atccttcaag ttacaggcag aaatcattac cagatgtgtg  301200
gtggagtcac acgggggatg tgagtcctaa tgcctgtgca gatgcatggg gaatgcagtg  301260
tcttttttgaa ggactggttt tagcgctgca agaagtaaag taaattctct tttacctgca  301320
ttcttgttcc ctctggtgct tttatgagga cctaggcaag aatagtattg aaccacttat  301380
accatccatc tgttagaaga acctataata cagaaatatt tgctttgggc tgaactccaa  301440
acgtaatact taatgatttc tcttcaagtt tgttgacaca ttctacatct ccacatacaa  301500
tttgctccca gtcgtttctg agatatgcta cagaaagtac aattgatcaa acgttggctg  301560
```

```
tagggattca agaacagtcc tgtgactgca ttttcgttcc ttcctgaaac tattccaagg   301620
ccataaaaca ccttttttgt gtgaactgtc tttctgtatc ccatttcaga tgatatcttc   301680
tttcctttaa atacagtctt ttatatttt ctaattgtct gattgccaaa acaatatatc    301740
tgcattgcta taaatttaca gtatcaaaga tcatacagaa gaaaatcttt ttttaacaaa   301800
agaaaaccat tgttgataat ttagtttaca tacatacata tgtacataca tgtatcctct   301860
tagcactctg gggcccggag tagagagcaa acctgtgaaa cagatagata gatagataga   301920
tagatagata gatagataga tagatagaag atatagagat atgttagagc tatagagata   301980
tagtctctag atagatagat aagaatatct gtattctctc tctctagaca aatgattagg   302040
aaacagtcta taagaacgtg tgtgtgtgtg tgtgtgtgtg tgtgtgtgtg tgtatgctct   302100
ctagaggtag aatatatctc tctgtaggga gagagactta tgcatgtgta tgtatgtata   302160
aaacaaagaa acaataaaaa cacaaaggcc caaatatcaa ccagaagaaa ctgaccagct   302220
gtaatgggac aattgaaaca tctgtaagaa tatttgtact ggatttaaaa tgataaagac   302280
ataaaagttc atgtattcat catgacaccc agaataaaac tcactggtta tattactagg   302340
ccacgatcgc attttcctga atcttgatca ataaaagaat catgattttt tcccactttt   302400
cctatatata ttgaatttca gagtaactaa aaaattggtg attacaagta aaatttcaga   302460
taatatatgc agaaagaaca atactatctg aaaatcatta ttttgtgaaa ctccaaatta   302520
agtaagtata ttaatctgtc ctcacactga tctaaagaac tgctggacac taggtaattt   302580
attaaggaaa gaggtttact tgacttgcag ttccacatgg ctggggaggc ctcaggaagc   302640
ttacaattgt ggcagaaagg gcagcaaacg tgtctttctt cacatggtgg tggcaggaga   302700
gagaaatgag tgcccattga aaggggaaat cccttataaa accatcagat cttgtgaaaa   302760
ctgactcact accacgagaa caccatgggg gaaactgccc ccatgattca attatctcca   302820
cctggttcct cccacaacat gtggccatgg aactacaatt caagatggga tttgggtggg   302880
gacacagcca aaccatatca ataagagatc taggaaatta tctctgatta tttgaaaagc   302940
ttcgcaggtt tatatatata tatatatata tatatatata tatatatata tatatatata   303000
tgtgtgtatg tatatatata tatatatata tgtgtatgta tatatatata tatatatggt   303060
gggattcatt accaactgaa tgtaattatc aaccactctt aagataatta aaagtaacac   303120
tagcaggtat catgtaagtc cttattaaat tcagtataaa gtacagagca gttcctgggt   303180
gcgttgtttc ctacaaaggg caccataacc ctaaggaaga aaaacaagat gtgattagga   303240
aacattctgt taattctaga acatggggtg ttcttcagca gtaatgttca aaatgtggtt   303300
cacaaagcag caacttgtta gaaatgcaaa atttaagatc ctatacctgg gaggaggctt   303360
cctgaatcta aaattgaggg tgtgggttgc aaactattat ttctttccca aacccatctg   303420
tgatgtttat gcttgataaa atttgatggg acggttcatt gatttccata aggaattaac   303480
gatgtaagaa aatgagaaga agaattgtat tatggaaaag agggtgtcaa tattttcact   303540
tgctttctct ttaaatgtgt ggatcacaag atttgctttt cattaaaagt attcagatat   303600
atatacgtat ttgaaataca tgtgcctata cactaacccc aaaacagctc attaagaatc   303660
tcttccactg ggacataggc atcagtattt gttaaaatat cactaagtgt ttagtgtggt   303720
tgatgagtgt agaaagaata tattttcacc aagcttatga gatgggcagt ttggggccag   303780
gagaagaagg cagtgaaaga acttgggtga taagcagctg tctacttgca aaacaactta   303840
ttattaatga attgggactt taaatttttt tttttatttt cataggtttt aggggaacaa   303900
```

```
gtggtatttg cttacatgag tcacttcttt agtggtgatt tgtgagattt tggtgcaccc    303960
attacccaag cagtatacac tgaacccaat ttgtagtatt ttatccccca accccctccc    304020 acccttccc tctgagtccc cagagtccat tgtgtcattc ttatgccttt gcatcctcat    304080
agctcagctc ccacttatga atgagaacat aagatgtttg gttttccatt cctgagttac    304140
ttcacttcca ataatagtct ccagtcccat ccaggtagct gtgaatgcca ttaattcatt    304200
tctttgtatg gctgagtagc attccatcat atatttatgt accacagttt ctttatccgc    304260
tcgttgattg atgggcattg ggttggttcc acattgtgac ccaatgcttt taaaataatg    304320
tgtgtgtttg gccacgaaca taagccagaa cactagaaaa attgtttact gaaagccatc    304380
ttagtttcag gaacacaaag gaaatgaggt aatgtgtgaa aagaacttta aaaattgtaa    304440
ggcattttgc ataaagatgt taggtgcttt ttgaagtttc tatttaaatg tggtcaatta    304500
gagaggtttt ttttttttca ttttatgttt gccttgaaag catttagaag tatgagaata    304560
tataatttca ttttgtaaaa cacaatatgt tgaacctaat aggatctttc ttggaaactg    304620
aacattgtcc tgggttttgg aggcatccca ttgaaattta gccatgattc catattcagc    304680
aaattgctgt ggacccagat acatcttcgc tgaccagaag tctttccaga gtggaagatt    304740
ttagtaaatg tacaagtcaa tcttgtagaa ttagataaaa tgcattctgt tttccatcac    304800
ttgccgatat ccccccactg ctaattaaag gaaacacaat ccacaattga tttacttatg    304860
taaatgtaga ttacaaacca acaacatgat tttaagagtc ttaagaagtt gagggctatt    304920
ttgaatgttt actcttggag acatgtatat ttaggtgtcc tggtcaacaa gatcaattgt    304980
aggaatggtt ggtgcaatca cattggtcat taaatacaga catcacacat aatcaagcag    305040
atttagctca gggtatgggt aactcaacat atgaacacca ttcaaagtat ttccccaaaa    305100
ggctggcatg gtggctgaca tggtttggtt gtgtccccac ccaaatctcg tcttgaattc    305160
ttgtgagagg gacccagcgg gaggcaagtg aatcatgggg gcaggcccctt cctgtgctgt    305220 tctcatgata gtgaataagt ctcatgagat ctgatggttt taaaaagggg agtttccctg    305280
cataagctct cttctgttgt ctgctgccat gtgagacatg ccttttacct tccaccatga    305340
ttgtgaggcc tccccaggca cgtggaactg ttaagtccat taaacctgtt tcttttgtaa    305400
attgcccagt ctcaggcatg tctctatgag cagtgtgaaa atggactgat atagtggctt    305460
acgcctgtaa tcctagcact tgggagggc aaggcaggca gatcgcttga gctttgcagt    305520
ttgagaccag cctgggcaac atggtgaaac cctgtctcta taaaaatac aaaaattagc    305580 tgggtgcagt ggcacaagtg tgtattccca gctacttggg gacactgggt caggaggatt    305640
gcttgagcac aggattgctt gagctagaga tgcccaatgc atctcaaggg tgcagtgagc    305700
cgagatggcg ccacttcagc ctgggtgaca aagtgagatc ctgtctcaaa aaataaaaaa    305760
atatttcccc aatggggaca tatggcttaa tagttagggt tattgtttgt agtgatgaat    305820
aggtttggaa ataggtagtg gtgataatta taccacattg tgaatgtaat gaatcccact    305880
gaattgtaca ttttaaaatg atcaaaatgg caaacttatc ccacacacaa ataaatagat    305940
atagatatac atagatatct tcatatggtt tttcttgttt tttaattttt tattttttta    306000
ttttatttat ttatttattt gagatggtgc ctccctctgt cgcccaggct ggtgtgcagt    306060
ggcatgatct cggctcactg caacctcctc ctcccaggtt caagcgattc tcctgcctca    306120
gcctctcaag tagctggtat tacaggcctg tgccaccatg ctctgctaat ttttgtattt    306180
ttagtagaga cgaggtttca ccatgttggc caggatgatc tcgaactcct gacctcaggt    306240
gatccgcctg cctcagcctc ccaaagtgct gggattacag gtgtgagcca ctgcgccctg    306300
```

```
ccttcatata ggtttaata ttagttttgc ttaatttaaa gacagtttga ggcagtacag 306360
cataaagtac tccccacatt tcatttattt agttttaatt gacaagtaat aattgtacat 306420
atttacgggg tgcatactga tgttccaata catgtaatat acagtgatca gatctaagta 306480
attagcatat ccattatcta aaacatttat catttctttg tgttgggaac attcaatttc 306540
ctccttctag ctatttgaaa ctacatatta tattattttt aactacagtc accctgcagt 306600
gctatggaac acgagaacct atttctcctg tttccccccc tccccacgaa gaaataaaag 306660
aggtgaaatc tgacacacaa agcaaaagga acaaagacat tcaggtactg gagttgagca 306720
taaattttac ctcacaattt ctggcagata aagcaaaaag agagagaaaa acaattggtt 306780
ctgggattag tatttccggc aagagaaacc ttctcccttt tccctctgat tcttggtgaa 306840
gagcagttat gatgttggag ataaaaggag aagatggcag tgatggttcc ttgttctttc 306900
cttctgcagt ggctgtcagc ttcgcctgtg atattaacag taagacagga aagcctgaga 306960
ccgcctcact aaagacagac ccttcccatt atgtgtcacg gcagccttca cccttgaatc 307020
tagaaaatac tacctgggcc gtgctaagtt tattcttaaa agcctaacac cgtgtagcta 307080
ccgctgccca atgcatctgc ccaaaacagc actccccaaa tcctgaatat gcatagaaat 307140
aactttcag ttttcatgcc tactgctgaa ttgtaccaac agagattctg atttggaagt 307200
cagcggagga gtctatgcag tttaaatttt tacagacaac tcaaggtttt gtggatatat 307260
cctgagacag ctcagccctc ccaggctgtt ggtaccatag gggctgggag agattgccct 307320
cacttacccc gcaaacacct tgcaggatgc agaacagctc ttaataaata tgtgttatgg 307380
aaataaagga atgcccctgt gcttggaagt attaggctgc ctctctctct ctctgtctct 307440
gtctctcctc tctctctctc tctctctctc tctctctctc tctctctctc tggttcattt 307500
tcaatgccgc tgagtcatac agtgagaagc agcttagggt cattaagaga ttgaaacatc 307560
ggagaaaaaa agtgaatatg ttttcatttg aatctctatt tttaactctt tctgaccttg 307620
tctgtcaaat ttggctacct tgagactgtt gcagtgataa tgaaataagc ctatgctgtt 307680
ctttggaatc attttagaca tatacatgtc taatatatat atatatatat atatgtatat 307740
atatatataa aaaatactta ccatatgtga tcttgtttga catgccttt ttctatacaa 307800
aagcacatga atcaccatgc ttcagcaatg aagatgttgt gttttggact aaaggcagtg 307860
taaacacaac atgctattag cgttttctt aatcatcact accacccagc cgttgtcttc 307920
ttgcacaaga taataatagc atctcacatt tccatggagc tttataatgc atgaaggtct 307980
ttcacattca tcgtttttgtt caatgtcata gggagaggga gcttcagtaa cctcaaagcc 308040
cagtgtgcag aaagagaaac tgggattgat tcaatcattt ggccacagtc ctaggactct 308100
tgaatgtgtg tgtaactcag gcagggtgaa aatcccagaa gatacgtccc catcccaagg 308160
gcacctaccc aggttcaata acttggttac aactgacact cttggatga tgctgcactc 308220
ttcacaaaca cgtatccaaa cctatcatga acccaaacca gagcaaacat caaatcccca 308280
ctcctaccac atattcacat cttgtattaa caccaaagcc tgaagcaccc tgacaacatg 308340
tgtccagaag atgttgaatg tcttccaccc tgactgccac taacctggtt aaagccagga 308400
ccaactttca cctggacaac tgcagtgac ttcttccaaa tgcacgctcc tgcagtcctg 308460
tccaccagtg gctcctgtga gctttacgaa accataaatc ctatcacatc cctgccatgt 308520
tccaactctt atgccttgtc attgctttac aataaattcc aacatttac tctctctttc 308580
aagtgtgaac tcacttttgcc tactactgga ataacgttct ttcacatttc cttgctaatt 308640
```

```
atgagtcagc tacaccggga ctccttctgt tctcctcacc ctttaaacat atttcccatt  308700
tgaaacttcg caactcgtaa ttcttttcag gaatgtttcc ctttcatcat cttgtagctg  308760
cttcgttgtc atcatttcct ttcatttcca cctcttcaga gaggctttgt ttagaagaaa  308820
acataggagc aaatatttgc cagctagggt tatgcaaaag tttcttacat agaacacaaa  308880
atgtaagaac cgcaagagaa tgtattgacg gggccttcca gacaccatga agaactcaga  308940
gagcaagctt cagattgaga gaaacatttt acaactaata tagcagagaa ttgacttgta  309000
actagaatat ataaaaatat ctcccaactc aatgataagt caggcaacct gcagagcagc  309060
agtcctcaac acttttggca ccagggacta atttcacgga agataatttt ttccaagtag  309120
gggaacggtt tcagtatgaa acttccacct cagatcatca ggcattagat tctcataagg  309180
agcaggcaac ctagatccct cacatgtgca gttcacagta gggttcacac tcctatgaga  309240
atctaatgcc accgctgaac tgacgagagg tggagctcag gtggtaatgt gagtggtagg  309300
gagtggctgt aaatacagat gaagcttccc tcgcttgccc accactcacc tcctgctggc  309360
ccagtcccta accaaaactg gtccatggcc tggggcttgg ggacccctgc tgtagaggac  309420
agaataacag cccctacat atgttcacat cctaccttat gcagtaacac ggacttgact  309480
gacgtgataa agattttgag atggggagag tatcttcaag tatctaagtg agctcagtgt  309540
aataaaaata tccttataag acagaaactg gaagcttgga acaatagaag agctgaaggt  309600
gaaacagacg tcagacagag attaagatgc tatgctacat atatatatat attgcccagg  309660
aggattgctt tgttggagcc tataaaggtt tgtgagataa agttctgaa gtggagaatt  309720 gttactatga tggttgctta aaatctagtt tttagaacag atgagtttt gactgtagct  309780 actctggtat gtgatccatt taatcatttt tttgtttaat taattctcag agagaaatct  309840
tagccccagc tatttaaatc tctccgtaaa taaagacttc caagcaccac tgggacagtt  309900
accaaaaatg acaaatcatt ggcaattcta acaataaact tcagtatagt aagagatata  309960
atggaactct gtaactgctc tcaaatcaaa catccctcct gcttagtgaa aacagaattg  310020
cactaatttc tctgatgcag tctcaaaatc gagccaccat ttcaggtttt gtaagaaaag  310080
ttgcggactt caggcttaga aaagacatcc cagttatgca ttgtggctga ggataacagg  310140
aagatgagaa ttaggatgta gctatcttca aaaagaaaag tggcaaaaag aaaagaaaaa  310200
ccttaatgtt agaacatata aaaatagtat aaataattaa gaacttaaag aggcagagag  310260
tttggttaaa gcggcaagcc agcaggacaa ttttagtgtg tagcttaagg tacaatacat  310320
gcataatttg cccttcctca attctagaaa atattgtctg tcttcttcaa taaccttct  310380 attcctgaaa ctaagcattc cactgggatt ttagctattt tatgtgctgt catatttact  310440
ttgctagcgt gcatgtgatt acacctaagt tctaattcgt ctaatatatg tgcattactt  310500
tttcattcat ctaatatgaa ttctagttca tctaatatag tgttgtataa gttgtctttt  310560
tacttatgtg cattttacag tgccctgaat agcactgaag tacaaaaatg tatcttaata  310620
tgtgttttat ctccatactt tgatggtgaa aaatattact ttccattcaa atgagttta  310680 aaatagtctc attaaaaaca aatgaaaacg taaataaaaa aaaaaaaacc ttttctgtaa  310740
tttttcaaga tatctatgga aatgcactga actaccgcat cattttcccc cagattttgc  310800
ttgggtcatc atggctactt catacattgt tgaatgagca tttgccgtaa atctcatagc  310860
ataagtaaaa gctatgatgt gttttttgcc ttgtctttct cttttcactt taaacacata  310920
ataaacactt agtaagcaga ttgaataaat acatacccc tttatgcaaa attattcaca  310980
aataaatggt atctaattca ttctttaaaa taccatcaga gaacacacaa tctcgcttta  311040
```

```
ccatctgtat aattttagag tcagagtcta atttgaccag cagtcaattt tttcccttg    311100
gactcctttc atatatttga aggacatttc tttgttccta gtatgtgtag atgaagcaaa   311160
actaaactgc atggcttctg atattcatga aagcaggcta gtaggtaacc attttgaac    311220
acattccaca ccaagcgcaa tgctgttct tgtgcattgt ccagttgagt tcctcagctt    311280
gctatgggag ggctactatt ctcctcccca tttcacatat aaagaaagtg ggactttgaa   311340
atcttaagtc atgtgcttaa ggcttttgcaa tagattccac cacaaggatg tccaactgaa  311400
tccactgcaa gcaataactc caaaagcagt caccaagcaa atgcccttgg tgtaaagtga   311460
tacgttctgt aacagaaatt cattgaaagc catttactgt gccgagagaa taagataat    311520
cacacaggac acttttggaa aggggcccac attggtagaa agagatggcc aggttctacc   311580
tgagtatgca ggtgacccct gcggaagatg cagagactga ccttcaggtc acactgacct   311640
ttcaaatggt gctgggtcca tgagctagcc gtgcagcttt gtgtgcggcc atagcccaca   311700
ggaaggtgtg ctcaggcaag gtgttcaggg caatttatgg tcgcccagca gccctgcaga   311760
gggcgcccta gatcttgggg attttatata aaaaggcaag catatcaaaa tgcaaggcat   311820
attctggaaa tagctagcaa gtgttgtggt ggatttgcag gctccagaac ataagtaggg   311880
catcccttga gaaggtcaca tgggcccaca cagaatgacc cttggattcc cagtaatgaa   311940
tttgtttctc caacacattc actttattgt gtgggtgtga ttgttgttgc taaaaaggga   312000
gatttaaatt atgaactaaa tataaacaga tattagcaat aaaacgtgaa tattccctat   312060
agtcacatgc ttcgaaataa tcaccctcca ctgtttgaat tccttccaga ttttatttt    312120
taataaaaca aatgggctgg acgcagtggt tcatgcctta atcccaggac tttgggaggc   312180
cgaggcgggt ggatcacttg aagtcaggag ttcaagacta gcctggacaa cattgcaaaa   312240
ccccatctct acaaaatata caaaaattag cagcaaatgg tggcacattc ctgtaatccc   312300
agctatttgg tgggctgagg caggagagtc gcttgaatcc aggaggcaga ggttgtagtg   312360
agctgagatt gcaccactgc actccagtct gggaagcaga gcgaaactct gtctcaaaaa   312420
aaatacataa aaatataaaa taaaataaat gatatgtagt attcagtagc ccactattt    312480
ttcttgagat accttagatg tgtttctgtg tccatgagtg taaatactcc ttagcacttt   312540
atgcagacaa acagcatctc ataatatgga tccaaccaag acaatccatt caaatctctg   312600
acttgtgaac attcagcttg ctgctattgt ttgtttttaa aattacaatc cgtgtgaatt   312660
gtggagcctt gggtggctat ttttatgcat cagaataaag attttcatag aaagcattca   312720
aagaattagg actcctgggt cagaagtttc caatttcat tttcctgggt tttacccatt    312780
ctcttacact ggagaccatc atgatgatgt tgatggtgtg gaaattcaga ggaagctaaa   312840
aggacgtagc acccaaatga gcaggtcctg gggaactgta gttctcatct cagacactag   312900
gatgcagacc cagggaggga caagatgtac aagctctttg aaaactaaaa ccaaaggatg   312960
tgacagccaa ttgaatgaga gtcagcagca aatctggaga aatatctaag gagaaagtgt   313020
tcagttgaaa atactcaaag ttggctgggc atggtggttc acacctgtaa tcccagcact   313080
ttttggaggc tgaggcaggg agatcacttg agctcaggag ttcgagacca gcctggccaa   313140
catgatgaaa ccccgtctct actaaacata caaaaatcag ctgggtgtgg tggcgtgtgc   313200
ctgtaatccc agctactctt gaggctgagg caggagaatt gcttgaatcc aggaagtgga   313260
ggttgcagtg agccaagatc acactgctgc actccagctt aggcgacaga gcgagagtct   313320
gtctcaaaaa caaaaaaaga ctcaaagttg actcaaagag atttgtttcc aggctggcta   313380
```

```
ttcccaaatt ttcatttgca tgaaactcat gtatcaatta tcttcagatt ttgatgtttt  313440
attatttaat aaacaagctg tatttattat tttatatttt gttcctaaaa tatgatcaat  313500
ttcagttttt ttttatttca tgtaatttaa actaaagcac ttaaaaaata cctatgcagc  313560
ttaattctag ataaatgtgt ggagatatta tcttttatga aaatactgca aggaatctca  313620
gtagtagttc ataggcccca gagtttggaa acctgtggta taaaaatcat ttgtctctta  313680
taattgtttt agattttctc tactgatatt ggaaatagac tttggttctg tgcaatactg  313740
ctgtgataac atgatacaaa tggagaatgg tctgctagta ctcattccat ttttaagtaa  313800
aaactaaaaa taaaaggcac tgaatttcaa gcagccctgc ctatcaggca acagaatttg  313860
aatgcagtgc atcagcttcc ctcccttcca gcccatcctg tgcaatgtgt gcttctgtgt  313920
taaatcctac atgttttcag tcagaaagtt aaaggttcac cttgtaataa atgcatttca  313980
tgaatgattt cctataaccg tcaaagatta gttttgcatc tgtttgactg attttttgttt  314040 tttatgcttc tgctttcatt ctaaccaaac agatttcttt ttgacctcat ttgcatgatc  314100
taacacaaat tctgttatt ctcactgaag aattttatt taaacatttt ctgttggtg  314160 tcacttcttt agtttaaagg tgcacaaatg tatgtctgtg tacatataca tttatagtca  314220
cacatgcata tatgggtta tatatgcata tatatatata tatacataca tatattatat  314280
atatatacat acacacatat caggtgaatt acacacactg aaatggtgaa agatatttaa  314340
cttctgtatt cacttaatta tctcctggtt acttgtctcc aaaaaatgcc tactgtgttt  314400
atgcaaggaa tgatctccta aaagaaaatg gattgcagct ttaacgtcat gtaacaatgt  314460
cttttgttaa ttgaaagaaa aacaatatct gaccccattg ggttccttac catttacttg  314520
cagtgcatgg agaaacaaaa gacctgcagt cattctccta agccctgtga tgtaattcaa  314580
aatgagagga aacatctaca ttattatcta taataaaaat tggaaacttt tctgttgtga  314640
caacaatatt aagcctgaat agaaatattc atgtttatat gatattcact tcagtcaaca  314700
tgcagcagga aaaactgtga ttcctatttt tagtcatctt ttccatgaaa cctgtttcta  314760
aataaccata ctaactaaat gtactagtct gttctcatgc tgctaataaa gacatacctg  314820
agactgggta atgtataaag aaaagaagtt taatggactc acagttccac atggctgggg  314880
aggcctcacg atcatggcag aagacaaagg agaagcaaag tcacatctta catggtggca  314940
ggcaagagaa tgtgtccagg ggaactgcca tttataaaac catcagattt catgacactt  315000
attcactatc atgagaacag catgacaaaa acccaccccc atgattcagt tacctcctac  315060
tgggtccctc ccatgacaca tggggattat ggggagctaca gttcaagatg agatttgggt  315120
gaggagacag ccaaaccaga tcactgaacg tatctattga tatctcttgt gtgtgtatat  315180
ttgttattgt tgttccttcc aggacccctgg atgaaacttg gcatcaatgt agccattaac  315240
atggattcat tcacatggtc tcttttgcat cttttctttcg ttgttcaatt attggaggag  315300
aggttgctga ttcaagctt catattaggg agagtaaagc tcagaaacca aaatttcatc  315360
ggctaaaatg cttagagagt ttgtagccta aaggacctgt cagttaaagg agccatttgt  315420
tgtaaatctc tggttttaga caatcaagta gcttgttctc ttcattcacc ttgaacatat  315480
atttaaagtt aagtgatcta tccgaggaat gacttctcag gagcagcact catctttggt  315540
atcatgtgtg gctctttcca agttgatgag ctaccatcat tttgctttct acaatcagga  315600
ggcaaaaccc agtggtttag gtttgcagga ttcctaaaaa tattaatttt aatttgctac  315660
aataaatacc aggattcctg gtgtcaaaaa gcttgcaaaa aatcacacca ttagaatttt  315720
ttaagatcac tcttttattta cacttaagaa gatagctttg ccaggaaaat gcctgccttc  315780
```

```
cttctttcct tccctccttc cttccttcct ttcttccttc cttccttcct tccctccctc 315840
cctcccacct tccttacttc cttccctccc tccctcctac cttccttcct tccttcctcc 315900
tgctctccct ccctccctcc ttccctccct ccctccttcc ctccctccct ccttccctcc 315960
ctccctcctt ccctccctcc ctcctgcctt ccttccttcc ttccttcctc cctcctgctc 316020
tccctccctc cctccttccc tccttccctc tccctgctcc atcacatcac agagctgtag 316080
tgtgctgcct gttccttgcc tccagtctta ttcacaggaa aacctggcca ggtgctgatg 316140
aataaagaag aagacagatt gatagtgaga tctaattttc acagatcagg cgacttggga 316200
aaacaggtct ttttattttc aaatgctaac tttctgggct catagaattc tgtatcagta 316260
agcccacatg cttttaagt ctgatttata gaaaacatga tttggccctc aaaacaatgt 316320
aacctcccaa cagattcatc tttaccacta cacagataga gctgattagt caagacagaa 316380
gaattgcaat agataaaggg tttaattcct gcagagctgg ctaaatggga gactggagtt 316440
ttattgttac tcaaatcagc cttcccaaaa atttggaggc ttgggttttt ccagaatact 316500
ttggcagaca ggggctaggg aatgagtgct gctgattggt tgaggatgca atgataggg 316560
tgtggaaaac agccctggtg cacccagtcg gcctctatgt ggggacacag aggagtcact 316620
ggtcctagta ggaccaatca gttgtcagaa atgcaaaagc ctgaaaagac atcttaaaag 316680
gccaatctgt actatgctta ttacctgggt aatgagataa cctgtacatc aaaccctgt 316740
gacatgcagt tcacctacat aataaaccta caggtatacc cctgaaccta aaataaaagt 316800
tttaaaaagg caaattttag cttctagtga ttggggaagt tgcaaatctt gtgacctctg 316860
gaataatggc tggtaatcat tcaactaagc ttacatctta gcagaattca ggcctctctc 316920
attctttaac ctggtggcct ttcattactt ttacaaaggt ggtttagttt taagaggggc 316980
tattatcatt taaactacaa gttcaatttc tcccaaagtt agcttggccc gtgcccagga 317040
atgatcaaga acagtatgga ggttaaaggc aagatggagt tggttaggtc agatctcttt 317100
cactgtcata attgtctgac tattgtaagt tttgcaaagg tggtttcaag gtgaaaggac 317160
tatactctta aagagcataa aattattgca ttcattgtgt acctgaaaca ggcactcccc 317220
cttgttgata gtttaaaaag aaaaaaataa taatccctgg atgttgcaat aaatgaaaat 317280
gccatggcag aaactgtgga acaccagcc tcaaaacacc acattgattt gttaaacttc 317340
agagatccat ggattgtcgt ttccctcagc cagcctgtag gatatttgga agaatttcag 317400
aacctcaaag atcaaaccat ccataggat gctgttagaa gaactaagat ttttgaaggc 317460
aggggatatt cattagcctg cttttggaaa ggttaaaaca ctctgatttt gctagggagg 317520
aagagtttat ggtggaagaa aggccaatga tttcctgcgt gttgaaaatc ttcatactcc 317580
tccacagaaa caaaataagt caacaagtca ttctgcagaa ttgagaaaga gaacagtg 317640
agtgaagaaa agacgtgctg aagacagaat cgttctgtta gaaaattgct cgtgccttag 317700
gaattaatca cctctttctt taataggga agaaagcatt gccctgtggt attataggc 317760
acctaaactg acatgattcg tcattgtcat ataaggatct tcgatctttt ctcccaagca 317820
aagcctgatg cctttatga acgatcgtgt caaagatata gtgatggaga caggtgttgc 317880
agaacatttt tggcatgaag cactaattag taattgctaa ttaaatgggg gaggaggctt 317940
gggtaatgtc tgatcgcacc cactaatcgt agctaatctc ccgtcacatc cctctgaact 318000
ttaaagaaga tcacattggt aggatgtgtc ttaagtatcc aacctcgcag ttgcgacgct 318060
gcctctcttt gaagctgcag gagatagtga ctcccgattc aggcttggag tttttattgt 318120
```

```
cattgttgaa cgaaaatcgt cctgtgactt tctttggagc caggccattt cctcctttcc   318180
agctcagagc attttttccac aggtgctcag gaaagctcat ggaagaaatg ctggttgact  318240
caattggtat gcagcctcat cctctactct ttttgtttta aaagtagaag ccggcactca   318300
gtcactcctt ggaatgccgt caactttggt tagggacgtg ctttgaggga attggtttga   318360
tgttatttta gggcttaaag cagcctgtct tcatacaaac atgactgcag gtggccataa   318420
taatgtgctg agcatccctt gaaatgagtg aatgacatgg ctcttggaaa aaagaaattg   318480
tatagaaggg gcaaatatca tagttgggta gttggggaag gctcaaataa ggacgtgaaa   318540
atggttaaaa aaaaaaactt ttaaaaattc tttgtctttt tggaaggcat atccagtaca   318600
gatttggaca taaagttgga ttaaagtttta tgcaatgaac taaacttgca ggaggcctta   318660
gaaaatattc ctagttttga atctgagtag gagagtgtat gtcttcccaa acttgacttc   318720
aaaacatcag aagaaagcag ttttttccagg tcaagctatt tttcaataca gaaggaacaa   318780
aaaataaaat agattaactc ataactttgc tatcattaat accaaaattg ccattttttca  318840 actactaagg agaaattaag aatcgtatgc cttgagtaaa atctagatcc tcaactcaca   318900
gaatccttct ttttaaaata aggaaggcca gttcctgata ttttgggaac agttggggag   318960
atgtgaatat tcattagctt ttgggtgagg ttcaataatt acattttttt gtatgtgact   319020
aatattttcg ctatgtagga aaatagaggt gtatactatt tacgagtcgg atctagtgga   319080
gtctgtaact tacgttgttt cttaagcatt gaaaggagtt aaaacaaaat gttaataact   319140
aattcagtga gaaagacagg cgcacactgc ctttgtatac atgcacatat tcttagacac   319200
agacacacat gtgcacttac gccccctccc cccccacac acgtactgtt ttcccctgaaa   319260 aatttcttgt aggagtctgt tgcattttttc aaaaagaaa atgaaaatgt gcacagaaat   319320
gataccttga acctagtaaa atttacgacg tcttctggga ttgcttcatg ttattaatat   319380
tttagattca ttttgccttc tctattagcc acatatatac acaaagatgc catggtatca   319440
taacatcaac ctaaaataac cattatttat ataattattt ctgccacaaa attttttctc   319500
ctgttcttcc tctaattggt gggggtgaga gttgaggaga gagagaatga agaagacaag   319560
ctatgagata tctttttcaaa tagcagagac acgtatgcac ttttttctatt tggccaccaa  319620 aaatatcttg tgttcttttg tagggttttt aagtaccggt gaccaggcag caaaaggcaa   319680
ctatgggctc ctggatcaga ttcaagcact gcggtggatt gaggagaatg tgggagcctt   319740
tggcggggac cccaagagag tgaccatctt tggctcgggg gctggggcct cctgtgtcag   319800
cctgttgacc ctgtcccact actcagaagg taataatggc accccagggg tgggcgggca   319860
aataccctga accaagaaat gaatggtcag agttcatatc tcagatgcat gtcctggtta   319920
ccagaagtca ctctggcaac agaaaatgcc caaaagatca aatgaatcca tcttcatgtc   319980
ttttaactca gcttttgttc catttgctct gtcacccagg ctggagtgca gtggtatgat   320040
catagctcat tgtagcttcc aactcctggg cttaaggctt ctcccatctc agtctcctga   320100
atacctggga ctactggctg cttttttaaaa ttttttatag agaagtggtc ttgctatgtt   320160
tgcctgggct ggtctcaaac tccaggactc aagcgatcct cctgccttgg cctctcaaag   320220
tgctgggatg acagatgtga gccaccatgc ttgatcagta atatttttct cctaatttaa   320280
atgtgtgaca attaggtgtt ggttacaatg attggaacaa ataactact ttagaagtcc    320340 tgacactttt gttttttttt gccattctga ctgtatttga ctatttgaaa ttttattaac   320400
ttctagctac aacttagtaa aagtagtatg gaagagagac agtatgtcga taagggatgc   320460
gggtgtatag attttgtaac catcagggct tttagccaca tgttttttaa gaagtcgctc    320520
```

```
ctctctctaa ttcatattaa ttctttaaat cttctggaaa tattgaaaca cgtctggtgc 320580
attcatttag aagtagattc tgggtagaag tagattctac ccagaggaat agtgtctctc 320640
tccctgatgg tctccctccc tcccttgctc ttcccctccc attcttctct ttccctctct 320700
cgtcctctct gtctctctcc ctctctatgt cctcctccct ctacctctct cctgctccct 320760
ctctctcttt tgctctgtct ctcaccctct ctctccccct ccttccactg tctctcctcc 320820
ctccctctct ctctccccct cacactgtcc ccccactctc cctgtctttc tccctctctc 320880
tctcttcctc tctctccttt tctctgtctc cccactctct tactcactat ctcctttcct 320940
ctctctcttt ccccccttc cctctgtccc tctctctctt tgtttctttc tctctctctc 321000 cctcccttc ttcttctcct gcaaatatga ctttcaccaa aggacctcct tcctggtcag 321060
gtcagcatgc agcactaggg agtgtccaga gtttgctttc ccctctccct tcctctctct 321120
ctctcctgca aatatgactt tcacgaagga cctccttgct gggccagtca gcacgaggtc 321180
ctctgcttgt ccccgtggga gctccaaacc ctccctgggg cctgctatt aacctggaaa 321240 aagctgatgt tggcaaagtg gagaaagagg aaaccacaaa aacacatgtg catcatgtta 321300
cctcaaccag atgtgcactt gaacgtgtag tcagcatagg cacccgtacc caaccagatg 321360
tgcacttgga cgcctaagca gtagatggtt atgctgccta agtaatggtc agcataggca 321420
gccacacccc tgagccctgc tggagtgcct gaggctttcc ccggaggctc actcagtgga 321480
ttcccagctg tcccttttgtg aaggaggctc cctgcagtat ccgatgagag acttcaaaga 321540
ggagtccaca ggaatttgag gcaattggtt ctggaagcag gatcacaaat tcctggctgt 321600
ggcctaaaag gaagaggcag gaaaatctgc agtgcagatc cagccctggg ttgcctggcc 321660
acacgcaagt gaatattcct aatagccgtc tcagtcatca agacagcttt gtaatttgtt 321720
ctgtgttgtc agtggtcttc agaatggcac cacactgact gaacctgaag ttctcaaaac 321780
cttcatggaa tttttttttt ttttcaggga gtctcactct gtctcccagg caggagtgca 321840
gtggcacaat cttggcttac cgcaacatcc accttctgga ttcaaagcga ttctcctgcc 321900
tcagcctccc gagttgctgg gattacaggc gcccaccact gtgcccggct aattttttgta 321960 tttttagtag agatgggctt tcaccgtgtt ggccaggcta gtctcgaact tcctgacctc 322020
aagtggccca cccacctcga cctcccgaat gattatttt aaagttatca gctggatatg 322080
gtggctcatg gctgttatcc cagcactttg ggaggctgag cggggaggat ggcttgagcc 322140
caggagtttg agaccagcct ggtcaacata gcgagacccc gtttgtacaa aaatgaaaat 322200
aaaaaccagc tgggcctggt ggcgcatgct tgtggtccca gttactgggg gggctgaggt 322260
gggaggatcg cttgagccag ggatgtcgag gctgcagtga gctgtgaggt tccactccag 322320
cctgggtgac agagtgagac cctgtctcaa catacataca tacatacata aaattaaaaa 322380
gtatctttct ttagagtaac tgcaggactt tcttcacttc ggcaccgtct ggacaagttt 322440
ctggatcgct gtgctcctca gtgtcttcat tggcaagata ggacagatga gggtttcctg 322500
aaatcctcca aactctgaat tccttgagtt tttagttcat aatgttttgc ccatgagacc 322560
aaatggcctt tgatttctta ctagtgctaa tgagaggaaa ggctcatatt tgtattaact 322620
ttatttcaaa aacacgataa gtgaagaatc tgatgaacca tttggtagag agatttctat 322680 ggcattttg aaaatacctc gatttcact tttctcaatt gatataatca caattgtaga 322740
tttagaaagc agtcagaacc aacttcagga gtaatcaaac acatgtaagc cacattaatt 322800
ggagggaggt gttaattatt taagtcaata ggttggaaat tattatactt ttgcatcggt 322860
```

```
catttctgca aggcatgctt ctaaacagcc catcaatata atcacgaatt atgaaaaata 322920
caagccaggc actgaggctc ctgcctgtct atcatcccag caatttggga ggccaaggtg 322980
ggcagattgc ttgagtccag gagttcaaga caagcctgaa caacatggcg aaaccccgtc 323040
tctacaaaaa agagacgcat ctgttgtccc agctacttgg gaggctgagg tggaaggatc 323100
atttgagcct ggaaggcaga ggctccagcg agccaagatc ccgccactgc actccagcct 323160
gggtagcaga gtgataccrt gtctaaaata aaaataaata tagccagact gtttgcctta 323220
ggaattcctt gcctggttat atggtctaat gaagacaaag tacacgtgga aagtgatagt 323280
tttatgaaga tgttcaccac agtattagta tcgtagcaaa gaatgaaatg aaaagctaca 323340
agatcaaaag gagaggaaaa ttataatgaa ccatatgtat ttactcaata ataatttaag 323400
aatttaccta agatatacat cagctggaaa aacagtttag acagctatat aaatattggg 323460
ctcagctatg caaacagac atttgaatgg agggaaagag ctaagaatta tgtgaactcc 323520
tagcatactc attacgctaa ggtgagttgt gtttaaagta tgaattctgg gtgatttttt 323580
tcattatcca actattttag tcttatcagg agttctgtta cttccctaac atacaaataa 323640
atgtttatg tatgttactt tatatacact actgcctaaa ttattgccag tacttatgag 323700
aagggcggga aaggaacttc tcacagcatt ttttccaatt ctgaatgttt taactaatga 323760
aagtatccaa tagaatacat attgactttc tcttttggtt tttttttttt tggacatttt 323820
aaaataatct tcagagccaa gcactcaagt caatacttgc acatttctga cagaaacgtt 323880
cccaggatgg ctttgatgac atactggtca aagccatatt ggtttcaagt tgcggtcctg 323940
tgtgtcatct ttgggcaatc ctccagtctt taaaatcacg tcttcctgat gacagttata 324000
ttttcctcat atttgattgc ttctgtgacc ttaaaaatcg acagggcatg aacttctgga 324060
ctcacaactg aatgccttat tctttagtgc ccgactcggg ctgggattca cggaaatggc 324120
aggaagcaag tgtaaatgga atgctgattt ttacagcgca cctctcttgt cctatcgtag 324180
ttaaaaatac agattttata cttctggaca tccgtgtagt agactgaact catggagaat 324240
tttaagctac acagaatttt actcctaaaa ttgcccatgc ttttcaagt ttctcagcaa 324300
gtggagcatt tttatatgtg gcaaaataaa atatacacat ctctgagttt ccaatggatg 324360
tagttttgaa agaagtgacc taaaaaatac tccttacttg ggcacccagt tgaggatttc 324420
tttaagcata gctagctgaa tgtatttatt ttaattggca aatcttaata tcttcattag 324480
actcaaggta gaagtagaaa tgcgctcctg aattagcact ctgaagttga ttcaagtgga 324540
tttcttttt tcccataatg aagagatacc tagttttgct tgtgagacaa gagggccttt 324600
gaactggtac tagcttaaag cattttttt cttggaaatg gggaatgcag ttgctcttgg 324660
agttttata tatggcatct ggaggcaagg aagcaaaaac gacactaaat tgtggaagga 324720
aaaagaaatc acatgtattt taccagtgca ggagaagtgt caatgtggtt tcatttcctt 324780
aaactcgtgt gtgtgtgtgt gtgtgtagaa taacattccc taaaatgaat gttcaggagg 324840
aggggtgaag ggggaatgga aatgaaaatg ggtaaagggg cccctgacag agctgaatgc 324900
tactacatcc agaaactcac atgcctgaga gacaatcaca gccttcattg ctcagtaaaa 324960
gctgcatttc tgtcctgtgg gttttcattt gcatgtccac aattttgcac ctgcaggtct 325020
cttccagaag gccatcattc agagcggcac cgccctgtcc agctgggcag tgaactacca 325080
gccggccaag tacactcgga tattggcaga caaggtcggc tgcaacatgc tggacaccac 325140
ggacatggta gaatgcctgc ggaacaagaa ctacaaggga ctcatccagc agaccatcac 325200
cccggccacc taccacatag ccttcgggcc ggtgatcgac ggcgacgtca tcccagacga 325260
```

```
cccccagatc ctgatggagc aaggcgagtt cctcaactac gacatcatgc tgggcgtcaa 325320 ccaagggaa ggcctgaagt tcgtggacgg catcgtggat aacgaggacg gtgtgacgcc 325380
caacgacttt gacttctccg tgtccaactt cgtggacaac ctttacggct accctgaagg 325440
gaaagacact ttgcgggaga ctatcaagtt catgtacaca gactgggccg ataaggaaaa 325500
cccggagacg cggcggaaaa ccctggtggc tctctttact gaccaccagt gggtggcccc 325560
cgccgtggcc accgccgacc tgcacgcgca gtacggctcc cccacctact tctatgcctt 325620
ctatcatcac tgccaaagcg aaatgaagcc cagctgggca gattcggccc atggtgatga 325680
ggtcccctat gtcttcggca tccccatgat cggtcccacc gagctcttca gttgtaactt 325740
ttccaagaac gacgtcatgc tcagcgccgt ggtcatgacc tactggacga acttcgccaa 325800
aactgggtac gttcatcttc gtgttggggt atcactatcc ttgccacttg tttgtgtcct 325860
caatataggt gttgcttcta ctgccacgtg caggagcaca cacgcataca cacacataca 325920
catgcatgca cacacataca cacagacaca cgcttacaca cacagcagta acaggcagct 325980
tctcccccaa catctatggc aactcatttt tttctttact cctaaagtgt tataggagta 326040
aaacacttaa ctgtcaaacc agattttac tagagttcta attgcccatt gggaattcca 326100
gagttcctac ctgcaggtgc aggactcata catatatgat ggttctgtta acagctgatt 326160
aaacggtttt gttttgtcc ttgttgtttt agagacacag tctcactctg ttgcccacac 326220
tggagtgcag tggtgcaaca gtagctcact acagcctcct gaactccta ggctcaagcc 326280 atcctcctgc ctcagcctcc tgagtagctg ggactacagg tgcctgccac catgcctggc 326340
taatttttaa tttttttttt ttggtagaaa gagggtctca ctctgttgcc taggctggag 326400
tatagtggcg caatcatagc tcactgaagc ctcgagctca tgggttcatg tgatcctccc 326460
atctcagcct cttgagtagc tgggactaca ggcgtgcacc accatgccct tacatggatt 326520
tttgtagaca cagggtttgc tatgttgccc aggcttctct caaactcctg gctcaagggg 326580
atcctcccac atcagccttc tgaatagctg ggactacagg tgcacaccac cttactcagc 326640 taatttatt ttgttagaga cagggttttg ctgtgtcacc cgagctggtc tcaaactctt 326700
gggctcaagt gatcttccca cctcagcctc caaaagtgct gagattacag gtgtgagcca 326760
tcacaccagc cctcattaca gagttttaag tctaatttca accatatctc ttttgttaat 326820
ttgcaaggat atcacagcac atgtaccact tggggaactg tgttgattgc ctggccatag 326880
gaatgaaaac aaatatcata ataattataa agaaatataa atatatattc ctatatatat 326940
ttaatgtcta tataaaaata tagatattcc tatttgtata atatagtaca tttatatttg 327000
tatttgtata tatatacaca caaatatatt tgtatataca aatacaaata tatatacaaa 327060
tactatatat atacaatata tatcaaaata caaatatata tatacacaaa tacgtttgta 327120
ttttctctgc tatataaata actagagaga gaaaatgaaa atatatgata tttgtatcat 327180
attgctatat gtcatgcata cataaacaca cacacacaaa cacacataca tgtgtatctc 327240
acaggaaagc tcatttattg gcctaaatat agtagaaaat ataaaatata caaaaagcat 327300
atatacaaca gagtctgcca atattctgct gagcggattc tctgcaaacc atgggagaaa 327360
agaacccaaa acaacctaaa tagctccaaa cattgtggca tttttttcatt ttctcttgtc 327420 taataatgta actgtggaaa tggatggggt gtcattctgt tctaccagtg tgtgcctcca 327480
tcatcaccct gagcctcttt acactgaatg agagagaaag atgtgcctgt cgcccaggga 327540
gggtaaatct tcccgtgcgg aatgaggctc tgagactgca gtggccctgc cacacatgag 327600
```

```
ttatgcacag taatccttag aagatctggg gatgctggtg gtttcaatgc ctacgtgttt    327660
agcagctggc atactgtaca aagattccaa agtggtttgg gtagggagtg gtttgagaat    327720
gttttgtgcc cttggcgaaa gtacagcatg tttttggagt ggaaaaggta tcacctggat    327780
accacctttc aataatcaga ctttgtagat ttggtctgag aaaggctacc cagaggaaaa    327840
gagaggaggg acccacattt gatgcaaatg cttgtctatc actcaacggt tcttttttgt    327900
gtgaagaaat gattgaaatc aaattaatac ttttttttaaa gtaaaccttg tttattagtt    327960
tgttgggact gctgttatca gagtatccaa aactgtatgg ctatgctggg cgcagtggct    328020
catgcctgta accccagcac tttgggaggc cgaggcagga ggatcacctg aggaggccaa    328080
gagtttaaga ccagcctagg caacatagtg agagtccgtc tctacaaaac aaatgaaaaa    328140
atttagctgt gcatggtagc atatgccgag agtctcagct tctcaggagg ctgaggcaga    328200
gggatcactt gagctcagga ggtcaaggct gcagtgggcc atgtttgcac cactgcactc    328260
caacctgggt gacagaccga aacctttatc tttaaaaaaa aaaaaaaaa aaaaaaaaa    328320 aagcaccaaa aacggtgtgt cttataacaa cagaaatgta tcggttcacg ctttctaagg    328380
ccagaagttg caaatgaagg tgcttgcagg gccaagttcc ctccaaatct gtaggggag    328440 ggtatttcct tgctccttct tagttactgg tgtttgggtg cagtctttgg cattcctacc    328500
ttgcaggtgc accatcccac tctgtgtctt tgtcatctta cggcctccct gtgtgtctct    328560
gtctccacat ggccgtcttc atataagagc atctgccaag gtgcattaga agctcaccct    328620
actctagtat gacctcaact taacataaat agtcatatct gcagttaccc tatttccaaa    328680
taagctcaca tactgagata ctggggttat gacttcagcg tatcttaatt tatggggaga    328740
cagtattcaa tctctaatac cctgtgaaat cagggccagg ccctcttttg tgacagcact    328800
gagataggcg gtgtctgccc ttgcagagaa tttcatcctc ttgaagccta aagacttcca    328860
tgagagtttc ccaacatggc tatactcatt caatcttcgc tacattggca tccaaacgta    328920
ttaccgactt ggtctgcaaa cactctcttt acttactctc attaaaaaca tatgcttttt    328980
cttttcctcc ttacatgatt tgaaaataaa ctttatatga ttatcttaag tggaaagcta    329040
gaatcattcc tcatacattt tatggaacca ttaaaacaat agtgaaatct aaataatgct    329100
gttaaattct cattagctct tcctgacttc caaaggctat gagactgagg ctggctctct    329160
cattattaaa aaaaaataaa aaaaaaaaaa aaggaaaaaa gacagaaaaa gataaaggaa    329220
gttaattagt tccatgaggt gatcgttatc actgctgaca ccaaatggac gcttttacca    329280
agacatcacg aaggtctgag agagccgtga gaagagaata ccacaatgat ctctctgtta    329340
ttgagtgctt ttaatgccat gaatctgttt cttaaaatca cttggcttag agcctgtgat    329400
ttccaccctg catttaggga atacattcac gttgccattc atggtctgtg ttgagggtgc    329460
ttctagcttt catgaaggcc ctgacatggc tggaagagat gaggaaggaa taactgctag    329520
aacttggaga gacgctctga tgctactgaa atcaaaagct gcaggtagag agagttcatt    329580
gaggtaccca gagctcgaat gtcagtccgt ctgaagcctc tattttgtt tcttccgccc    329640 atgggaaaca tccctgaaat aacactgagt gtattaatgc agtgagctct tttaattcat    329700
tggaaaggta ttagaatgac tcaaatgatt cctcaaggaa gttactcaga acttacatct    329760
catgtgaaat gcaacgtgtg gattcaaata caaatagttt aagtgatcac acctccatgg    329820
cagccccata aaagaaggaa atggggaatt tcactgtcgg gcacagtctg gtgagctagg    329880
tattcgtcag tggatgacaa ggacttcagt tgcagttggt agttatttgt ttattgtaaa    329940
ttgggtggtg gcccgatcac tccagggcag agaaggattc cctggtcacc aggtgcagag    330000
```

```
aatgaaccaa actgatgccc gcaaggagaa agtatgggat gcaccttatc tgctgtcatg    330060
gtgtgagctg ccaagtttaa cgccattttg cagagcacac actcagatga tgactcacag    330120
aacaggaggg catatttctg cataccatca ctgttccctt ccagcactgg aggtgacagg    330180
aggaaacaag aatagctccc agcgtgtctg tcactacacg gtgccgtgga gaaaggatcg    330240
cattgtgcca ggacatactt caccactctc agtgggcgtt aagtcaagcg ttctaaacct    330300
gcaggcacag ccagtctctc gatggcgcat gtgtttgcca agatgaagtg gatgggtct    330360 ggatgcttct atatagacat ctcaaagtag atggttctga cctttagtct aggtttgaag    330420
gcacatatac ctggtataca taaacctttg gttttgggat gagcacagaa aaatgatgtt    330480
gggatgtgca tggcggagaa aaggaaggaa ggagggaggg aatggaggaa agagagttca    330540
gacaaaggaa cgaagggagg gaaggaggga gggaggagg aaaagaaaag gagggcggga    330600
gggaatcaag aaaggagtaa aggaagggag gaagggagga agaaagagg taaggggga    330660 ggagaggaag gaaagaagaa gggaaggaag gagggaggga aggtgaaagg aagaaaggga    330720
ggaaggaaga aaagatggaa ggaaggaaag gaaagagaga aagagggaa gagaggaagg    330780 gagaagggag aaagaagaga ggaaggaagg aaagtagcga gggaaggaag gaaaaaatgg    330840
agggagagag aaagaaggaa gggagggagg aaggaagagg gaggaaaaag ggaatggagg    330900
aggagaggaa gaagggaggg agggaaagaa ggaaaacagg gaaaaggagg gtaagagaga    330960
gaaagagggg aagggggaga ggaggaagga aagaaggagg gagggaggga caattggatc    331020
tttgcttata aattatgtca cctgtatatt ttcatggtag cattaggtga gagggctctc    331080
ccatcttaga aaggcggagt cagcgagtac gcatagtaga aatgaggagg aagtccctac    331140
ggaggctcta aattatgaaa accttgatca agaaaggatg ttgaaatcat tgaatgccag    331200
ggcctcaagt aatccttgct atttcttttt tattattatt ttgaataggg aagcagttgc    331260
ccaggcctgt gcctgagggg gatcctcccc tgtagcaagg aggtgtttca atgttagtcc    331320
aggtcagagg actaaaatca tgctggaaga gaaccgtgtg agcccaaaca tgcagaggca    331380
ttgtagaaat aaggtagatt gagaccgttt ttggaaatca gctgcagtgt caaggagaag    331440
tgaaaactaa ctctaaagtt tcaaaagggt tctagagcat taaagtcctt ttcctggaaa    331500
attactttgg gaataggaga aaaagggttc gtccaagctg atcaatgaaa ttcaggtgct    331560
cagtgatcca ggattctttc attttgagct ctgtgtggaa agagatggac aaaaaggagt    331620
ggggaatctt ggtttattta aaggtatga caaagaacag tgctttaaag taaccaaaca    331680
atgcattata atatagaata gaagacctta tgtgctattg gaagtcagat atgagaagag    331740
agttttgtaa tggaaaatca gatcaacaca tattttgatt tttttatgtt gttccatcga    331800
gtctggggtt tgtacggcag attgatttct gtcctgtttg catcagctac catcactgct    331860
tttgaatgtg ctggtatcct atgattaatt tacgttcaac tattgttaaa tctttgggaa    331920
aaaaaagaag ttccaatgag gtatttagtg gggatgggtt acagagagtt gcagcgtaat    331980
tctggctgta aaggcgacct ttattaccaa aaaggaattt taagctgaat gaatgaacat    332040
ccccacctgg tgtggaagag gagtcactga atgcataata aactagtccg gtaataatcg    332100
ttaactgcga acaatgtttt gggtatgagg aaaacctgta ctacttaaag gaacagctga    332160
gaggattcac agatattttt agagagatca tagtactata tccatctcca gctaaagaaa    332220
tgaactagac cttagaaagg cacttgagtc tctgctgcca agatgacatc tcaaatataaa    332280 caggacaggt ggaaatggct gtgttaggtg ctgggggata aggaggaaga catgcattga    332340
```

-continued

```
gtcttttact agagagacca acttgtgttt ctgtcctcaa tcattatagt ctttaatttt 332400
actcacagga gtttaaacac ttcttaggct gaataaagtc taaaaaacaa aacactgata 332460
ccccacatct agacctcact gtctggaggg tttggtaagg gagaatgact tgggctatca 332520
taatctccac aagtttatct ggctttaaga attctggctg tgcatctccg agatctttaa 332580
tagacagacg gtatcaggtg gcagctcatt tatatggatt ttccaaatcc tctgctttat 332640
tcttcaagaa caaatataaa tgtgttttct ttaccttca aatatacct gagttccttc 332700
gaaaatagcc ttgtacccaa catgaacaga atactccttt tcctagatgc tcactgctta 332760
atagatgagg tagccacaca tctaatagat ccaattcagt aaaattggat ccatggaaaa 332820
aaaggtagaa tcttcacttc catttgtttc tttagaatat taaaaatcaa taactaatat 332880
tagtggattt ttttcctaaa atattcattc acttatttt ctttcagtac acgttaaata 332940
actgaaaatt ttaaaattat ttcagaggac ttaaagagca aaagaaacat gagttgctgc 333000
attgaatcca acatttttc aaaccatgt aagaatacat gcataataaa taaaaaagc 333060
agaagacttt tcaaatatat tgtttatcag taaataagaa aactcatggt attagaacct 333120
atgagattat atatatttgt tctcacccta ttagtaaagt gaaaacacag cagttagtgt 333180
gcattcaact aaagggtaga ggtcaactt cttttctcc tgtattatgt tatacatcta 333240
atatctatat ctatagatag atatacacat acacatatat acacatgaca tacatatata 333300
tactgcatat agtatatagt tagtatgcag tataaactgt ggtatgcagt atacttgtat 333360
atagtatgta atatacaata tactttatg cactctacaa tgtatacaat atagaaattc 333420
agtatgtact ctgatataca gtatatcact ccctacttct ccctcccttg caatattata 333480
ggtgttctat tttttatatt ggaagagagg gggtaatatt tcctgaattc ttaccatatg 333540
ccagacatct tgtcattatc tttcaacctt catcacttac ctccaaccct gatatttca 333600
tcagccatgt agaggagtaa gttaaggcca atactggctg gaaaacttgc ttaagatttc 333660
acagctctta actagccaga gctgcagaaa gttgaataca gggaaatgat ttatttatc 333720
accaccacag actcagactg aggggataaa atcttccttc agcaagtgtg gcgcctctgg 333780
ctcaagtata ttgttgaat cctgcacagt gtctggtaat ggctacagat acatgatctt 333840
ccttggtcct gcagccttct gccatgcagg ccatgcaatg actggaggca gtttcacaga 333900
agtcccgcca aggagaagtt acctggaaga tagcccttag ctcacacctg gagccattga 333960
tcaggatgtt gcaactccct gcttgcctgg ttctgcacat cacatctcaa tgctcagtgc 334020
taactagtac ataacatttt gccatgcata atctcaaatc gtttttataa caaataaacc 334080
ttaagacgta attgttttt agcttacttt acaagccata aaaaaatgg aagaaatgag 334140
catttggtaa tttatttttt gaaggggaag tgttatccta aaagagtcag ttgcaaagat 334200
gtttattaaa ggccctatgt tttatgaatt atctccaaat tttatgatt ctccttctac 334260
ctgtgaccac ttgtgcaaat aataagaaga taattctttg gctcatagtt tccaagcaca 334320
acttagcatc tgtaacagcc cttgacttgt ttctgggtgt cttttttatc ttaaacatgt 334380
taacctcatc ataactatat gtaccatttt agcaaacttc ttacagctaa catagcgtgc 334440
tttcatcttt ttaccttcaa atagagagca aacacatggt gcatatgtct atttacaaac 334500
actttgtaat tataaagcct atttttattt ctactgttaa tatcaatttt cattgctaaa 334560
actgcaacat ttattcattt acttcaaaag caattcttga gcaagaaaga gaatacccat 334620
ttcttggaca atagcttctt aatcagaatt tctcaacctc agtactgtta acatttgggt 334680
ccagataact tctttgctgt gggggtctct cctgtgcacc agagggtatt tagtagcatc 334740
```

```
cctcacctcc acccttcata gaacaaccct tcgtctacgg aaaccaaaag tgtctccaga  334800
tactgccaaa tatccctttg gagcaaatca gtcctggatg agttttacag ttcgacaaga  334860
gtgaaacttg aaatactgaa attttttccta gagacactta gttttccttc tttcccttta  334920
tttttgaaga tcatttgatg ccttaaaaaa tagtaaacat gttataaaaa ttgcataatg  334980
ctgctatcag gatttatatt taaagaaaa ataagagcaa ttttttaaagg aaaagacaac  335040 atggtagaca ggtctaggat taaagcagaa tgtaccttg ctgcttgggt attttgtgct  335100
cattgataaa tatatatgaa gagcagattg taacttcctg atttattggt ttaagataat  335160
ttcacgtcac atgtggaaga gtatgacctt tcttttttc ttccttctat cctcagtgat  335220
ccaaatcaac cagttcctca ggataccaag ttcattcaca caaaacccaa ccgctttgaa  335280
gaagtggcct ggtccaagta taatcccaaa gaccagctct atctgcatat tggcttgaaa  335340
cccagagtga gagatcacta ccgggcaacg aaagtggctt tctggttgga actcgttcct  335400
catttgcaca acttgaacga gatattccag tatgtttcaa caaccacaaa ggttcctcca  335460
ccagacatga catcatttcc ctatggcacc cggcgatctc ccgccaagat atggccaacc  335520
accaaacgcc cagcaatcac tcctgccaac aatcccaaac actctaagga ccctcacaaa  335580
acagggcctg aggacacaac tgtcctcatt gaaaccaaac gagattattc caccgaatta  335640 agtgtccacca ttgccgtcgg ggcgtcgctc ctcttcctca acatcttagc ttttgcggcg  335700
ctgtactaca aaaaggacaa gaggcgccat gagactcaca ggcgccccag tcccagaga  335760 aacaccacaa atgatatcgc tcacatccag aacgaagaga tcatgtctct gcagatgaag  335820
cagctggaac acgatcacga gtgtgagtcg ctgcaggcac acgacacact gaggctcacc  335880
tgcccgccag actacaccct cacgctgcgc cggtcgccag atgacatccc acttatgacg  335940
ccaaacacca tcaccatgat tccaaacaca ctgacgggga tgcagccttt gcacactttt  336000
aacaccttca gtggaggaca aaacagtaca aatttacccc acggacattc caccactaga  336060
gtatagcttt gccctatttc ccttcctatc cctctgccct acccgctcag caacatagaa  336120
gagggaagga aagagagaag gaaagagaga gagaaagaaa gtctccagac caggaatgtt  336180
tttgtcccac tgacttaaga caaaaatgca aaaaggcagt catcccatcc cggcagaccc  336240
ttatcgttgg tgttttccag tattacaaga tcaacttctg accctgtgaa atgtgagaag  336300
tacacatttc tgttaaaata actgcttaa gatctctacc actccaatcg atgtttagtg  336360
tgataggaca tcaccatttc aaggccccgg gtgtttccaa cgtcatggaa gcagctgaca  336420
cttctgaaac tcagccaagg acacttgata tttttttaatt acaatggaag tttaaacatt  336480
tctttctgtg ccacacaatg gatggctctc cttaagtgaa gaaagagtca atgagatttt  336540
gcccagcaca tggagctgta atccagagag aaggaaacgt agaaatttat tattaaaaga  336600
atggactgtg cagcgaaatc tgtacggttc tgtgcaaaga ggtgttttgc cagcctgaac  336660
tatatttaag agactttgta aaaagaaaa atgtatatag ctgtgagttt aaacaaaaac  336720
cacaaacaga caaacaagaa aaaagctttt tattggtgtt ttcactttga aagagctttt  336780
agcaaggttg tgcttttcat tgtgctctgt acgtatataa atatatatat atatacacac  336840
acacacacac attagtcata tcacctctgt ttcctcccca acaaaagagg cttttcttct  336900
taattacttg tggtaaacaa agacatggga ttttcttaca tgagattctc atttgtagga  336960
ggatgtgatg tcccacagaa gacccagacg gtctgtgtgg cctatttccc ccgtcaggtt  337020
gcacaggtgc atgcaagagc attcttagga gaccactgtt ttgaaaaact tttgacttgt  337080
```

```
acgtgttagc cttcatgaaa ttgcagtaca gagatgggtc cccaaagtgg agtgtattta  337140
cagcttgtta aattagagac atgcacacac aaagaatcag tagggagaaa caaaaataca  337200
agtcccgttc tgtagctctg gcccttgaa tatgtttagg aagagttgct tcccatttca  337260
gggccctgcc aaaaaagaa gaaagcttgc ctttggtggg gctatgcccc ttggagtaaa  337320
tacggctctg tgttccctag cagctgcggg agggtttggc cgatgaagta cctgctcagc  337380
ttagctaatc agattgaagg aagacatgtg tctttccttt ttgtttaagc actcggtccc  337440
ttatttatca gtaagcaggt ttttaaaaat cttttatatc atttatggga tcaaacatat  337500
gattgtctga aaacatcact ttttgtggat ttgtgtatcc ggtcaccaaa cggtgaatat  337560
tatagaagaa tgggggaaga aaggatagaa tattaaaact gctttgcatg ggttttctgg  337620
gaaattagga taacttcact gagaagacat tgaatggaaa ttattcaccc attttaaatt  337680
ggtgacctag ggatcagaga tttgtctttc caacagcttg tcatttttc atttctcttc  337740
tcattttca ggaaagtttt gagtgttata aggtggaagg aaacatagta gcaatggata  337800
cttttttgaa aaattattgc attaccaaga aacagtagcc aaagatattt gaagatcatg  337860
ttcctcggct ccattgtggg ttattctaga aatccagtct taaatctctc cgctaaagtg  337920
gacattcccc ataaaaattg tccagctgcc tggctctttt gcaataacaa cctttgatta  337980
ctgaatccct acactcaaac tatagtgata tatcagtgtt tgagagtgac ctctagaaaa  338040
aagaaaagtg ttttttagaaa tgcgtacaag tcacccccaa atcctattgc ttatcttggg  338100
ttaaatttga gagtgattct ctgtatataa atatgtgaaa tattattatc tcaacttagc  338160
acacgtgaag caacatttct ttcctacaga gaggtgtcat ggtaagattt cattccgaat  338220
tcattgtttc atagagctat gatcaggcca tttctgcaag caatgtatga ccccacctga  338280
gcaaccacaa ataggctctc tgtgaaacta caaaggaagt tatgtgtggc atccatgttg  338340
gtttcgtctg tctgtaatgt gaattccagt atttgtttag tatttccagt tgtctcctgc  338400
tagcaatatg tacagtaacg cgtcaggctt gtgacatttg aataaggaaa acagagttc  338460
ctgttaagtg aataacttta gcttttacag gggattatga tcaaaagtga ttttagtaca  338520
tcttaaatga tatcttattt ctacatggaa agaagttata gaatcttcat agagttctat  338580
gagaaaaaat atacttgcta tctataaaaa agagaaaaaa gaaaaaaaat gagaaaaaag  338640
taagaaaaaa aaaatcctg tcctaggctt ttactcttga tcttcaaagg cacgcagggt  338700
ttaatggttc cttgggttat tattttgcag ttttgtttt tattttgcct taagtaatga  338760
tagaagatat atatggccgg acacatatgt ataaactttt cagcagcatt tttaataata  338820
aaatatcaca gtattttcta atgctttgtg caaataa                           338857
```

<210> SEQ ID NO 2
<211> LENGTH: 5672
<212> TYPE: DNA
<213> ORGANISM: Homo sapiens

<400> SEQUENCE: 2

```
agaaggggaa ggctcctggg ctttcaatac atcctcctga atcatacctc gtttcgggtt       60
ccctagaaaa atctggacgt gtaaaaagaa ctcttaacgg ccgatgcagc tcttccaaag      120
ctaaggctgc cttggagttt tcataagaaa ttgtccctgg aggtgttgga tgatcacagc      180
ttccttggag cattgcagtt gctggaatcc agtttcagga ttaagggagg gctgcctcct      240
tgcaatgggc tgccaagaaa acggctgtgc ttgttcttaa cctcaggctc tgtctgtgat      300
cagtctgaga gtctctccca ggtctactgc tccctggaaa gccctatctc tctgcaggct      360
```

```
cgcctctggg ctttgtctcc ttggagccac atcactggga cagctgtgga tgtggatgca    420
gatttgaacc atgtcacggc cccagggact gctatggctt cctttgttgt tcaccccggt    480
ctgcgtcatg ttaaactcca atgtcctcct gtggttaact gctcttgcca tcaagttcac    540
cctcattgac agccaagcac agtatccagt tgtcaacaca aattatggca aaatccgggg    600
cctaagaaca ccgttaccca atgagatctt gggtccagtg gagcagtact taggggtccc    660
ctatgcctca ccccccactg gagagaggcg gtttcagccc ccagaacccc cgtcctcctg    720
gactggcatc cgaaatacta ctcagtttgc tgctgtgtgc ccccagcacc tggatgagag    780
atccttactg catgacatgc tgcccatctg gtttaccgcc aatttggata ctttgatgac    840
ctatgttcaa gatcaaaatg aagactgcct ttacttaaac atctacgtgc ccacggaaga    900
tgatattcat gatcagaaca gtaagaagcc cgtcatggtc tatatccatg ggggatctta    960
catggagggc accggcaaca tgattgacgg cagcattttg gcaagctacg aaacgtcat    1020 cgtgatcacc attaactacc gtctgggaat actagggttt ttaagtaccg gtgaccaggc    1080
agcaaaaggc aactatgggc tcctggatca gattcaagca ctgcggtgga ttgaggagaa    1140
tgtgggagcc tttggcgggg accccaagag agtgaccatc tttggctcgg gggctggggc    1200
ctcctgtgtc agcctgttga ccctgtccca ctactcagaa ggtctcttcc agaaggccat    1260
cattcagagc ggcaccgccc tgtccagctg ggcagtgaac taccagccgg ccaagtacac    1320
tcggatattg cagacaagg tcggctgcaa catgctggac accacggaca tggtagaatg    1380
cctgcggaac aagaactaca aggagctcat ccagcagacc atcaccccgg ccacctacca    1440
catagccttc gggccggtga tcgacggcga cgtcatccca gacgacccc agatcctgat    1500 ggagcaaggc gagttcctca actacgacat catgctgggc gtcaaccaag ggaaggcct    1560 gaagttcgtg gacggcatcg tggataacga ggacggtgtg acgcccaacg actttgactt    1620
ctccgtgtcc aacttcgtgg acaaccttta cggctaccct gaagggaaag acactttgcg    1680
ggagactatc aagttcatgt acacagactg ggccgataag gaaaacccgg agacgcggcg    1740
gaaaaccctg gtggctctct ttactgacca ccagtgggtg gccccgccg tggccaccgc    1800 cgacctgcac gcgcagtacg gctcccccac ctacttctat gccttctatc atcactgcca    1860
aagcgaaatg aagcccagct gggcagattc ggcccatggt gatgaggtcc cctatgtctt    1920
cggcatcccc atgatcggtc ccaccgagct cttcagttgt aacttttcca gaacgacgt    1980 catgctcagc gccgtggtca tgacctactg gacgaacttc gccaaaactg gtgatccaaa    2040
tcaaccagtt cctcaggata ccaagttcat tcacacaaaa cccaaccgct ttgaagaagt    2100
ggcctggtcc aagtataatc ccaaagacca gctctatctg catattggct gaaacccag    2160 agtgagagat cactaccggg caacgaaagt ggctttctgg ttggaactcg ttcctcattt    2220
gcacaacttg aacgagatat tccagtatgt ttcaacaacc acaaaggttc ctccaccaga    2280
catgacatca tttccctatg gcacccggcg atctcccgcc aagatatggc aaccaccaa    2340 acgcccagca atcactcctg ccaacaatcc caaacactct aaggaccctc acaaaacagg    2400
gcctgaggac acaactgtcc tcattgaaac caaacgagat tattccaccg aattaagtgt    2460
caccattgcc gtcgggcgt cgctcctctt cctcaacatc ttagcttttg cggcgctgta    2520 ctacaaaag acaagaggc gccatgagac tcacaggcgc cccagtcccc agagaaacac    2580
cacaaatgat atcgctcaca tccagaacga agagatcatg tctctgcaga tgaagcagct    2640
ggaacacgat cacgagtgtg agtcgctgca ggcacacgac acactgaggc tcacctgccc    2700
```

```
gccagactac accctcacgc tgcgccggtc gccagatgac atcccactta tgacgccaaa    2760
caccatcacc atgattccaa acacactgac ggggatgcag cctttgcaca cttttaacac    2820
cttcagtgga ggacaaaaca gtacaaattt accccacgga cattccacca ctagagtata    2880
gctttgccct atttcccttc ctatccctct gccctacccg ctcagcaaca tagaagaggg    2940
aaggaaagag agaaggaaag agagagagaa agaaagtctc cagaccagga atgttttttgt   3000
cccactgact taagacaaaa atgcaaaaag gcagtcatcc catcccggca gacccttatc    3060
gttggtgttt tccagtatta caagatcaac ttctgaccct gtgaaatgtg agaagtacac    3120
atttctgtta aaataactgc tttaagatct ctaccactcc aatcgatgtt tagtgtgata    3180
ggacatcacc atttcaaggc cccgggtgtt tccaacgtca tggaagcagc tgacacttct    3240
gaaactcagc caaggacact tgatattttt taattacaat ggaagtttaa acatttcttt    3300
ctgtgccaca caatggatgg ctctccttaa gtgaagaaag agtcaatgag attttgccca    3360
gcacatggag ctgtaatcca gagagaagga aacgtagaaa tttattatta aaagaatgga    3420
ctgtgcagcg aaatctgtac ggttctgtgc aaagaggtgt tttgccagcc tgaactatat    3480
ttaagagact ttgtaaaaaa gaaaaatgta tatagctgtg agtttaaaca aaaaccacaa    3540
acagacaaac aagaaaaaaa gcttttattg gtgttttcac tttgaaagag cttttagcaa    3600
ggttgtgctt tcattgtgc tctgtacgta tataaatata tatatatata cacacacaca    3660
cacacattag tcatatcacc tctgtttcct ccccaacaaa agaggctttt cttcttaatt    3720
acttgtggta aacaaagaca tgggattttc ttacatgaga ttctcatttg taggaggatg    3780
tgatgtccca cagaagaccc agacggtctg tgtggcctat ttccccgtc aggttgcaca     3840
ggtgcatgca agagcattct taggagacca ctgttttgaa aaacttttga cttgtacgtg    3900
ttagccttca tgaaattgca gtacagagat gggtccccaa agtggagtgt atttacagct    3960
tgttaaatta gagacatgca cacacaaaga atcagtaggg agaaacaaaa atacaagtcc    4020
cgttctgtag ctctggccct ttgaatatgt ttaggaagag ttgcttccca tttcagggcc    4080
ctgccaaaaa aagaagaaag cttgcctttg gtggggctat gccccttgga gtaaatacgg    4140
ctctgtgttc cctagcagct gcgggagggt ttggccgatg aagtacctgc tcagcttagc    4200
taatcagatt gaaggaagac atgtgtcttt ccttttttgtt taagcactcg gtcccttatt   4260
tatcagtaag caggttttta aaaatctttt atatcattta tgggatcaaa catatgattg    4320
tctgaaaaca tcacttttttg tggatttgtg tatccggtca ccaaacggtg aatattatag   4380
aagaatgggg gaagaaagga tagaatatta aaactgcttt gcatgggttt tctgggaaat    4440
taggataact tcactgagaa gacattgaat ggaaattatt cacccatttt aaattggtga    4500
cctagggatc agagatttgt ctttccaaca gcttgtcatt ttttcatttc tcttctcatt    4560
tttcaggaaa gttttgagtg ttataaggtg gaaggaaaca tagtagcaat ggatacttttt   4620
ttgaaaaatt attgcattac caagaaacag tagccaaaga tatttgaaga tcatgttcct    4680
cggctccatt gtgggttatt ctagaaatcc agtcttaaat ctctccgcta aagtggacat    4740
tccccataaa aattgtccag ctgcctggct cttttgcaat aacaaccttt gattactgaa    4800
tccctacact caaactatag tgatatatca gtgtttgaga gtgacctcta gaaaaaagaa    4860
aagtgttttt agaaatgcgt acaagtcacc cccaaatcct attgcttatc ttgggttaaa    4920
tttgagagtg attctctgta tataaatatg tgaaatatta ttatctcaac ttagcacacg    4980
tgaagcaaca tttcttttcct acagagaggt gtcatggtaa gatttcattc cgaattcatt   5040
gtttcataga gctatgatca ggccattttct gcaagcaatg tatgaccccca cctgagcaac  5100
```

-continued

```
cacaaatagg ctctctgtga aactacaaag gaagttatgt gtggcatcca tgttggtttc    5160
gtctgtctgt aatgtgaatt ccagtatttg tttagtattt ccagttgtct cctgctagca    5220
atatgtacag taacgcgtca ggcttgtgac atttgaataa ggaaaaacag agttcctgtt    5280
aagtgaataa ctttagcttt tacaggggat tatgatcaaa agtgatttta gtacatctta    5340
aatgatatct tatttctaca tggaagaagg ttatagaatc ttcatagagt tctatgagaa    5400
aaaatatact tgctatctat aaaaaagaga aaaagaaaa aaaatgagaa aaagtaaga     5460 aaaaaaaaaa tcctgtccta ggctttact cttgatcttc aaaggcacgc agggtttaat   5520
ggttccttgg gttattattt tgcagttttg ttttttattt tgccttaagt aatgataaa    5580 gatatatatg gccggacaca tatgtataaa cttttcagca gcattttaa taataaaata    5640 tcacagtatt ttctaaaaaa aaaaaaaaaa aa                                 5672
```

<210> SEQ ID NO 3
<211> LENGTH: 21
<212> TYPE: DNA
<213> ORGANISM: Artificial sequence
<220> FEATURE:
<223> OTHER INFORMATION: polynucleotide

<400> SEQUENCE: 3
cggctgcaac ttctcgcgca a                                              21

<210> SEQ ID NO 4
<211> LENGTH: 816
<212> TYPE: PRT
<213> ORGANISM: Homo sapiens

<400> SEQUENCE: 4

Met Ser Arg Pro Gln Gly Leu Leu Trp Leu Pro Leu Leu Phe Thr Pro
1               5                   10                  15

Val Cys Val Met Leu Asn Ser Asn Val Leu Leu Trp Leu Thr Ala Leu
            20                  25                  30

Ala Ile Lys Phe Thr Leu Ile Asp Ser Gln Ala Gln Tyr Pro Val Val
        35                  40                  45

Asn Thr Asn Tyr Gly Lys Ile Arg Gly Leu Arg Thr Pro Leu Pro Asn
    50                  55                  60

Glu Ile Leu Gly Pro Val Glu Gln Tyr Leu Gly Val Pro Tyr Ala Ser
65                  70                  75                  80

Pro Pro Thr Gly Glu Arg Arg Phe Gln Pro Pro Glu Pro Pro Ser Ser
                85                  90                  95

Trp Thr Gly Ile Arg Asn Thr Thr Gln Phe Ala Ala Val Cys Pro Gln
            100                 105                 110

His Leu Asp Glu Arg Ser Leu Leu His Asp Met Leu Pro Ile Trp Phe
        115                 120                 125

Thr Ala Asn Leu Asp Thr Leu Met Thr Tyr Val Gln Asp Gln Asn Glu
    130                 135                 140

Asp Cys Leu Tyr Leu Asn Ile Tyr Val Pro Thr Glu Asp Asp Ile His
145                 150                 155                 160

Asp Gln Asn Ser Lys Lys Pro Val Met Val Tyr Ile His Gly Gly Ser
                165                 170                 175

Tyr Met Glu Gly Thr Gly Asn Met Ile Asp Gly Ser Ile Leu Ala Ser
            180                 185                 190

Tyr Gly Asn Val Ile Val Ile Thr Ile Asn Tyr Arg Leu Gly Ile Leu
        195                 200                 205

```
Gly Phe Leu Ser Thr Gly Asp Gln Ala Ala Lys Gly Asn Tyr Gly Leu
    210                 215                 220

Leu Asp Gln Ile Gln Ala Leu Arg Trp Ile Glu Glu Asn Val Gly Ala
225                 230                 235                 240

Phe Gly Gly Asp Pro Lys Arg Val Thr Ile Phe Gly Ser Gly Ala Gly
                245                 250                 255

Ala Ser Cys Val Ser Leu Leu Thr Leu Ser His Tyr Ser Glu Gly Leu
            260                 265                 270

Phe Gln Lys Ala Ile Ile Gln Ser Gly Thr Ala Leu Ser Ser Trp Ala
        275                 280                 285

Val Asn Tyr Gln Pro Ala Lys Tyr Thr Arg Ile Leu Ala Asp Lys Val
    290                 295                 300

Gly Cys Asn Met Leu Asp Thr Thr Asp Met Val Glu Cys Leu Arg Asn
305                 310                 315                 320

Lys Asn Tyr Lys Glu Leu Ile Gln Gln Thr Ile Thr Pro Ala Thr Tyr
                325                 330                 335

His Ile Ala Phe Gly Pro Val Ile Asp Gly Asp Val Ile Pro Asp Asp
            340                 345                 350

Pro Gln Ile Leu Met Glu Gln Gly Glu Phe Leu Asn Tyr Asp Ile Met
        355                 360                 365

Leu Gly Val Asn Gln Gly Glu Gly Leu Lys Phe Val Asp Gly Ile Val
    370                 375                 380

Asp Asn Glu Asp Gly Val Thr Pro Asn Asp Phe Asp Phe Ser Val Ser
385                 390                 395                 400

Asn Phe Val Asp Asn Leu Tyr Gly Tyr Pro Glu Gly Lys Asp Thr Leu
                405                 410                 415

Arg Glu Thr Ile Lys Phe Met Tyr Thr Asp Trp Ala Asp Lys Glu Asn
            420                 425                 430

Pro Glu Thr Arg Arg Lys Thr Leu Val Ala Leu Phe Thr Asp His Gln
        435                 440                 445

Trp Val Ala Pro Ala Val Ala Thr Ala Asp Leu His Ala Gln Tyr Gly
    450                 455                 460

Ser Pro Thr Tyr Phe Tyr Ala Phe Tyr His His Cys Gln Ser Glu Met
465                 470                 475                 480

Lys Pro Ser Trp Ala Asp Ser Ala His Gly Asp Glu Val Pro Tyr Val
                485                 490                 495

Phe Gly Ile Pro Met Ile Gly Pro Thr Glu Leu Phe Ser Cys Asn Phe
            500                 505                 510

Ser Lys Asn Asp Val Met Leu Ser Ala Val Val Met Thr Tyr Trp Thr
        515                 520                 525

Asn Phe Ala Lys Thr Gly Asp Pro Asn Gln Pro Val Pro Gln Asp Thr
    530                 535                 540

Lys Phe Ile His Thr Lys Pro Asn Arg Phe Glu Glu Val Ala Trp Ser
545                 550                 555                 560

Lys Tyr Asn Pro Lys Asp Gln Leu Tyr Leu His Ile Gly Leu Lys Pro
                565                 570                 575

Arg Val Arg Asp His Tyr Arg Ala Thr Lys Val Ala Phe Trp Leu Glu
            580                 585                 590

Leu Val Pro His Leu His Asn Leu Asn Glu Ile Phe Gln Tyr Val Ser
        595                 600                 605

Thr Thr Thr Lys Val Pro Pro Pro Asp Met Thr Ser Phe Pro Tyr Gly
    610                 615                 620
```

Thr Arg Arg Ser Pro Ala Lys Ile Trp Pro Thr Lys Arg Pro Ala
625                 630                 635                 640

Ile Thr Pro Ala Asn Asn Pro Lys His Ser Lys Asp Pro His Lys Thr
            645                 650                 655

Gly Pro Glu Asp Thr Thr Val Leu Ile Glu Thr Lys Arg Asp Tyr Ser
        660                 665                 670

Thr Glu Leu Ser Val Thr Ile Ala Val Gly Ala Ser Leu Leu Phe Leu
            675                 680                 685

Asn Ile Leu Ala Phe Ala Ala Leu Tyr Tyr Lys Lys Asp Lys Arg Arg
690                 695                 700

His Glu Thr His Arg Arg Pro Ser Pro Gln Arg Asn Thr Thr Asn Asp
705                 710                 715                 720

Ile Ala His Ile Gln Asn Glu Glu Ile Met Ser Leu Gln Met Lys Gln
            725                 730                 735

Leu Glu His Asp His Glu Cys Glu Ser Leu Gln Ala His Asp Thr Leu
        740                 745                 750

Arg Leu Thr Cys Pro Pro Asp Tyr Thr Leu Thr Leu Arg Arg Ser Pro
        755                 760                 765

Asp Asp Ile Pro Leu Met Thr Pro Asn Thr Ile Thr Met Ile Pro Asn
770                 775                 780

Thr Leu Thr Gly Met Gln Pro Leu His Thr Phe Asn Thr Phe Ser Gly
785                 790                 795                 800

Gly Gln Asn Ser Thr Asn Leu Pro His Gly His Ser Thr Thr Arg Val
            805                 810                 815

<210> SEQ ID NO 5
<211> LENGTH: 21
<212> TYPE: DNA
<213> ORGANISM: Artificial sequence
<220> FEATURE:
<223> OTHER INFORMATION: Primer

<400> SEQUENCE: 5
aaagccctat ctctctgcag g                                          21

<210> SEQ ID NO 6
<211> LENGTH: 22
<212> TYPE: DNA
<213> ORGANISM: Artificial sequence
<220> FEATURE:
<223> OTHER INFORMATION: Primer

<400> SEQUENCE: 6
tgagtagtat ttcggatgcc ag                                         22

<210> SEQ ID NO 7
<211> LENGTH: 22
<212> TYPE: DNA
<213> ORGANISM: Artificial sequence
<220> FEATURE:
<223> OTHER INFORMATION: Primer

<400> SEQUENCE: 7
aagaacaccg ttacccaatg ag                                         22

<210> SEQ ID NO 8
<211> LENGTH: 23
<212> TYPE: DNA
<213> ORGANISM: Artificial sequence
<220> FEATURE:
<223> OTHER INFORMATION: Primer -continued

<400> SEQUENCE: 8
gagacattat aaaaccctcc tag                                                          23

<210> SEQ ID NO 9
<211> LENGTH: 22
<212> TYPE: DNA
<213> ORGANISM: Artificial sequence
<220> FEATURE:
<223> OTHER INFORMATION: Primer

<400> SEQUENCE: 9
ttagcattgg tgagtcagtg tg                                                           22

<210> SEQ ID NO 10
<211> LENGTH: 22
<212> TYPE: DNA
<213> ORGANISM: Artificial sequence
<220> FEATURE:
<223> OTHER INFORMATION: Primer

<400> SEQUENCE: 10
ccgtcaaaac gagaagtgga ct                                                           22

<210> SEQ ID NO 11
<211> LENGTH: 20
<212> TYPE: DNA
<213> ORGANISM: Artificial sequence
<220> FEATURE:
<223> OTHER INFORMATION: Primer

<400> SEQUENCE: 11 cttttttctat ttggccacca                                                             20

<210> SEQ ID NO 12
<211> LENGTH: 21
<212> TYPE: DNA
<213> ORGANISM: Artificial sequence
<220> FEATURE:
<223> OTHER INFORMATION: Primer

<400> SEQUENCE: 12
ttcttggttc agggtatttg c                                                            21

<210> SEQ ID NO 13
<211> LENGTH: 20
<212> TYPE: DNA
<213> ORGANISM: Artificial sequence
<220> FEATURE:
<223> OTHER INFORMATION: Primer

<400> SEQUENCE: 13
agctgcattt ctgtcctgtg                                                              20

<210> SEQ ID NO 14
<211> LENGTH: 20
<212> TYPE: DNA
<213> ORGANISM: Artificial sequence
<220> FEATURE:
<223> OTHER INFORMATION: Primer

<400> SEQUENCE: 14
tctcccgcaa agtgtctttc                                                              20

<210> SEQ ID NO 15

```
<211> LENGTH: 20
<212> TYPE: DNA
<213> ORGANISM: Artificial sequence
<220> FEATURE:
<223> OTHER INFORMATION: Primer

<400> SEQUENCE: 15
ccaacttcgt ggacaacctt                                           20

<210> SEQ ID NO 16
<211> LENGTH: 20
<212> TYPE: DNA
<213> ORGANISM: Artificial sequence
<220> FEATURE:
<223> OTHER INFORMATION: Primer

<400> SEQUENCE: 16
accccaacac gaagatgaac                                           20

<210> SEQ ID NO 17
<211> LENGTH: 20
<212> TYPE: DNA
<213> ORGANISM: Artificial sequence
<220> FEATURE:
<223> OTHER INFORMATION: Primer

<400> SEQUENCE: 17
cacgtcacat gtggaagagt                                           20

<210> SEQ ID NO 18
<211> LENGTH: 20
<212> TYPE: DNA
<213> ORGANISM: Artificial sequence
<220> FEATURE:
<223> OTHER INFORMATION: Primer

<400> SEQUENCE: 18
gacggcaatg gtgacactta                                           20

<210> SEQ ID NO 19
<211> LENGTH: 20
<212> TYPE: DNA
<213> ORGANISM: Artificial sequence
<220> FEATURE:
<223> OTHER INFORMATION: Primer

<400> SEQUENCE: 19
tcctcattga aaccaaacga                                           20

<210> SEQ ID NO 20
<211> LENGTH: 20
<212> TYPE: DNA
<213> ORGANISM: Artificial sequence
<220> FEATURE:
<223> OTHER INFORMATION: Primer

<400> SEQUENCE: 20
aacattcctg gtctggagac                                           20
```

MODULATION OF NLGN4 EXPRESSION, NK CELL ACTIVITY IN NON-ALCOHOLIC FATTY LIVER DISEASE (NAFLD)

CROSS REFERENCE TO RELATED APPLICATIONS

This application claims priority from U.S. Provisional application Ser. No. 61/884,153 filed on Sep. 30, 2013.

FIELD OF THE INVENTION

The present invention relates to the involvement of NK cells in Nonalcoholic-Fatty-Liver-Disease (NAFLD), mediated by a novel Neuroligin-4 (NLGn4) synaptic pathway. The present invention provides compositions and methods for modulating the action of NLGn4 to attenuate Nonalcoholic-Fatty-Liver-Disease (NAFLD).

BACKGROUND OF THE INVENTION

Nonalcoholic fatty-liver disease (NAFLD) is one of the most prevalent liver diseases in western countries. The full pathophysiology of NAFLD is still unknown. Both obesity and insulin resistance are considered to play a strong role in the disease process. Indeed, the rising rates of obesity and diabetes mellitus correlate with the increasing incidence of NAFLD, which is the hepatic and early manifestation of metabolic syndrome. Estimates suggest that about 20% to 30% of adults in developed countries have excess fat accumulation in the liver, 50% among people with diabetes, and about 80% in the obese and morbidly obese individuals.

Non-alcoholic steatohepatitis (NASH) is the most severe form of NAFLD, and can progress to more severe forms of liver disease, including fibrosis progression, cirrhosis, and even hepatocellular carcinoma.

The disease begins with the aberrant accumulation of triglycerides in the liver, resulting in simple steatosis; most patients who develop steatosis are stable and further disease does not develop. However, some individuals progress to NASH, the severe form of NAFLD. In NASH, up to 20% of patients' progress into cirrhosis.

The normal liver is composed of hepatocytes and non-parenchymal cells, which include kupffer cells, sinusoidal endothelial cells, and myofibroblasts known as Hepatic Stellate Cells (HSCs). HSCs are considered to be involved in the pathogenesis of liver fibrosis from any etiology, including NASH-related hepatic fibrosis. In normal liver, HSCs are described as being in a quiescent state and serve to store retinoids (vitamin A). Quiescent stellate cells represent 5-8% of the total number of liver cells. When the liver is damaged, HSCs can change into an activated state characterized by contractions, loss of lipid droplets and enhanced of proliferation, cell migration as well as cellular adhesion. HSCs are also unequivocally the main cells involved in the production of excessive ECM seen in liver fibrosis. Since activated HSCs themselves secrete inflammatory chemokines, a vicious cycle is formed, whereby fibrogenic and inflammatory cells stimulate each other and perpetuate a process of liver damage and repair.

Natural killer (NK) cells are a key component of the innate immune system, and play a critical role in the early stages of the immune response against tumor cells, as well as those infected by viral and microbial pathogens.

In humans, two NK-cell subsets have been characterized according to the cell-surface density of CD56 and expression of CD16. $CD56^{dim}CD16^{bright}$ NK cells (hereinafter $CD56^{dim}$) compose approximately 90% of circulating NK cells; $CD56^{bright}CD16^{dim}$ NK cells (hereinafter $CD56^{bright}$) constitute approximately 10%. $CD56^{bright}$ NK cells proliferate and produce interferon in response to stimulation with interleukin-12 (IL-12), whereas $CD56^{dim}$ NK cells are more cytolytic and produce significant amounts of cytokine when their activating receptors are engaged.

In a paper published by some of the inventors it was found that, as opposed to CD8 immune cells, NK cells have anti-fibrotic activity through stimulation of HSC killing. (Melhhem et al., J. Hepatology; 2006; 45: 60-71). It has also been reported that the function of NK cells decreases when the liver disease progresses into cirrhosis, suggesting that attenuating NK function is a prerequisite for the progression of the disease (Seki et al.; Clin Dev Immunol.; 2011; Article ID 868345).

Human neuroligin-4 (NLG4, NLGn4, NLGn4X) encodes a member of a family of neuronal cell surface proteins called the Neuroligins. FIG. 1 illustrates the neuroligins and their interactions. Members of this family may act as splice site-specific ligands for beta-neurexins and may be involved in the formation and remodeling of central nervous system synapses. The encoded protein interacts with discs, large (Drosophila) homolog 4 (DLG4). Mutations in this gene have been associated with autism and Asperger syndrome. NLGn4 is also detected with high levels of expression in heart and lower in liver, skeletal muscle and pancreas.

The clinical implications of NAFLD are derived mostly from its potential to progress to cirrhosis and liver failure. There is an unmet medical for compositions and methods for treating NAFLD and preventing the progression to cirrhosis. Nowhere in the art has it been suggested that disease progression of NAFLD can be modulated by attenuating NLGn4 expression and thereby NK cell activity.

SUMMARY OF THE INVENTION

The present invention relates to preventing, treating and attenuating liver disease by inhibiting NLGn4 expression and thereby modulating the activity of NK cells. The invention, according to some embodiments relates to attenuation of the progression of NAFLD into cirrhosis and liver failure by modulating the expression of human neuroligin-4 (NLGn4, NLGn4, NLGn4X) and thereby activating cytotoxic NK cells.

There is provided herein according to some embodiments, a method of treating, attenuating and/or preventing progression of a liver disorder in a subject, the method comprising administering to the subject a composition comprising a therapeutically effective amount of an agent capable of inhibiting expression of a NLGn4 gene product, thereby treating, attenuating and/or preventing progression of the liver disorder.

According to some embodiments, the human NLGn4 gene product is encoded by a nucleic acid sequence comprising SEQ ID NO: 1. According to some embodiments, the NLGn4 gene product is encoded by a nucleic acid sequence with the accession number NM_020742. According to some embodiments, the NLGn4 gene product is encoded by a nucleic acid sequence with the accession number NM_181332. According to some embodiments, the NLGn4 gene product is encoded by a nucleic acid sequence with the accession number NM_001282145. According to some embodiments, the NLGn4 gene product is encoded by a nucleic acid sequence with the accession number NM_001282146.

According to some embodiments, the NLGn4 gene product comprises an mRNA sequence set forth in SEQ ID NO: 2. According to some embodiments, the accession number of the NLGn4 mRNA is AY358562. According to some embodiments, the accession number of the NLGn4 mRNA is BC032567. According to some embodiments, the accession number of the NLGn4 mRNA is BC034018.

According to some embodiments, the NLGn4 gene product comprises a peptide sequence set forth in SEQ ID NO: 4. According to some embodiments, the accession number of the NLGn4 polypeptide is NP_001269075.1. According to some embodiments, the accession number of the NLGn4 polypeptide is NP_001269074.1. According to some embodiments, the accession number of the NLGn4 polypeptide is NP_851849.1. According to some embodiments, the accession number of the NLGn4 polypeptide is NP_065793.1.

According to some embodiments, the agent comprises one or more inhibitory nucleic acids complementary to at least a portion of SEQ ID NO: 2.

According to some embodiments, the one or more inhibitory nucleic acids is selected from the group consisting of: an antisense molecule, an siRNA, and an shRNA. Each possibility is a separate embodiment of the invention.

According to some embodiments, the siRNA comprises a sequence set forth in SEQ ID NO: 3. According to some embodiments, the accession number of the siRNA sequence is SI03083395.

According to some embodiments, the liver disorder is selected from the group consisting of: non-alcoholic fatty liver disease (NAFLD), non-alcoholic steatohepatitis (NASH), cirrhosis, hepatitis, liver adenoma, insulin hypersensitivity, liver cancer and any combination thereof. Each possibility is a separate embodiment of the invention.

According to some embodiments, the liver disorder is characterized by NLGn4 overexpression. According to some embodiments, NLGn4 overexpression comprises a 2, 3, 4, 5-10 fold or more increase in NLGn4 expression relative to the expression level obtained in normal subjects. According to some embodiments, the overexpression attenuates NK cell activity, inhibits the expression of NLGn4 and modulates and/or activates the function of the NK cell.

According to some embodiments, administering to the subject the composition comprising a therapeutically effective amount of an agent capable of inhibiting expression of a NLGn4 gene product comprises administering the composition to an immune cell population of the subject. According to some embodiments, administering the composition to an immune cell population comprises infecting the immune cell population with a vector comprising the agent capable of inhibiting NLGn4 expression.

According to some embodiments, inhibiting the expression of the NLGn4 gene product reduces the activity of hepatic stellate cells. According to some embodiments, inhibiting the expression of the NLGn4 gene product increases apoptosis of the hepatic stellate cells.

According to some embodiments, the composition further comprises a GLUT4 antagonist. According to some embodiments, NLGn4 expression is regulated by a specific type of ionotropic glutamate receptor N-methyl-D-aspartate (NMDA or GLUT4 receptor; NMDAR). According to some embodiments, NLGn4 is linked to NMDR and both localize and bind PSD-95; a post synaptic density protein (PSD) According to some embodiments, the composition comprises an NMDAR antagonist selected from the group consisting of: Ketamin, Amantadine, Phencyclidine, Nitrous oxide, Dextromethorphan (and dextrorphan), Memantine, Ethanol, Riluzole, Xenon, HU-211, Lead (Pb2+), Conantokins, and Huperzine A.

According to an alternative embodiment, administering an N-methyl D aspartate receptor (NMDAR) agonist can increase NMDAR-mediated NLGn4 expression and as a result attenuate NK cell activity. Non-limiting examples of NMDAR agonists are Aminocyclopropanecarboxylic acid, D-Cycloserine, cis-2,3-Piperidinedicarboxylic acid, L-aspartate, L-alanine, Quinolinate, Homocysterate, D-serine, and ACPL.

There is provided herein according to some embodiments, a pharmaceutical composition for the use in treating, attenuating and/or preventing progression of a liver disorder in a subject, the composition comprising a therapeutically effective amount of an agent capable of inhibiting expression of a NLGn4 gene product, wherein the composition is capable of treating, attenuating and/or preventing progression of the liver disorder.

According to some embodiments, the pharmaceutical composition further comprises a pharmaceutically acceptable carrier.

There is provided herein according to some embodiments, a method of diagnosing and/or monitoring a liver disorder in a subject, the method comprising: isolating an immune cell population from a biological sample of the subject; detecting expression level of an NLGn4 gene product in the immune cell population and diagnosing and/or monitoring the liver disorder according to the NLGn4 gene product expression level.

According to some embodiments, the NLGn4 gene product is encoded by a nucleic acid sequence comprising SEQ ID NO: 1. According to some embodiments, the NLGn4 gene product comprises SEQ ID NO: 2.

According to some embodiments, the agent comprises one or more inhibitory nucleic acids complementary to at least a portion of SEQ ID NO: 2. According to some embodiments, the one or more inhibitory nucleic acids are selected from the group consisting of: an antisense molecule, an siRNA, and an shRNA. Each possibility is a separate embodiment of the invention.

According to some embodiments, the siRNA comprises a sequence set forth in SEQ ID NO: 3.

According to some embodiments, the liver disorder is selected from the group consisting of: non-alcoholic fatty liver disease (NAFLD), non-alcoholic steatohepatitis (NASH), cirrhosis, hepatitis, liver adenoma, insulin hypersensitivity, liver cancer and any combination thereof. Each possibility is a separate embodiment of the invention.

According to some embodiments, the immune cell population is a natural killer (NK) cell population. Additionally or alternatively, the immune cell population is a subpopulation of NK cells According to some embodiments; the NK subpopulation is the $CD56^{dim}$ subpopulation. According to some embodiments; the NK subpopulation is the $CD56^{bright}$ subpopulation. According to some embodiments, the method comprises modulating the activity of the NK cells and/or a subpopulation of NK cells. According to some embodiments, modulating the activity of NK cells comprises enhancing the cytotoxicity of the NK cells. According to some embodiments, enhancing the cytotoxicity of NK cells comprises, but is not limited to, elevating CD107a expression in the NK cell and/or NK subpopulation.

According to some embodiments, the NK cell is a liver NK cell, and the activity of the NK cell is attenuated in patients with a liver disorder. According to yet another embodiment, NK cells from patients with a liver disorder, overexpresses NLGn4.

According to some embodiments, the biological sample comprises a blood sample, a tissue sample, a biological fluid, or any combination thereof.

According to some embodiments, the NLGn4 gene product expression level is detected by Polymerase Chain Reaction (PCR), Reverse-Transcriptase-PCR (RT-PCR), Northern Blot, Real-time PCR, hybridization to an oligonucleotide or any combination thereof. Each possibility is a separate embodiment of the invention.

According to some embodiments, the oligonucleotide comprises deoxyribonucleic acid (DNA), RNA, complementary deoxyribonucleic acid (cDNA), genomic DNA, synthetic oligonucleotide, or any combination thereof. Each possibility is a separate embodiment of the invention.

There is provided herein according to some embodiments, a kit for diagnosing a liver disorder, the kit comprising: means for isolating an immune cell population from a biological sample of a patient; and at least one reagent capable of detecting NLGn4 gene product expression level.

According to some embodiments, the reagent comprises NLGn4 specific primers.

According to some embodiments, the NLGN4 primers were designed to specifically amplify the NLGN4 copy on the X chromosome (Xp22.32-p22.31).

DETAILED DESCRIPTION

Figure 1:
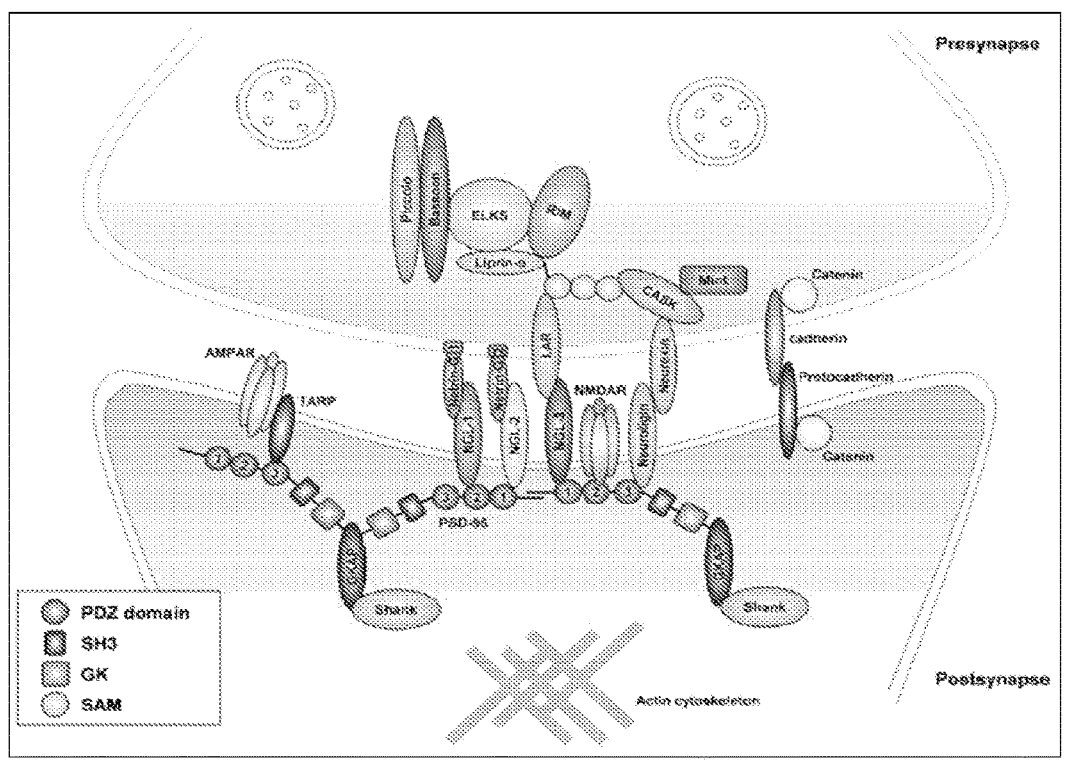
FIG. 1 shows a schematic representation of the Neuroligins and NLG interactions.

The present invention provides methods and compositions for treating and diagnosing liver disorders by activating attenuated natural killer (NK) cells and thereby reducing Hepatic stellate cell (HCSs) induced fibrosis.

In the following description, various aspects of the invention will be described. For the purpose of explanation, specific details are set forth in order to provide a thorough understanding of the invention. However, it will also be apparent to one skilled in the art that the invention may be practiced without specific details being presented herein. Furthermore, well-known features may be omitted or simplified in order not to obscure the invention.

The following are terms which are used throughout the description and which should be understood in accordance with the various embodiments to mean as follows:

As referred to herein, the terms "liver disorder", "liver disease" and "hepatic disease" are used interchangeably and refer to diseases and disorders that cause the liver to function improperly or stop functioning.

As referred to herein, the term "gene product" refers to a DNA sequence that is transcribed into mRNA that is then translated into a sequence of amino acids characteristic of a specific polypeptide. Hence it is understood by the skilled in the art that the term gene product encompasses non-processed RNA, mRNA, splice variants thereof, corresponding cDNA sequences, polypeptides and proteins.

As used herein the terms "polynucleotide" "polynucleotide molecules", "oligonucleotide", "nucleic acid" and "nucleotide" may interchangeably be used. The terms are directed to polymers of deoxyribonucleotides (DNA), ribonucleotides (RNA), and modified forms thereof in the form of a separate fragment or as a component of a larger construct, linear or branched, single stranded, double stranded, triple stranded, or hybrids thereof. The term also encompasses RNA/DNA hybrids. The polynucleotides may include sense and antisense oligonucleotide or polynucleotide sequences of DNA or RNA. The DNA or RNA molecules may be, for example, but not limited to: complementary DNA (cDNA), genomic DNA, synthesized DNA, recombinant DNA, or a hybrid thereof or an RNA molecule such as, for example, mRNA, shRNA, siRNA, miRNA, and the like. Accordingly, as used herein, the terms "polynucleotide molecules", "oligonucleotide", "polynucleotide", "nucleic acid" and "nucleotide" sequences are meant to refer to both DNA and RNA molecules and refers to nucleic acid or ribonucleic acid sequence.

As used herein the term "complementary" is directed to base pairing between strands of nucleic acids. As known in the art, each strand of a nucleic acid may be complementary to another strand in that the base pairs between the strands are non-covalently connected via two or three hydrogen bonds. Two nucleotides on opposite complementary nucleic acid strands that are connected by hydrogen bonds are called a base pair. According to the Watson-Crick DNA base pairing, adenine (A) forms a base pair with thymine (T) and guanine (G) with cytosine (C). In RNA, thymine is replaced by uracil (U). The degree of complementarity between two strands of nucleic acid may vary, according to the number (or percentage) of nucleotides that form base pairs between the strands. For example, "100% complementarity" indicates that all the nucleotides in each strand form base pairs with the complement strand. For example, "95% complementarity" indicates that 95% of the nucleotides in each strand from base pair with the complement strand. The term sufficient complementarity may include any percentage of complementarity from about 30% to about 100%.

As used herein the term "short hairpin RNA" and "shRNA are used interchangeably and refer to, refer to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region.

As used herein the term "small interfering RNA" and "siRNA" are used interchangeably and refer to a nucleic acid molecule mediating RNA interference or gene silencing. The siRNA inhibits expression of a target gene and provides effective gene knock-down.

As used herein the term "antisense oligonucleotide" refer to nucleic acids, preferably, DNA, RNA or its derivatives, that are complementary to the nucleotide sequences of a target mRNA, characterized in that they binds to the target mRNA and interfere its translation to protein.

As used herein the term "vector" refers to expression constructs engineered to express shRNAs such as, but not limited to, retroviral and lentiviral vectors. Such expression constructs may include one or more inducible promoters, RNA Pol III promoter systems such as U6 snRNA promoters or H1 RNA polymerase III promoters, or other promoters known in the art.

According to an aspect of the invention, provided is a method of treating, attenuating or preventing a liver disorders such as Non-alcoholic fatty liver disease (NAFLD), and Non-alcoholic steatohepatitis (NASH) in a patient in need thereof. Alternatively other disorders such as cirrhosis, hepatitis, liver adenoma, insulin resistance, and liver cancer, or any NK related inflammatory or neoplastic disorder, can be the subject of treatment as well. The clinical implications of NAFLD are derived mostly from its potential to progress to Non-alcoholic steatohepatitis, cirrhosis and liver failure. In accordance, the invention, addresses the long felt need to attenuate the progression of NAFLD into cirrhosis and liver failure by inhibiting NLGn4 expression and thereby modulating the cytotoxic activity of NK cells. According to some embodiments, the invention provides a method for modulating the activity of a natural killer (NK) cell.

According to some embodiments, the method comprises administering to the patient in need thereof, a composition comprising a therapeutically effective amount of an agent capable of inhibiting the expression of the ribonucleic acid (RNA) encoded by NLGn4 nucleic acid molecule. The agent can for example be one or more polynucleotides, capable of hybridizing with the NLGn4 nucleic acid, such an inhibitory nucleic acid that is complementary and specific to at least a portion of NLGn4. The inhibitory nucleic acid can for example be an antisense molecule, an siRNA, or an shRNA. According to some embodiments, the siRNA comprises the sequence set forth in SEQ ID NO: 3. CGGCTGCAACTCTCGCGCAA.

The NLGn4 mRNA sequence is set forth in the following sequence SEQ ID NO:2:

agaaggggaaggctcctgggctttcaatacatcctcctgaatcataccte gtttcgggttccctagaaaaatctggacgtgtaaaaagaactcttaacgg ccgatgcagctcttccaaagctaaggctgccttggagttttcataagaaa ttgtccctggaggtgttggatgatcacagcttccttggagcattgcagtt gctggaatccagtttcaggattaagggagggctgcctccttgcaatgggc tgccaagaaaacggctgtgcttgttcttaacctcaggctctgtctgtgat cagtctgagagtctctcccaggtctactgctccctggaaagccctatctc tctgcaggctcgcctctggctttgtctccttggagccacatcactggga cagctgtggatgtggatgcagatttgaaccatgtcacggccccagggact gctatggcttcctttgttgttcacccggtctgcgtcatgttaaactcca atgtcctcctgtggttaactgctcttgccatcaagttcaccctcattgac agccaagcacagtatccagttgtcaacacaaattatggcaaaatccgggg cctaagaacaccgttacccaatgagatcttgggtccagtggagcagtact taggggtcccctatgcctcaccccccactggagagaggcggtttcagccc ccagaaccccgtcctcctggactggcatccgaaatactactcagtttgc tgctgtgtgcccccagcacctggatgagagatccttactgcatgacatgc tgcccatctggtttaccgccaatttggatactttgatgacctatgttcaa gatcaaaatgaagactgcctttacttaaacatctacgtgcccacggaaga tgatattcatgatcagaacagtaagaagcccgtcatggtctatatccatg ggggatcttacatggagggcaccggcaacatgattgacggcagcattttg gcaagctacggaaacgtcatcgtgatcaccattaactaccgtctgggaat actagggttttaagtaccggtgaccaggcagcaaaaggcaactatgggc tcctggatcagattcaagcactgcggtggattgaggagaatgtgggagcc tttggcggggaccccaagagagtgaccatctttggctcgggggctgggc ctcctgtgtcagcctgttgaccctgtcccactactcagaaggtctcttcc agaaggccatcattcagagcggcaccgccctgtccagctgggcagtgaac taccagccggccaagtacactcggatattggcagacaaggtcggctgcaa catgctggacaccacgacatggtagaatgcctgcggaacaagaactaca aggagctcatccagcagaccatcaccccggccacctaccacatagccttc gggccggtgatcgacggcgacgtcatcccagacgaccccagatcctgat ggagcaaggcgagttcctcaactacgacatcatgctgggcgtcaaccaag gggaaggcctgaagttcgtggacggcatcgtggataacgaggacggtgtg acgcccaacgactttgacttctccgtgtccaacttcgtggacaaccttta cggctaccctgaagggaaagacactttgcgggagactatcaagttcatgt acacagactgggccgataaggaaaacccggagacgcggcggaaaaccctg gtggctctctttactgaccaccagtgggtggccccgccgtggccaccgc cgacctgcacgcgcagtacggctcccccacctacttctatgccttctatc atcactgccaaagcgaaatgaagcccagctgggcagattcggcccatggt gatgaggtcccctatgtcttcggcatcccatgatcggtcccaccgagct cttcagttgtaacttttccaagaacgacgtcatgctcagcgccgtggtca tgacctactggacgaacttcgccaaaactggtgatccaaatcaaccagtt cctcaggataccaagttcattcacacaaaacccaaccgctttgaagaagt ggcctggtccaagtataatcccaaagaccagctctatctgcatattggct tgaaacccagagtgagagatcactaccgggcaacgaaagtggctttctgg ttggaactcgttcctcatttgcacaacttgaacgagatattccagtatgt ttcaacaaccacaaaggttcctccaccagacatgacatcatttccctatg gcacccggcgatctcccgccaagatatggccaaccaccaaacgcccagca atcactcctgccaacaatcccaaacactctaaggaccctcacaaaacagg gcctgaggacacaactgtcctcattgaaaccaaacgagattattccaccg aattaagtgtcaccattgccgtcggggcgtcgctcctcttcctcaacatc ttagcttttgcggcgtgtactacaaaaaggacaagaggcgccatgagac tcacaggcgccccagtcccagagaaacaccacaaatgatatcgctcaca -continued

```
tccagaacgaagagatcatgtctctgcagatgaagcagctggaacacgat
cacgagtgtgagtcgctgcaggcacacgacacactgaggctcacctgccc
gccagactacaccctcacgctgcgccggtcgccagatgacatcccactta
tgacgccaaacaccatcaccatgattccaaacacactgacggggatgcag
cctttgcacacttttaaccacttcagtggaggacaaaacagtacaaattt
accccacggacattccaccactagagtatagctttgccctatttccttc
ctatccctctgccctacccgctcagcaacatagaagagggaaggaaagag
agaaggaaagagagagagaaagaaagtctccagaccaggaatgttttgt
cccactgacttaagacaaaaatgcaaaaaggcagtcatcccatcccggca
gaccctatcgttggtgttttccagtattacaagatcaacttctgaccct
gtgaaatgtgagaagtacacatttctgttaaaataactgctttaagatct
ctaccactccaatcgatgtttagtgtgataggacatcaccatttcaaggc
cccgggtgtttccaacgtcatggaagcagctgacacttctgaaactcagc
caaggacacttgatatttttaattacaatggaagtttaaacatttcttt
ctgtgccacacaatggatgctctccttaagtgaagaaagagtcaatgag
attttgcccagcacatggagctgtaatccagagagaaggaaacgtagaaa
tttattattaaaagaatggactgtgcagcgaaatctgtacggttctgtgc
aaagaggtgttttgccagcctgaactatatttaagagactttgtaaaaaa
gaaaaatgtatatagctgtgagtttaaacaaaaaccacaaacagacaaac
aagaaaaaaagcttttattggtgttttcactttgaaagagcttttagcaa
ggttgtgcttttcattgtgctctgtacgtatataaatatatatatata
cacacacacacacattagtcatatcacctctgtttcctccccaacaaa
agaggcttttcttcttaattacttgtggtaaacaaagacatgggattttc
ttacatgagattctcatttgtaggaggatgtgatgtcccacagaagaccc
agacggtctgtgtggcctatttcccccgtcaggttgcacaggtgcatgca
agagcattcttaggagaccactgttttgaaaaacttttgacttgtacgtg
ttagccttcatgaaattgcagtacagagatgggtccccaaagtggagtgt
atttacagcttgttaaattagagacatgcacacacaaagaatcagtaggg
agaaacaaaaatacaagtcccgttctgtagctctggcccttgaatatgt
ttaggaagagttgcttcccatttcagggccctgccaaaaaagaagaaag
cttgcctttggtggggctatgcccttggagtaaatacggctctgtgttc
cctagcagctgcgggagggtttggccgatgaagtacctgctcagcttagc
taatcagattgaaggaagacatgtgtcttttcctttttgtttaagcactcg
gtcccttatttatcagtaagcaggttttttaaaaatcttttatatcattta
tgggatcaaacatatgattgtctgaaaacatcactttttgtggatttgtg
tatccggtcaccaaacggtgaatattatagaagaatggggaagaaagga
tagaatattaaaactgctttgcatgggttttctgggaaattaggataact
tcactgagaagacattgaatggaaattattcacccattttaaattggtga
cctagggatcagagatttgtctttccaacagcttgtcatttttcatttc
tcttctcattttttcaggaaagttttgagtgttataaggtggaaggaaaca
tagtagcaatggatactttttttgaaaaattattgcattaccaagaaacag
tagccaaagatatttgaagatcatgttcctcggctccattgtgggttatt
ctagaaatccagtcttaaatctctccgctaaagtggacattccccataaa
aattgtccagctgcctggctcttttgcaataacaacctttgattactgaa
tccctacactcaaactatagtgatatatcagtgtttgagagtgacctcta
gaaaaagaaaagtgtttttagaaatgcgtacaagtcaccccccaaatcct
attgcttatcttgggttaaatttgagagtgattctctgtatataaatatg
tgaaatattattatctcaacttagcacacgtgaagcaacatttcttttcct
acagagaggtgtcatggtaagatttcattccgaattcattgtttcataga
gctatgatcaggccatttctgcaagcaatgtatgaccccacctgagcaac
cacaaataggctctctgtgaaactacaaaggaagttatgtgtggcatcca
tgttggtttcgtctgtctgtaatgtgaattccagtatttgtttagtattt
ccagttgtctcctgctagcaatatgtacagtaacgcgtcaggcttgtgac
atttgaataaggaaaaacagagttcctgttaagtgaataactttagctttt
tacaggggattatgatcaaaagtgattttagtacatcttaaatgatatct
tatttctacatggaaagaagttatagaatcttcatagagttctatgagaa
aaaatatacttgctatctataaaaaagagaaaaaagaaaaaaaatgagaa
aaaagtaagaaaaaaaaaatcctgtcctaggcttttactcttgatcttc
aaaggcacgcagggttaatggttccttgggttattattttgcagttttg
ttttttattttgccttaagtaatgatagaagatatatatggccggacaca
tatgtataaacttttcagcagcatttttaataataaaatatcacagtatt
ttctaaaaaaaaaaaaaaaaa
```

Additionally or alternatively, the method comprises administering to the patient in need thereof, a composition comprising a therapeutically effective amount of an agent (such as for example an antibody) capable of inhibiting the expression and/or function of NLGn4 protein.

The NLGn4 polypeptide sequence is set forth in the following sequence SEQ ID NO: 4:

```
MSRPQGLLWLPLLFTPVCVMLNSNVLLWLTALAIKFTLIDSQAQYPVVNT
NYGKIRGLRTPLPNEILGPVEQYLGVPYASPPTGERRFQPPEPPSSWTGI
RNTTQFAAVCPQHLDERSLLHDMLPIWFTANLDTLMTYVQDQNEDCLYLN
IYVPTEDDIHDQNSKKPVMVYIHGGSYMEGTGNMIDGSILASYGNVIVIT
INYRLGILGFLSTGDQAAKGNYGLLDQIQALRWIEENVGAFGGDPKRVTI
FGSGAGASCVSLLTLSHYSEGLFQKAIIQSGTALSSWAVNYQPAKYTRIL
ADKVGCNMLDTTDMVECLRNKNYKELIQQTITPATYHIAFGPVIDGDVIP
DDPQILMEQGEFLNYDIMLGVNQGEGLKFVDGIVDNEDGVTPNDFDFSVS
NEVDNLYGYPEGKDTLRETIKFMYTDWADKENPETRRKTLVALFTDHQWV
APAVATADLHAQYGSPTYFYAFYHHCQSEMKPSWADSAHGDEVPYVEGIP
MIGPTELFSCNFSKNDVMLSAVVMTYWTNFAKTGDPNQPVPQDTKFIHTK
PNRFEEVAWSKYNPKDQLYLHIGLKPRVRDHYRATKVAFWLELVPHLHNL
NEIFQYVSTTTKVPPPDMTSFPYGTRRSPAKIWPTTKRPAITPANNPKHS
```

```
-continued
KDPHKTGPEDTTVLIETKRDYSTELSVTIAVGASLLFLNILAFAALYYKK

DKRRHETHRRPSPQRNTTNDIAHIQNEEIMSLQMKQLEHDHECESLQAHD

TLRLTCPPDYTLTLRRSPDDIPLMTPNTITMIPNTLTGMQPLHTFNTFSG

GQNSTNLPHGHSTTRV
```

According to some embodiments, the NK cells are liver NK cells which are attenuated in patients having a liver disorder. According to yet another embodiment, the liver disorder is characterized by overexpression of NLGn4 RNA. Such overexpression can attenuate NK cell activity.

According to some embodiments inhibiting the expression of NLGn4 modulates the function of the NK cell for example by activating the NK cell and/or the CD56$^{dim}$ NK cell subset. As a result of NK activation, the activity of hepatic stellate cells (HSCs) and hence fibrosis is reduced. In addition, and according to yet another embodiment, modulating and/or activating the NK cells increases the apoptosis of the HSCs.

According to yet another embodiment there is provided a method for modulating the activity of a natural killer (NK) cell and/or treating, preventing and/or attenuating a liver disorder by administering to a patient a composition comprising a GLUT4 antagonist. Such antagonist can according to the present invention inhibit GLUT4 mediated NLGn4 expression. The antagonist can be selected from the group comprising Ketamine, Amantadine, Phencyclidine, Nitrous oxide, Dextromethorphan (and dextrorphan), Memantine, Ethanol, Riluzole (used in ALS), Xenon, HU-211 (also a cannabinoid), Lead (Pb2+), Conantokins, and Huperzine A. According to an alternative embodiment administering a NMDAR (also known as GLUT4) agonist can increase GLUT4 mediated NLGn4 expression and as a result attenuate NK cell activity. Examples of a GLUT4 agonists are Aminocyclopropanecarboxylic acid, D-Cycloserine, cis-2, 3-Piperidinedicarboxylic acid, L-aspartate, L-alanine, Quinolinate, Homocysterate, D-serine, and ACPL.

According to another aspect of the invention, there is provided a method of modulating the expression of the ribonucleic acid (RNA) encoded by NLGn4 nucleic acid. According to one embodiment, modulating the expression NLGn4 can serve to treat, attenuate or prevent a liver disorder, such as Non-alcoholic fatty liver disease (NAFLD), Non-alcoholic steatohepatitis (NASH), cirrhosis, hepatitis, liver adenoma, insulin resistance, a liver cancer, any NK related inflammatory or neoplastic disorder, or any combination thereof.

According to another embodiment, modulating the expression of NLGn4 comprises contacting the immune cell, such as an NK cell and/or a CD56$^{dim}$ NK cell subset, with a composition comprising an effective amount of an agent that inhibits NLGn4 expression. Such agent can for example be an inhibitory nucleic acid that is complementary and specific to at least a portion of the NLGn4 nucleic acid molecule.

According to yet another embodiment, the inhibitory nucleic acid can for example be an antisense molecule, an siRNA, or an shRNA.

Inhibiting NLGn4 can according to the present invention enhance the cytotoxicity of the NK cells and or specific NK cell subpopulations. According to certain embodiments enhancing the cytotoxicity comprises enhancing the expression of CD107a on said NK cell.

In certain liver disorders NK cell function can be attenuated. According to the present invention such attenuation can be a result of NLGn4 overexpression. In accordance, inhibiting the expression of NLGn4 modulates and/or activates the function of attenuated NK cell. In turn, activating the NK cell may reduce HSC activity and/or increase their apoptosis.

According to yet another aspect of the invention there is provided a method of diagnosing or monitoring a liver disorder and/or the severity of a liver disorder in a patient such as Non-alcoholic fatty liver disease (NAFLD), Non-alcoholic steatohepatitis (NASH), cirrhosis, hepatitis, a liver adenoma, insulin resistance, a liver cancer, any NK related inflammatory or neoplastic disorder, or any combination thereof. The method comprises, according to one embodiment, detecting the expression level of a ribonucleic acid (RNA) encoded by NLGn4 nucleic acid molecule in a biological sample, such as a blood sample, a tissue sample and/or a biological fluid, of a patient.

According to some embodiments, the method further comprises isolating the RNA from the biological sample prior to detecting the NLGn4 RNA expression level. The detection of NLGn4 expression comprises Polymerase Chain Reaction (PCR), Reverse-Transcriptase-PCR (RT-PCR), Northern Blot, Real-time PCR, Flow Cytometry (FACS) or any combination thereof.

Alternatively, the expression level of NLGn4 is detected by hybridization to an oligonucleotide such as a deoxyribonucleic acid (DNA), an RNA, complementary deoxyribonucleic acid (cDNA), a genomic DNA, a synthetic oligonucleotide, or any combination thereof.

According to yet another aspect of the invention, there is provided a pharmaceutical composition comprising a therapeutically effective amount of an agent that inhibits the expression or function of NLGn4.

The agent can be one or more polynucleotides, capable of hybridizing with said nucleic acid. For example the agent can be an inhibitory nucleic acid, such as an antisense molecule, an siRNA, or an shRNA that is complementary and specific to at least a portion of said NLGn4 nucleic acid molecule According to some embodiments, the pharmaceutical composition further comprises a vector capable of expressing the inhibitory nucleic acid molecule. Non-limiting examples of vectors comprise lentiviral vectors, retroviral vectors, plasmids as well as other suitable vectors.

According to another embodiment, the composition comprises or additionally comprises a GLUT4 antagonist. Such antagonist can according to the present invention inhibit GLUT4 mediated NLGn4 expression. The antagonist can be selected from the group consisting of Ketamin, Amantadine, Phencyclidine, Nitrous oxide, Dextromethorphan (and dextrorphan), Memantine, Ethanol, Riluzole (used in ALS), Xenon, HU-211 (also a cannabinoid), Lead (Pb2+), Conantokins, and Huperzine A According to an alternative embodiment administering a GLUT4 agonist can increase GLUT4 mediated NLGn4 expression and as a result attenuate NK cell activity. Examples of a GLUT4 agonists are alanine, Aminocyclopropanecarboxylic acid, D-Cycloserine, cis-2, 3-Piperidinedicarboxylic acid, L-aspartate, L-alanine, Quinolinate, Homocysterate, D-serine, and ACPL According to yet another aspect of the invention, there is provided a kit for prevention, treatment or attenuation of a liver disorder such as, but not limited to, Non-alcoholic fatty liver disease (NAFLD), Non-alcoholic steatohepatitis (NASH), cirrhosis, hepatitis, a liver adenoma, insulin resistance, a liver cancer, any NK related inflammatory or neoplastic disorder, or any combination thereof. The kit comprises the pharmaceutical composition as essentially described above and a pharmaceutically acceptable carrier.

According to yet another aspect of the invention, there is provided a kit for diagnosing a liver disorder such as but not limited to Non-alcoholic fatty liver disease (NAFLD), Non-alcoholic steatohepatitis (NASH), cirrhosis, hepatitis, a liver adenoma, insulin hypersensitivity, a liver cancer or any combination thereof. The kit comprises at least one reagent capable of detecting the expression of a nucleic acid in a biological sample such as a blood sample, a tissue sample, and/or a biological fluid.

According to some embodiments, the reagent comprises NLGn4 specific primers. According to some embodiments, the NLGn4 specific primers are selected from the group set forth in table 1 below.

TABLE 1

NLGn4 specific primers

| Exon | Forward | Reverse |
|---|---|---|
| 2.1 | AAAGCCCTATCTCTCTGCAGG (SEQ ID NO: 5) | TGAGTAGTATTTCGGATGCCAG (SEQ ID NO: 6) |
| 2.2 | AAGAACACCGTTACCCAATGAG (SEQ ID NO: 7) | GAGACATTATAAAACCCTCCTAG (SEQ ID NO: 8) |
| 3 | TTAGCATTGGTGAGTCAGTGTG (SEQ ID NO: 9) | CCGTCAAAACGAGAAGTGGACT (SEQ ID NO: 10) |
| 4 | CTTTTTCTATTTGGCCACCA (SEQ ID NO: 11) | TTCTTGGTTCAGGGTATTTGC (SEQ ID NO: 12) |
| 5.1 | AGCTGCATTTCTGTCCTGTG (SEQ ID NO: 13) | TCTCCCGCAAAGTGTCTTTC (SEQ ID NO: 14) |
| 5.2 | CCAACTTCGTGGACAACCTT (SEQ ID NO: 15) | ACCCCAACACGAAGATGAAC (SEQ ID NO: 16) |
| 6.1 | CACGTCACATGTGGAAGAGT (SEQ ID NO: 17) | GACGGCAATGGTGACACTTA (SEQ ID NO: 18) |
| 6.2 | TCCTCATTGAAACCAAACGA (SEQ ID NO: 19) | AACATTCCTGGTCTGGAGAC (SEQ ID NO: 20) |

The following examples are presented to provide a more complete understanding of the invention. The specific techniques, conditions, materials, proportions and reported data set forth to illustrate the principles of the invention are exemplary and should not be construed as limiting the scope of the invention.

EXAMPLES

Example 1: Methods Used for Evaluating the Role of NLGn4 in NK Activity a) Knockdown of NLGn4:

Lentivirus expressing NLGn4 siRNA were used to infect NK cells of either mouse or human origin and thereby inhibiting NLGn4 expression.

b) NLGn4 Expression:

NLGn4 expression level was evaluated by real-time PCR. In short, RNA was extracted from the cells using Tri Reagent. The extracted RNA was converted to cDNA using random hexamers and reverse transcriptase. NLGn4 expression level was assessed by real time PCR using NLGn4 specific primers. The results were normalized to the expression levels of $a$-actin using $a$-actin specific primers.

c) Isolation of NK Cells from Human Blood Samples:

Blood samples obtained from patients were centrifuged at 4000 rpm for 5 min. After centrifugation, the buffy coat fraction of the blood containing most of the leukocytes was collected and NK cells were isolated using the RosetteSep NK isolation kit according to manufactures instruction.

d) Flow cytometry using FACS analysis of CD107a, NLGn4, $a$-SMA, annexin.

Example 2: NLGn4 is Overexpressed in Patients with Cirrhosis and in a Non-Alcoholic Fatty Liver Disease (NAFLD) Mouse Model Human peripheral blood cells (PBLs) were isolated in accordance with Example 1c from cirrhotic patients and healthy controls, as well as from NAFLD/control mice. RNA was extracted and converted into cDNA and a gene array analysis was performed using an Affymetrix expression array. The results were collated in order to identify the genes having an at least two-fold change in the expression profile. It was found that NLGn4 showed the most significant change in that an approximately 4-fold up-regulation was observed among the cirrhotic patients.

Example 3: NLGn4 Expression can be Reduced Using siRNA

Figure 2:
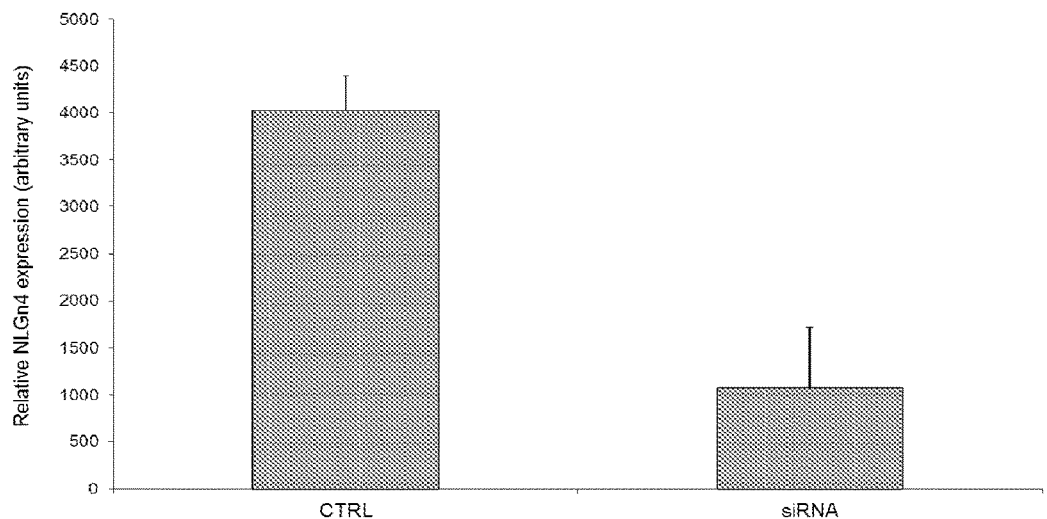
FIG. 2 shows NLGn4 expression upon NLGn4 siRNA expression in mouse NK cells.

Mouse liver NK cells were infected with a lentiviral vector expressing an siRNA against NLGn4 or a scrambled control. 48 hours post infection, the cells were harvested, RNA extracted and converted into cDNA in accordance with example 1b. NLGn4 Expression levels in cells infected with the NLGn4 siRNA or the scrambled control were evaluated using real-time PCR using primes specific for NLGn4. The expression levels obtained were normalized to those obtained for α-actin. As seen in FIG. 2, a significant reduction in NLGn4 expression is observed in cells infected with the siRNA expressing vector, as compared to the control.

Figure 3A:
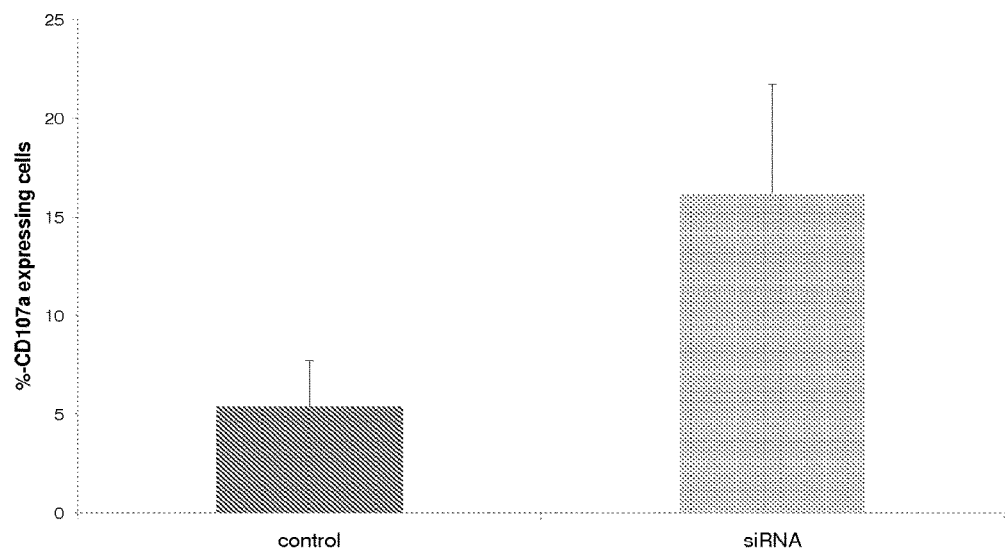
FIG. 3A presents the percentage of viable NK cells expressing CD107a (control or infected with NLGn4 siRNA) co-cultured with HSCs isolated from a WT mouse.

Example 4: NLGn4 Knockdown (KD) Increases NK Activation and Hepatic Stellate Cell (HSC) Apoptosis and Reduces HSC Activity NK cells obtained from mice livers were pre-incubated with IL2 in order to obtain a mature NK cell population. Following infection with the NLGn4 siRNA or with the scrambled control, the cells were co-cultured with freshly isolated HSC from a NAFLD mouse model. The activity of the NK cells was evaluated by the expression of CD107a, a marker of active NK cells. The percentage of viable NK cells expressing CD107a was evaluated by FACS using an anti-CD107a antibody and gating annexin negative cells. As seen in FIG. 3A, as a result of the KD of NLGn4 a significant increase in CD107a positive cells amongst the viable NK cell population was observed.

Figure 3B:
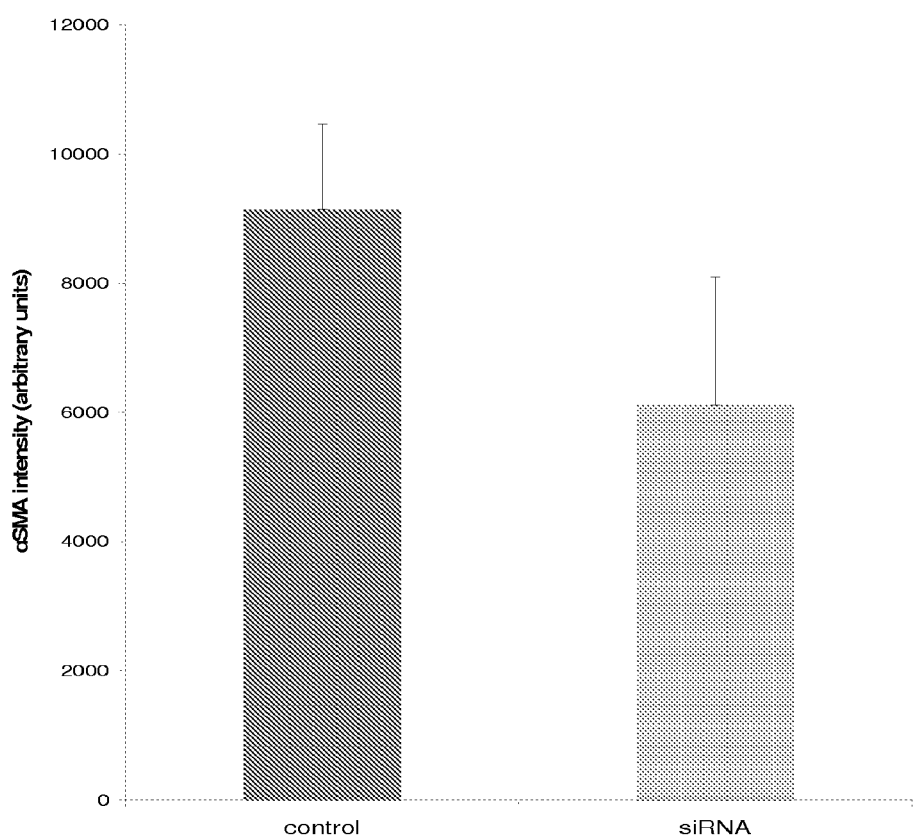
FIG. 3B presents a SMA intensity of en HSCs co-cultured with control or NLGn4 siRNA infected NK cells.
Figure 3C:
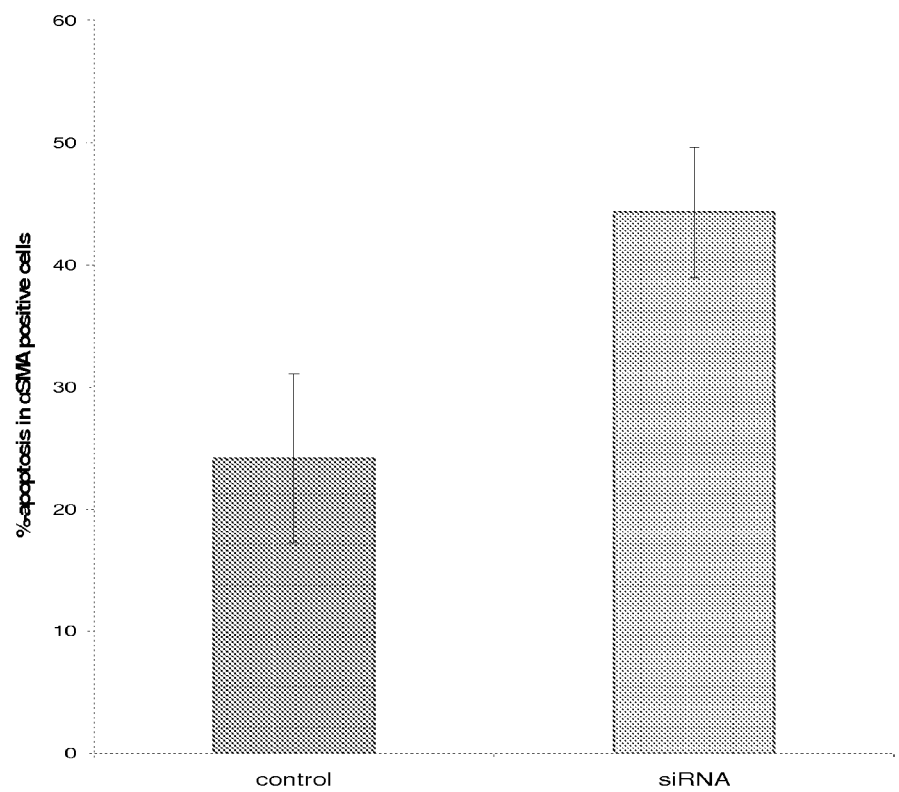
FIG. 3C shows apoptosis of HCS upon co-culturing with control or NLGn4 siRNA infected NK cells.
Figure 4:
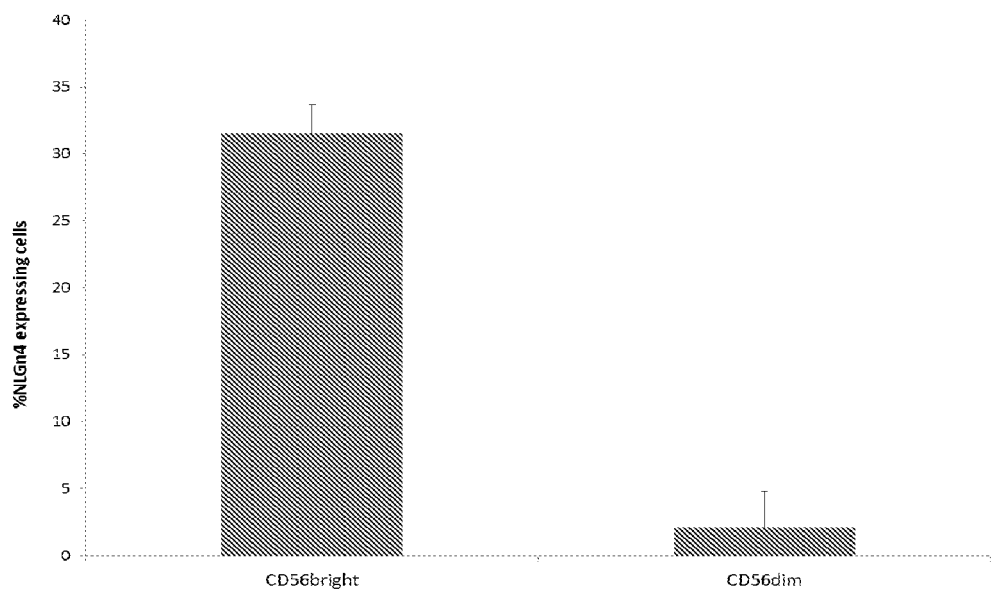
FIG. 4 presents NLGn4 expression in the $CD56^{bright}$ and $CD56^{dim}$ NK subpopulation.

The impact of NK cell activation by NLGn4 KD on HCSs was evaluated by co-culturing the HSCs with the control or the NLGn4 KD NK cells and assessing a SMA intensity (marker of HSC activation). $a$-SMA intensity was significantly decreased upon co-culture with NLGn4 KD NK cells (FIG. 3B) and amongst the $a$-SMA expressing cells an increase in apoptosis was observed (FIG. 3C).

Example 5: NLGn4 is Expression is High in the CD56$^{bright}$ NK Subpopulation and Low in the CD56$^{dim}$ NK Subpopulation Human peripheral blood cells (PBLs) were isolated in accordance with Example 1c. The isolated NK cells were

Figure 5:
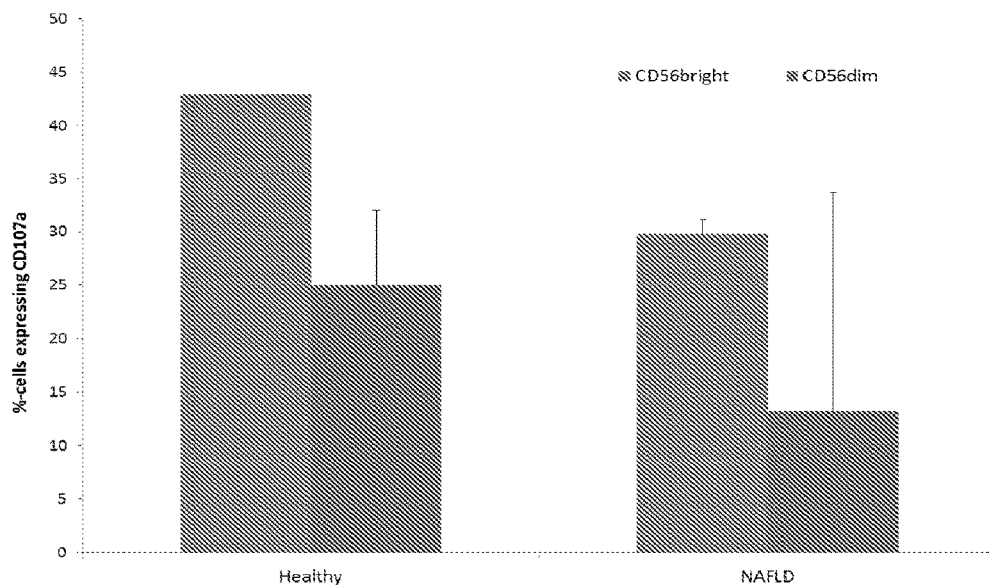
FIG. 5 presents CD107a expression in NAFLD patients and healthy controls.

Example 6: NK Activity as Assessed by CD107a Expression is Attenuated in NAFLD Patients Human peripheral blood cells (PBLs) from NAFLD patients (n=9) and healthy controls (n=3) were isolated in accordance with Example 1c. The isolated NK cells were then co-stained with an anti-CD56 antibody and with an anti-CD107a antibody. FACS analysis showed that CD107a expression was reduced, corresponding to an attenuated NK activity in NAFLD patients (FIG. 5).

Figure 6:
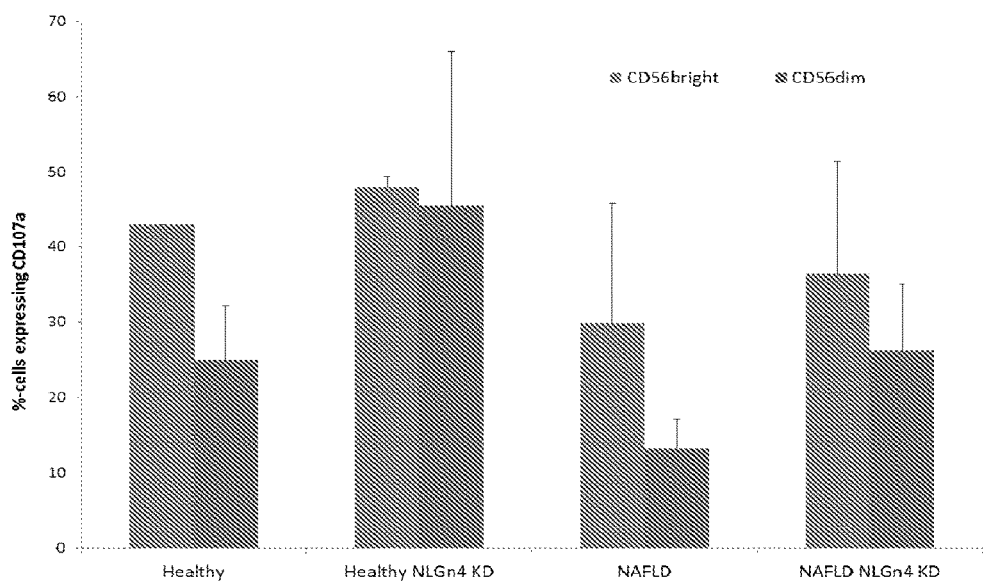
FIG. 6 presents on NK cell activity as assessed by CD107a expression.

Example 7: NLGn4 KD Increases CD56$^{dim}$ NK Cell Activity as Assessed by CD107a Expression Human peripheral blood cells (PBLs) from NAFLD patients (n=9) and healthy controls (n=3) were isolated in accordance with Example 1c. The isolated NK cells were then infected with a lentiviral vector expressing an siRNA against human NLGn4 or a scrambled control. NK activity in response to NLGn4 KD was assessed by CD107a expression. That is, the isolated NK cells were co-stained with an anti-CD56 antibody and with an anti-CD107a antibody. As seen from FIG. 6, CD107a expression was significantly elevated in the CD56$^{dim}$ subpopulation. This might suggest that reducing the expression of NLGn4 can effectively enhance NK cytotoxicity. Since NLGn4 is primarily expressed in CD56$^{bright}$ cells it may be suggested that overexpression of NLGn4 by CD56$^{bright}$ cells inhibits the cytotoxicity of CD56$^{dim}$ cells.

Example 8: NLGn4 KD does not Alter NK Viability

Figure 7A:
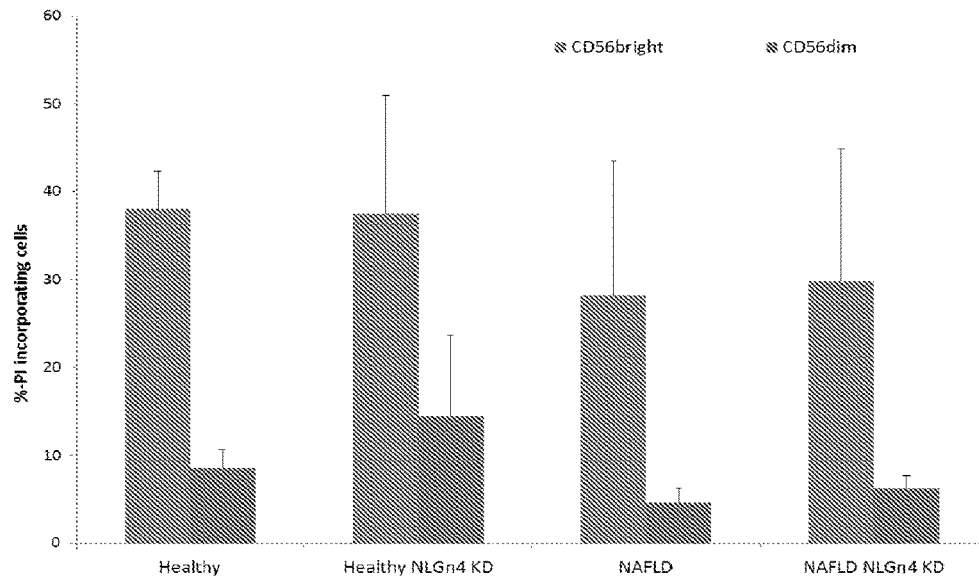
FIG. 7A presents the effects of NLGn4 KD on NK cell viability, as estimated by PI incorporation.
Figure 7B:
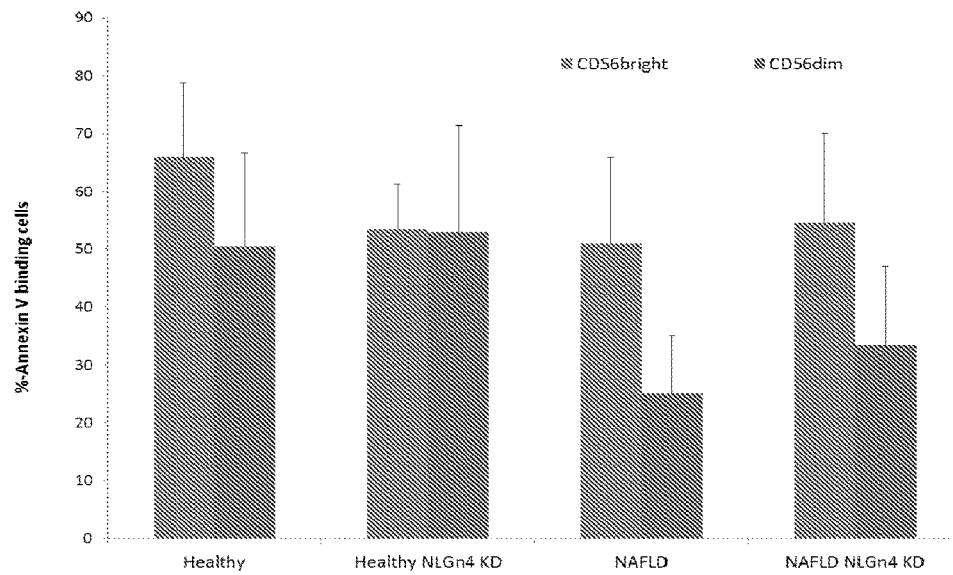
FIG. 7B presents the effects of NLGn4 KD on NK cell viability, as estimated by annexin binding.

Human peripheral blood cells (PBLs) from NAFLD patients (n=9) and healthy controls (n=3) were isolated in accordance with Example 1c. The isolated NK cells were then infected with a lentiviral vector expressing an siRNA against human NLGn4 or a scrambled control. The viability of the NK cells was assessed by FACS analysis estimating annexin binding and PI incorporation. As seen in FIGS. 7A and B, NLGn4 knockdown did not alter cellular viability neither of CD56$^{bright}$ nor of CD56$^{dim}$ NK cells in either NAFLD patients or healthy controls. This indicates that CD56$^{dim}$ cytotoxicity toward foreign cells is elevated without compromising self-recognition.

Example 9: NLGn4 Overexpression Correlates with High Insulin Levels

Figure 8:
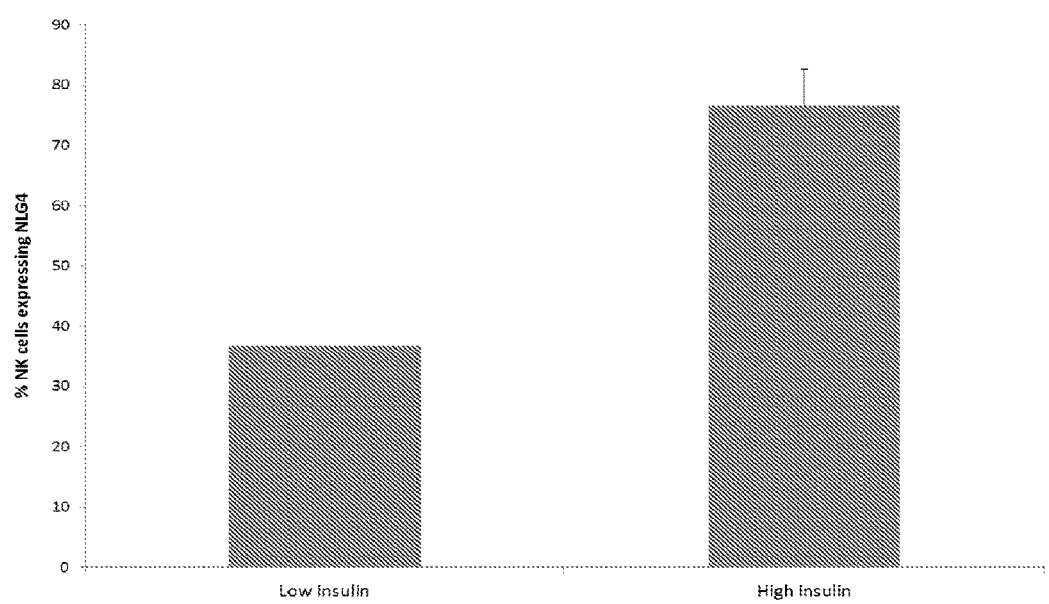
FIG. 8 shows the correlation between insulin and NLGn4 expression.

Human peripheral blood cells (PBLs) from patients with low insulin levels (n=3) and patients with high insulin levels controls (n=3) were isolated in accordance with Example 1c. The isolated NK cells were stained with an anti-NLGn4 antibody. FACS analysis of the cells showed that NLGn4 was significantly higher in NK cells from patients with high insulin levels as compared to those with low insulin levels (FIG. 8). This may suggest that the increased prevalence of NAFLD among insulin resistant subjects may be due to insulin mediated NLGn4 overexpression.

Example 10: Treatment of Mice with a GLUT4 Agonist Elevates NLGn4 Expression NK cells from livers of mice treated with the GLUT4 agonist alanine or control mice are isolated. The isolated NK cells are then co-stained with an anti-CD56 antibody and with an anti-NLGn4 antibody.

Example 11: Treatment of Mice with a GLUT4 Antagonist Reduces NLGn4 Expression NK cells from livers of mice treated with the GLUT4 agonist or control mice are isolated. The isolated NK cells are then co-stained with an anti-CD56 antibody and with an anti-NLGn4 antibody.

---

The invention claimed is:

1. A method of diagnosing and/or monitoring a liver disorder in a subject, the method comprising:
   (a) isolating an immune cell population from a biological sample of the subject, wherein the immune cell population is a natural killer (NK) cell population;
   (b) detecting expression level of an NLGn4 gene product in the immune cell population using NLGn4 specific primer or NLGn4 specific probes, wherein the NLGN4 specific primer or probe comprises a sequence selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20; and
   (c) diagnosing and/or monitoring the liver disorder according to the NLGn4 gene product increased expression level, wherein the liver disorder is non-alcoholic fatty liver disease (NAFLD) or cirrhosis.

2. The method of claim 1, wherein the NLGn4 gene product is encoded by a nucleic acid sequence comprising SEQ ID NO: 1.

3. The method of claim 1, wherein the NLGn4 gene product comprises SEQ ID NO: 2.

4. The method of claim 1, wherein the liver disorder is NAFLD.

5. The method of claim 1, wherein the biological sample comprises a blood sample, a tissue sample, a biological fluid, or any combination thereof.

6. The method of claim 5, wherein the biological sample is a blood sample.

7. The method of claim 1, wherein the NLGn4 gene product expression level is detected by Polymerase Chain Reaction (PCR), Reverse-Transcriptase-PCR (RT-PCR), Northern Blot, Real-time PCR, hybridization to an oligonucleotide or any combination thereof.

8. The method of claim 7, wherein the oligonucleotide comprises deoxyribonucleic acid (DNA), RNA, complementary deoxyribonucleic acid (cDNA), genomic DNA, synthetic oligonucleotide, or any combination thereof.

9. The method of claim 1, further comprising isolating RNA from the immune cell population prior to the detecting of the expression level of the NLGn4 gene product.

* * * * *